(12) United States Patent
Yamamoto et al.

(10) Patent No.: US 8,729,264 B2
(45) Date of Patent: May 20, 2014

(54) AGENT FOR PREVENTION AND/OR TREATMENT OF SKIN DISEASES

(75) Inventors: Keisuke Yamamoto, Sunto-gun (JP); Seiji Aratake, Sunto-gun (JP); Daisuke Nakashima, Sunto-gun (JP); Kimihisa Ueno, Sunto-gun (JP); Mirai Mizutani, Sunto-gun (JP); Daisuke Harada, Sunto-gun (JP); Katsuya Kobayashi, Sunto-gun (JP); Kazuki Hemmi, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 684 days.

(21) Appl. No.: 12/680,484

(22) PCT Filed: Sep. 26, 2008

(86) PCT No.: PCT/JP2008/067563
§ 371 (c)(1),
(2), (4) Date: Mar. 26, 2010

(87) PCT Pub. No.: WO2009/041663
PCT Pub. Date: Apr. 2, 2009

(65) Prior Publication Data
US 2010/0256134 A1    Oct. 7, 2010

(30) Foreign Application Priority Data
Sep. 28, 2007 (JP) .................................. 2007-252804

(51) Int. Cl.
*C07D 487/00* (2006.01)

(52) U.S. Cl.
USPC ........................................................ 544/281

(58) Field of Classification Search
USPC ........................................................ 544/281
See application file for complete search history.

(56) References Cited

U.S. PATENT DOCUMENTS

| 5,055,472 | A  | 10/1991 | Fujikawa et al. |
| 5,420,128 | A  | 5/1995  | Kiyokawa et al. |
| 2004/0043998 | A1 | 3/2004 | Kato et al. |
| 2006/0089362 | A1 | 4/2006 | Seno et al. |
| 2007/0037883 | A1 | 2/2007 | Dusting et al. |
| 2007/0082901 | A1 * | 4/2007 | Guzi et al. ................. 514/234.5 |
| 2007/0179161 | A1 | 8/2007 | Parratt et al. |

FOREIGN PATENT DOCUMENTS

| EP | 0 328 700 A1 | 8/1989 |
| EP | 1 149 835 A1 | 10/2001 |
| JP | 04-270285 A | 9/1992 |
| JP | 05-112571 A | 5/1993 |
| JP | 07-157485 A | 6/1995 |
| JP | 09-169762 A | 6/1997 |
| JP | 10-101672 A | 4/1998 |
| JP | 2000-038350 A | 2/2000 |
| JP | 2002-501532 A | 1/2002 |
| JP | 2006-520326 A | 9/2006 |
| WO | WO 98/54093 A1 | 12/1998 |
| WO | WO 00/44754 A1 | 8/2000 |
| WO | WO 00/53605 A1 | 9/2000 |
| WO | WO 00/59908 A2 | 10/2000 |
| WO | WO 02/40485 A1 | 5/2002 |
| WO | WO 03/091256 A1 | 11/2003 |
| WO | WO 03/101993 A1 * | 12/2003 |
| WO | WO 2004/087707 A1 | 10/2004 |
| WO | WO 2004/110454 A1 | 12/2004 |
| WO | WO 2006/052913 A1 | 5/2006 |

OTHER PUBLICATIONS

European Patent Office, Extended European Search Report in European Application No. 08833967.6-2101 (May 4, 2011).
Japanese Patent Office, Notice of Reasons for Refusal in Japanese Patent Application 2009-534444 (Jun. 11, 2013).

* cited by examiner

*Primary Examiner* — Kara R McMillian
(74) *Attorney, Agent, or Firm* — Leydig, Voit & Mayer, Ltd.

(57) ABSTRACT

Provided is an agent for the prevention and/or treatment of a skin disease containing, as an active ingredient, a pyrazolopyrimidine derivative represented by the formula (I)

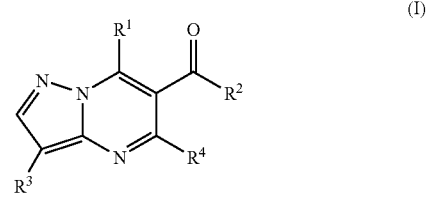

(wherein each symbol is as defined in the specification), or a pharmacologically acceptable salt thereof, and the like.

11 Claims, No Drawings

AGENT FOR PREVENTION AND/OR TREATMENT OF SKIN DISEASES

TECHNICAL FIELD

The present invention relates to an agent for the prevention and/or treatment of a skin disease containing, as an active ingredient, a pyrazolopyrimidine derivative or a pharmacologically acceptable salt thereof, and the like.

BACKGROUND ART

Pyrazolo[1,5-a]pyrimidine derivatives are known to be useful as corticotrophin-releasing factor receptor antagonist (patent documents 1 and 2), adenosine enhancer (patent document 3), angiotensin II antagonist (patent document 4), tyrosine kinase inhibitor (patent documents 5 and 6), HMG-CoA inhibitor (patent document 7), NAD(H) oxidase inhibitor (patent document 8), adenosine $A_{2A}$ receptor agonist (patent documents 9 and 10), therapeutic drug for prostatic hyperplasia (patent document 11), therapeutic drug for cerebral circulatory disturbance (patent document 12), anti-obesity drug (patent document 13) and anti-inflammatory drug (patent document 14).

patent document 1: WO00/59908
    patent document 2: JP-A-2000-38350
    patent document 3: JP-A-10-101672
    patent document 4: JP-A-7-157485
    patent document 5: WO00/53605
    patent document 6: WO98/54093
    patent document 7: JP-A-4-270285
    patent document 8: WO03/091256
    patent document 9: WO02/40485
    patent document 10: WO2004/110454
    patent document 11: JP-A-5-112571
    patent document 12: EP-A-0328700
    patent document 13: WO00/44754
    patent document 14: JP-A-9-169762.

DISCLOSURE OF THE INVENTION

Problems to be Solved by the Invention

An object of the present invention is to provide an agent for the prevention and/or treatment of a skin disease containing, as an active ingredient, a pyrazolopyrimidine derivative or a pharmacologically acceptable salt thereof, and the like.

Means of Solving the Problems

The present invention relates to the following (1)-(37).
(1) An agent for the prevention and/or treatment of a skin disease comprising, as an active ingredient, a pyrazolopyrimidine derivative represented by the formula (I)

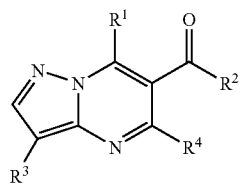

[wherein $R^1$ represents $-NR^{1a}R^{1b}$ (wherein $R^{1a}$ and $R^{1b}$ are the same or different and each represents a hydrogen atom, lower alkyl optionally having substituent(s), cycloalkyl optionally having substituent(s), lower alkoxy optionally having substituent(s), lower alkanoyl optionally having substituent(s), aryl optionally having substituent(s), aralkyl optionally having substituent(s), an aromatic heterocyclic group optionally having substituent(s) or an aliphatic heterocyclic group optionally having substituent(s), or $R^{1a}$ and $R^{1b}$ form, together with the adjacent nitrogen atom, a nitrogen-containing heterocyclic group optionally having substituent(s)), $-OR^{1c}$ (wherein $R^{1c}$ represents a hydrogen atom, lower alkyl optionally having substituent(s), cycloalkyl optionally having substituent(s), aryl optionally having substituent(s), aralkyl optionally having substituent(s), an aromatic heterocyclic group optionally having substituent(s) or an aliphatic heterocyclic group optionally having substituent(s)) or $-SR^{1d}$ (wherein $R^{1d}$ is as defined for the aforementioned $R^{1c}$),
$R^2$ represents

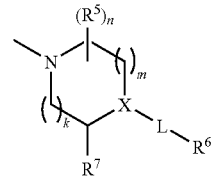

[wherein k and m each represents an integer of 0-2 wherein the total of k and m is not more than 3,
    n represents an integer of 0-4, and when n is 2, 3 or 4, respective $R^5$s may be the same or different,
    L represents a single bond, alkylene, C(=O) or $SO_2$,
    $R^5$ represents halogen, hydroxy, lower alkyl optionally having substituent(s) or lower alkoxy optionally having substituent(s),
    $R^6$ represents lower alkyl optionally having substituent(s), cycloalkyl optionally having substituent(s), aryl optionally having substituent(s), an aromatic heterocyclic group optionally having substituent(s) or an aliphatic heterocyclic group optionally having substituent(s),
    X represents a nitrogen atom or $-CR^8$ (wherein $R^8$ represents a hydrogen atom, halogen, hydroxy, cyano, lower alkyl optionally having substituent(s) or lower alkoxy optionally having substituent(s), or forms a bond together with $R^7$), and
    $R^7$ forms a bond together with $R^8$, or represents a hydrogen atom, halogen, hydroxy, lower alkyl optionally having substituent(s) or lower alkoxy optionally having substituent(s)], or

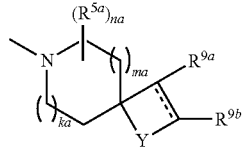

{wherein ka, ma and na are as defined for the aforementioned k, m and n, respectively,
    $R^{5a}$ is as defined for the aforementioned $R^5$,
    ===== represents a single bond or a double bond,
    $R^{9a}$ and $R^{9b}$ are the same or different and each represents a hydrogen atom or lower alkyl optionally having substituent(s), or $R^{9a}$ and $R^{9b}$ form, together with the respectively adjacent carbon atoms, an aliphatic ring optionally having substituent(s) or an aromatic ring optionally having substituent(s), Y represents —CHR$^{10a}$—CHR$^{10b}$— (wherein R$^{10a}$ and R$^{10b}$ are the same or different and each represents a hydrogen atom, hydroxy, lower alkyl optionally having substituent(s) or lower alkoxy optionally having substituent(s), or R$^{10a}$ and R$^{10b}$ form, together with the respectively adjacent carbon atoms, an aliphatic ring optionally having substituent(s)), —CR$^{10c}$=CR$^{10d}$— (wherein R$^{10c}$ and R$^{10d}$ are the same or different and each represents a hydrogen atom or lower alkyl optionally having substituent(s), or R$^{10c}$ and R$^{10d}$ form, together with the respectively adjacent carbon atoms, an aliphatic ring optionally having substituent(s) or an aromatic ring optionally having substituent(s)), —Z$^{a}$—CR$^{11a}$R$^{11b}$— [wherein R$^{11a}$ and R$^{11b}$ are the same or different and each represents a hydrogen atom or lower alkyl optionally having substituent(s), or R$^{11a}$ and R$^{11b}$ form carbonyl together with the adjacent carbon atom, Z$^{a}$ represents C(=O), O, S, SO, SO$_2$ or NR$^{12}$ (wherein R$^{12}$ represents a hydrogen atom, lower alkyl optionally having substituent(s), lower alkanoyl optionally having substituent(s), lower alkoxycarbonyl optionally having substituent(s) or aralkyl optionally having substituent(s))], or —CR$^{11c}$R$^{11d}$—Z$^{b}$— (wherein R$^{11c}$, R$^{11d}$ and Z$^{b}$ are as defined for the aforementioned R$^{11a}$, R$^{11b}$ and Z$^{a}$, respectively)}, R$^{3}$ represents carboxy, lower alkoxycarbonyl optionally having substituent(s), lower alkyl optionally having substituent(s), lower alkanoyl optionally having substituent(s), aralkyl optionally having substituent(s), an aromatic heterocyclic group optionally having substituent(s), —C(=O)NR$^{13a}$R$^{13b}$ [wherein R$^{13a}$ and R$^{13b}$ are the same or different and each represents a hydrogen atom, lower alkyl optionally having substituent(s), lower alkanoyl optionally having substituent(s), aralkyl optionally having substituent(s) or —S(O)$_2$R$^{14}$ (wherein R$^{14}$ represents lower alkyl optionally having substituent(s), cycloalkyl optionally having substituent(s), N-mono-lower alkylamino optionally having substituent(s), N,N-di-lower alkylamino optionally having substituent(s), aryl optionally having substituent(s), aralkyl optionally having substituent(s), an aromatic heterocyclic group optionally having substituent(s) or an aliphatic heterocyclic group optionally having substituent(s)), or R$^{13a}$ and R$^{13b}$ form, together with the adjacent nitrogen atom, a nitrogen-containing heterocyclic group optionally having substituent(s)] or —NR$^{13c}$R$^{13d}$ (wherein R$^{13c}$ and R$^{13d}$ are as defined for the aforementioned R$^{13a}$ and R$^{13b}$, respectively), and R$^{4}$ represents a hydrogen atom, halogen, lower alkyl optionally having substituent(s), aralkyl optionally having substituent(s), —NR$^{15a}$R$^{15b}$ (wherein R$^{15a}$ and R$^{15b}$ are as defined for the aforementioned R$^{1a}$ and R$^{1b}$, respectively), —OR$^{15c}$ (wherein R$^{15c}$ is as defined for the aforementioned R$^{1c}$), or —SR$^{15d}$ (wherein R$^{15d}$ is as defined for the aforementioned R$^{1c}$)], or a pharmacologically acceptable salt thereof.

(2) The agent for the prevention and/or treatment of a skin disease of the aforementioned (1), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(3) The agent for the prevention and/or treatment of a skin disease of the aforementioned (1), wherein the skin disease is dermatitis.

(4) The agent for the prevention and/or treatment of a skin disease of the aforementioned (1), wherein the skin disease is a skin disease selected from contact dermatitis and atopic dermatitis.

(5) A pyrazolopyrimidine derivative represented by the formula (IA)

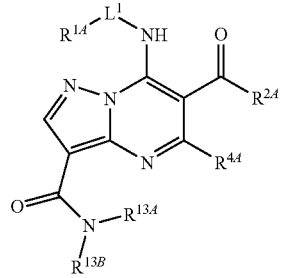

(IA)

[wherein L$^{1}$ represents a single bond or alkylene,

R$^{1A}$ represents cycloalkyl optionally having substituent(s), aryl optionally having substituent(s), an aromatic heterocyclic group optionally having substituent(s) or an aliphatic heterocyclic group optionally having substituent(s), R$^{2A}$ represents

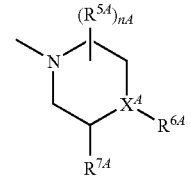

[wherein nA represents an integer of 0-2, and when nA is 2, respective R$^{5A}$s may be the same or different, R$^{5A}$ represents halogen or lower alkyl, R$^{6A}$ represents cycloalkyl optionally having substituent(s), aryl optionally having substituent(s), an aromatic heterocyclic group optionally having substituent(s) or an aliphatic heterocyclic group optionally having substituent(s), X$^{A}$ represents a nitrogen atom or —CR$^{8A}$ (wherein R$^{8A}$ represents a hydrogen atom, halogen or lower alkyl, or forms a bond together with R$^{7A}$), and R$^{7A}$ forms a bond together with R$^{8A}$, or represents a hydrogen atom, halogen or lower alkyl], or

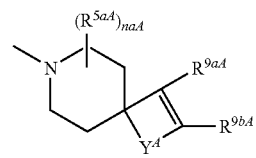

{wherein naA and R$^{5aA}$ are as defined for the aforementioned nA and R$^{5A}$, respectively, R$^{9aA}$ and R$^{9bA}$ form, together with the respectively adjacent carbon atom, an aromatic ring optionally having substituent(s), Y$^{A}$ represents —CHR$^{10aA}$—CHR$^{10bA}$— (wherein $R^{10aA}$ and $R^{10bA}$ are the same or different and each represents a hydrogen atom, hydroxy, lower alkyl optionally having substituent(s) or lower alkoxy optionally having substituent(s)), —$CR^{10cA}$=$CR^{10dA}$— (wherein $R^{10cA}$ and $R^{10dA}$ are the same or different and each represents a hydrogen atom or lower alkyl optionally having substituent(s)), —$Z^{aA}$—$CR^{11aA}R^{11bA}$— [wherein $R^{11aA}$ and $R^{11bA}$ are the same or different and each represents a hydrogen atom or lower alkyl optionally having substituent(s), or $R^{11aA}$ and $R^{11bA}$ form carbonyl together with the adjacent carbon atom, $Z^{aA}$ represents C(=O), O, S, SO, $SO_2$ or $NR^{12A}$ (wherein $R^{12A}$ represents a hydrogen atom, lower alkyl optionally having substituent(s), lower alkanoyl optionally having substituent(s), lower alkoxycarbonyl optionally having substituent(s) or aralkyl optionally having substituent(s))], or —$CR^{11cA}R^{11dA}$—$Z^{bA}$— (wherein $R^{11cA}$, $R^{11dA}$ and $Z^{bA}$ are as defined for the aforementioned $R^{11aA}$, $R^{11bA}$ and $Z^{aA}$, respectively)}, $R^{13A}$ and $R^{13B}$ are the same or different and each represents a hydrogen atom, lower alkyl optionally having substituent(s), lower alkanoyl optionally having substituent(s), aralkyl optionally having substituent(s) or —$S(O)_2R^{14A}$ (wherein $R^{14A}$ represents lower alkyl optionally having substituent(s), cycloalkyl optionally having substituent(s), N-mono-lower alkylamino optionally having substituent(s), N,N-di-lower alkylamino optionally having substituent(s), aryl optionally having substituent(s), aralkyl optionally having substituent(s), an aromatic heterocyclic group optionally having substituent(s) or an aliphatic heterocyclic group optionally having substituent(s)), or $R^{13A}$ and $R^{13B}$ form, together with the adjacent nitrogen atom, a nitrogen-containing heterocyclic group optionally having substituent(s), and $R^{4A}$ represents a hydrogen atom or lower alkyl optionally having substituent(s)], or a pharmacologically acceptable salt thereof.

(6) The pyrazolopyrimidine derivative or the pharmacologically acceptable salt thereof of the aforementioned (5) wherein $L^1$ is a single bond or methylene.

(7) The pyrazolopyrimidine derivative or the pharmacologically acceptable salt thereof of the aforementioned (5) or (6), wherein $R^{1A}$ is aryl optionally having substituent(s).

(8) The pyrazolopyrimidine derivative or the pharmacologically acceptable salt thereof of the aforementioned (5) or (6), wherein $R^{1A}$ is phenyl optionally having substituent(s).

(9) The pyrazolopyrimidine derivative or the pharmacologically acceptable salt thereof of the aforementioned (5) or (6), wherein $R^{1A}$ is an aromatic heterocyclic group optionally having substituent(s).

(10) The pyrazolopyrimidine derivative or the pharmacologically acceptable salt thereof of any of the aforementioned (5)-(9), wherein $R^{4A}$ is a hydrogen atom.

(11) The pyrazolopyrimidine derivative or the pharmacologically acceptable salt thereof of any of the aforementioned (5)-(10), wherein $R^{13A}$ is a hydrogen atom, and $R^{13B}$ is —$S(O)_2R^{14A}$ (wherein $R^{14A}$ is as defined above).

(12) The pyrazolopyrimidine derivative or the pharmacologically acceptable salt thereof of any of the aforementioned (5)-(10), wherein $R^{13A}$ is a hydrogen atom, and $R^{13B}$ is —$S(O)_2R^{14B}$ (wherein $R^{14B}$ represents lower alkyl, halogen-substituted lower alkyl or cycloalkyl).

(13) The pyrazolopyrimidine derivative or the pharmacologically acceptable salt thereof of any of the aforementioned (5)-(12), wherein $R^{2A}$ is

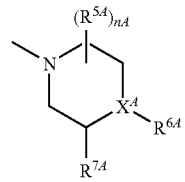

(wherein nA, $R^{5A}$, $R^{6A}$, $R^{7A}$ and $X^A$ are each as defined above), or a pharmacologically acceptable salt thereof.

(14) The pyrazolopyrimidine derivative or the pharmacologically acceptable salt thereof of the aforementioned (13), wherein $R^{6A}$ is phenyl optionally having substituent(s).

(15) The pyrazolopyrimidine derivative or the pharmacologically acceptable salt thereof of any of the aforementioned (5)-(12), wherein $R^{2A}$ is

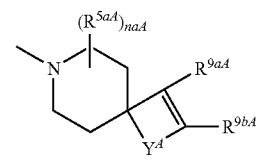

(wherein naA, $R^{5aA}$, $R^{9aA}$, $R^{9bA}$ and $Y^A$ are each as defined above).

(16) The pyrazolopyrimidine derivative or the pharmacologically acceptable salt thereof of the aforementioned (15), wherein $R^{9aA}$ and $R^{9bA}$ form, together with the respectively adjacent carbon atom, a benzene ring optionally having substituent(s), $Y^A$ is —$CHR^{10aA}$—$CHR^{10bA}$— (wherein $R^{10aA}$ and $R^{10bA}$ are each as defined above), —$CR^{10cA}$=$CR^{10dA}$— (wherein $R^{10cA}$ and $R^{10dA}$ are each as defined above), —O—$CR^{11aA}R^{11bA}$— (wherein $R^{11aA}$ and $R^{11bA}$ are each as defined above) or —$CR^{11cA}R^{11dA}$—O— (wherein $R^{11cA}$ and $R^{11dA}$ are each as defined above).

(17) A pharmaceutical agent comprising, as an active ingredient, the pyrazolopyrimidine derivative of any of the aforementioned (5)-(16), or the pharmacologically acceptable salt thereof.

(18) An agent for the prevention and/or treatment of a skin disease comprising, as an active ingredient, the pyrazolopyrimidine derivative of any of the aforementioned (5)-(16), or the pharmacologically acceptable salt thereof.

(19) The agent for the prevention and/or treatment of a skin disease of the aforementioned (18), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(20) The agent for the prevention and/or treatment of a skin disease of the aforementioned (18), wherein the skin disease is dermatitis.

(21) The agent for the prevention and/or treatment of a skin disease of the aforementioned (18), wherein the skin disease is a skin disease selected from contact dermatitis and atopic dermatitis.

(22) A method for the prevention and/or treatment of a skin disease, comprising a step of administering an effective amount of the pyrazolopyrimidine derivative of any of the aforementioned (5)-(16), or the pharmacologically acceptable salt thereof to a subject in need thereof.

(23) The method of the aforementioned (22), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(24) The method of the aforementioned (22), wherein the skin disease is dermatitis.

(25) The method of the aforementioned (22), wherein the skin disease is a skin disease selected from contact dermatitis and atopic dermatitis.

(26) Use of the pyrazolopyrimidine derivative of any of the aforementioned (5)-(16) or the pharmacologically acceptable salt thereof for the manufacture of an agent for the prevention and/or treatment of a skin disease.

(27) The use of the aforementioned (26), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(28) The use of the aforementioned (26), wherein the skin disease is dermatitis.

(29) The use of the aforementioned (26), wherein the skin disease is a skin disease selected from contact dermatitis and atopic dermatitis.

(30) A method for the prevention and/or treatment of a skin disease, comprising a step of administering, to a subject in need thereof, an effective amount of a pyrazolopyrimidine derivative represented by the formula (I)

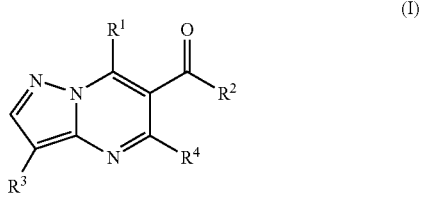

(wherein $R^1$, $R^2$, $R^3$ and $R^4$ are each as defined above), or a pharmacologically acceptable salt thereof.

(31) The method of the aforementioned (30), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(32) The method of the aforementioned (30), wherein the skin disease is dermatitis.

(33) The method of the aforementioned (30), wherein the skin disease is a skin disease selected from contact dermatitis and atopic dermatitis.

(34) Use of a pyrazolopyrimidine derivative represented by the formula (I)

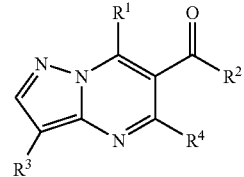

(wherein $R^1$, $R^2$, $R^3$ and $R^4$ are each as defined above), or a pharmacologically acceptable salt thereof for the manufacture of an agent for the prevention and/or treatment of a skin disease.

(35) The use of the aforementioned (34), wherein the skin disease is a skin disease selected from acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(36) The use of the aforementioned (34), wherein the skin disease is dermatitis.

(37) The use of the aforementioned (34), wherein the skin disease is a skin disease selected from contact dermatitis and atopic dermatitis.

Effect of the Invention

The present invention provides an agent for the prevention and/or treatment of a skin disease containing, as an active ingredient, a pyrazolopyrimidine derivative or a pharmacologically acceptable salt thereof, and the like.

BEST MODE FOR CARRYING OUT THE INVENTION

In the present specification, the compounds represented by the formula (I) and the formula (IA) are referred to as compound (I) and compound (IA). The same applies to the compounds having other formula numbers.

In the definition of each group in the formula (I) and the formula (IA),

Examples of the lower alkyl, and the lower alkyl moiety of the lower alkoxy, the lower alkoxycarbonyl, the lower alkanoyl, the N-mono-lower alkylamino and the N,N-di-lower alkylamino include straight chain or branched alkyl having a carbon number of 1-10, more specifically, methyl, ethyl, propyl, isopropyl, butyl, isobutyl, sec-butyl, tert-butyl, pentyl, isopentyl, neopentyl, hexyl, heptyl, octyl, nonyl, decyl and the like. Two lower alkyl moieties of the N,N-di-lower alkylamino may be the same or different.

The alkylene and the alkylene moiety of the halogen-substituted lower alkyl has the same meaning as the group formed by removing one hydrogen atom from the aforementioned lower alkyl.

Examples of the cycloalkyl include cycloalkyl having 3 to 8 carbon atoms, and more specific examples thereof include cyclopropyl, cyclobutyl, cyclopentyl, cyclohexyl, cycloheptyl, cyclooctyl and the like.

Examples of the aryl include aryl having a carbon number of 6-14, and more specific examples thereof include phenyl, naphthyl, azulenyl, anthryl, pentalenyl, indenyl, biphenylenyl and the like.

The alkylene moiety of the aralkyl has the same meaning as the group formed by removing one hydrogen atom from the aforementioned lower alkyl, and the aryl moiety is as defined for the aforementioned aryl.

Examples of the aliphatic heterocyclic group include a 3- to 7-membered monocyclic aliphatic heterocyclic group containing at least one atom selected from a nitrogen atom, an oxygen atom and a sulfur atom, a bicyclic or tricyclic condensed aliphatic heterocyclic group containing at least one atom selected from a nitrogen atom, an oxygen atom and a sulfur atom, wherein 3- to 8-membered rings are condensed, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic condensed aromatic heterocyclic group containing at least one atom selected from a nitrogen atom, an oxygen atom and a sulfur atom, wherein 3- to 8-membered rings are condensed, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, azepinyl, diazepinyl, pyranyl, oxepinyl, thiopyranyl, thiepinyl, furazanyl, oxadiazolyl, oxazinyl, oxadiazinyl, oxazepinyl, oxadiazepinyl, thiazinyl, thiadiazinyl, thiazepinyl, thiadiazepinyl, indolizinyl, isobenzofuranyl, isobenzothiophenyl, dithianaphthalenyl, quinolizinyl, pteridinyl, benzoxazolidinyl, chromenyl, benzoxepinyl, benzoxadiazepinyl, benzothiepinyl, benzothiazepinyl, benzothiadiazepinyl, benzoazepinyl, benzodiazepinyl, benzofurazanyl, benzothiadiazolinyl, carbazolyl, β-carbolinyl, acrydinyl, phenazinyl, dibenzofuranyl, xanthenyl, dibenzothiophenyl, phenothiazinyl, phenoxazinyl, phenoxathinyl, thianthrenyl, phenanthridinyl, phenanthrolinyl, perimidinyl and the like.

Examples of the nitrogen-containing heterocyclic group formed together with the adjacent nitrogen atom thereto include a 5-membered or 6-membered monocyclic heterocyclic group containing at least one nitrogen atom (said monocyclic heterocyclic group may contain another nitrogen atom, an oxygen atom or a sulfur atom), a bicyclic or tricyclic condensed heterocyclic group containing at least one nitrogen atom (said condensed heterocyclic group may contain other nitrogen atom, oxygen atom or sulfur atom), wherein 3- to 8-membered rings are condensed, and the like, and more specific examples thereof include aziridinyl, azetidinyl, pyrrolidinyl, piperidino, azepanyl, pyrrolinyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl and the like.

Examples of the aliphatic ring include aliphatic rings corresponding to the aforementioned cycloalkyl and aliphatic heterocyclic group.

Examples of the aromatic ring include aromatic rings corresponding to the aforementioned aryl and aromatic heterocyclic group.

The halogen and the halogen moiety of the halogen-substituted lower alkyl mean each atom of fluorine, chlorine, bromine or iodine.

The substituent(s) (substituent group-1) in the lower alkyl optionally having substituent(s), the lower alkoxy optionally having substituent(s), the N-mono-lower alkylamino optionally having substituent(s), the N,N-di-lower alkylamino optionally having substituent(s), the lower alkoxycarbonyl optionally having substituent(s) and the lower alkanoyl optionally having substituent(s) are the same or different and examples thereof include 1 to 3 substituents selected from the group consisting of halogen; sulfanyl; nitro; cyano; $C_{3-8}$ cycloalkyl optionally having 1 to 3 substituents selected from the following substituent group C; an aliphatic heterocyclic group optionally having 1 to 3 substituents selected from the following substituent group C; an aromatic heterocyclic group optionally having 1 to 3 substituents selected from the following substituent group B; $C_{1-10}$ alkylsulfanyl optionally having 1 to 3 substituents selected from the following substituent group A; $C_{6-14}$ arylsulfanyl optionally having 1 to 3 substituents selected from the following substituent group B; $C_{1-10}$ alkylsulfonyl optionally having 1 to 3 substituents selected from the following substituent group A; $C_{6-14}$ arylsulfonyl optionally having 1 to 3 substituents selected from the following substituent group B; $OR^{16}$ (wherein $R^{16}$ represents a hydrogen atom, $C_{1-10}$ alkyl optionally having 1 to 3 substituents selected from the following substituent group A, $C_{3-8}$ cycloalkyl optionally having 1 to 3 substituents selected from the following substituent group C, $C_{6-14}$ aryl optionally having 1 to 3 substituents selected from the following substituent group B, $C_{7-16}$ aralkyl optionally having 1 to 3 substituents selected from the following substituent group B, an aromatic heterocyclic group optionally having 1 to 3 substituents selected from the following substituent group B, $C_{2-11}$ alkanoyl optionally having 1 to 3 substituents selected from the following substituent group A, $C_{7-15}$ aroyl optionally having 1 to 3 substituents selected from the following substituent group B, $C_{1-10}$ alkylsulfonyl optionally having 1 to 3 substituents selected from the following substituent group A or $C_{6-14}$ arylsulfonyl optionally having 1 to 3 substituents selected from the following substituent group B); C(=O)R$^{17}$ (wherein R$^{17}$ represents amino, hydroxy, $C_{1-10}$ alkyl optionally having 1 to 3 substituents selected from the following substituent group A, $C_{3-8}$ cycloalkyl optionally having 1 to 3 substituents selected from the following substituent group C, $C_{6-14}$ aryl optionally having 1 to 3 substituents selected from the following substituent group B, an aliphatic heterocyclic group optionally having 1 to 3 substituents selected from the following substituent group C, an aromatic heterocyclic group optionally having 1 to 3 substituents selected from the following substituent group B, $C_{1-10}$ alkoxy optionally having 1 to 3 substituents selected from the following substituent group A, $C_{6-14}$ aryloxy optionally having 1 to 3 substituents selected from the following substituent group B, $C_{1-10}$ alkylamino optionally having 1 to 3 substituents selected from the following substituent group A, di-$C_{1-10}$ alkylamino optionally having 1 to 3 substituents selected from the following substituent group A or $C_{6-14}$ arylamino optionally having 1 to 3 substituents selected from the following substituent group B); and —NR$^{18a}$R$^{18b}$ (wherein R$^{18a}$ and R$^{18b}$ are the same or different and each represents a hydrogen atom, formyl, $C_{1-10}$ alkyl optionally having 1 to 3 substituents selected from the following substituent group A, $C_{3-8}$ cycloalkyl optionally having 1 to 3 substituents selected from the following substituent group C, $C_{6-14}$ aryl optionally having 1 to 3 substituents selected from the following substituent group B, an aliphatic heterocyclic group optionally having 1 to 3 substituents selected from the following substituent group C, an aromatic heterocyclic group optionally having 1 to 3 substituents selected from the following substituent group B, $C_{2-11}$ alkanoyl optionally having 1 to 3 substituents selected from the following substituent group A, $C_{7-15}$ aroyl optionally having 1 to 3 substituents selected from the following substituent group B, $C_{1-10}$ alkoxycarbonyl optionally having 1 to 3 substituents selected from the following substituent group A, $C_{1-10}$ alkylsulfonyl optionally having 1 to 3 substituents selected from the following substituent group A or $C_{6-14}$ arylsulfonyl optionally having 1 to 3 substituents selected from the following substituent group B). Examples of the substituent in the lower alkoxy optionally having substituent(s), the lower alkoxycarbonyl optionally having substituent(s) and the lower alkanoyl optionally having substituent(s) also include $C_{6-14}$ aryl optionally having 1 to 3 substituents selected from the following substituent group B, in addition to the aforementioned substituents.

The substituent(s) in the aryl optionally having substituent(s), the phenyl optionally having substituent(s), the aralkyl optionally having substituent(s), the aromatic heterocyclic group optionally having substituent(s), the aromatic ring optionally having substituent(s) and the benzene ring optionally having substituent(s) are the same or different and examples thereof include 1 to 3 substituents selected from the group consisting of $C_{1-10}$ alkyl optionally having 1 to 3 substituents selected from the following substituent group A, $C_{6-14}$ aryl optionally having 1 to 3 substituents selected from the following substituent group B and the substituents of the aforementioned substituent group-1. The substituent in the aryl optionally having substituent(s) may form a condensed ring of $C_{4-8}$ cycloalkyl ring optionally having 1 to 3 substituents selected from the following substituent group C with the aryl moiety or a condensed ring of an aliphatic heterocyclic group optionally having 1 to 3 substituents selected from the following substituent group C with the aryl moiety in addition to the above substituent(s). The substituent in the phenyl optionally having substituent(s) may form a condensed ring of $C_{4-8}$ cycloalkyl ring optionally having 1 to 3 substituents selected from the following substituent group C with the phenyl moiety or a condensed ring of an aliphatic heterocyclic group optionally having 1 to 3 substituents selected from the following substituent group C with the phenyl moiety in addition to the above substituent(s). The substituent in the aryl moiety of the aralkyl optionally having substituent(s) may form a condensed ring of $C_{4-8}$ cycloalkyl ring optionally having 1 to 3 substituents selected from the following substituent group C with the aryl moiety of the aralkyl or a condensed ring of aliphatic heterocycle optionally having 1 to 3 substituents selected from the following substituent group C with the aryl moiety of the aralkyl in addition to the above substituent(s).

The substituent(s) in the cycloalkyl optionally having substituent(s), the aliphatic heterocyclic group optionally having substituent(s), the nitrogen-containing heterocyclic group optionally having substituent(s), which is formed together with the adjacent nitrogen atom and the aliphatic ring optionally having substituent(s) are the same or different and examples thereof include 1 to 3 substituents selected from the group consisting of oxo, $C_{1-10}$ alkyl optionally having 1 to 3 substituents selected from the following substituent group A, $C_{6-14}$ aryl optionally having 1 to 3 substituents selected from the following substituent group B and the substituents of the aforementioned substituent group-1. The substituent in the cycloalkyl optionally having substituent(s) may form a condensed ring of a benzene ring optionally having 1 to 3 substituents selected from the following substituent group B with the cycloalkyl moiety in addition to the above substituent(s).

The substituent group A means the group consisting of halogen; hydroxy; sulfanyl; nitro; cyano; carboxy; carbamoyl; $C_{3-8}$ cycloalkyl; $C_{6-14}$ aryl optionally having 1 to 3 substituents selected from the group consisting of halogen, hydroxy, amino, nitro, carboxy, $C_{1-10}$ alkoxycarbonyl, $C_{1-10}$ alkoxy and trifluoromethyl (substituent group a); an aliphatic heterocyclic group; an aromatic heterocyclic group; $C_{1-10}$ alkoxy optionally having 1 to 3 substituents selected from the group consisting of halogen, hydroxy, amino, carboxy, $C_{1-10}$ alkoxy, $C_{1-10}$ alkylamino, di-$C_{1-10}$ alkylamino and $C_{1-10}$ alkoxycarbonyl (substituent group b); $C_{3-8}$ cycloalkoxy; $C_{6-14}$ aryloxy optionally having 1 to 3 substituents selected from the aforementioned substituent group a; $C_{7-16}$ aralkyloxy optionally having 1 to 3 substituents selected from the aforementioned substituent group a; $C_{2-11}$ alkanoyloxy; $C_{7-15}$ aroyloxy; $C_{1-10}$ alkylsulfonyloxy; trifluoromethanesulfonyloxy; $C_{6-14}$ arylsulfonyloxy; p-toluenesulfonyloxy; $C_{1-10}$ alkylsulfanyl; $C_{6-14}$ arylsulfanyl; —NR$^{19a}$R$^{19b}$ (wherein R$^{19a}$ and R$^{19b}$ are the same or different and each represents a hydrogen atom; formyl; $C_{1-10}$ alkyl optionally having 1 to 3 substituents selected from the aforementioned substituent group b; $C_{3-8}$ cycloalkyl; $C_{6-14}$ aryl optionally having 1 to 3 substituents selected from the aforementioned substituent group a; an aromatic heterocyclic group; $C_{7-16}$ aralkyl optionally having 1 to 3 substituents selected from the aforementioned substituent group a; $C_{2-11}$ alkanoyl; $C_{7-15}$ aroyl; $C_{1-10}$ alkoxycarbonyl; $C_{7-16}$ aralkyloxycarbonyl; $C_{1-10}$ alkylsulfonyl; trifluoromethanesulfonyl; $C_{6-14}$ arylsulfonyl or p-toluenesulfonyl); $C_{2-11}$ alkanoyl; $C_{3-8}$ cycloalkylcarbonyl; $C_{7-15}$ aroyl; aliphatic heterocyclylcarbonyl; aromatic heterocyclylcarbonyl; $C_{1-10}$ alkoxycarbonyl; $C_{6-14}$ aryloxycarbonyl;

$C_{7-16}$ aralkyloxycarbonyl; $C_{1-10}$ alkylcarbamoyl; di-$C_{1-10}$ alkylcarbamoyl and $C_{6-14}$ arylcarbamoyl.

The substituent group B means the group consisting of $C_{1-10}$ alkyl, trifluoromethyl and the substituents of the aforementioned substituent group A.

The substituent group C means the group consisting of oxo, $C_{1-10}$ alkyl, trifluoromethyl and the substituents of the aforementioned substituent group A.

Examples of the $C_{1-10}$ alkyl and the $C_{1-10}$ alkyl moiety of the $C_{1-10}$ alkoxy, the $C_{2-11}$ alkanoyloxy, the $C_{1-10}$ alkylsulfanyl, the $C_{2-11}$ alkanoyl, the $C_{1-10}$ alkoxycarbonyl, the $C_{1-10}$ alkylcarbamoyl, the di-$C_{1-10}$ alkylcarbamoyl, the $C_{1-10}$ alkylsulfonyl, the $C_{1-10}$ alkylsulfonyloxy, the $C_{1-10}$ alkylamino and the di-$C_{1-10}$ alkylamino shown here include the groups exemplified as the aforementioned lower alkyl. Two $C_{1-10}$ alkyls of di-$C_{1-10}$ alkylcarbamoyl and di-$C_{1-10}$ alkylamino may be the same or different.

Examples of the $C_{3-8}$ cycloalkyl and the $C_{3-8}$ cycloalkyl moiety of the $C_{3-8}$ cycloalkoxy and the $C_{3-8}$ cycloalkylcarbonyl include the groups exemplified as the aforementioned cycloalkyl.

Examples of the aryl condensed with the $C_{4-8}$ cycloalkyl ring and the aryl moiety of the aralkyl condensed with the $C_{4-8}$ cycloalkyl ring include a cycloalkyl-condensed aryl having 8 to 16 carbon atoms, and more specific examples thereof include indanyl, 1,2,3,4-tetrahydronaphthalenyl and the like.

Examples of the phenyl condensed with the $C_{4-8}$ cycloalkyl ring include a cycloalkyl-condensed phenyl having 8 to 12 carbon atoms, and more specific examples thereof include indanyl, 1,2,3,4-tetrahydronaphthalenyl and the like.

Examples of the cycloalkyl condensed with the benzene ring include a benzene ring-condensed cycloalkyl having 8 to 12 carbon atoms, and more specific examples thereof include indanyl, 1,2,3,4-tetrahydronaphthalenyl and the like.

Examples of the $C_{6-14}$ aryl, and the aryl moiety of the $C_{6-14}$ aryloxy, the $C_{6-14}$ arylamino, the $C_{6-14}$ arylsulfanyl, the $C_{7-15}$ aroyl, the $C_{7-15}$ aroyloxy, the $C_{6-14}$ aryloxycarbonyl, the $C_{6-14}$ arylsulfonyl, the $C_{6-14}$ arylsulfonyloxy and the $C_{6-14}$ arylcarbamoyl include the groups exemplified as the aforementioned aryl.

Examples of the aryl moiety of the $C_{7-16}$ aralkyloxy, the $C_{7-16}$ aralkyl and the $C_{7-16}$ aralkyloxycarbonyl include the group exemplified as the aforementioned aryl, and examples of the alkylene moiety thereof include $C_{1-10}$ alkylene and more specifically, the group formed by removing one hydrogen atom from the aforementioned lower alkyl can be mentioned.

Examples of the aliphatic heterocyclic group and the aliphatic heterocyclic group moiety of the aliphatic heterocyclylcarbonyl include the groups exemplified as the aforementioned aliphatic heterocyclic group.

Examples of the aromatic heterocyclic group and the aromatic heterocyclic group moiety of the aromatic heterocyclylcarbonyl include the groups exemplified as the aforementioned aromatic heterocyclic group.

Examples of the aryl condensed with the aliphatic heterocycle and the aryl moiety of the aralkyl condensed with the aliphatic heterocycle include aryl condensed with a 4- to 7-membered monocyclic aliphatic heterocyclic group containing at least one atom selected from a nitrogen atom, an oxygen atom and a sulfur atom, and more specific examples thereof include dihydrobenzofuranyl, dihydroisobenzofuranyl, indolinyl, isoindolinyl, chromanyl, isochromanyl and the like.

Examples of the phenyl condensed with the aliphatic heterocycle include phenyl condensed with a 4- to 7-membered monocyclic aliphatic heterocyclic group containing at least one atom selected from a nitrogen atom, an oxygen atom and a sulfur atom, and more specific examples thereof include dihydrobenzofuranyl, dihydroisobenzofuranyl, indolinyl, isoindolinyl, chromanyl, isochromanyl and the like.

Examples of the halogen include the atom exemplified as the aforementioned halogen.

In each group of compound (I), $R^1$ is preferably $NR^{1a}R^{1b}$ (wherein $R^{1a}$ and $R^{1b}$ are each as defined above), more preferably, one of $R^{1a}$ and $R^{1b}$ is a hydrogen atom, and the other is lower alkyl optionally having substituent(s), cycloalkyl optionally having substituent(s), aralkyl optionally having substituent(s), aryl optionally having substituent(s), an aromatic heterocyclic group optionally having substituent(s) or an aliphatic heterocyclic group optionally having substituent(s), and more preferably, one of $R^{1a}$ and $R^{1b}$ is a hydrogen atom, and the other is aralkyl optionally having substituent(s) or aryl optionally having substituent(s). In addition, it is also more preferable that one of $R^{1a}$ and $R^{1b}$ be a hydrogen atom, and the other be an aromatic heterocyclic group optionally having substituent(s).

When $R^2$ is

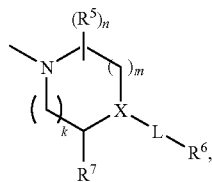

$R^5$ is preferably lower alkyl optionally having substituent(s), more preferably lower alkyl.

$R^6$ is preferably aryl optionally having substituent(s) or an aromatic heterocyclic group optionally having substituent(s), more preferably aryl optionally having substituent(s), still more preferably phenyl optionally having substituent(s).

$R^7$ is preferably a hydrogen atom or lower alkyl.

X is preferably a nitrogen atom or $CR^{8a}$ (wherein $R^{8a}$ represents a hydrogen atom, halogen or lower alkyl), more preferably $CR^{8a}$ (wherein $R^{8a}$ is as defined above).

L is preferably a single bond.

k and m are each preferably 1.

n is preferably 0 or 1, more preferably 0.

When $R^2$ is

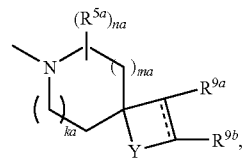

$R^{5a}$ is preferably lower alkyl optionally having substituent(s), more preferably lower alkyl.

$R^{9a}$ and $R^{9b}$ preferably form, together with the respectively adjacent carbon atom, an aromatic ring optionally having substituent(s), more preferably form, together with the respectively adjacent carbon atom, a benzene ring optionally having substituent(s).

Y is preferably $—CHR^{10a}—CHR^{10b}—$ (wherein $R^{10a}$ and $R^{10b}$ are each as defined above), $—CR^{10c}=CR^{10d}—$ (wherein $R^{10c}$ and $R^{1d}$ are each as defined above), $—O—CR^{11a}R^{11b}—$ (wherein $R^{11a}$ and $R^{11b}$ are each as defined above) or $—CR^{11c}R_{11d}—O—$ (wherein $R^{11c}$ and $R^{11d}$ are each as defined above), more preferably —CHR$^{10aa}$—CHR$^{10ba}$— (wherein R$^{10aa}$ and R$^{10ba}$ are the same or different and each represents a hydrogen atom or lower alkyl), —CR$^{10ca}$=CR$^{10da}$— (wherein R$^{10ca}$ and R$^{10da}$ are the same or different and each represents a hydrogen atom or lower alkyl), —O—CR$^{11aa}$R$^{11ba}$— (wherein R$^{11ca}$ and R$^{11ba}$ are the same or different and each represents a hydrogen atom or lower alkyl), or —CR$^{11ca}$R$^{11da}$—O— (wherein R$^{11ca}$ and R$^{11da}$ are the same or different and each represents a hydrogen atom or lower alkyl).

ka and ma are each preferably 1.

na is preferably 0 or 1, more preferably 0.

$R^3$ is preferably carboxy or —(C=O)NR$^{13a}$R$^{13b}$ (wherein R$^{13a}$ and R$^{13b}$ are each as defined above), more preferably one of R$^{13a}$ and R$^{13b}$ is a hydrogen atom, and the other is —S(O)$_2$R$^{14}$ (wherein R$^{14}$ is as defined above), and still more preferably, one of R$^{13a}$ and R$^{13b}$ is a hydrogen atom, and the other is —S(O)$_2$R$^{14C}$ (wherein R$^{14C}$ is as defined for the aforementioned R$^{14B}$).

$R^4$ is preferably a hydrogen atom.

As compound (I), a compound wherein one or more of the above-mentioned preferable substituent embodiments are combined is preferable.

In each group of compound (IA), $R^{1A}$ is preferably aryl optionally having substituent(s) or an aromatic heterocyclic group optionally having substituent(s), more preferably aryl optionally having substituent(s), still more preferably phenyl optionally having substituent(s). Another more preferable embodiment is an aromatic heterocyclic group optionally having substituent(s).

$L^1$ is preferably a single bond or methylene.

When $R^{2A}$ is

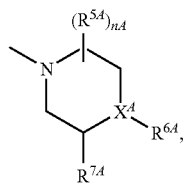

$R^{5A}$ is preferably lower alkyl.

$R^{6A}$ is preferably aryl optionally having substituent(s) or an aromatic heterocyclic group optionally having substituent(s), more preferably aryl optionally having substituent(s), still more preferably phenyl optionally having substituent(s).

$R^{7A}$ is preferably a hydrogen atom or lower alkyl.

$X^A$ is preferably a nitrogen atom or CR$^{8Aa}$ (wherein R$^{8Aa}$ represents a hydrogen atom, halogen or lower alkyl), more preferably CR$^{8Aa}$ (wherein R$^{8Aa}$ is as defined above).

nA is preferably 0 or 1, more preferably 0.

When $R^{2A}$ is

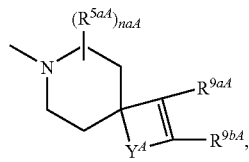

$R^{5aA}$ is preferably lower alkyl.

$R^{9aA}$ and $R^{9bA}$ preferably form, each together with the adjacent carbon atom, a benzene ring optionally having substituent(s).

$Y^A$ is preferably —CHR$^{10aA}$—CHR$^{10bA}$— (wherein R$^{10aA}$ and R$^{10bA}$ are each as defined above), —CR$^{10cA}$=CR$^{10dA}$— (wherein R$^{10cA}$ and R$^{10dA}$ are each as defined above), —O—CR$^{10aA}$R$^{11bA}$— (wherein R$^{11aA}$ and R$^{11bA}$ are each as defined above) or —CR$^{11cA}$R$^{11dA}$—O— (wherein R$^{11cA}$ and R$^{11dA}$ are each as defined above), more preferably —CHR$^{10aAa}$—CHR$^{10bAa}$— (wherein R$^{10aAa}$ and R$^{10bAa}$ are the same or different and each represents a hydrogen atom or lower alkyl), —CR$^{10cAa}$=CR$^{10dAa}$— (wherein R$^{10cAa}$ and R$^{10dAa}$ are the same or different and each represents a hydrogen atom or lower alkyl), —O—CR$^{11aAa}$R$^{11bAa}$— (wherein R$^{11aAa}$ and R$^{11bAa}$ are the same or different and each represents a hydrogen atom or lower alkyl), or —CR$^{11cAa}$R$^{11dAa}$—O— (wherein R$^{11cAa}$ and R$^{11dAa}$ are the same or different and each represents a hydrogen atom or lower alkyl).

naA is preferably 0 or 1, more preferably 0.

$R^{13A}$ and $R^{13B}$ are the same or different and each is preferably a hydrogen atom or —S(O)$_2$R$^{14A}$ (wherein R$^{14A}$ is as defined above), more preferably one of R$^{13A}$ and R$^{13B}$ is a hydrogen atom, and the other is —S(O)$_2$R$^{14A}$ (wherein R$^{14A}$ is as defined above) and still more preferably one of R$^{13A}$ and R$^{13B}$ is a hydrogen atom, and the other is —S(O)$_2$R$^{14B}$ (wherein R$^{14B}$ is as defined above).

$R^{4A}$ is preferably a hydrogen atom.

As compound (IA), a compound wherein one or more of the above-mentioned preferable substituent embodiments are combined is preferable.

The pharmacologically acceptable salts of compound (I) and (IA) comprise, for example, pharmacologically acceptable acid addition salts, metal salts, ammonium salts, organic amine addition salts, amino acid addition salts and the like. Examples of the pharmacologically acceptable acid addition salts of compounds (I) and (IA) include, but are not limited to, inorganic acid salts such as hydrochloride, hydrobromide, nitrate, sulfate, phosphate and the like, organic acid salts such as acetate, oxalate, maleate, fumarate, citrate, benzoate, methanesulfonate, para-toluenesulfonate, benzenesulfonate, tartrate, succinate, lactate, gluconate, embonate and the like. Examples of the pharmacologically acceptable metal salts include, but are not limited to, sodium salt, potassium salt, magnesium salt, calcium salt, aluminum salt, zinc salt and the like. Examples of the pharmacologically acceptable ammonium salt include, but are not limited to, ammonium salt, tetramethylammonium salt and the like. Examples of the pharmacologically acceptable organic amine addition salt include, but are not limited to, addition salts of morpholine, piperidine and the like. Examples of the pharmacologically acceptable amino acid addition salt include, but are not limited to, addition salts of lysine, glycine, phenylalanine, aspartic acid, glutamic acid and the like.

The pharmacologically acceptable salts of compounds (I) and (IA) include quaternary ammonium salt. The quaternary ammonium salt means one wherein the nitrogen atom in the compound is quaternarized by Rx (Rx is lower alkyl or lower alkyl substituted phenyl where lower alkyl is as defined above).

The pharmacologically acceptable salts of compounds (I) and (IA) also include N-oxide. N-oxide is a compound wherein the nitrogen atom in the compound is oxidized. Compounds (I) and (IA) can be converted to N-oxide by any oxidization method, for example, by using m-chloroperbenzoic acid, air oxidization, an oxidation reagent such as liver extract and the like.

In the present invention, the skin diseases refer to those where the lesion appears on the skin. Specific examples thereof include, but are not limited to, acne vulgaris, drug eruption, contact dermatitis, dermatitis due to venomous moth, pollen dermatitis, urticaria, psoriasis, atopic dermatitis, candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis and the like.

In the present invention, dermatitis refers to, from among the aforementioned skin diseases, one wherein immune system is endogenously or exogenously activated to cause skin symptoms. Specific examples thereof include, but are not limited to, acne vulgaris, contact dermatitis, atopic dermatitis, pollen dermatitis, psoriasis, drug eruption, lupus erythematosus, seborrheic dermatitis, eczema, Stevens-Johnson syndrome, toxic epidermal necrosis and the like.

The treatment in the present invention refers to reversing the progression of, mitigating or inhibiting the disease or condition to be applied, or one or more symptoms of such disease or condition. Moreover, it includes application to inhibit progression before remission of disease, or when the symptom is mild. In skin diseases, aggravation and remission may be repeated regularly or chronically. The therapeutic agent and/or preventive agent are/is also used for extending the remission period and preventing aggravation. The preventive agent is also used for preventing the onset of a disease.

The aggravation used in the present specification refers to aggravation of the symptoms of a disease.

The remission used in the present specification refers to a temporary or permanent reduction or disappearance of the symptoms of a disease. In addition, the remission time refers to the state of remission, and the remission period refers to the period during which the state of remission continues.

Compound (I) used in the present invention and compound (IA) of the present invention also include a prodrug. The prodrug is a compound that can be converted to compound (I) or (IA) by a reaction by an enzyme, gastric acid and the like in the body. As the prodrug applicable in the present invention, many kinds are known, and a suitable prodrug may be selected from a known literature (for example, Iyakuhin no Kaihatsu, Hirokawa Shoten, 1990, vol. 7, p. 163) and synthesized by a known method. For example, as a prodrug of compound (I) or (IA), when compound (I) or (IA) has amino, a compound wherein the amino is acylated, alkylated or phosphorylated, when compound (I) or (IA) has hydroxy, a compound wherein the hydroxy is acylated, alkylated, phosphorylated or borated, when compound (I) or (IA) has carboxy, a compound wherein the carboxy is esterified or amidated, and the like can be mentioned. The prodrug of compound (I) or (IA) may be any of hydrate, non-hydrate and solvate, and may form a salt with a pharmacologically acceptable acid or base, like in the case of compounds (I) and (IA).

A preferable compound used in the present specification is a compound having desirable properties in one or more items from various evaluation items required for an agent for the prevention and/or treatment of skin diseases, pharmaceutical products or object of use, such as pharmacological activity, as well as physical stability, stability under physiological conditions, safety to the body and the like.

Compound (I) used in the present invention, compound (IA) of the present invention, and pharmacologically acceptable salts thereof may show an unpreferable action on living organisms. Even in such a case, the usefulness of an agent for the prevention and/or treatment, and a pharmaceutical product of the present invention can be exhibited while reducing an unpreferable action by using appropriate dose and administration method.

The compound (I) used in the present invention and compound (IA) of the present invention include those possibly having a stereoisomer such as geometric isomer, optical isomer and the like, tautomer and the like. The present invention encompasses all possible isomers and mixtures thereof including them, and the mixing ratio thereof may be any.

The compound (I) used in the present invention, compound (IA) of the present invention, and pharmacologically acceptable salts thereof may be present as adducts with water or various solvents, and the present invention also encompasses such adducts.

The present invention encompasses a compound which is included in compound (I) used in the present invention and compound (IA) of the present invention, wherein one or more atoms are labeled with isotope. A compound incorporating a radioisotope from isotopes, such as $^3$H(tritium) or $^{14}$C is useful for examining tissue distribution of compound and screening for an agent for the prevention and/or treatment of skin diseases.

The isotope used in the present specification refers to an atom having an atomic value or a mass number different from those generally found naturally. Examples of the isotope in the compound of the present invention include $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, and the like.

The inert solvent used in the present specification is an organic or inorganic solvent, which is liquid at room temperature or reaction temperature, and shows no change in the chemical structure before and after reaction. Specific examples thereof include, but are not limited to, tetrahydrofuran (THF), dioxane, carbon tetrachloride, acetone, ethyl acetate, methyl acetate, isopropyl acetate, diethyl ether, ethylene glycol, triethylene glycol, glyme, diglyme, 1,2-dimethoxyethane (DME), acetonitrile, methanol, ethanol, butanol, 2-propanol, methylene chloride, chloroform, benzene, water, toluene, pyridine, N,N-dimethylformamide (DMF), dimethylimidazole, N-methylpyrrolidine, N-methylpyrrolidinone, dimethylpropyleneurea, hexane, pentane, nitrobenzene, dimethyl sulfoxide(DMSO), diphenyl ether, Dowtherm A (registered trade mark), polychlorinated diphenyl, tetralin, heptane, octane, xylene, methylethylketone, methylisobutylketone, N,N-dimethylacetamide, sulfolane, 1,2-dichloroethane and the like.

The production methods of compound (I) are explained in the following.

In the production methods shown below, when the defined groups change under the conditions of the production methods or are inappropriate for performing the production methods, the desired compound can be produced by performing the methods for the introduction and removal of the protecting groups conventionally performed in the synthetic organic chemistry (e.g., methods described in Protective Groups in Organic Synthesis, third edition, T. W. Greene, John Wiley & Sons Inc., 1999 etc.) or the like. If necessary, the order of the reaction steps can also be changed.

Production method 1

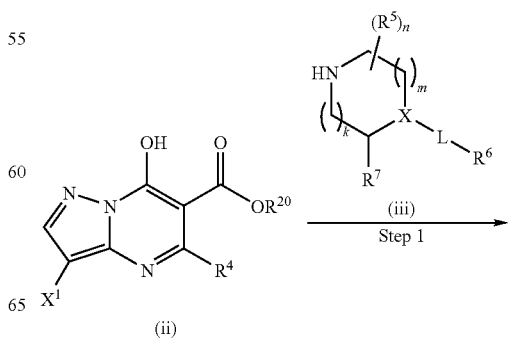

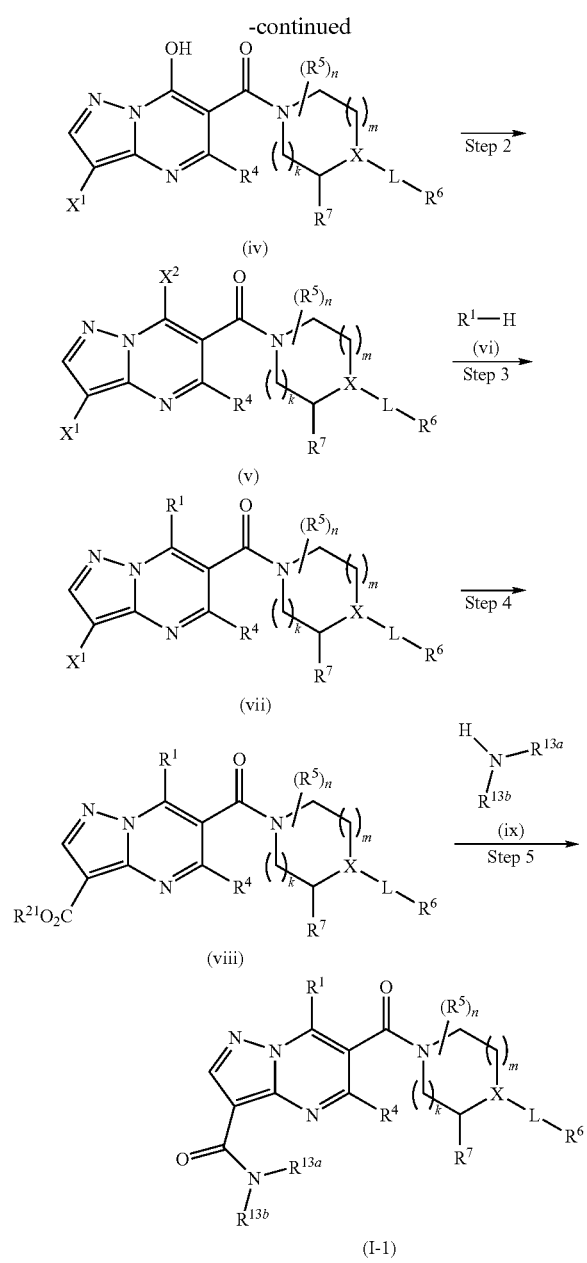

(wherein $R^1$, $R^4$, $R^5$, $R^6$, $R^7$, $R^{13a}$, $R^{13b}$, X, L, k, m and n are each as defined above, $R^{20}$ and $R^{21}$ are the same or different and each represents a hydrogen atom or lower alkyl, and $X^1$ and $X^2$ are the same or different and each represents a leaving group. Examples of the leaving group include sulfonyloxy such as benzenesulfonyloxy, methanesulfonyloxy, p-toluenesulfonyloxy and the like, a group obtained by removing one hydrogen atom from carboxylic acids, such as lower alkanoyloxy, arylcarbonyloxy, aromatic heterocyclic carbonyloxy and the like, chlorine atom, bromine atom, iodine atom and fluorine atom).

The conversion reaction of each of $R^1$, $R^4$, $R^5$, $R^6$, $R^7$, $R^{13a}$, $R^{13b}$, $R^{20}$, $R^{21}$, X, $X^1$ and $X^2$ can be performed between any steps of step 1-step 5 of this production method.

Compound (viii) in this production method is encompassed in compound (I).

[Step 1]

Compound (iv) can be obtained by reacting compound (ii) with compound (iii) by the following methods 1-4.

Compound (ii) wherein $R^{20}$ is lower alkyl can be synthesized by a known method [for example, the method described in Journal of Medicinal Chemistry, vol. 25, p. 235 (1982)] or a method analogous thereto.

Compound (ii) wherein $R^{20}$ is a hydrogen atom can be obtained by the following method 5 from compound (ii) wherein $R^{20}$ is lower alkyl.

(Method 1)

compound (ii) wherein $R^{20}$ is a hydrogen atom is treated in an inert solvent or without solvent using 1-20 equivalents, preferably 1-5 equivalents, of an acid halogenating agent at a temperature between −20° C. and the boiling point of the solvent to be used, preferably between −10° C. and 30° C., for 15 min-48 hr, preferably 1-18 hr, to give acid halide of compound (ii). Where necessary, 0.01-0.5 equivalent of DMF, pyridine or the like may be added. Compound (iv) can be obtained by reacting the obtained acid halide with 0.5-2 equivalents, preferably 1-1.2 equivalents, of compound (iii) in an inert solvent in the presence of 1-5 equivalents, preferably 1-3 equivalents, of a base at a temperature between −20° C. and the boiling point of the solvent to be used, preferably between —10° C. and 30° C., for 15 min-48 hr, preferably 1-10 hr.

Examples of the inert solvent to be used in the reaction to obtain acid halide include chloroform, methylene chloride, pyridine, THF, DME, toluene, DMF, dioxane, ethyl acetate and the like, and these can be used alone or in a mixture. Among these, methylene chloride or toluene is preferable.

Examples of the acid halogenating agent include thionyl chloride, oxalyl chloride and the like.

Examples of the inert solvent to be used for the reaction of acid halide with compound (iii) include chloroform, methylene chloride, pyridine, THF, DME, toluene, DMF, dioxane, ethyl acetate and the like, and these can be used alone or in a mixture. Among these, methylene chloride or DMF is preferable.

Examples of the base include pyridine, triethylamine, (dimethylamino) pyridine, N,N-diisopropylethylamine, aqueous sodium hydrogen carbonate solution, aqueous sodium hydroxide solution and the like. Among these, triethylamine is preferable.

(Method 2)

compound (ii) wherein $R^{20}$ is a hydrogen atom is reacted with 1-20 equivalents, preferably 1-5 equivalents, of a mixed acid anhydride reagent in an inert solvent or without solvent in the presence of 1-5 equivalents, preferably 1-3 equivalents, of a base at a temperature between −30° C. and 40° C., preferably between −30° C. and 0° C., for 5 min-24 hr, preferably 10 min-2 hr, to give a mixed acid anhydride of compound (ii). The obtained mixed acid anhydride is reacted with 0.5-2 equivalents, preferably 1-1.2 equivalents, of compound (iii) at a temperature between −30° C. and 40° C., preferably between −30° C. and 30° C., for 5 min-24 hr, preferably 10 min-2 hr, to give compound (iv).

Examples of the inert solvent include chloroform, methylene chloride, pyridine, THF, DME, toluene, DMF, dioxane, acetonitrile, ethyl acetate and the like, and these can be used alone or in a mixture. Among these, THF, DMF or acetonitrile is preferable.

Examples of the base include pyridine, triethylamine, 4-(dimethylamino)pyridine, N-methylmorpholine, N,N-diisopropylethylamine and the like. Among these, N-methylmorpholine or triethylamine is preferable.

Examples of the mixed acid anhydride reagent include isobutyl chloroformate, ethyl chloroformate, pivaloyl chloride, tosyl chloride, mesyl chloride and the like. Among these, isobutyl chloroformate or mesyl chloride is preferable.

(Method 3)

Compound (ii) wherein $R^{20}$ is a hydrogen atom is reacted with 0.5-10 equivalents, preferably 0.5-5 equivalents, of compound (iii) in an inert solvent or without solvent in the presence or absence of 1-20 equivalents, preferably 1-10 equivalents, of a base in the presence of 1-20 equivalents, preferably 1-5 equivalents, of a condensing agent at a temperature between −30° C. and 60° C., preferably between −30° C. and 40° C., for 30 min-72 hr, preferably 1-18 hr, to give compound (iv). At this time, 0.5-2 equivalents of, for example, 1-hydroxybenzotriazole (HOBt) or a hydrate thereof (HOBt.H$_2$O), or 3-hydroxy-4-oxo-3,4-dihydro-1,2,3-benzotriazine or the like may be added.

Examples of the inert solvent include chloroform, methylene chloride, pyridine, THF, DME, toluene, DMF, DMSO, dioxane, acetonitrile, ethyl acetate and the like, and these can be used alone or in a mixture. Among these, methylene chloride, DMF, THF or acetonitrile is preferable.

Examples of the base include pyridine, triethylamine, 4-(dimethylamino)pyridine, N-methylmorpholine, N,N-diisopropylethylamine and the like. Among those, N,N-diisopropylethylamine or triethylamine is preferable.

Examples of the condensing agent include 1,3-dicyclohexylcarbodiimide, 1-ethyl-3-[3-(dimethylamino)propyl]carbodiimide or hydrochloride thereof, 1,1'-carbonyldiimidazole, 1,3-diisopropylcarbodiimide, diphenylphosphoryl azide, 2-Chloro-1-methylpyridinium iodide, 1-benzotriazolyl mesylate, 1-benzotriazolyl tosylate, 1-benzotriazolyl benzenesulfonate, benzotriazol-1-yloxytripyrrolidinophosphonium hexafluorophosphate, 1-propylphosphonic acid anhydride cyclic trimer and the like. Among these, 1-ethyl-3-[3-(dimethylamino)propyl]carbodiimide or hydrochloride thereof, or 1-propylphosphonic acid anhydride cyclic trimer is preferable.

(Method 4)

Compound (ii) wherein $R^{20}$ is lower alkyl is treated and reacted with 1-20 equivalents of compound (iii) and 1-10 equivalents of an organic metal compound in an inert solvent or without solvent at a temperature between −78° C. and the boiling point of the solvent to be used, preferably between −30° C. and the boiling point of the solvent to be used for 15 min-48 hr, preferably 1-18 hr, to give compound (iv).

Examples of the inert solvent include THF, diethyl ether, toluene, benzene, hexane, pentane and the like, and these can be used alone or in a mixture.

Examples of the organic metal compound include n-butyllithium, sec-butyllithium, trimethylaluminum and the like. Among these, n-butyllithium or trimethylaluminum is preferable.

(Method 5)

Compound (ii) wherein $R^{20}$ is lower alkyl is treated and reacted with 0.5-50 equivalents of a suitable base in a solvent or without solvent at a temperature between −30° C. and the boiling point of the solvent to be used, preferably between 0° C. and the boiling point of the solvent to be used, for 5 min-48 hr to give compound (ii) wherein $R^{20}$ is a hydrogen atom.

Examples of the solvent include water, methanol, ethanol, THF, DME, DMF, DMSO, dioxane, acetonitrile, pyridine and the like, and these can be used alone or in a mixture.

Examples of the base include sodium hydroxide, potassium carbonate, sodium hydrogen carbonate, potassium hydroxide, sodium methoxide, potassium ethoxide, lithium iodide/pyridine and the like. Among these, sodium hydroxide or lithium iodide/pyridine is preferable.

[Step 2]

Compound (v) can be obtained by reacting compound (iv) with 0.5-50 equivalents, preferably a solvent amount, of a leaving group-introducing reagent in an inert solvent or without solvent at a temperature between −30° C. and 150° C. for 15 min-48 hr.

As the leaving group-introducing reagent, a suitable reagent can be selected according to the leaving group to be used. For example, when $X^2$ is a halogen atom such as a chlorine atom, a bromine atom and the like, phosphorus oxychloride, phosphorus oxybromide, phosphorus pentachloride, trichloroacetyl chloride, phosphorus trichloride, phosphorus tribromide, acetyl chloride, thionyl chloride or the like can be used. At this time, 0.5-3 equivalents of, for example, N,N-diisopropylethylamine, N,N-diethylaniline or the like may be added.

Preferably, the reaction is performed using phosphorus oxychloride without solvent at 80-120° C.

[Step 3]

Compound (vii) can be obtained by reacting compound (v) with 0.5-10 equivalents, preferably 1-3 equivalents, of compound (vi) in an inert solvent or without solvent at a temperature between the melting point and the boiling point of the solvent to be used for 15 min-48 hr, and using a base where necessary, and when further necessary, by irradiating microwave with 100-500 (W) energy under pressurization conditions of 1-20 atm.

Examples of the base include sodium hydroxide, potassium carbonate, sodium hydrogen carbonate, barium hydroxide, cesium carbonate, potassium hydroxide, sodium methoxide, potassium ethoxide, lithium hydroxide, lithium hexamethyldisilazane, sodium hydride, potassium hydride, n-butyllithium, lithium diisopropylamide, potassium tert-butoxide, triethylamine, N,N-diisopropylethylamine, tributylamine, dicyclohexylmethylamine, N-methylmorpholine, pyridine, N-methylpiperidine, 2,6-di-tert-butylpyridine, 1,8-diazabicyclo[5.4.0]undec-7-ene (DBU), 1,5-diazabicyclo[4.3.0]non-5-ene (DBN), 4-(dimethylamino)pyridine, Amberlyst A-21 (manufactured by ROHM AND HAAS JAPAN KK.), AG 1-X8 (Bio-Rad, manufactured by Richmond, Calif.), polyvinyl pyridine, morpholinomethyl polystyrene and the like.

The microwave refers to 1 GHz-1 THz electromagnetic wave, and 2450 MHz is preferably used.

The irradiation energy is more preferably 300 watt.

The reaction is preferably performed using DMF, N,N-dimethylacetamide or N-methylpyrrolidinone as an inert solvent, and potassium carbonate, triethylamine or N,N-diisopropylethylamine as a base at 80-120° C. for 1-24 hr.

[Step 4]

Compound (viii) can be obtained from compound (vii) by the following method 1 or 2.

(Method 1)

Compound (vii) is treated with 1-20 equivalents of a metal reagent in an inert solvent or without solvent at a temperature between −78° C. and the boiling point of the solvent to be used, preferably between −30° C. and the boiling point of the solvent to be used for 15 min-48 hr, preferably 1-18 hr, to give a metalated compound of compound (vii). The obtained metalated compound is reacted with 50-300 equivalents, preferably 100-200 equivalents, of carbon dioxide or carbon dioxide bubbling (for 5 min-24 hr) at a temperature between −30° C. and 40° C., preferably −30° C. and 30° C., for 5 min-24 hr, preferably 10 min-2 hr, to give compound (viii) wherein $R^{21}$ is a hydrogen atom.

For the preparation of a metalated compound, many methods are known (Jikken Kagaku Koza, the 4th edition, Maruzen, 1992, vol. 25, p. 10, p. 51, p. 60 etc.) and they are applicable.

Examples of the metal reagent include n-butyllithium, sec-butyllithium, isopropylmagnesium chloride, phenylmagnesium bromide, methyllithium, sodium, magnesium and the like. In this case, 1-20 equivalents of, for example, N,N-diisopropylethylamine, bis[2-(N,N-dimethylamino)ethyl] ether, N,N,N',N'-tetramethylethylenediamine and the like may be added. Among these, a combination of n-butyllithium and N,N-diisopropylethylamine or a combination of isopropylmagnesium chloride and bis[2-(N,N-dimethylamino) ethyl]ether is preferable.

Examples of the inert solvent include THF, DME, toluene, dioxane, diethyl ether and the like, and these can be used alone or in a mixture. Among these, THF or diethylether is preferable.

(Method 2)

Compound (viii) can be obtained by reacting compound (vii) with 1-20 equivalents of water or alcohol in an inert solvent or without solvent in the presence of 1-20 equivalents, preferably 1-5 equivalents, of a base and 0.05-1 equivalent, preferably 0.05-0.10 equivalent, of a palladium catalyst, under a carbon monoxide atmosphere. The reaction is generally performed at a temperature between 0 and 150° C., preferably between 20° C. and 120° C., for 1-72 hr.

Examples of the inert solvent include pentane, hexane, heptane, octane, benzene, toluene, xylene, diethyl ether, dioxane, THF, glyme, acetone, methylethylketone, methylisobutylketone, acetonitrile, pyridine, DMF, N,N-dimethylacetamide, DMSO, sulfolane and the like, and these can be used alone or in a mixture. Among these, toluene, DMF or N,N-dimethylacetamide is preferable. In this step, water or alcohol is used as a reaction agent, and they can also be used as solvents.

Examples of the alcohol include methanol, ethanol, n-propyl alcohol, i-propyl alcohol, n-butyl alcohol, i-butyl alcohol, sec-butyl alcohol, tert-butyl alcohol, n-pentyl alcohol, n-hexyl alcohol, n-heptyl alcohol, n-octyl alcohol, n-nonyl alcohol, n-decyl alcohol and the like. Among these, ethanol or n-propyl alcohol is preferable.

As the palladium catalyst, palladium acetate(II), palladium chloride(II), dichlorobis(triphenylphosphine)palladium(II), bis(acetonitrile)dichloropalladium(II), bis(benzonitrile) dichloropalladium(II), [1,2-bis(diphenylphosphino)ethane] dichloropalladium(II), [1,1'-bis(diphenylphosphino)ferrocene]palladium(II)dichloride, [2,2'-bis(diphenylphosphino)-1,1'-binaphthyl]palladium(II)chloride, dichlorobis(tricyclohexylphosphine)palladium(II), dichlorobis(tri-o-toluylphosphine)palladium(II), [1,4-bis(diphenylphosphino)butane]palladium(II)dichloride, bis(acetate) bis(triphenylphosphine)palladium(II), palladium(II) trifluoroacetate, tetrakis(triphenylphosphine)palladium(0), tris(dibenzylideneacetone)dipalladium(0) or the like can be used. In addition, 0.05-1 equivalent, preferably 0.05-0.15 equivalent, of an organic phosphate compound, such as triphenylphosphine, o-toluylphosphine, tri-tert-butylphosphine, tri-2-furylphosphine, 1,2-bis(diphenylphosphino)ethane, 1,1'-bis(diphenylphosphino)ferrocene, 2,2'-bis(diphenylphosphino)-1,1'-binaphthyl, tricyclohexylphosphine, 1,2-bis(diphenylphosphino)ethane, 1,3-bis(diphenylphosphino) propane, 1,4-bis(diphenylphosphino)butane or the like can also be used by further adding to the above-mentioned palladium catalyst. Among these, tetrakis(triphenylphosphine) palladium(0), dichlorobis(triphenylphosphine)palladium (II), dichlorobis(tri-o-toluylphosphine)palladium(II) or [1,1'-bis(diphenylphosphino)ferrocene]palladium(II)dichloride is preferable.

As the base, organic bases such as triethylamine, N,N-diisopropylethylamine, DBU, N,N-dimethylaniline, pyridine, quinoline or the like, inorganic bases such as cesium carbonate, potassium carbonate, sodium carbonate, lithium carbonate, sodium hydrogen carbonate, potassium hydroxide, sodium hydroxide, lithium hydroxide, potassium tert-butoxide, thallium hydroxide, thallium carbonate, silver carbonate, silver oxide or the like, basic anion exchange resins such as Amberlyst A-21 (manufactured by ROHM AND HAAS JAPAN KK.), AG 1-X8 (manufactured by Bio-Rad, Richmond, Calif.) or the like, a base carried on a solid phase such as polyvinyl pyridine, morpholinomethyl polystyrene or the like, or the like can be used. Among these, cesium carbonate is preferable.

As the carbon monoxide pressure, normal pressure −30 kg/cm$^2$ is generally preferable.

Compound (viii) wherein $R^{21}$ is lower alkyl can be converted to compound (viii) wherein $R^{21}$ is a hydrogen atom by a method similar to the aforementioned Method 5, Step 1.

[Step 5]

Compound (I-1) can be obtained by reacting compound (viii) with compound (ix) according to the following Methods 1-4.

(Method 1)

Compound (viii) wherein $R^{21}$ is a hydrogen atom is treated with 1-20 equivalents, preferably 1-5 equivalents, of an acid halogenating agent in an inert solvent or without solvent at a temperature between −20° C. and the boiling point of the solvent to be used, preferably between −10° C. and 30° C. for 15 min-48 hr, preferably 1-18 hr, to give an acid halide of compound (viii). In this case, 0.01-0.5 equivalent of DMF, pyridine or the like may be added as necessary. The obtained acid halide is reacted with 0.5-2 equivalents, preferably 1-1.2 equivalents, of compound (ix) in an inert solvent in the presence of 1-5 equivalents, preferably 1-3 equivalents, of a base at a temperature between −20° C. and the boiling point of the solvent to be used, preferably between −10° C. and 30° C. for 15 min-48 hr, preferably 1-10 hr, to give compound (I-1).

Examples of the inert solvent to be used in the reaction to obtain acid halide include chloroform, methylene chloride, pyridine, THF, DME, toluene, DMF, dioxane, ethyl acetate and the like, and these can be used alone or in a mixture. Among these, methylene chloride or toluene is preferable.

Examples of the acid halogenating agent include thionyl chloride, oxalyl chloride and the like.

Examples of the inert solvent to be used for the reaction of acid halide with compound (ix) include chloroform, methylene chloride, pyridine, THF, DME, toluene, DMF, dioxane, ethyl acetate and the like, and these can be used alone or in a mixture. Among these, methylene chloride or DMF is preferable.

Examples of the base include pyridine, triethylamine, 4-(dimethylamino)pyridine, N,N-diisopropylethylamine, aqueous sodium hydrogen carbonate solution, aqueous sodium hydroxide solution and the like. Among these, triethylamine is preferable.

(Method 2)

Compound (viii) wherein $R^{21}$ is a hydrogen atom is reacted with 1-20 equivalents, preferably 1-5 equivalents, of a mixed acid anhydride reagent in an inert solvent or without solvent in the presence of 1-5 equivalents, preferably 1-3 equivalents, of a base at a temperature between −30° C. and 40° C., preferably between −30-0° C., for 5 min-24 hr, preferably 10 min-2 hr, to give a mixed acid anhydride of compound (viii). The obtained mixed acid anhydride is reacted with 0.5-2 equivalents, preferably 1-1.2 equivalents, of compound (ix) at a temperature between −30° C. and 40° C., preferably between −30° C. and 30° C., for 5 min-24 hr, preferably 10 min-2 hr, to give compound (I-1).

Examples of the inert solvent include chloroform, methylene chloride, pyridine, THF, DME, toluene, DMF, dioxane, acetonitrile, ethyl acetate and the like, and these can be used alone or in a mixture. Among these, THF, DMF or acetonitrile is preferable.

Examples of the base include pyridine, triethylamine, 4-(dimethylamino)pyridine, N-methylmorpholine, N,N-diisopropylethylamine and the like. Among these, N-methylmorpholine or triethylamine is preferable.

Examples of the mixed acid anhydride reagent include isobutyl chloroformate, ethyl chloroformate, pivaloyl chloride, tosyl chloride, mesyl chloride and the like. Among these, isobutyl chloroformate or mesyl chloride is preferable.

(Method 3)

Compound (viii) wherein $R^{21}$ is a hydrogen atom is reacted with 0.3-20 equivalents, preferably 0.4-10 equivalents, of compound (ix) in an inert solvent or without solvent in the presence or absence of 1-20 equivalents, preferably 1-10 equivalents, of a base in the presence of 1-20 equivalents, preferably 1-5 equivalents, of a condensing agent at a temperature between −30° C. and 100° C., preferably between −30° C. and 70° C., for 30 min-72 hr, preferably 1-18 hr, to give compound (I-1). In this case, 0.5-2 equivalents of, for example, HOBt, HOBt.H$_2$O, 3-hydroxy-4-oxo-3,4-dihydro-1,2,3-benzotriazine or the like may be added.

Examples of the inert solvent include chloroform, methylene chloride, pyridine, THF, DME, toluene, DMF, DMSO, dioxane, acetonitrile, ethyl acetate and the like, and these can be used alone or in a mixture. Among these, methylene chloride, DMF, THF or acetonitrile is preferable.

Examples of the base include pyridine, triethylamine, 4-(dimethylamino)pyridine, N-methylmorpholine, N,N-diisopropylethylamine, DBU, DBN and the like. Among these, DBU, N,N-diisopropylethylamine or triethylamine is preferable.

Examples of the condensing agent include 1,3-dicyclohexylcarbodiimide, 1-ethyl-3-[3-(dimethylamino)propyl]carbodiimide or hydrochloride thereof, 1,1'-carbonyldiimidazole, 1,3-diisopropylcarbodiimide, diphenylphosphoryl azide, 2-Chloro-1-methylpyridinium iodide, 1-benzotriazolyl mesylate, 1-benzotriazolyl tosylate, 1-benzotriazolyl benzenesulfonate, benzotriazol-1-yloxytripyrrolidinophosphonium hexafluorophosphate, 1-propylphosphonic acid anhydride cyclic trimer and the like. Among these, 1-ethyl-3-[3-(dimethylamino)propyl]carbodiimide or hydrochloride thereof, or 1,1'-carbonyldiimidazole is preferable.

(Method 4)

Compound (viii) wherein $R^{21}$ is lower alkyl is reacted with 1-20 equivalents of compound (ix) in an inert solvent or without solvent, using 1-10 equivalents of an organic metal compound at a temperature between −78° C. and the boiling point of the solvent to be used, preferably −30° C. and the boiling point of the solvent to be used, for 15 min-48 hr, preferably 1-18 hr, to give compound (I-1).

Examples of the inert solvent include THF, diethyl ether, toluene, benzene, hexane, pentane and the like, and these can be used alone or in a mixture.

Examples of the organic metal compound include n-butyllithium, sec-butyllithium, trimethylaluminum and the like. Among these, n-butyllithium or trimethylaluminum is preferable.

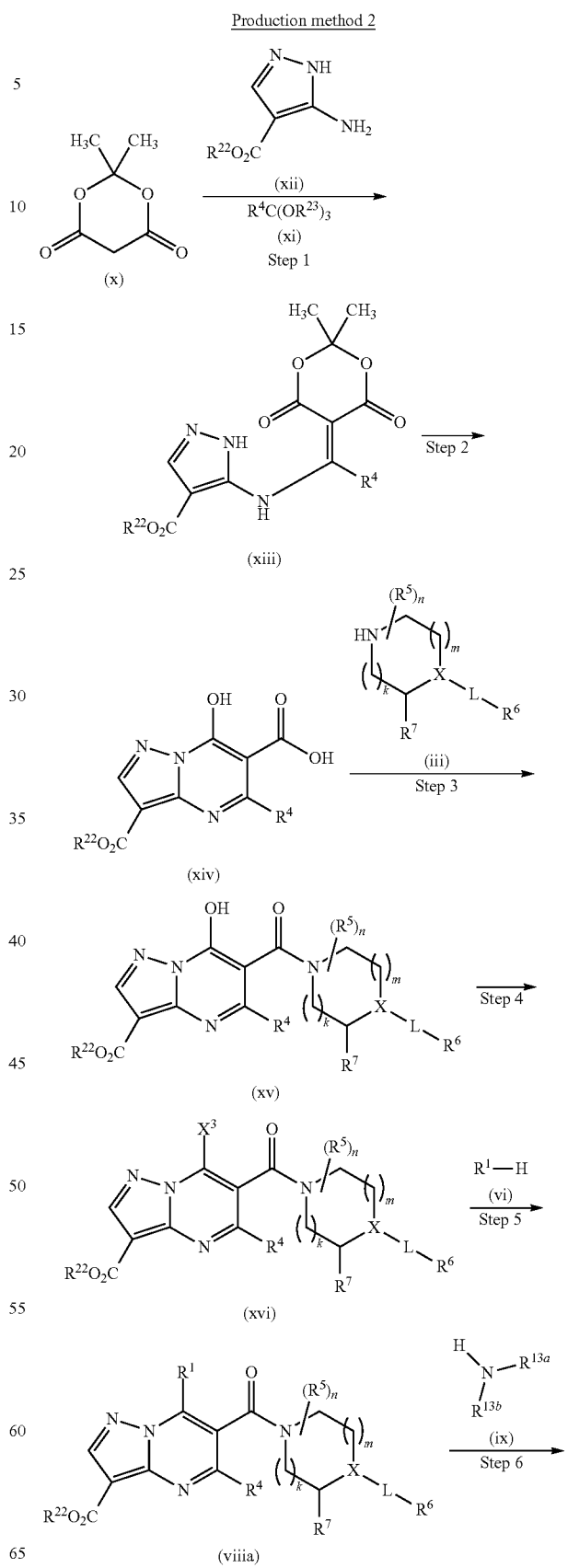

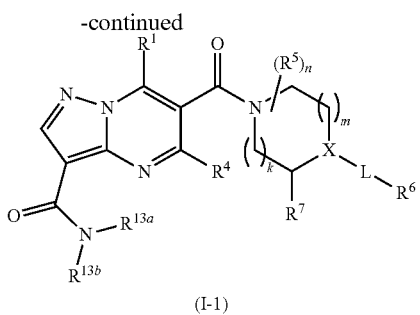

(wherein $R^1$, $R^4$, $R^5$, $R^6$, $R^7$, $R^{13a}$, $R^{13b}$, X, L, k, m and n are each as defined above, $R^{22}$ and $R^{23}$ are the same or different and each represents lower alkyl, $R^{24}$ represents a hydrogen atom or lower alkyl, and $X^3$ represents a leaving group. Examples of the leaving group include sulfonyloxy such as benzenesulfonyloxy, methanesulfonyloxy, p-toluenesulfonyloxy or the like, a group obtained by removing one hydrogen atom from carboxylic acids, such as lower alkanoyloxy, arylcarbonyloxy, aromatic heterocyclic carbonyloxy or the like, a chlorine atom, a bromine atom, an iodine atom, a fluorine atom).

The conversion reaction of each of $R^1$, $R^4$, $R^5$, $R^6$, $R^7$, $R^{13a}$, $R^{13b}$, $R^{22}$, $R^{24}$, X and $X^3$ can be performed between any steps of step 1-step 6 of this production method.

Compounds (viiia) and (xv) in this production method are encompassed in compound (I).

[Step 1]

Compound (x) is reacted with 1-20 equivalents, preferably 1-5 equivalents, of compound (xi) in an inert solvent or without solvent at a temperature between 80° C. and 150° C., preferably between 100° C. and 140° C., for 10 min-24 hr, preferably 30 min-4 hr, and then with 0.5-2 equivalents, preferably 0.8-1.2 equivalents, of compound (xii) at a temperature between 0° C. and 150° C., preferably between 100° C. and 140° C., for 10 min-24 hr, preferably 30 min-4 hr, to give compound (xiii).

Compounds (x), (xi) and (xii) can be obtained as commercially available products, or can be synthesized by a known method.

Examples of the inert solvent include 1,2-dichloroethane, DME, toluene, DMF, dioxane, acetonitrile, ethyl acetate and the like, and these can be used alone or in a mixture. Among these, toluene is preferable.

[Step 2]

Compound (xiii) is reacted with 1-20 equivalents, preferably 1-5 equivalents, of a Lewis acid reagent in an inert solvent or without solvent in the presence of 1-10 equivalents, preferably 1-5 equivalents, of a base at a temperature between −30° C. and 40° C., preferably between −30° C. and 30° C., for 5 min-24 hr, preferably 10 min-2 hr, to give compound (xiv).

Examples of the inert solvent include chloroform, methylene chloride, pyridine, THF, DMF, toluene, DMF, dioxane, acetonitrile, ethyl acetate and the like, and these can be used alone or in a mixture. Among these, chloroform or methylene chloride is preferable.

Examples of the base include pyridine, triethylamine, 4-(dimethylamino)pyridine, N-methylmorpholine, N,N-diisopropylethylamine and the like. Among these, N-methylmorpholine or triethylamine is preferable.

Examples of the Lewis acid reagent include boron trifluoride diethyl ether complex, aluminum chloride, trimethylsilyl trifluoromethanesulfonate, triethylsilyl trifluoromethanesulfonate, triisopropylsilyl trifluoromethanesulfonate, tert-butyldimethylsilyl trifluoromethanesulfonate and the like. Among these, trimethylsilyl trifluoromethanesulfonate or triethylsilyl trifluoromethanesulfonate is preferable.

[Step 3]

Compound (xv) can be obtained by reacting compound (xiv) with compound (iii) by the following methods 1-3.

(Method 1)

Compound (xiv) is treated in an inert solvent or without solvent using 1-20 equivalents, preferably 1-5 equivalents, of an acid halogenating agent at a temperature between −20° C. and the boiling point of the solvent to be used, preferably between −10° C. and 30° C., for 15 min-48 hr, preferably 1-18 hr, to give acid halide of compound (xiv). Where necessary, 0.01-0.5 equivalent of DMF, pyridine or the like may be added. Compound (xv) can be obtained by reacting the obtained acid halide with 0.5-2 equivalents, preferably 1-1.2 equivalents, of compound (iii) in an inert solvent in the presence of 1-5 equivalents, preferably 1-3 equivalents, of a base at a temperature between −20° C. and the boiling point of the solvent to be used, preferably between −10° C. and 30° C., for 15 min-48 hr, preferably 1-10 hr.

Examples of the inert solvent to be used in the reaction to obtain acid halide include chloroform, methylene chloride, pyridine, THF, DME, toluene, DMF, dioxane, ethyl acetate and the like, and these can be used alone or in a mixture. Among these, methylene chloride or toluene is preferable.

Examples of the acid halogenating agent include thionyl chloride, oxalyl chloride and the like.

Examples of the inert solvent to be used for the reaction of acid halide with compound (iii) include chloroform, methylene chloride, pyridine, THF, DME, toluene, DMF, dioxane, ethyl acetate and the like, and these can be used alone or in a mixture. Among these, methylene chloride or DMF is preferable.

Examples of the base include pyridine, triethylamine, 4-(dimethylamino)pyridine, N,N-diisopropylethylamine, aqueous sodium hydrogen carbonate solution, aqueous sodium hydroxide solution and the like. Among these, triethylamine is preferable.

(Method 2)

compound (xiv) is reacted with 1-20 equivalents, preferably 1-5 equivalents, of a mixed acid anhydride reagent in an inert solvent or without solvent in the presence of 1-5 equivalents, preferably 1-3 equivalents, of a base at a temperature between −30° C. and 40° C., preferably between −30° C. and 0° C., for 5 min-24 hr, preferably 10 min-2 hr, to give a mixed acid anhydride of compound (xiv). The obtained mixed acid anhydride is reacted with 0.5-2 equivalents, preferably 1-1.2 equivalents, of compound (iii) at a temperature between −30° C. and 40° C., preferably between −30° C. and 30° C., for 5 min-24 hr, preferably 10 min-2 hr, to give compound (xv).

Examples of the inert solvent include chloroform, methylene chloride, pyridine, THF, DME, toluene, DMF, dioxane, acetonitrile, ethyl acetate and the like, and these can be used alone or in a mixture. Among these, THF, DMF or acetonitrile is preferable.

Examples of the base include pyridine, triethylamine, 4-(dimethylamino)pyridine, N-methylmorpholine, N,N-diisopropylethylamine and the like. Among these, N-methylmorpholine or triethylamine is preferable.

Examples of the mixed acid anhydride reagent include isobutyl chloroformate, ethyl chloroformate, pivaloyl chloride, tosyl chloride, mesyl chloride and the like. Among these, isobutyl chloroformate or mesyl chloride is preferable.

(Method 3)

Compound (xiv) is reacted with 0.5-10 equivalents, preferably 0.5-5 equivalents, of compound (iii) in an inert solvent or without solvent in the presence or absence of 1-20 equivalents, preferably 1-10 equivalents, of a base in the presence of 1-20 equivalents, preferably 1-5 equivalents, of a condensing agent at a temperature between −30° C. and 60° C., preferably between −30° C. and 40° C., for 30 min-72 hr, preferably 1-18 hr, to give compound (xv). At this time, 0.5-2 equivalents of, for example, HOBt, HOBt.H₂O, 3-hydroxy-4-oxo-3,4-dihydro-1,2,3-benzotriazine or the like may be added.

Examples of the inert solvent include chloroform, methylene chloride, pyridine, THF, DME, toluene, DMF, DMSO, dioxane, acetonitrile, ethyl acetate and the like, and these can be used alone or in a mixture. Among these, methylene chloride, DMF, THF or acetonitrile is preferable.

Examples of the base include pyridine, triethylamine, 4-(dimethylamino)pyridine, N-methylmorpholine, N,N-diisopropylethylamine and the like. Among those, N,N-diisopropylethylamine or triethylamine is preferable.

Examples of the condensing agent include 1,3-dicyclohexylcarbodiimide, 1-ethyl-3-[3-(dimethylamino)propyl]carbodiimide or hydrochloride thereof, 1,1'-carbonyldiimidazole, 1,3-diisopropylcarbodiimide, diphenylphosphoryl azide, 2-chloro-1-methylpyridinium iodide, 1-benzotriazolyl mesylate, 1-benzotriazolyl tosylate, 1-benzotriazolyl benzenesulfonate, benzotriazol-1-yloxytripyrrolidinophosphonium hexafluorophosphate, 1-propylphosphonic acid anhydride cyclic trimer and the like. Among these, 1-ethyl-3-[3-(dimethylamino)propyl]carbodiimide or hydrochloride thereof, or 1-propylphosphonic acid anhydride cyclic trimer is preferable.

[Step 4]

Compound (xvi) can be obtained by reacting compound (xv) with 0.5-50 equivalents, preferably a solvent amount, of a leaving group-introducing reagent in an inert solvent or without solvent at a temperature between −30° C. and 150° C. for 15 min-24 hr.

As the leaving group-introducing reagent, a suitable reagent can be selected according to the leaving group to be used. For example, when $X^3$ is a halogen atom such as a chlorine atom, a bromine atom and the like, phosphorus oxychloride, phosphorus oxybromide, phosphorus pentachloride, trichloroacetyl chloride, phosphorus trichloride, phosphorus tribromide, acetyl chloride, thionyl chloride or the like can be used. At this time, 0.5-3 equivalents of, for example, N,N-diisopropylethylamine, N,N-diethylaniline or the like may be added.

Preferably, the reaction is performed using phosphorus oxychloride without solvent at 80-120° C.

[Step 5]

Compound (viiia) can be obtained by reacting compound (xvi) with 0.5-10 equivalents, preferably 1-3 equivalents, of compound (vi) in an inert solvent or without solvent at a temperature between the melting point and the boiling point of the solvent to be used for 15 min-24 hr, and using a base where necessary, and when further necessary, by irradiating microwave with 100-500 (W) energy under pressurization conditions of 1-20 atm.

Examples of the base include sodium hydroxide, potassium carbonate, sodium hydrogen carbonate, barium hydroxide, cesium carbonate, potassium hydroxide, sodium methoxide, potassium ethoxide, lithium hydroxide, lithium hexamethyldisilazane, sodium hydride, potassium hydride, n-butyllithium, lithium diisopropylamide, potassium tert-butoxide, triethylamine, N,N-diisopropylethylamine, tributylamine, dicyclohexylmethylamine, N-methylmorpholine, pyridine, N-methylpiperidine, 2,6-di-tert-butylpyridine, DBU, DBN, 4-(dimethylamino)pyridine, Amberlyst A-21 (manufactured by ROHM AND HAAS JAPAN KK.), AG 1-X8 (Bio-Rad, manufactured by Richmond, Calif.), polyvinyl pyridine, morpholinomethyl polystyrene and the like.

The microwave refers to 1 GHz-1 THz electromagnetic wave, and 2450 MHz is preferably used.

The irradiation energy is more preferably 300 watt.

The reaction is preferably performed using DMF, N,N-dimethylacetamide or N-methylpyrrolidinone as an inert solvent, and potassium carbonate, triethylamine or N,N-diisopropylethylamine as a base at a temperature between 80° C. and 120° C. for 1-24 hr.

Compound (viiia) wherein $R^{24}$ is a hydrogen atom can be obtained from compound (viiia) wherein $R^{24}$ is lower alkyl by a method similar to the method 5 of the aforementioned Production method 1, step 1.

[Step 6]

Compound (I-1) can be obtained by reacting compound (viiia) with compound (ix) by a method similar to the methods 1-4 of the aforementioned Production method 1, step 5.

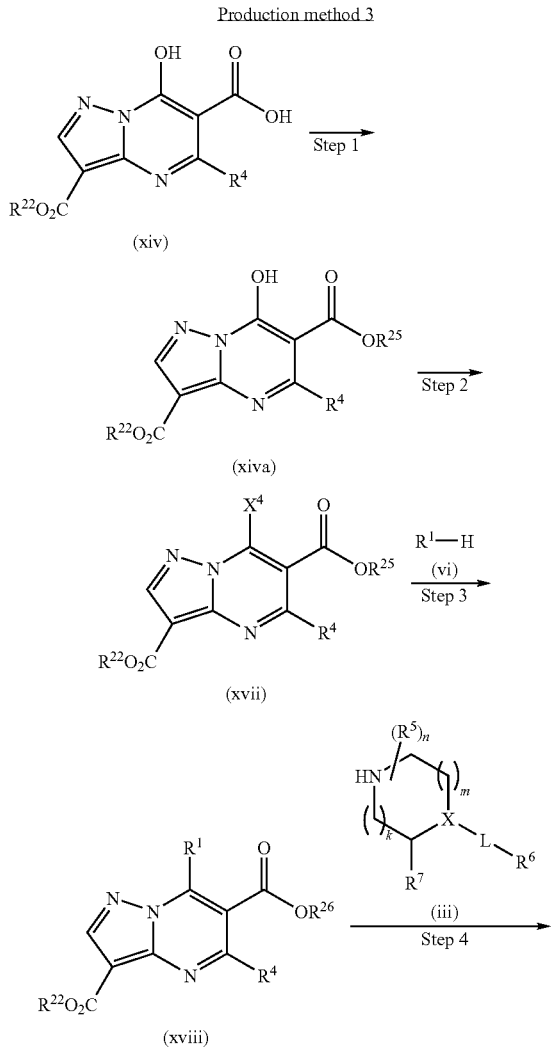

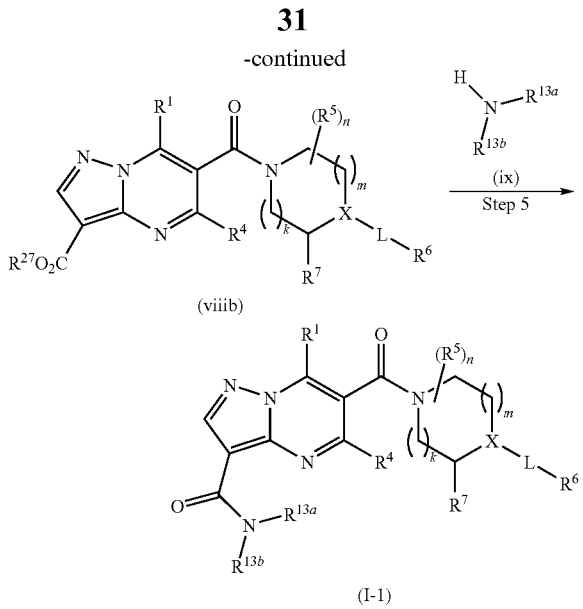

(wherein $R^1$, $R^4$, $R^5$, $R^6$, $R^7$, $R^{13a}$, $R^{13b}$, $R^{22}$, X, L, k, m and n are each as defined above, $R^{25}$ represents lower alkyl, $R^{26}$ and $R^{27}$ are the same or different and each represents a hydrogen atom or lower alkyl, and $X^4$ represents a leaving group. Examples of the leaving group include sulfonyloxy such as benzenesulfonyloxy, methanesulfonyloxy, p-toluenesulfonyloxy and the like, a group obtained by removing one hydrogen atom from carboxylic acids, such as lower alkanoyloxy, arylcarbonyloxy, aromatic heterocyclic carbonyloxy and the like, a chlorine atom, a bromine atom, an iodine atom and a fluorine atom).

The conversion reaction of each of $R^1$, $R^4$, $R^5$, $R^6$, $R^7$, $R^{13a}$, $R^{13b}$, $R^{22}$, $R^{25}$, $R^{26}$, $R^{27}$, X and $X^4$ can be performed between any steps of step 1-step 5 of this Production method.

Compound (viiib) in this production method is encompassed in compound (I).

[Step 1]

Compound (xiva) can be obtained by the following method from compound (xiv) obtained in the aforementioned production method 2, step 2.

Compound (xiv) is treated in an inert solvent or without solvent using 1-20 equivalents, preferably 1-5 equivalents, of an acid halogenating agent at a temperature between –20° C. and the boiling point of the solvent to be used for 15 min-48 hr, preferably 1-18 hr, to give acid halide of compound (xiv). Where necessary, 0.01-0.5 equivalent of DMF, pyridine or the like may be added. Compound (xiva) can be obtained by reacting the obtained acid halide with 0.5-2 equivalents, preferably 1-1.2 equivalents, or a solvent amount of alcohol in an inert solvent in the presence of 1-10 equivalents, preferably 1-5 equivalents, of a base at a temperature between –20° C. and the boiling point of the solvent to be used, preferably between –10° C. and 30° C., for 15 min-48 hr, preferably 1-10 hr.

Examples of the inert solvent to be used in the reaction to obtain acid halide include 1,2-dichloroethane, chloroform, methylene chloride, pyridine, THF, DME, toluene, DMF, dioxane, ethyl acetate and the like, and these can be used alone or in a mixture. Among these, 1,2-dichloroethane, methylene chloride or toluene is preferable.

Examples of the acid halogenating agent include thionyl chloride, oxalyl chloride and the like.

Examples of the inert solvent to be used for the reaction of acid halide with alcohol include 1,2-dichloroethane, chloroform, methylene chloride, pyridine, THF, DME, toluene, DMF, dioxane, ethyl acetate and the like, and these can be used alone or in a mixture. Among these, 1,2-dichloroethane, methylene chloride or DMF is preferable.

Examples of the base include pyridine, triethylamine, 4-(dimethylamino)pyridine, N,N-diisopropylethylamine, aqueous sodium hydrogen carbonate solution, aqueous sodium hydroxide solution and the like. Among these, triethylamine is preferable.

Examples of the alcohol include methanol, ethanol, n-propyl alcohol, i-propyl alcohol, n-butyl alcohol, i-butyl alcohol, sec-butyl alcohol, tert-butyl alcohol, n-pentyl alcohol, n-hexyl alcohol, n-heptyl alcohol, n-octyl alcohol, n-nonyl alcohol, n-decyl alcohol and the like. Among these, ethanol or methanol is preferable.

[Step 2]

Compound (xvii) can be obtained from compound (xiva) by a method similar to the aforementioned Production method 2, step 4.

[Step 3]

Compound (xviii) wherein $R^{26}$ is lower alkyl can be obtained from compound (xvii) by a method similar to the method of the aforementioned Production method 2, step 5.

In this reaction, when $R^{22}$ and/or $R^{25}$ are/is converted to a hydrogen atom, each can be converted to lower alkyl by a method similar to step 1 of this production method.

Compound (xviii) wherein $R^{26}$ is a hydrogen atom can be obtained from compound (xviii) wherein $R^{26}$ is lower alkyl by a method similar to the method 5 of the aforementioned Production method 1, step 1.

[Step 4]

Compound (viiib) wherein $R^{27}$ is lower alkyl can be obtained by reacting compound (xviii) with compound (iii) by a method similar to the methods 1-4 of the aforementioned Production method 1, step 1.

Compound (viiib) wherein $R^{27}$ is a hydrogen atom can be obtained from compound (viiib) wherein $R^{27}$ is lower alkyl by a method similar to the method 5 of the aforementioned Production method 1, step 1.

[Step 5]

Compound (I-1) can be obtained by reacting compound (viiib) with compound (ix) by a method similar to the methods 1-4 of the aforementioned Production method 1, step 5.

The following compound (I-2) can be produced by a method similar to the above-mentioned Production methods 1-3 and using compound (XX)

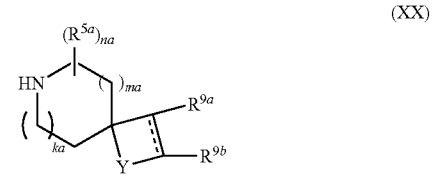

(wherein - - - - -, $R^{5a}$, $R^{9a}$, $R^{9b}$, Y, ka, ma and na are each as defined above), which is a corresponding cyclic amine.

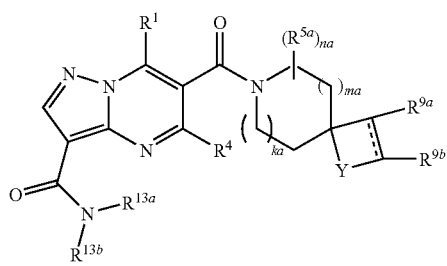

(wherein ----, $R^1$, $R^4$, $R^{5a}$, $R^{9a}$, $R^{9b}$, $R^{13a}$, $R^{13b}$, Y, ka, ma and na are each as defined above).

Each functional group in compound (I) and compound (IA) can also be converted by a known method (e.g., the method described in Comprehensive Organic Transformations 2nd edition, R. C. Larock, Vch Verlagsgesellschaft Mbh, 1999 and the like) or similar methods thereto.

The intermediates and the desired compounds in the above-mentioned respective production methods can be isolated and purified by applying separation purification methods usually used in the synthetic organic chemistry such as filtration, extraction, washing, drying, concentration, recrystallization, various chromatographies or the like. In addition, intermediates can also be subjected to a next reaction without particular purification.

When a salt of compound (I) or (IA) is to be obtained, compound (I) or (IA) obtained in the form of a salt can be directly purified. When it is obtained in a free form, compound (I) or (IA) may be dissolved or suspended in a suitable solvent, and an acid or base is added thereto to form a salt, which may be isolated and purified.

Specific examples of the structural formulas of compounds (I) and (IA) obtained by the present invention are shown in Table 1 and Table 2. However, the compounds of the present invention are not limited thereto. In the Tables, Ph means phenyl.

TABLE 1-continued
(I-1)
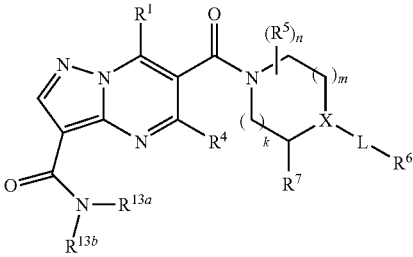
| Compound No. | R¹ | | R⁴ | R¹³ᵃ | R¹³ᵇ |
|---|---|---|---|---|---|
| a-6 | 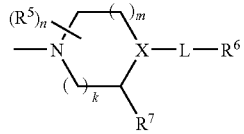 | 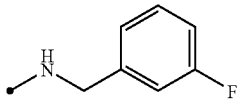 | H | H | 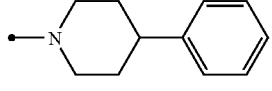 |
| a-7 |  | 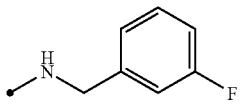 | H | H | 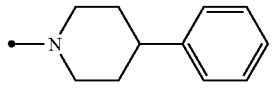 |
| a-8 | 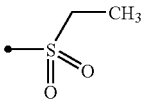 | 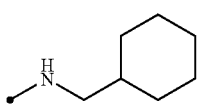 | H | H | 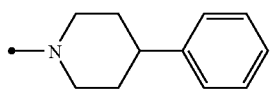 |
| a-9 |  | 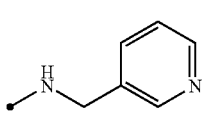 | H | H | 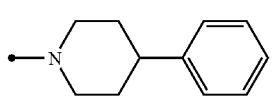 |
| a-10 |  | 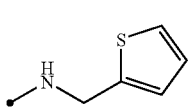 | H | H | 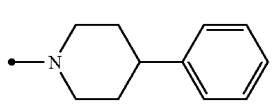 |
| a-11 |  | 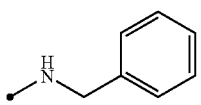 | H | —CH₂CH₂—O—CH₂CH₂— | |
| a-12 | 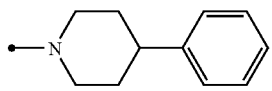 | 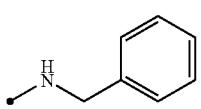 | H | H | H |
| a-13 | 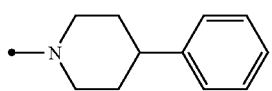 | 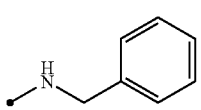 | H | H | 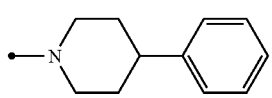 |
| a-14 | 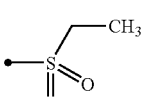 | 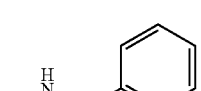 | H | H | 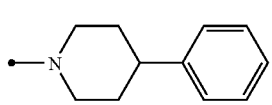 |
| a-15 |  | 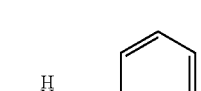 | H | H | 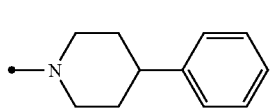 |

TABLE 1-continued (I-1)

| Compound No. | R¹ | [piperidine group] | R⁴ | R¹³ᵃ | R¹³ᵇ |
|---|---|---|---|---|---|
| a-16 | NH-benzyl | 4-phenylpiperidin-1-yl | H | H | morpholin-4-ylsulfonyl |
| a-17 | NH-CH₂-(3-methoxyphenyl) | 4-phenylpiperidin-1-yl | H | H | methylsulfonyl |
| a-18 | NH-CH₂-(3-chlorophenyl) | 4-phenylpiperidin-1-yl | H | H | methylsulfonyl |
| a-19 | NH-CH(CH₃)-phenyl | 4-phenylpiperidin-1-yl | H | H | methylsulfonyl |
| a-20 | NH-(indan-1-yl) | 4-phenylpiperidin-1-yl | H | H | methylsulfonyl |
| a-21 | NH-benzyl | 3-methyl-4-phenylpiperidin-1-yl | H | H | methylsulfonyl |
| a-22 | NH-benzyl | 4-(2-methoxyphenyl)piperidin-1-yl | H | H | methylsulfonyl |
| a-23 | NH-benzyl | 4-(thien-2-yl)piperidin-1-yl | H | H | methylsulfonyl |

TABLE 1-continued
(I-1)
| Compound No. | R¹ | (structure) | R⁴ | R¹³ᵃ | R¹³ᵇ |
|---|---|---|---|---|---|
| a-24 | 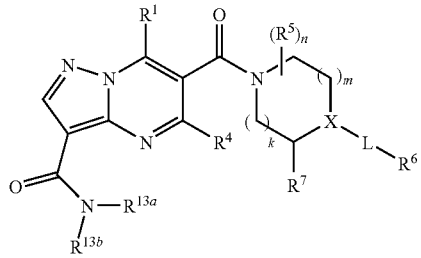 | 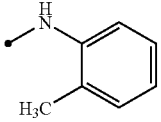 | H | H | 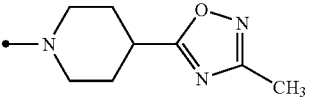 |
| a-25 | 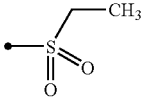 | 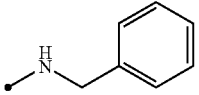 | H | H | 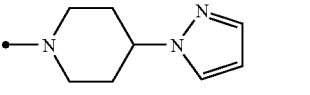 |
| a-26 | 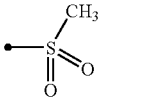 | 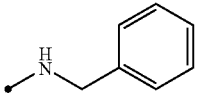 | H | H | 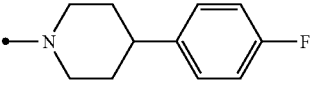 |
| a-27 | 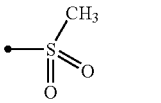 | 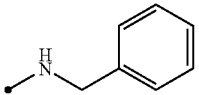 | H | H | 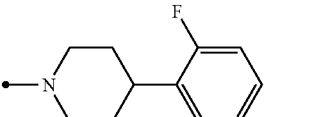 |
| a-28 | 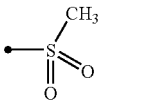 | 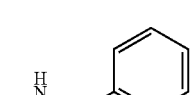 | H | H | 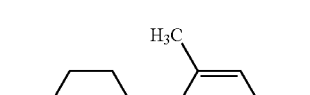 |
| a-29 | 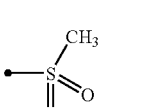 | 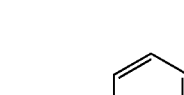 | H | H | 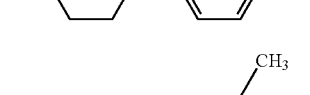 |
| a-30 | 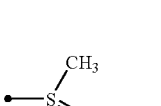 | 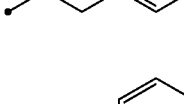 | H | H | 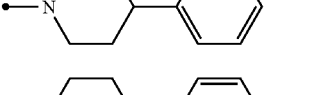 |
| a-31 | 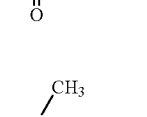 | 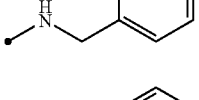 | H | H | 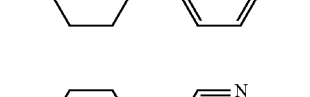 |
| a-32 | 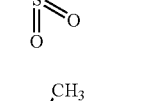 | 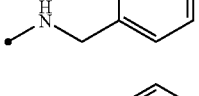 | H | H | 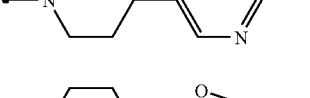 |

TABLE 1-continued
(I-1)
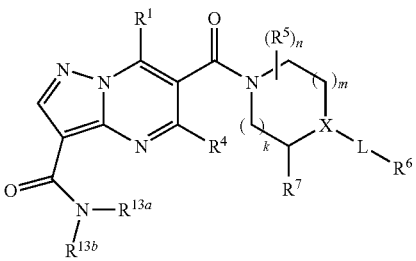
| Compound No. | R¹ |  | R⁴ | R¹³ᵃ | R¹³ᵇ |
|---|---|---|---|---|---|
| a-33 |  | 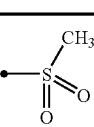 | H | H |  |
| a-34 |  |  | H | H |  |
| a-35 |  |  | H | H |  |
| a-36 |  |  | H | H |  |
| a-37 |  |  | H | H |  |
| a-38 |  |  | H | H |  |
| a-39 |  |  | H | H |  |
| a-40 |  |  | H | H |  |

TABLE 1-continued (I-1)

| Compound No. | R¹ | [piperidine group] | R⁴ | R¹³ᵃ | R¹³ᵇ |
|---|---|---|---|---|---|
| a-41 | NH-(4-methylphenyl) | 4-phenylpiperidin-1-yl | H | H | -S(O)₂-CH₂CH₃ |
| a-42 | NH-(3-methylphenyl) | 4-phenylpiperidin-1-yl | H | H | -S(O)₂-CH₂CH₃ |
| a-43 | NH-(2-chlorophenyl) | 4-phenylpiperidin-1-yl | H | H | -S(O)₂-CH₂CH₃ |
| a-44 | NH-(2-methoxyphenyl) | 4-phenylpiperidin-1-yl | H | H | -S(O)₂-CH₂CH₃ |
| a-45 | NH-(2-methylthiophenyl) | 4-phenylpiperidin-1-yl | H | H | -S(O)₂-CH₂CH₃ |
| a-46 | NH-(2-methylsulfonylphenyl) | 4-phenylpiperidin-1-yl | H | H | -S(O)₂-CH₂CH₃ |
| a-47 | NH-(2-phenylphenyl) | 4-phenylpiperidin-1-yl | H | H | -S(O)₂-cyclopropyl |
| a-48 | NH-(2-benzyloxyphenyl) | 4-phenylpiperidin-1-yl | H | H | -S(O)₂-CH₂CH₃ |

TABLE 1-continued
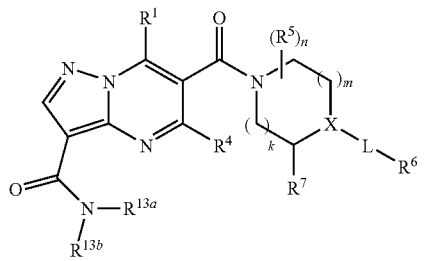
(I-1)
| Compound No. | –R¹ | 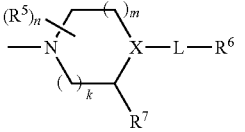 | –R⁴ | –R¹³ᵃ | –R¹³ᵇ |
|---|---|---|---|---|---|
| a-49 | 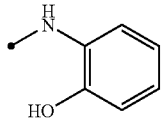 |  | –H | –H | 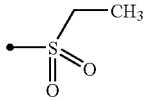 |
| a-50 | 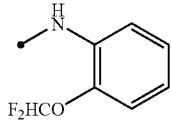 | 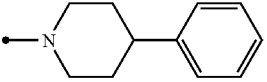 | –H | –H | 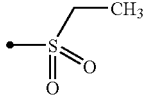 |
| a-51 | 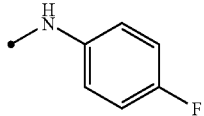 | 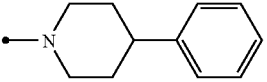 | –H | –H | 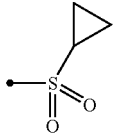 |
| a-52 | 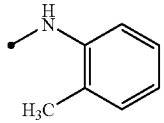 | 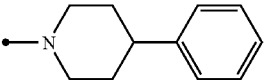 | –H | –H | 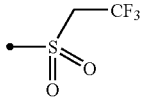 |
| a-53 | 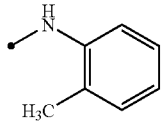 | 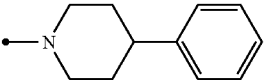 | –H | –H | 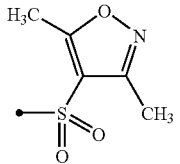 |
| a-54 | 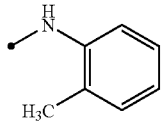 | 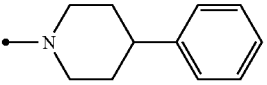 | –H | –H | 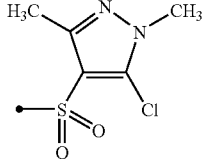 |
| a-55 | 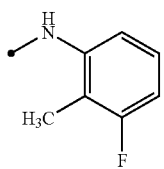 | 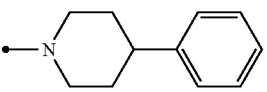 | –H | –H | 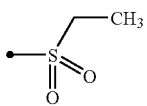 |

TABLE 1-continued (I-1)

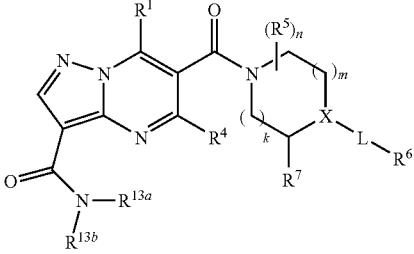

| Compound No. | R¹ | (piperidine-X-L-R⁶ group) | R⁴ | R¹³ᵃ | R¹³ᵇ |
|---|---|---|---|---|---|
| a-56 | 3-fluoro-2-methylanilino | 4-phenylpiperidin-1-yl | H | H | cyclopropylsulfonylmethyl |
| a-57 | 4-fluoro-2-methylanilino | 4-phenylpiperidin-1-yl | H | H | ethylsulfonylmethyl |
| a-58 | 3-chloro-2-methylanilino | 4-phenylpiperidin-1-yl | H | H | ethylsulfonylmethyl |
| a-59 | 2-fluoro-5-methylanilino | 4-phenylpiperidin-1-yl | H | H | ethylsulfonylmethyl |
| a-60 | 2-fluoro-5-methylanilino | 4-phenylpiperidin-1-yl | H | H | cyclopropylsulfonylmethyl |
| a-61 | 2,5-dimethylanilino | 4-phenylpiperidin-1-yl | H | H | ethylsulfonylmethyl |
| a-62 | 2-methyl-5-(trifluoromethyl)anilino | 4-phenylpiperidin-1-yl | H | H | cyclopropylsulfonylmethyl |

TABLE 1-continued (I-1)

| Compound No. | —R¹ | | —R⁴ | —R¹³ᵃ | —R¹³ᵇ |
|---|---|---|---|---|---|
| a-63 | 3-methyl-4-fluoroanilino | 4-phenylpiperidin-1-yl | —H | —H | —S(O)₂CH₂CH₃ |
| a-64 | 2-fluoro-3-methylanilino | 4-phenylpiperidin-1-yl | —H | —H | —S(O)₂CH₂CH₃ |
| a-65 | 2-chloro-3-fluoroanilino | 4-phenylpiperidin-1-yl | —H | —H | —S(O)₂CH₂CH₃ |
| a-66 | 2-chloro-5-methylanilino | 4-phenylpiperidin-1-yl | —H | —H | —S(O)₂CH₂CH₃ |
| a-67 | 2-chloro-4-fluoroanilino | 4-phenylpiperidin-1-yl | —H | —H | —S(O)₂CH₂CH₃ |
| a-68 | indan-4-ylamino | 4-phenylpiperidin-1-yl | —H | —H | —S(O)₂CH₂CH₃ |
| a-69 | (1-methyl-1H-pyrazol-5-yl)amino | 4-phenylpiperidin-1-yl | —H | —H | —S(O)₂CH₂CH₃ |

US 8,729,264 B2

TABLE 1-continued (I-1)

| Compound No. | –R¹ | | –R⁴ | –R¹³ᵃ | –R¹³ᵇ |
|---|---|---|---|---|---|
| a-70 | 3-NH-(2-methylpyridin-3-yl) | 4-phenylpiperidin-1-yl | H | H | ethylsulfonyl |
| a-71 | 3-NH-(4-methylthiophen-3-yl) | 4-phenylpiperidin-1-yl | H | H | cyclopropylsulfonyl |
| a-72 | 4-NH-(1H-indol-4-yl) | 4-phenylpiperidin-1-yl | H | H | ethylsulfonyl |
| a-73 | 7-NH-(1H-indol-7-yl) | 4-phenylpiperidin-1-yl | H | H | ethylsulfonyl |
| a-74 | 5-NH-(1H-indol-5-yl) | 4-phenylpiperidin-1-yl | H | H | ethylsulfonyl |
| a-75 | 6-NH-(1H-indol-6-yl) | 4-phenylpiperidin-1-yl | H | H | ethylsulfonyl |
| a-76 | 5-NH-(1-methyl-1H-indol-5-yl) | 4-phenylpiperidin-1-yl | H | H | ethylsulfonyl |
| a-77 | 4-NH-(1-methyl-1H-indol-4-yl) | 4-phenylpiperidin-1-yl | H | H | ethylsulfonyl |

TABLE 1-continued (I-1)

| Compound No. | •—R¹ | (structure with R⁵, X, L, R⁶, R⁷) | •—R⁴ | •—R¹³ᵃ | •—R¹³ᵇ |
|---|---|---|---|---|---|
| a-78 | 5-quinolinylamino | 4-phenylpiperidin-1-yl | —H | —H | ethylsulfonyl (–SO₂CH₂CH₃) |
| a-79 | 8-quinolinylamino | 4-phenylpiperidin-1-yl | —H | —H | ethylsulfonyl |
| a-80 | (2,2-dimethyl-2,3-dihydrobenzofuran-7-yl)amino | 4-phenylpiperidin-1-yl | —H | —H | ethylsulfonyl |
| a-81 | (2-fluoro-5-methylphenyl)amino | 4-(4-fluorophenyl)piperidin-1-yl | —H | —H | ethylsulfonyl |
| a-82 | (2-fluoro-5-methylphenyl)amino | 4-(4-fluorophenyl)piperidin-1-yl | —H | —H | cyclopropylsulfonyl |
| a-83 | (3-methylphenyl)amino | 4-(4-fluorophenyl)piperidin-1-yl | —H | —H | ethylsulfonyl |
| a-84 | (4-fluoro-2-methylphenyl)amino | 4-(4-fluorophenyl)piperidin-1-yl | —H | —H | ethylsulfonyl |

TABLE 1-continued (I-1)

| Compound No. | R¹ | (R⁵)ₙ, X—L—R⁶ with R⁷ | R⁴ | R¹³ᵃ | R¹³ᵇ |
|---|---|---|---|---|---|
| a-85 | 4-fluoro-3-methylanilino | 4-(4-fluorophenyl)piperidin-1-yl | H | H | ethylsulfonyl |
| a-86 | 2,5-dimethylanilino | 4-(4-fluorophenyl)piperidin-1-yl | H | H | ethylsulfonyl |
| a-87 | 2,5-dimethylanilino | 4-(4-fluorophenyl)piperidin-1-yl | H | H | cyclopropylsulfonyl |
| a-88 | 2,5-dimethylanilino | 4-(3,4-difluorophenyl)piperidin-1-yl | H | H | ethylsulfonyl |
| a-89 | 2,5-dimethylanilino | 4-(3,4-difluorophenyl)piperidin-1-yl | H | H | cyclopropylsulfonyl |
| a-90 | 2-fluoro-5-methylanilino | 4-(3,4-difluorophenyl)piperidin-1-yl | H | H | ethylsulfonyl |
| a-91 | 2-fluoro-5-methylanilino | 4-(2,4-difluorophenyl)piperidin-1-yl | H | H | ethylsulfonyl |
| a-92 | 2-fluoro-5-methylanilino | 4-(4-methoxyphenyl)piperidin-1-yl | H | H | ethylsulfonyl |

TABLE 1-continued (I-1)

| Compound No. | R¹ | (R⁵)ₙ—N—(  )ₖ—X—L—R⁶ with R⁷ | R⁴ | R¹³ᵃ | R¹³ᵇ |
|---|---|---|---|---|---|
| a-93 | 2-fluoro-5-methylphenylamino | 4-(naphthalen-2-yl)piperidin-1-yl | H | H | ethylsulfonyl |
| a-94 | 2-methyl-5-methylphenylamino (2,5-dimethylphenylamino) | 4-(6-fluoropyridin-3-yl)piperidin-1-yl | H | H | cyclopropylsulfonyl |
| a-95 | 2,5-dimethylphenylamino | 4-cyclohexylpiperidin-1-yl | H | H | ethylsulfonyl |
| a-96 | benzylamino | 4-fluoro-4-phenylpiperidin-1-yl | H | H | methylsulfonyl |
| a-97 | 2-methyl-4-fluorophenylamino | 4-fluoro-4-phenylpiperidin-1-yl | H | H | ethylsulfonyl |
| a-98 | 2-methyl-4-fluorophenylamino | 4-fluoro-4-phenylpiperidin-1-yl | H | H | cyclopropylsulfonyl |
| a-99 | 2-fluoro-5-methylphenylamino | 4-fluoro-4-phenylpiperidin-1-yl | H | H | ethylsulfonyl |

TABLE 1-continued
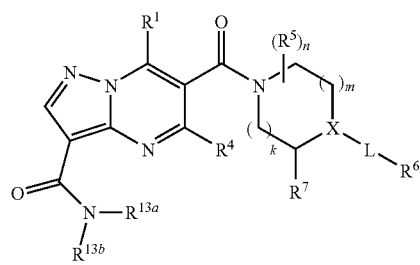
(I-1)
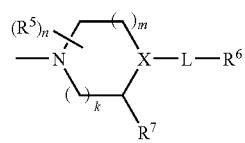
| Compound No. | •—R¹ | | •—R⁴ | •—R¹³ᵃ | •—R¹³ᵇ |
|---|---|---|---|---|---|
| a-100 | 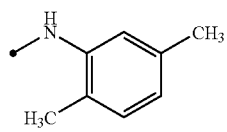 | 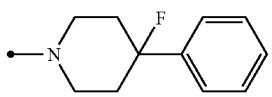 | •—H | •—H | 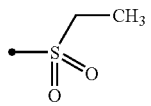 |
| a-101 | 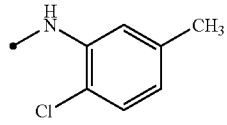 | 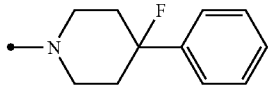 | •—H | •—H | 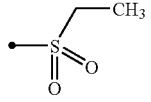 |
| a-102 | 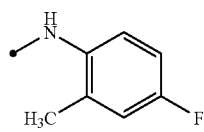 | 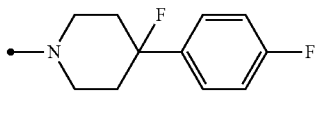 | •—H | •—H | 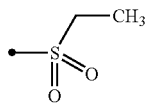 |
| a-103 | 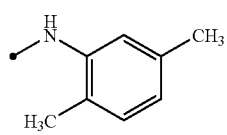 | 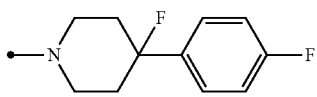 | •—H | •—H | 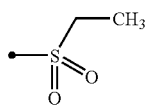 |
| a-104 | 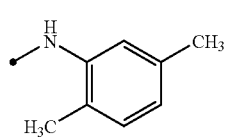 | 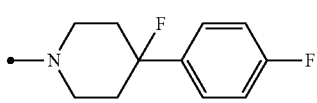 | •—H | •—H | 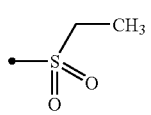 |

TABLE 2
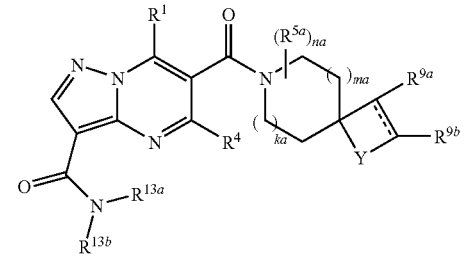

TABLE 2-continued

| Compound No. | R¹ | (structure) | R⁴ | R¹³ᵃ | R¹³ᵇ |
|---|---|---|---|---|---|
| a-112 | NH-benzyl | 3-methyl-spiro[indene-1,4'-piperidine] | H | H | -S(=O)₂-CH₃ |
| a-113 | NH-(2,5-dimethylphenyl) | 3-methyl-spiro[indene-1,4'-piperidine] | H | H | -S(=O)₂-CH₂CH₃ |
| a-114 | NH-phenyl | 3-methyl-spiro[indene-1,4'-piperidine] | H | H | -S(=O)₂-CH₃ |
| a-115 | NH-phenyl | 3-methyl-spiro[indene-1,4'-piperidine] | H | H | -S(=O)₂-CH₂CH₃ |
| a-116 | NH-(4-fluorophenyl) | 3-methyl-spiro[indene-1,4'-piperidine] | H | H | -S(=O)₂-CH₃ |

TABLE 2-continued
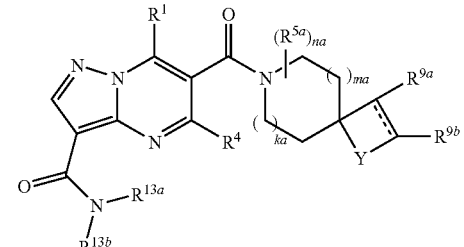
(I-2)
| Compound No. | —R¹ | 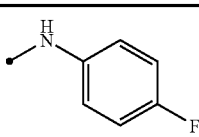 | —R⁴ | —R¹³ᵃ | —R¹³ᵇ |
|---|---|---|---|---|---|
| a-117 | 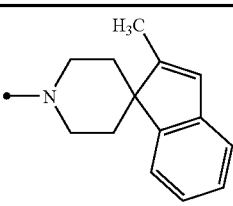 |  | —H | —H | 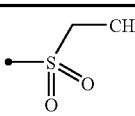 |
| a-118 | 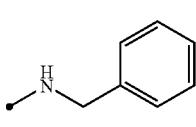 | 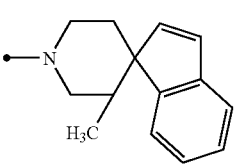 | —H | —H |  |
| a-119 | 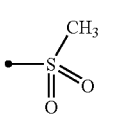 | 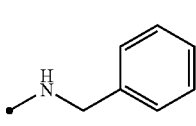 | —H | —H | 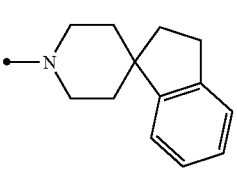 |
| a-120 |  | 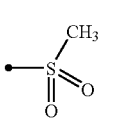 | —H | —H | 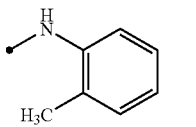 |
| a-121 | 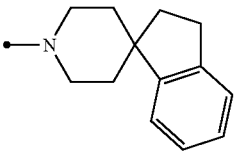 |  | —H | —H | 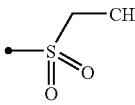 |
| a-122 | 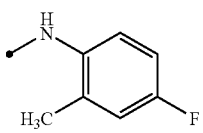 | 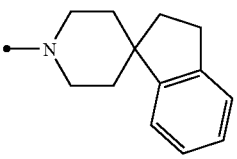 | —H | —H |  |
| a-123 | 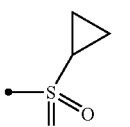 | 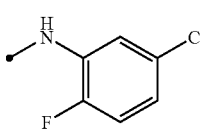 | —H | —H | 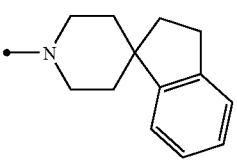 |

TABLE 2-continued
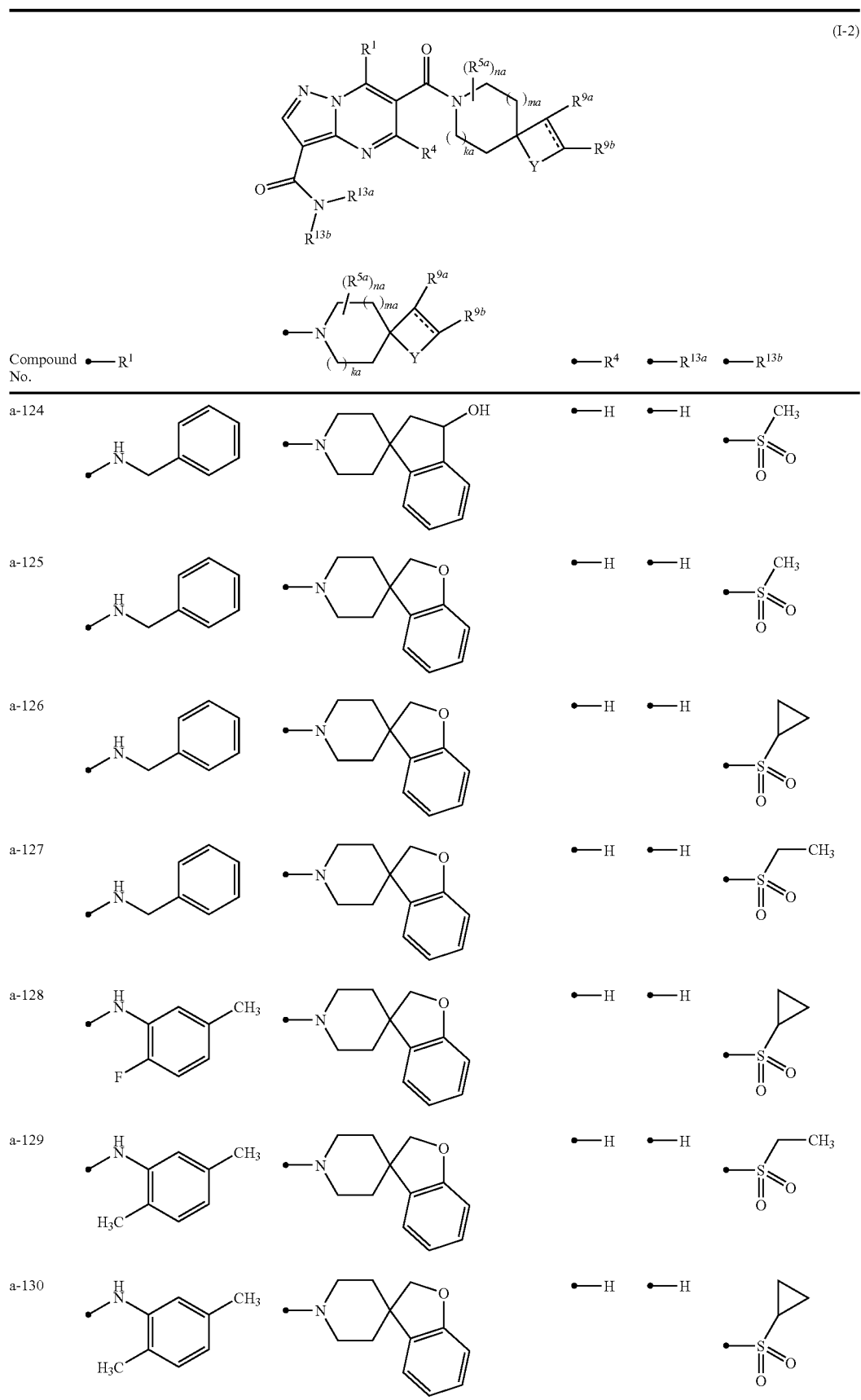

TABLE 2-continued (I-2)

| Compound No. | R¹ | (structure) | R⁴ | R¹³ᵃ | R¹³ᵇ |
|---|---|---|---|---|---|
| a-131 | 2-methylanilino | spiro-benzofuran-piperidine | H | H | S(O)₂CH₂CH₃ |
| a-132 | 3-methylanilino | spiro-benzofuran-piperidine | H | H | S(O)₂CH₂CH₃ |
| a-133 | 2-fluoro-3-methylanilino | spiro-benzofuran-piperidine | H | H | S(O)₂CH₂CH₃ |
| a-134 | benzylamino | fluoro-spiro-benzofuran-piperidine | H | H | S(O)₂CH₃ |
| a-135 | 3-methylanilino | fluoro-spiro-benzofuran-piperidine | H | H | S(O)₂CH₂CH₃ |
| a-136 | 2-fluoro-5-methylanilino | fluoro-spiro-benzofuran-piperidine | H | H | S(O)₂CH₂CH₃ |

TABLE 2-continued
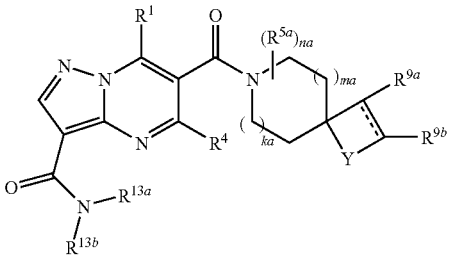
(I-2)
| Compound No. | R¹ | (R⁵ᵃ)ₙₐ R⁹ᵃ / N—...—Y—R⁹ᵇ (ka, ma) | R⁴ | R¹³ᵃ | R¹³ᵇ |
|---|---|---|---|---|---|
| a-137 | 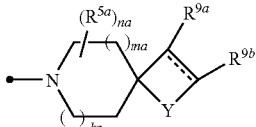 | 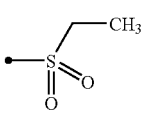 | —H | —H | 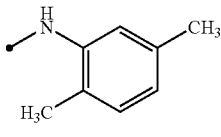 |
| a-138 | 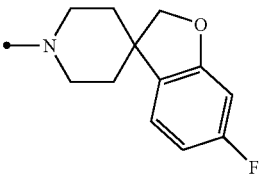 | 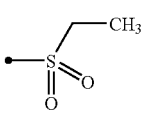 | —H | —H | 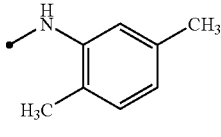 |
| a-139 | 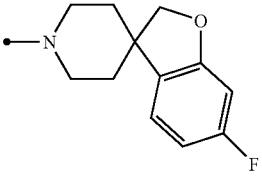 | 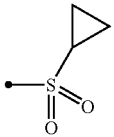 | —H | —H | 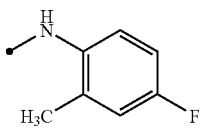 |
| a-140 | 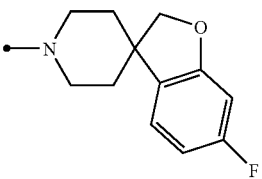 | 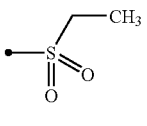 | —H | —H | 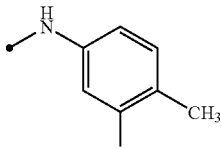 |
| a-141 | 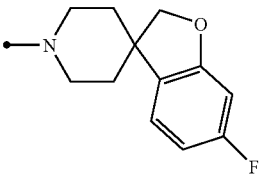 | 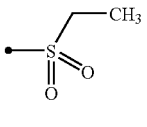 | —H | —H | 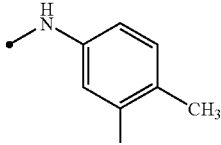 |
| a-142 | 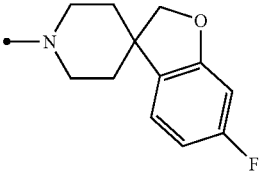 | 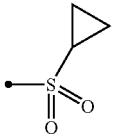 | —H | —H | 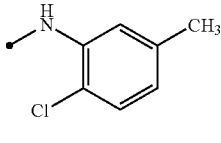 |

TABLE 2-continued (I-2)

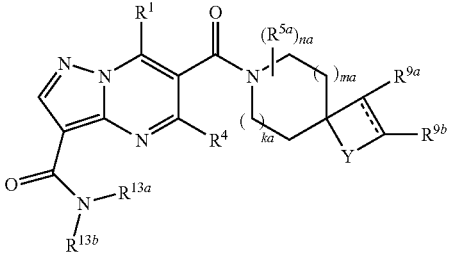

| Compound No. | R¹ | (structure) | R⁴ | R¹³ᵃ | R¹³ᵇ |
|---|---|---|---|---|---|
| a-143 | 2-Cl-5-CH₃-anilino (NH) | spiro[piperidine-benzofuran]-6-F | H | H | cyclopropylsulfonyl |
| a-144 | 4-CH₃-anilino (NH) | spiro[piperidine-benzofuran]-6-F | H | H | ethylsulfonyl |
| a-145 | benzylamino (NH-CH₂-Ph) | spiro[piperidine-benzofuran]-7-F | H | H | methylsulfonyl |
| a-146 | 2-F-5-CH₃-anilino (NH) | spiro[piperidine-benzofuran]-7-F | H | H | cyclopropylsulfonyl |
| a-147 | 2-CH₃-5-CH₃-anilino (NH) | spiro[piperidine-benzofuran]-7-F | H | H | ethylsulfonyl |
| a-148 | 2-CH₃-4-F-anilino (NH) | spiro[piperidine-benzofuran]-7-F | H | H | cyclopropylsulfonyl |
| a-149 | 2-CH₃-4-F-anilino (NH) | spiro[piperidine-benzofuran]-4-F | H | H | ethylsulfonyl |

TABLE 2-continued
(I-2)
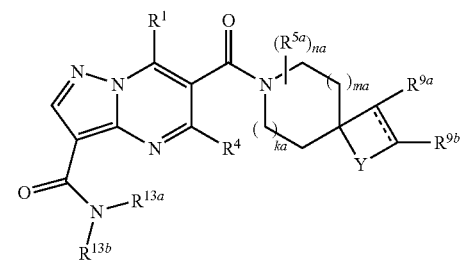
| Compound No. | —R¹ | 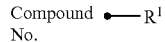 | —R⁴ | —R¹³ᵃ | —R¹³ᵇ |
|---|---|---|---|---|---|
| a-150 |  |  | —H | —H | 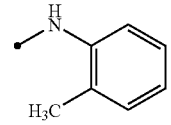 |
| a-151 | 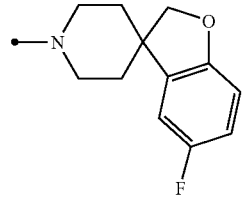 |  | —H | —H | 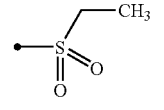 |
| a-152 | 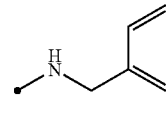 | 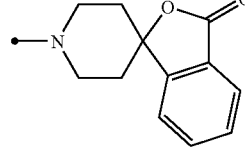 | —H | —H |  |
| a-153 | 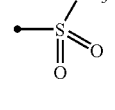 | 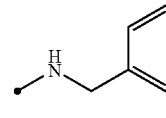 | —H | —H | 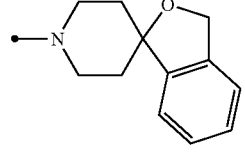 |
| a-154 |  | 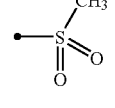 | —H | —H | 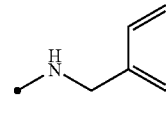 |
| a-155 | 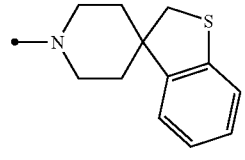 |  | —H | —H | 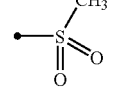 |

TABLE 2-continued (I-2)

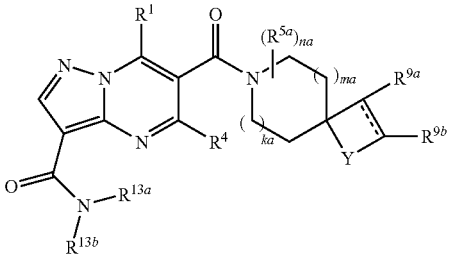

| Compound No. | •—R¹ | 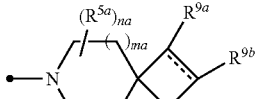 | •—R⁴ | •—R¹³ᵃ | •—R¹³ᵇ |
|---|---|---|---|---|---|
| a-156 | 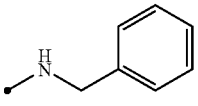 | 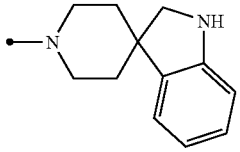 | •—H | •—H |  |
| a-157 |  |  | •—H | •—H | 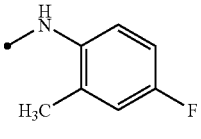 |
| a-158 | 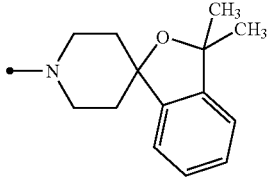 |  | •—H | •—H |  |
| a-159 | 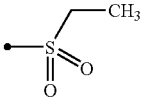 | 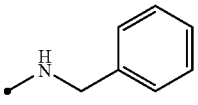 | •—H | •—H | 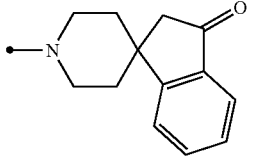 |

Next, the pharmacological action of the representative compound is specifically explained by Test Examples.

TEST EXAMPLE 1

Suppressive Action on Dinitrofluorobenzene-induced Ear Edema Reaction in Mouse

5-Week to 6-week old BALE/c mice (female, supplied by CHARLES RIVER LABORATORIES JAPAN, INC) were purchased and, after quarantine and habituation, those showing satisfactory body weight increase and free of abnormal appearance were used to start the test from 7 weeks of age. The animals were housed and bred in plastic cages (6 mice per cage) in a breeding chamber set at room temperature 19-25° C., humidity 30-70%, 12 hr illumination per day (7 a.m.-7 p.m.), with free access to a commercially available solid feed and water.

One day before the test, the abdomen was shaved, and a solution of dinitrofluorobenzene (manufactured by Nacalai Tesque) in acetone (manufactured by Wako Pure Chemical Industries, Ltd.) {concentration 0.5% [weight (w)/volume (v) %]} was applied to the shaved part of BALE/c mice by 100 μL for sensitization. On day 5 after sensitization, a dinitrofluorobenzene-acetone solution [concentration 0.2% (w/v %)] was applied to the front and the back of the auricle by 10 μL each (total 20 μL) to induce reaction. A test compound dissolved in acetone to the concentration of 1% (w/v %) was applied to the front and the back of the auricle 1 hr before and 3 hr after the induction of reaction each by 10 μL or 40 μL (total 20 μL or 80 μL). After the application, the applied part was air-dried by a dryer.

A group administered with the test compound by coating was taken as a test compound administration group, and a group administered with acetone (solvent) by coating instead of the test compound was taken as a solvent administration group. In addition, a group free of sensitization and induction of reaction and administered with acetone by coating instead of the test compound was taken as a normal group. The thickness of the auricle was measured immediately before induction of reaction and 24 hr after the induction with a dial thickness gauge (manufactured by OZAKI MFG. CO., LTD., G-1A), and the difference between them was taken as ear edema. The ear edema suppressive rate (%) was calculated according to the following formula. The results are shown in Table 3.

$$\text{ear edema suppressive rate (\%)} = \frac{\text{(value of solvent administration group)} - \text{(value of test compound administration group)}}{\text{(value of solvent administration group)} - \text{(value of normal group)}} \times 100$$

TABLE 3

| compound No. | test compound concentration (%) | ear edema suppressive rate (%) |
|---|---|---|
| a-1 | 1 | 20 |
| a-57 | 1 | 35 |
| a-59 | 1 | 6 |
| a-81 | 1 | 25 |
| a-84 | 1 | 25 |
| a-96 | 1 | 10 |
| a-126 | 1 | 10 |
| a-137 | 1 | 5 |

From the above results, the compound of the present invention was found to have an action to suppress ear edema and treat skin diseases.

While compound (I) to be used in the present invention, compound (IA) of the present invention and pharmaceutically acceptable salts thereof can be administered alone as they are, generally, they are desirably provided as various pharmaceutical preparations. In addition, such pharmaceutical preparations are used for animals and humans.

The pharmaceutical preparation relating to the present invention can contain, as an active ingredient, compound (I) to be used in the present invention or compound (IA) of the present invention or a pharmaceutically acceptable salt thereof alone or as a mixture with an active ingredient for any other treatment. Moreover, the pharmaceutical preparation can be produced by mixing the active ingredient with one or more kinds of pharmaceutically acceptable carriers (e.g., diluent, solvent, excipient or the like) according to any method well known in the technical field of pharmaceutical science.

As the administration route, a route most effective for the treatment is desirably employed, which may be an oral or parenteral route such as intravenous route, external route or the like.

The dosage form may be, for example, tablet, injection, ointment or the like.

Tablet can be produced by using an excipient such as lactose or the like, a disintegrant such as starch or the like, a lubricant such as magnesium stearate or the like, a binder such as hydroxypropylcellulose or the like, and is suitable for oral administration.

Injection or the like can be produced by using a diluent such as a salt solution, a glucose solution or a mixture of salt solution and a glucose solution or the like, or a solvent or the like.

Ointment can be produced from a base such as petrolatum and the like and an additive such as stearyl alcohol and the like.

While the dose and administration frequency of compound (I) to be used in the present invention or compound (IA) of the present invention or a pharmaceutically acceptable salt thereof varies depending on the mode of administration, age and body weight of patients, nature and severity of the symptom to be treated or the like, it is generally within the range of 0.01 to 1000 mg, preferably 0.05 to 100 mg, for oral administration to an adult, which is administered at once or in several portions a day. In the case of intravenous administration, external administration or the like, 0.001 to 1000 mg, preferably 0.01 to 100 mg, is administered to an adult at once or in several portions a day. However, these doses and administration frequencies vary depending on the aforementioned various conditions.

The present invention is explained in more detail in the following by Examples and Reference Examples, which are not to be construed as limitative.

The proton nuclear magnetic resonance spectrum ($^1$H NMR) used in the Examples and Reference Examples were measured at 270 MHz or 300 MHz, and exchanging protons may not be clearly observed depending on the compound and measurement conditions. The indication of the multiplicity of the signals is conventional, where br means an apparently broad signal.

EXAMPLE 1

N-[7-Benzylamino-6-(4-phenylpiperidine-1-carbonyl)pyrazolo[1,5-a]pyrimidine-3-carbonyl]methanesulfonamide (compound a-1)

[Step 1]

3-Bromo-7-hydroxypyrazolo[1,5-a]pyrimidine-6-carboxylic acid

Ethyl 3-bromo-7-hydroxypyrazolo[1,5-a]pyrimidine-6-carboxylate (Journal of Medicinal Chemistry, vol. 25, p. 235, 1982) (11.0 g, 38.5 mmol) was dissolved in ethanol (134 mL), 2 mol/L aqueous sodium hydroxide solution (134 mL, 269 mmol) was added, and the mixture was stirred at 60° C. for 1 hr. The reaction mixture was cooled to room temperature, and ethanol was evaporated under reduced pressure. 2 mol/L Hydrochloric acid (140 mL) was added under ice-cooling, and the mixture was stirred at room temperature for 30 min. The precipitate was collected by filtration, and washed with water (100 mL) and 2-propanol (50 mL) to give the title compound (9.9 g, 99%).

ESI-MS m/z: 259 (M+H)$^+$; $^1$H-NMR (DMSO-d$_6$, δ): 8.14 (s, 1H), 8.71 (s, 1H).

[Step 2]

3-Bromo-7-hydroxy-6-(4-phenylpiperidine-1-carbonyl)pyrazolo[1,5-a]pyrimidine

3-Bromo-7-hydroxypyrazolo[1,5-a]pyrimidine-6-carboxylic acid (6.3 g, 24.5 mmol) obtained in step 1 and 4-phenylpiperidine (7.9 g, 49.0 mmol) were suspended in methylene chloride (120 mL), triethylamine (13.7 ml, 98.1 mmol) and 50% 1-propylphosphonic acid anhydride cyclic trimerethyl acetate solution (6.0 g, 49.0 mmol) were added at 0° C., and the mixture was stirred at 0° C. for 2 hr. 4-Phenylpiperidine (7.9 g, 49.0 mmol), triethylamine (13.7 mL, 98.1 mmol) and 50% 1-propylphosphonic acid anhydride cyclic trimerethyl acetate solution (6.0 g, 49.0 mmol) were added to the reaction mixture, and the mixture was further stirred at 0° C. for 2 hr. 2 mol/L Hydrochloric acid (100 mL) was added to the reaction mixture, the organic layer and the aqueous layer were separated, and the organic layer was dried over anhydrous magnesium sulfate and concentrated under reduced pressure. 2 mol/L Hydrochloric acid (100 mL) was added to the residue, and the mixture was stirred at 30° C. for 2 hr. The precipitate was collected by filtration, and washed with water (100 mL) to give the title compound (7.7 g, 78%).

ESI-MS m/z: 401 (M+H)$^+$; $^1$H-NMR (DMSO-d$_6$, δ): 1.56-1.92 (m, 4H), 2.75-2.89 (m, 2H), 3.07-3.20 (m, 1H), 3.71-3.83 (m, 1H), 4.59-4.67 (m, 1H), 7.17-7.34 (m, 5H), 8.08 (s, 1H), 8.08 (s, 1H), 13.17 (br s, 1H).

[Step 3]

3-Bromo-7-chloro-6-(4-phenylpiperidine-1-carbonyl)pyrazolo[1,5-a]pyrimidine

To 3-bromo-7-hydroxy-6-(4-phenylpiperidine-1-carbonyl)pyrazolo[1,5-a]pyrimidine (7.7 g, 19.1 mmol) obtained in step 2 were added phosphorus oxychloride (100 mL) and N,N-diethylaniline (6.1 mL, 38.3 mmol), and the mixture was heated under reflux for 5 hr. The reaction mixture was concentrated under reduced pressure, the residue was diluted with ethyl acetate (100 mL) and neutralized with saturated aqueous sodium hydrogen carbonate solution (300 mL) under ice-cooling, and the organic layer and the aqueous layer were separated. The organic layer was washed with 10% aqueous citric acid solution (50 mL) and saturated brine (100 mL), dried over anhydrous magnesium sulfate, and concentrated under reduced pressure. The residue was purified by silica gel column chromatography (hexane/ethyl acetate=2/1) to give the title compound (7.5 g, 93%).

ESI-MS m/z: 420 (M+H)$^+$; $^1$H-NMR (CDCl$_3$, δ): 1.78-1.95 (m, 3H), 2.03-2.10 (m, 1H), 2.79-3.03 (m, 2H), 3.22-3.41 (m, 1H), 3.64-3.70 (m, 1H), 4.92-4.98 (m, 1H), 7.20-7.27 (m, 3H), 7.32-7.37 (m, 2H), 8.29 (s, 1H), 8.29 (br s, 0.5H), 8.54 (br s, 0.5H).

[Step 4]

7-Benzylamino-3-bromo-6-(4-phenylpiperidine-1-carbonyl)pyrazolo[1,5-a]pyrimidine 3-Bromo-7-chloro-6-(4-phenylpiperidine-1-carbonyl)pyrazolo[1,5-a]pyrimidine (3.0 g, 7.2 mmol) obtained in step 3 was dissolved in N-methylpyrrolidinone (30 mL), benzylamine (2.0 mL, 17.9 mmol) was added, and the mixture was stirred at 70° C. for 2 hr. 10% Aqueous citric acid solution (10 mL) and water (100 mL) were added to the reaction mixture, and the mixture was stirred at room temperature for 1 hr. The precipitate was collected by filtration, and washed with water (50 mL) to give the title compound (3.2 g, 90%).

ESI-MS m/z: 491 (M+H)$^+$; $^1$H-NMR (CDCl$_3$, δ): 1.51-1.59 (m, 2H), 1.80-1.84 (m, 2H), 2.60-2.68 (m, 3H), 4.11-4.36 (m, 2H), 4.85 (d, J=6.6 Hz, 2H), 7.11-7.14 (m, 2H), 7.20-7.44 (m, 9H), 8.04 (s, 1H), 8.18 (s, 1H).

[Step 5]

7-Benzylamino-6-(4-phenylpiperidine-1-carbonyl)pyrazolo[1,5-a]pyrimidine-3-carboxylic acid Bis[2-(N,N-dimethylamino)ethyl]ether (4.1 mL, 25.7 mmol) was dissolved in THF (15 mL), 2 mol/L isopropylmagnesium chloride-THF solution (13.0 mL, 25.7 mmol) was added dropwise under ice-cooling, and the mixture was stirred at room temperature for 5 min. A suspension (5 mL) of 7-benzylamino-3-bromo-6-(4-phenylpiperidine-1-carbonyl)pyrazolo[1,5-a]pyrimidine (1.4 g, 2.9 mmol) obtained in step 4 in THF was added to this mixture under ice-cooling, and the mixture was stirred at room temperature for 2 hr. Carbon dioxide gas was bubbled into the reaction mixture for 30 min under ice-cooling, and the reaction mixture was added dropwise to ice-cooled 1 mol/L hydrochloric acid (100 mL). The mixture was stirred at room temperature for 1 hr, and the precipitate was collected by filtration, and washed with water (50 mL) to give the title compound (0.9 g, 67%).

ESI-MS m/z: 456 (M+H)$^+$; $^1$H-NMR (CDCl$_3$, δ): 1.48-1.65 (m, 2H), 1.85-1.89 (m, 2H), 2.64-2.71 (m, 3H), 4.05-4.50 (m, 2H), 4.92 (d, J=5.9 Hz, 2H), 7.13-7.16 (m, 2H), 7.21-7.44 (m, 8H), 7.70 (br s, 1H), 8.25 (s, 1H), 8.53 (s, 1H).

[Step 6]

N-[7-Benzylamino-6-(4-phenylpiperidine-1-carbonyl)pyrazolo[1,5-a]pyrimidine-3-carbonyl]methanesulfonamide (compound a-1)

7-Benzylamino-6-(4-phenylpiperidine-1-carbonyl)pyrazolo[1,5-a]pyrimidine-3-carboxylic acid (0.9 g, 1.9 mmol) obtained in step 5 was dissolved in DMF (15 mL), 1,1'-carbonyldiimidazole (1.2 g, 7.6 mmol) was added, and the mixture was stirred at room temperature for 2 hr. Methanesulfonamide (0.9 g, 9.5 mmol) and DBU (1.4 g, 9.5 mmol) were added to the reaction mixture, and the mixture was stirred at 60° C. for 1 hr. 10% Aqueous citric acid solution (5 mL) and water (60 mL) were added to the reaction mixture, and the mixture was stirred at room temperature for 1 hr. The precipitate was collected by filtration, washed with water (50 mL), and purified by silica gel column chromatography (chloroform/methanol=95/5) to give compound a-1 (0.8 g, 81%).

ESI-MS m/z: 533 (M+H)$^+$; $^1$H-NMR (CDCl$_3$, δ): 1.48-1.64 (m, 2H), 1.85-1.91 (m, 2H), 2.65-2.73 (m, 3H), 3.43 (s, 3H), 3.68-4.11 (m, 2H), 4.91 (d, J=4.4 Hz, 2H), 7.15-7.18 (m, 2H), 7.22-7.44 (m, 8H), 7.68 (br s, 1H), 8.23 (s, 1H), 8.58 (s, 1H), 10.73 (br s, 1H).

EXAMPLE 2

N-[7-Benzylamino-6-(4-phenylpiperidine-1-carbonyl)pyrazolo[1,5-a]pyrimidine-3-carbonyl]cyclopropanesulfonamide (compound a-2)

In the same manner as in Example 1, step 6 and using cyclopropanesulfonamide (0.11 g, 0.88 mmol) instead of methanesulfonamide, compound a-2 (0.06 g, 63%) was obtained.

ESI-MS m/z: 559 (M+H)$^+$; $^1$H-NMR (CDCl$_3$, δ): 1.09-1.16 (m, 2H), 1.44-1.58 (m, 4H), 1.83-1.93 (m, 2H), 1.97-2.06 (m, 2H), 2.58-2.77 (m, 2H), 4.61-4.70 (m, 1H), 4.91 (d, J=4.5 Hz, 2H), 7.14-7.17 (m, 2H), 7.20-7.43 (m, 8H), 7.67 (br s, 1H), 8.22 (s, 1H), 8.58 (s, 1H), 10.68 (br s, 1H).

EXAMPLE 3

N-[7-Benzylamino-6-(4-phenylpiperidine-1-carbonyl)pyrazolo[1,5-a]pyrimidine-3-carbonyl]trifluoromethanesulfonamide (compound a-3)

In the same manner as in Example 1, step 6 and using trifluoromethanesulfonamide (0.38 g, 2.64 mmol) instead of methanesulfonamide, compound a-3 (0.17 g, 67%) was obtained.

ESI-MS m/z: 587(M+H)$^+$; $^1$H-NMR (CDCl$_3$, δ): 1.35-1.61 (m, 2H), 1.78-1.97 (m, 2H), 2.65-2.89 (m, 3H), 3.30-3.50 (m,

2H), 4.84 (d, J=5.6 Hz, 2H), 7.15-7.33 (m, 10H), 7.50-7.52 (m, 1H), 8.25 (s, 1H), 8.51 (s, 1H), 8.87 (s, 1H).

EXAMPLE 4

N-[7-Benzylamino-6-(4-phenylpiperidine-1-carbonyl)pyrazolo[1,5-a]pyrimidine-3-carbonyl]-N'-methylsulfamide (compound a-4)

In the same manner as in Example 1, step 6 and using N-methylsulfamide (WO01/83459, 0.25 g, 2.31 mmol) instead of methanesulfonamide, compound a-4 (0.02 g, 13%) was obtained.

ESI-MS m/z: 548 (M+H)$^+$; $^1$H-NMR (CDCl$_3$, δ): 1.54-1.63 (m, 2H), 1.84-1.94 (m, 2H), 2.65-2.75 (m, 3H), 3.43 (s, 3H), 4.17-4.32 (m, 2H), 4.96 (d, J=5.6 Hz, 2H), 7.01-7.42 (m, 10H), 7.80 (s, 1H), 8.24 (s, 1H), 8.59 (s, 1H), 10.72 (s, 1H).

EXAMPLE 5

N-[7-Benzylamino-6-(4-phenylpiperidine-1-carbonyl)pyrazolo[1,5-a]pyrimidine-3-carbonyl]-N',N'-dimethylsulfamide (compound a-5)

In the same manner as in Example 1, step 6 and using N,N-dimethylsulfamide (WO01/83459, 0.28 g, 2.31 mmol) instead of methanesulfonamide, compound a-5 (0.04 g, 23%) was obtained.

ESI-MS m/z: 562 (M+H)$^+$; $^1$H-NMR (CDCl$_3$, δ): 1.52-1.63 (m, 2H), 1.82-1.92 (m, 2H), 2.63-2.78 (m, 3H), 3.04 (s, 6H), 4.21-4.24 (m, 2H), 4.91 (d, J=5.9 Hz, 2H), 7.15-7.44 (m, 9H), 7.65-7.67 (m, 1H), 8.02 (s, 1H), 8.23 (s, 1H), 8.55 (s, 1H), 10.58 (s, 1H).

EXAMPLE 6

N-[7-(3-Fluorobenzylamino)-6-(4-phenylpiperidine-1-carbonyl)pyrazolo[1,5-a]pyrimidine-3-carbonyl] methanesulfonamide (compound a-6)

[Step 1]

3-bromo-7-(3-fluorobenzylamino)-6-(4-phenylpiperidine-1-carbonyl)pyrazolo[1,5-a]pyrimidine In the same manner as in Example 1, step 4 and using 3-fluorobenzylamine (1.0 g, 3.29 mmol) instead of benzylamine, the title compound (1.67 g, 98%) was obtained.
[Step 2]

7-(3-Fluorobenzylamino)-6-(4-phenylpiperidine-1-carbonyl)pyrazolo[1,5-a]pyrimidine-3-carboxylic acid In the same manner as in Example 1, step 5 and using 3-bromo-7-(3-fluorobenzylamino)-6-(4-phenylpiperidine-1-carbonyl)pyrazolo[1,5-a]pyrimidine (1.67 g, 3.26 mmol) obtained in step 1, the title compound (1.43 g, 80%) was obtained.
[Step 3]

N-[7-(3-Fluorobenzylamino)-6-(4-phenylpiperidine-1-carbonyl)pyrazolo[1,5-a]pyrimidine-3-carbonyl] methanesulfonamide (compound a-6)

In the same manner as in Example 1, step 6 and using 7-(3-fluorobenzylamino)-6-(4-phenylpiperidine-1-carbonyl)pyrazolo[1,5-a]pyrimidine-3-carboxylic acid (0.09 g, 0.18 mmol) obtained in step 2 and methanesulfonamide (0.1 g, 1.08 mmol), compound a-6 (0.06 g, 64%) was obtained.

ESI-MS m/z: 551 (M+H)$^+$; $^1$H-NMR (CDCl$_3$, δ): 1.55-1.61 (m, 2H), 1.86-1.95 (m, 2H), 2.64-2.82 (m, 3H), 3.43 (s, 3H), 4.10-4.40 (m, 2H), 4.96 (d, J=5.6 Hz, 2H), 7.01-7.42 (m, 9H), 7.82 (br s, 1H), 8.24 (s, 1H), 8.59 (s, 1H), 10.72 (br s, 1H).

EXAMPLE 7

N-[7-(3-Fluorobenzylamino)-6-(4-phenylpiperidine-1-carbonyl)pyrazolo[1,5-a]pyrimidine-3-carbonyl] ethanesulfonamide (compound a-7)

In the same manner as in Example 1, step 6 and using 7-(3-fluorobenzylamino)-6-(4-phenylpiperidine-1-carbonyl)pyrazolo[1,5-a]pyrimidine-3-carboxylic acid (0.09 g, 0.18 mmol) obtained in Example 6, step 2 and ethanesulfonamide (0.11 g, 1.08 mmol) instead of methanesulfonamide, compound a-7 (0.04 g, 38%) was obtained.

ESI-MS m/z: 565 (M+H)$^+$; $^1$H-NMR (CDCl$_3$, δ): 1.44 (t, J=7.3 Hz, 3H), 1.51-1.72 (m, 2H), 1.88-1.93 (m, 2H), 2.68-2.75 (m, 3H), 3.60 (q, J=7.3 Hz, 2H), 4.22-4.31 (m, 2H), 4.95 (d, J=5.3 Hz, 2H), 7.01-7.41 (m, 9H), 7.79-7.86 (m, 1H), 8.25 (s, 1H), 8.58 (s, 1H), 10.57 (s, 1H).

EXAMPLE 8

N-[7-Cyclohexylmethylamino-6-(4-phenylpiperidine-1-carbonyl)pyrazolo[1,5-a]pyrimidine-3-carbonyl]methanesulfonamide (compound a-8)

[Step 1]

3-Bromo-7-cyclohexylmethylamino-6-(4-phenylpiperidine-1-carbonyl)pyrazolo[1,5-a]pyrimidine In the same manner as in Example 1, step 4 and using cyclohexylmethylamine (1.0 g, 3.29 mmol) instead of benzylamine, the title compound (1.67 g, 98%) was obtained.
[Step 2]

7-Cyclohexylmethylamino-6-(4-phenylpiperidine-1-carbonyl)pyrazolo[1,5-a]pyrimidine-3-carboxylic acid In the same manner as in Example 1, step 5 and using 3-bromo-7-cyclohexylmethylamino-6-(4-phenylpiperidine-1-carbonyl)pyrazolo[1,5-a]pyrimidine (1.67 g, 3.26 mmol) obtained in step 1, the title compound (1.43 g, 80%) was obtained.
[Step 3]

N-[7-Cyclohexylmethylamino-6-(4-phenylpiperidine-1-carbonyl)pyrazolo[1,5-a]pyrimidine-3-carbonyl]methanesulfonamide (compound a-8)

In the same manner as in Example 1, step 6 and using 7-cyclohexylmethylamino-6-(4-phenylpiperidine-1-carbonyl)pyrazolo[1,5-a]pyrimidine-3-carboxylic acid (0.08 g, 0.17 mmol) obtained in step 2 and methanesulfonamide (0.11 g, 0.87 mmol), compound a-8 (80 mg, 32%) was obtained.

ESI-MS m/z: 539 (M+H)$^+$; $^1$H-NMR (CDCl$_3$, δ): 0.88-2.11 (m, 13H), 1.85-1.91 (m, 2H), 2.73-2.97 (m, 3H), 3.35 (br s, 2H), 3.42 (s, 3H), 3.45-3.63 (m, 2H), 7.13-7.35 (m, 5H), 7.65 (br s, 1H), 7.98 (s, 1H), 8.54 (s, 1H), 8.59 (br s, 1H).

EXAMPLE 9

N-[6-(4-Phenylpiperidine-1-carbonyl)-7-(pyridin-3-ylmethylamino)pyrazolo[1,5-a]pyrimidine-3-carbonyl]methanesulfonamide (compound a-9)

[Step 1]

3-Bromo-6-(4-phenylpiperidine-1-carbonyl)-7-(pyridin-3-ylmethylamino)pyrazolo[1,5-a]pyrimidine In the same manner as in Example 1, step 4 and using 3-picolylamine (0.53 g, 4.90 mmol) instead of benzylamine, the title compound (0.38 g, 81%) was obtained.

[Step 2]

6-(4-Phenylpiperidine-1-carbonyl)-7-(pyridin-3-ylmethylamino)pyrazolo[1,5-a]pyrimidine-3-carboxylic acid In the same manner as in Example 1, step 5 and using 3-bromo-6-(4-phenylpiperidine-1-carbonyl)-7-(pyridin-3-ylmethylamino)pyrazolo[1,5-a]pyrimidine (0.38 g, 0.77 mmol) obtained in step 1, the title compound (0.10 g, 28%) was obtained.

[Step 3]

N-[6-(4-Phenylpiperidine-1-carbonyl)-7-(pyridin-3-ylmethylamino)pyrazolo[1,5-a]pyrimidine-3-carbonyl]methanesulfonamide (compound a-9)

In the same manner as in Example 1, step 6 and using 6-(4-phenylpiperidine-1-carbonyl)-7-(pyridin-3-ylmethylamino)pyrazolo[1,5-a]pyrimidine-3-carboxylic acid (0.05 g, 0.11 mmol) obtained in step 2 and methanesulfonamide (0.052 g, 0.550 mmol), compound a-9 (0.03 g, 58%) was obtained.

ESI-MS m/z: 534 (M+H)$^+$; $^1$H-NMR (DMSO-d$_6$, δ): 1.21-2.04 (m, 4H), 2.31-2.80 (m, 2H), 3.19-3.58 (m, 5H), 4.32-4.71 (m, 1H), 4.75-4.90 (m, 2H), 7.13-7.43 (m, 6H), 7.62-7.71 (m, 2H), 8.39-8.51 (m, 3H), 8.75 (s, 1H), 9.34-9.49 (m, 1H).

EXAMPLE 10

N-[6-(4-Phenylpiperidine-1-carbonyl)-7-(2-thiophenemethylamino)pyrazolo[1,5-a]pyrimidine-3-carbonyl]methanesulfonamide (compound a-10)

[Step 1]

3-Bromo-6-(4-phenylpiperidine-1-carbonyl)-7-(2-thiophenemethylamino)pyrazolo[1,5-a]pyrimidine In the same manner as in Example 1, step 4 and using 2-thiophenemethylamine (0.41 g, 3.6 mmol) instead of benzylamine, the title compound (0.27 g, 85%) was obtained.

[Step 2]

6-(4-Phenylpiperidine-1-carbonyl)-7-(2-thiophenemethylamino)pyrazolo[1,5-a]pyrimidine-3-carboxylic acid In the same manner as in Example 1, step 5 and using 3-bromo-6-(4-phenylpiperidine-1-carbonyl)-7-(2-thiophenemethylamino)pyrazolo[1,5-a]pyrimidine (260 mg, 0.52 mmol) obtained in step 1, the title compound (0.21 g, 86%) was obtained.

[Step 3]

N-[6-(4-Phenylpiperidine-1-carbonyl)-7-(2-thiophenemethylamino)pyrazolo[1,5-a]pyrimidine-3-carbonyl]methanesulfonamide (compound a-10)

In the same manner as in Example 1, step 6 and using 6-(4-phenylpiperidine-1-carbonyl)-7-(2-thiophenemethylamino)pyrazolo[1,5-a]pyrimidine-3-carboxylic acid (0.06 g, 0.13 mmol) obtained in step 2 and methanesulfonamide (0.064 g, 0.65 mmol), compound a-10 (0.02 g, 29%) was obtained.

ESI-MS m/z: 539 (M+H)$^+$; $^1$H-NMR (DMSO-d$_6$, δ): 1.40-2.02 (m, 4H), 2.37-2.80 (m, 2H), 3.22-3.48 (m, 5H), 4.38-4.84 (m, 1H), 4.88-5.07 (m, 2H), 6.92-7.04 (m, 2H), 7.15-7.36 (m, 5H), 7.40-7.46 (m, 1H), 8.48 (s, 1H), 8.76 (s, 1H), 9.40-9.50 (m, 1H).

EXAMPLE 11

N-[7-Benzylamino-6-(4-phenylpiperidine-1-carbonyl)pyrazolo[1,5-a]pyrimidine-3-carbonyl]morpholine (compound a-11)

7-Benzylamino-6-(4-phenylpiperidine-1-carbonyl)pyrazolo[1,5-a]pyrimidine-3-carboxylic acid (0.08 g, 0.18 mmol) obtained in Example 1, step 5 was dissolved in DMF (1 mL), morpholine (0.02 mL, 0.21 mmol), 3-[(3-dimethylamino)propyl]-1-ethylcarbodiimide hydrochloride (0.04 g, 0.21 mmol) and HOBt (0.03 g, 0.21 mmol) were added, and the mixture was stirred at room temperature for 5 hr. 10% Aqueous citric acid solution (1 mL) and water (10 mL) were added to the reaction mixture, and the mixture was stirred at room temperature for 1 hr. The precipitate was collected by filtration, washed with water (20 mL), and purified by silica gel column chromatography (chloroform/methanol=90/10) to give compound a-11 (0.02 g, 18%).

ESI-MS m/z: 525 (M+H)$^+$; $^1$H-NMR (CDCl$_3$, δ): 1.50-1.61 (m, 2H), 1.79-1.86 (m, 2H), 2.56-2.68 (m, 3H), 3.69-3.81 (m, 9H), 4.83 (d, J=6.4 Hz, 2H), 7.12 (s, 1H), 7.15 (s, 1H), 7.20-7.41 (m, 8H), 7.49-7.52 (m, 1H), 8.18 (s, 1H), 8.35 (s, 1H).

EXAMPLE 12

7-Benzylamino-6-(4-phenylpiperidine-1-carbonyl)pyrazolo[1,5-a]pyrimidine-3-carboxamide (compound a-12)

In the same manner as in Example 11 and using 28% aqueous ammonia (1 mL) instead of morpholine, compound a-12 (0.01 g, 27%) was obtained.

ESI-MS m/z: 455 (M+H)$^+$; $^1$H-NMR (CDCl$_3$, δ): 1.50-1.60 (m, 2H), 1.80-1.89 (m, 2H), 2.60-2.71 (m, 4H), 4.86 (d, J=6.2 Hz, 2H), 5.64 (s, 1H), 7.13-7.42 (m, 10H), 7.61 (t, J=6.2 Hz, 1H), 7.88 (s, 1H), 8.17 (s, 1H), 8.56 (s, 1H).

EXAMPLE 13

N-[7-Benzylamino-6-(4-phenylpiperidine-1-carbonyl)pyrazolo[1,5-a]pyrimidine-3-carbonyl]ethanesulfonamide (compound a-13)

In the same manner as in Example 1, step 6 and using ethanesulfonamide (0.278 g, 2.64 mmol) instead of methanesulfonamide, the title compound (0.196 g, 82%) was obtained.

ESI-MS m/z: 547 (M+H)$^+$; $^1$H-NMR (DMSO-d$_6$, δ): 1.28 (t, J=8.1 Hz, 3H), 1.35-1.88 (m, 4H), 2.42-2.63 (m, 3H), 3.57 (q, J=8.1 Hz, 2H), 4.32-4.70 (m, 2H), 4.70-4.93 (m, 2H), 7.05-7.45 (m, 10H), 8.43 (s, 1H), 8.76 (s, 1H), 9.29-9.53 (m, 1H), 10.55-10.91 (m, 1H).

EXAMPLE 14

N-[7-Benzylamino-6-(4-phenylpiperidine-1-carbonyl)pyrazolo[1,5-a]pyrimidine-3-carbonyl]benzenesulfonamide (compound a-14)

In the same manner as in Example 1, step 6 and using benzenesulfonamide (0.17 g, 0.88 mmol) instead of methanesulfonamide, the title compound (0.08 g, 63%) was obtained.

ESI-MS m/z: 595(M+H)$^+$; $^1$H-NMR (CDCl$_3$, δ): 1.49-1.66 (m, 2H), 1.86-1.91 (m, 2H), 2.65-2.77 (m, 3H), 3.68-4.11 (m, 2H), 4.92 (d, J=4.4 Hz, 2H), 7.12-7.51 (m, 15H), 7.68 (br s, 1H), 8.25 (s, 1H), 8.59 (s, 1H), 10.73 (br s, 1H).

EXAMPLE 15

N-[7-Benzylamino-6-(4-phenylpiperidine-1-carbonyl)pyrazolo[1,5-a]pyrimidine-3-carbonyl]phenylmethanesulfonamide (compound a-15)

In the same manner as in Example 1, step 6 and using phenylmethanesulfonamide (0.15 g, 0.88 mmol) instead of methanesulfonamide, the title compound (0.08 g, 57%) was obtained.

ESI-MS m/z: 609(M+H)$^+$; $^1$H-NMR (CDCl$_3$, δ): 1.51-1.67 (m, 2H), 1.86-1.91 (m, 2H), 2.61-2.77 (m, 3H), 3.68-4.11 (m, 2H), 4.51 (s, 2H), 4.91 (d, J=4.4 Hz, 2H), 7.12-7.51 (m, 15H), 7.68 (br s, 1H), 8.25 (s, 1H), 8.58 (s, 1H), 10.73 (br s, 1H).

EXAMPLE 16

N-[7-Benzylamino-6-(4-phenylpiperidine-1-carbonyl)pyrazolo[1,5-a]pyrimidine-3-carbonyl]morpholine-4-sulfonamide (compound a-16)

In the same manner as in Example 1, step 6 and using morpholine-4-sulfonamide (0.182 g, 1.10 mmol) instead of methanesulfonamide, the title compound (0.088 g, 66%) was obtained.

ESI-MS m/z: 604 (M+H)$^+$; $^1$H-NMR (CDCl$_3$, δ): 1.48-1.72 (m, 2H), 1.77-2.01 (m, 2H), 2.51-2.89 (m, 3H), 3.43-3.55 (m, 4H), 3.71-3.86 (m, 4H), 4.03-4.51 (m, 2H), 4.84-4.97 (m, 2H), 7.08-7.49 (m, 10H), 7.57-7.79 (m, 1H), 8.23 (s, 1H), 8.55 (s, 1H), 10.63 (br s, 1H).

EXAMPLE 17

N-[7-(3-Methoxybenzylamino)-6-(4-phenylpiperidine-1-carbonyl)pyrazolo[1,5-a]pyrimidine-3-carbonyl]methanesulfonamide (compound a-17)

[Step 1]

3-Bromo-7-(3-methoxybenzylamino)-6-(4-phenylpiperidine-1-carbonyl)pyrazolo[1,5-a]pyrimidine In the same manner as in Example 1, step 4 and using 3-methoxybenzylamine (0.48 mL, 3.72 mmol) instead of benzylamine, the title compound (0.27 g, 73%) was obtained.

[Step 2]

7-(3-Methoxybenzylamino)-6-(4-phenylpiperidine-1-carbonyl)pyrazolo[1,5-a]pyrimidine-3-carboxylic acid In the same manner as in Example 1, step 5 and using 3-bromo-7-(3-methoxybenzylamino)-6-(4-phenylpiperidine-1-carbonyl)pyrazolo[1,5-a]pyrimidine (0.27 g, 0.52 mmol) obtained in step 1, the title compound (0.20 g, 79%) was obtained.

[Step 3]

N-[7-(3-Methoxybenzylamino)-6-(4-phenylpiperidine-1-carbonyl)pyrazolo[1,5-a]pyrimidine-3-carbonyl]methanesulfonamide (compound a-17)

In the same manner as in Example 1, step 6 and using 7-(3-methoxybenzylamino)-6-(4-phenylpiperidine-1-carbonyl)pyrazolo[1,5-a]pyrimidine-3-carboxylic acid (0.06 g, 0.12 mmol) obtained in step 2 and methanesulfonamide (0.06 g, 0.62 mmol), the title compound (0.06 g, 69%) was obtained.

ESI-MS m/z: 563 (M+H)$^+$; $^1$H-NMR (CDCl$_3$, δ): 1.49-1.64 (m, 2H), 1.81-1.91 (m, 2H), 2.60-2.77 (m, 3H), 3.43 (s, 3H), 3.66-3.89 (m, 2H), 3.80 (s, 3H), 4.89 (d, J=4.4 Hz, 2H), 6.80-6.89 (m, 3H), 7.15-7.35 (m, 6H), 7.65 (br s, 1H), 8.23 (s, 1H), 8.58 (s, 1H), 10.73 (br s, 1H).

EXAMPLE 18

N-[7-(3-Chlorobenzylamino)-6-(4-phenylpiperidine-1-carbonyl)pyrazolo[1,5-a]pyrimidine-3-carbonyl]methanesulfonamide (compound a-18)

[Step 1]

3-Bromo-7-(3-chlorobenzylamino)-6-(4-phenylpiperidine-1-carbonyl)pyrazolo[1,5-a]pyrimidine In the same manner as in Example 1, step 4 and using 3-chlorobenzylamine (0.44 mL, 3.58 mmol) instead of benzylamine, the title compound (0.19 g, 51%) was obtained.

[Step 2]

7-(3-Chlorobenzylamino)-6-(4-phenylpiperidine-1-carbonyl)pyrazolo[1,5-a]pyrimidine-3-carboxylic acid In the same manner as in Example 1, step 5 and using 3-bromo-7-(3-chlorobenzylamino)-6-(4-phenylpiperidine-1-carbonyl)pyrazolo[1,5-a]pyrimidine (0.19 g, 0.36 mmol) obtained in step 1, the title compound (0.16 g, 92%) was obtained.

[Step 3]

N-[7-(3-Chlorobenzylamino)-6-(4-phenylpiperidine-1-carbonyl)pyrazolo[1,5-a]pyrimidine-3-carbonyl]methanesulfonamide (compound a-18)

In the same manner as in Example 1, step 6 and using 7-(3-chlorobenzylamino)-6-(4-phenylpiperidine-1-carbonyl)pyrazolo[1,5-a]pyrimidine-3-carboxylic acid (0.08 g, 0.16 mmol) obtained in step 2 and methanesulfonamide (0.08 g, 0.82 mmol), the title compound (0.02 g, 22%) was obtained.

ESI-MS m/z: 568 (M+H)$^+$; $^1$H-NMR (CDCl$_3$, δ): 1.50-1.67 (m, 2H), 1.80-1.95 (m, 2H), 2.62-2.78 (m, 3H), 3.42 (s, 3H), 3.66-3.89 (m, 2H), 4.95 (br s, 2H), 7.09-7.34 (m, 9H), 8.04 (br s, 1H), 8.24 (s, 1H), 8.59 (s, 1H), 10.73 (br s, 1H).

EXAMPLE 19

N-[7-(1-Phenethylamino)-6-(4-phenylpiperidine-1-carbonyl)pyrazolo[1,5-a]pyrimidine-3-carbonyl]methanesulfonamide (compound a-19)

[Step 1]

Ethyl 5-[(2,2-dimethyl-4,6-dioxo-1,3-dioxane-5-ylidene)methylamino]-1H-pyrazole-4-carboxylate Meldrum's acid (15.3 g, 106 mmol) was dissolved in toluene (450 mL), triethyl orthoformate (17.6 mL, 106 mmol) was added, and the mixture was heated under reflux for 2 hr. The reaction mixture was allowed to cool to room temperature, ethyl 3-amino-4-pyrazolecarboxylate (15 g, 96.7 mmol) was added, and the mixture was heated under reflux for 3 hr. The reaction mixture was allowed to cool to room temperature, and stirred at room temperature for 10 hr. The precipitated crystals were collected by filtration, washed with diisopropylether (100 mL), and dried under reduced pressure at 40° C. overnight to give the title compound (26.3 g, 88%).

$^1$H-NMR (DMSO-d$_6$, δ): 1.33 (t, J=7.0 Hz, 3H), 1.69 (s, 6H), 4.31 (q, J=7.0 Hz, 2H), 8.41 (d, J=1.8 Hz, 1H), 8.79 (d, J=14.3 Hz, 1H), 11.7 (d, J=13.9 Hz, 1H), 13.5 (br s, 1H).

[Step 2]

3-Ethoxycarbonyl-7-hydroxypyrazolo[1,5-a]pyrimidine-6-carboxylic acid

Ethyl 5-[(2,2-dimethyl-4,6-dioxo-1,3-dioxane-5-ylidene)methylamino]1H-pyrazole-4-carboxylate (14.9 g, 45.6 mmol) obtained in step 1 was suspended in methylene chloride (227 mL), and triethylamine (25 mL, 182 mmol) was added. Trimethylsilyl trifluoromethanesulfonate (33.2 mL, 182 mmol) was added dropwise over about 10 min under ice-cooling while maintaining the reaction inside temperature at not more than 10° C., and the mixture was stirred at room temperature for 1 hr. The reaction mixture was cooled to 0° C., and ethanol (75 mL) was added dropwise over 10 min. After the completion of the dropwise addition, the mixture was stirred at room temperature for 10 hr. The precipitated crystals were collected by filtration, washed with cold ethanol (50 mL), and dried under reduced pressure at 40° C. overnight to give the title compound (10.5 g, 91%).

$^1$H-NMR (DMSO-d$_6$, δ): 1.33 (t, J=7.1 Hz, 3H), 4.34 (q, J=7.2 Hz, 2H), 8.30 (s, 1H), 8.42 (s, 1H).

[Step 3]

3-Ethoxycarbonyl-7-hydroxy-6-(4-phenylpiperidine-1-carbonyl)pyrazolo[1,5-a]pyrimidine In the same manner as in Example 1, step 2 and using 3-ethoxycarbonyl-7-hydroxypyrazolo[1,5-a]pyrimidine-6-carboxylic acid (2.48 g, 9.9 mmol) obtained in step 2 instead of 3-bromo-7-hydroxypyrazolo[1,5-a]pyrimidine-6-carboxylic acid, the title compound (2.64 g, 68%) was obtained.

$^1$H-NMR (DMSO-d$_6$, δ): 1.32 (t, J=7.0 Hz, 3H), 1.56-1.90 (m, 3H), 2.73-2.80 (m, 2H), 3.11-3.23 (m, 2H), 3.75-3.79 (m, 1H), 4.33 (q, J=7.0 Hz, 2H), 4.59-4.63 (m, 1H), 7.18-7.34 (m, 5H), 7.99 (s, 1H), 8.27 (s, 1H), 12.54 (br s, 1H).

[Step 4]

7-Chloro-3-ethoxycarbonyl-6-(4-phenylpiperidine-1-carbonyl)pyrazolo[1,5-a]pyrimidine In the same manner as in Example 1, step 3 and using 3-ethoxycarbonyl-7-hydroxy-6-(4-phenylpiperidine-1-carbonyl)pyrazolo[1,5-a]pyrimidine (1.0 g, 2.5 mmol) obtained in step 3 instead of 3-bromo-7-hydroxy-6-(4-phenylpiperidine-1-carbonyl)pyrazolo[1,5-a]pyrimidine, the title compound (0.614 g, 59%) was obtained.

$^1$H-NMR (CDCl$_3$, δ): 1.44 (t, J=7.1 Hz, 3H), 1.80-1.92 (m, 3H), 2.06-2.11 (m, 1H), 2.79-2.85 (m, 1H), 2.99 (dt, J=13.2, 2.6 Hz, 1H), 3.26-3.38 (m, 1H), 3.61-3.66 (m, 1H), 4.47 (q, J=7.0 Hz, 2H), 4.93-4.98 (m, 1H), 7.20-7.37 (m, 5H), 8.67 (br d, J=20.0 Hz, 1H), 8.74 (s, 1H).

[Step 5]

3-Ethoxycarbonyl-7-(1-phenethylamino)-6-(4-phenylpiperidine-1-carbonyl)pyrazolo[1,5-a]pyrimidine 7-Chloro-3-ethoxycarbonyl-6-(4-phenylpiperidine-1-carbonyl)pyrazolo[1,5-a]pyrimidine (0.30 g, 0.73 mmol) obtained in step 4 was dissolved in N,N-dimethylacetamide (2 mL), 1-phenethylamine (0.187 mL, 1.45 mmol) was added, and the mixture was heated at 70° C. for 2 hr. 10% Aqueous citric acid solution (10 mL) and water (10 mL) were added to the reaction mixture, and the mixture was stirred at room temperature for 1 hr. The precipitate was collected by filtration, and washed with water (10 mL) to give the title compound (0.399 g, 99%).

ESI-MS m/z: 498 (M+H)$^+$; $^1$H-NMR (CDCl$_3$, δ): 1.13-1.98 (m, 5H), 1.42 (t, J=7.1 Hz, 3H), 1.66 (d, J=6.8 Hz, 3H), 2.34-4.78 (m, 4H), 4.44 (q, J=7.1 Hz, 2H), 5.14-5.54 (m, 1H), 7.12 (d, J=7.1 Hz, 2H), 7.20-7.45 (m, 9H), 8.25 (s, 1H), 8.52 (s, 1H).

[Step 6]

7-(1-Phenethylamino)-6-(4-phenylpiperidine-1-carbonyl)pyrazolo[1,5-a]pyrimidine-3-carboxylic acid 3-Ethoxycarbonyl-7-(1-phenethylamino)-6-(4-phenylpiperidine-1-carbonyl)pyrazolo[1,5-a]pyrimidine (0.399 g, 0.73 mmol) obtained in step 5 was dissolved in ethanol (10 mL) and THF (15 mL), 2 mol/L aqueous sodium hydroxide solution (10 mL) was added, and the mixture was stirred at 75° C. for 3 hr. This mixture was cooled to room temperature, and ethanol and THF were evaporated under reduced pressure. 2 mol/L Hydrochloric acid (10 mL) was added under ice-cooling, and the mixture was stirred at room temperature for 30 min. The precipitate was collected by filtration, and washed with water (20 mL) to give the title compound (0.254 g, 74%).

ESI-MS m/z: 470 (M+H)$^+$; $^1$H-NMR (CDCl$_3$, δ): 1.04-2.70 (m, 5H), 1.68 (d, J=6.6 Hz, 3H), 4.39-5.82 (m, 5H), 7.00-7.76 (m, 10H), 8.17 (s, 1H), 8.57 (s, 1H).

[Step 7]

N-[7-(1-Phenethylamino)-6-(4-phenylpiperidine-1-carbonyl)pyrazolo[1,5-a]pyrimidine-3-carbonyl]methanesulfonamide (compound a-19)

In the same manner as in Example 1, step 6 and using 7-(1-phenethylamino)-6-(4-phenylpiperidine-1-carbonyl)pyrazolo[1,5-a]pyrimidine-3-carboxylic acid (0.05 g, 0.11 mmol) obtained in step 6 and methanesulfonamide (0.052 g, 0.55 mmol), the title compound (0.033 g, 55%) was obtained.

ESI-MS m/z: 547 (M+H)$^+$; $^1$H-NMR (CDCl$_3$, δ): 1.15-2.68 (m, 5H), 1.68 (d, J=7.0 Hz, 3H), 2.91-5.78 (m, 5H), 3.42 (s, 3H), 6.86-7.81 (m, 11H), 8.15 (s, 1H), 8.61 (s, 1H), 10.71 (s, 1H).

EXAMPLE 20

N-[7-(2,3-Dihydro-1H-inden-1-ylamino)-6-(4-phenylpiperidine-1-carbonyl)pyrazolo[1,5-a]pyrimidine-3-carbonyl]methanesulfonamide (compound a-20)

[Step 1]

7-(2,3-Dihydro-1H-inden-1-ylamino)-3-ethoxycarbonyl-6-(4-phenylpiperidine-1-carbonyl)pyrazolo[1,5-a]pyrimidine In the same manner as in Example 19, step 5 and using 1-aminoindane (0.09 mL, 0.71 mmol), the title compound (220 mg, 89%) was obtained.

[Step 2]

7-(2,3-Dihydro-1H-inden-1-ylamino)-6-(4-phenylpiperidine-1-carbonyl)pyrazolo[1,5-a]pyrimidine-3-carboxylic acid In the same manner as in Example 19, step 6 and using 7-(2,3-dihydro-1H-inden-1-ylamino)-3-ethoxycarbonyl-6-(4-phenylpiperidine-1-carbonyl)pyrazolo[1,5-a]pyrimidine (220 mg, 0.43 mmol) obtained in step 1, the title compound (154 mg, 74%) was obtained.

[Step 3]

N-[7-(2,3-Dihydro-1H-inden-1-ylamino)-6-(4-phenylpiperidine-1-carbonyl)pyrazolo[1,5-a]pyrimidine-3-carbonyl]methanesulfonamide (compound a-20)

In the same manner as in Example 1, step 6 and using 7-(2,3-dihydro-1H-inden-1-ylamino)-6-(4-phenylpiperidine-1-carbonyl)pyrazolo[1,5-a]pyrimidine-3-carboxylic acid (50 mg, 0.104 mmol) obtained in step 2 and methanesulfonamide (39 mg, 0.42 mmol), the title compound (33 mg, 57%) was obtained.

ESI-MS m/z: 559 (M+H)$^+$; $^1$H-NMR (CDCl$_3$, δ): 1.72 (br s, 2H), 1.98-2.11 (m, 3H), 2.68-3.17 (m, 8H), 3.43 (s, 3H), 4.48 (br s, 1H), 7.18-7.34 (m, 10H), 8.28 (s, 1H), 8.53 (s, 1H), 10.78 (br s, 1H).

EXAMPLE 21

N-[7-Benzylamino-6-(3-methyl-4-phenylpiperidine-1-carbonyl)pyrazolo[1,5-a]pyrimidine-3-carbonyl]methanesulfonamide (compound a-21)

[Step 1]

Methyl 3-ethoxycarbonyl-7-hydroxypyrazolo[1,5-a]pyrimidine-6-carboxylate

3-Ethoxycarbonyl-7-hydroxypyrazolo[1,5-a]pyrimidine-6-carboxylic acid (27.0 g, 0.11 mol) obtained in Example 19, step 2 was suspended in 1,2-dichloroethane (320 mL), and thionyl chloride (39 mL, 0.54 mol) was added. DMF (22 mL) was added, and the mixture was heated under reflux for 6 hr. The reaction mixture was cooled to room temperature, and the solvent was evaporated under reduced pressure. The residue was suspended in methylene chloride (300 mL), and triethylamine (75 mL, 0.54 mol) was added in an ice bath. Methanol (50 mL) was added dropwise over 30 min, and the mixture was stirred at room temperature for 2 hr. The solvent was evaporated under reduced pressure, and the residue was added to 2 mol/L hydrochloric acid containing ice (about 500 mL). The precipitated solid was collected by filtration, and washed with water (50 mL) to give the title compound (27.5 g, 95%).

$^1$H-NMR (DMSO-d$_6$, δ): 1.33 (t, J=7.0 Hz, 3H), 3.79 (s, 3H), 4.34 (q, J=7.0 Hz, 2H), 8.26 (s, 1H), 8.39 (s, 1H).

[Step 2]

Methyl 7-chloro-3-ethoxycarbonylpyrazolo[1,5-a]pyrimidine-6-carboxylate

In the same manner as in Example 1, step 3 and using methyl 3-ethoxycarbonyl-7-hydroxypyrazolo[1,5-a]pyrimidine-6-carboxylate (13.7 g, 51.0 mmol) obtained in step 1 instead of 3-bromo-7-hydroxy-6-(4-phenylpiperidine-1-carbonyl)pyrazolo[1,5-a]pyrimidine, the title compound (14.1 g, 96%) was obtained.

$^1$H-NMR (CDCl$_3$, δ): 1.43 (t, J=7.0 Hz, 3H), 4.05 (s, 3H), 4.46 (g, J=7.0 Hz, 2H), 8.74 (s, 1H), 9.20 (s, 1H).

[Step 3]

Methyl 7-benzylamino-3-ethoxycarbonylpyrazolo[1,5-a]pyrimidine-6-carboxylate

In the same manner as in Example 1, step 4 and using methyl 7-chloro-3-ethoxycarbonylpyrazolo[1,5-a]pyrimidine-6-carboxylate (7.0 g, 24.4 mmol) obtained in step 2 instead of 3-bromo-7-chloro-6-(4-phenylpiperidine-1-carbonyl)pyrazolo[1,5-a]pyrimidine, the title compound (6.4 g, 73%) was obtained.

$^1$H-NMR (CDCl$_3$, δ): 1.40 (t, J=7.0 Hz, 3H), 3.91 (s, 3H), 4.42 (q, J=7.0, 2H), 5.58 (br s, 2H), 7.26-7.38 (m, 5H), 8.42 (s, 1H), 8.92 (s, 1H), 10.01 (s, 1H).

[Step 4]

7-Benzylamino-3-ethoxycarbonylpyrazolo[1,5-a]pyrimidine-6-carboxylic acid

Methyl 7-benzylamino-3-ethoxycarbonylpyrazolo[1,5-a]pyrimidine-6-carboxylate (6.4 g, 17.7 mmol) obtained in step 3 was dissolved in pyridine (90 mL), lithium iodide (23.7 g, 0.18 mol) was added, and the mixture was stirred with heating at 95° C. for 4 hr. The reaction mixture was allowed to cool, added dropwise to 2 mol/L hydrochloric acid containing ice (about 500 mL), and the mixture was stirred at room temperature for 1 hr. The precipitated solid was collected by filtration, washed with isopropanol (100 mL), and dried under reduced pressure at 50° C. overnight to give the title compound (5.2 g, 85%).

$^1$H-NMR (DMSO-d$_6$, δ): 1.29 (t, J=7.0 Hz, 3H), 4.27 (q, J=7.0, 2H), 5.52 (br s, 2H), 7.27-7.37 (m, 5H), 8.51 (s, 1H), 8.78 (s, 1H), 10.17 (br s, 1H), 13.50 (br s, 1H).

[Step 5]

7-Benzylamino-3-ethoxycarbonyl-6-(3-methyl-4-phenylpiperidine-1-carbonyl)pyrazolo[1,5-a]pyrimidine 7-Benzylamino-3-ethoxycarbonylpyrazolo[1,5-a]pyrimidine-6-carboxylic acid (0.20 g, 0.58 mmol) obtained in step 4 was dissolved in DMF (2 mL), 3-methyl-4-phenylpiperidine hydrochloride (Journal of Heterocyclic Chemistry, vol. 12, page 709, 0.15 g, 0.70 mmol), 1-hydroxybenzotriazole (0.13 g, 0.70 mmol) and 1-ethyl-3-[3-(dimethylamino)propyl]carbodiimide hydrochloride (0.10 g, 0.70 mmol) were added, and the mixture was stirred at room temperature for 3 hr. Saturated aqueous sodium hydrogen carbonate solution (10 mL) was added dropwise to the reaction mixture, and the precipitated solid was m collected by filtration. The obtained solid was washed with water, and dried under reduced pressure at 50° C. overnight to give the title compound (0.23 g, 81%).

[Step 6]

7-Benzylamino-6-(3-methyl-4-phenylpiperidine-1-carbonyl)pyrazolo[1,5-a]pyrimidine-3-carboxylic acid In the same manner as in Example 19, step 6 and using 7-benzylamino-3-ethoxycarbonyl-6-(3-methyl-4-phenylpiperidine-1-carbonyl)pyrazolo[1,5-a]pyrimidine (0.23 g, 0.47 mmol) obtained in step 5 instead of 3-ethoxycarbonyl-7-(1-phenethylamino)-6-(4-phenylpiperidine-1-carbonyl)pyrazolo[1,5-a]pyrimidine, the title compound (0.21 g, 92%) was obtained.

[Step 7]

N-[7-Benzylamino-6-(3-methyl-4-phenylpiperidine-1-carbonyl)pyrazolo[1,5-a]pyrimidine-3-carbonyl]methanesulfonamide (compound a-21)

In the same manner as in Example 1, step 6 and using 7-benzylamino-6-(3-methyl-4-phenylpiperidine-1-carbonyl)pyrazolo[1,5-a]pyrimidine-3-carboxylic acid (0.209 g, 0.445 mmol) obtained in step 6 and methanesulfonamide (0.211 g, 2.23 mmol), the title compound (0.042 g, 17%) was obtained.

ESI-MS m/z: 547 (M+H)$^+$; $^1$H-NMR (CDCl$_3$, δ): 0.69-0.74 (m, 3H), 1.23-1.84 (m, 2H), 2.00-2.35 (m, 1H), 2.60-2.77 (m, 3H), 3.66-3.89 (m, 2H), 4.88 (br s, 2H), 7.09-7.42 (m, 10H), 7.64 (br s, 1H), 8.24 (s, 0.3H), 8.26 (s, 0.7H), 8.57 (s, 1H), 10.75 (br s, 1H).

EXAMPLE 22

N-[7-Benzylamino-6-(4-(2-methoxyphenyl)piperidine-1-carbonyl)pyrazolo[1,5-a]pyrimidine-3-carbonyl]methanesulfonamide (compound a-22)

[Step 1]

Ethyl 3-bromo-7-chloropyrazolo[1,5-a]pyrimidine-6-carboxylate

In the same manner as in Example 1, step 3 and using known ethyl 3-bromo-7-hydroxypyrazolo[1,5-a]pyrimidine-6-carboxylate (Journal of Medicinal Chemistry, vol. 25, page 235, 8.13 g, 28.6 mmol) instead of 3-bromo-7-hydroxy-6-(4-phenylpiperidine-1-carbonyl)pyrazolo[1,5-a]pyrimidine, the title compound (7.32 g, 84%) was obtained.

[Step 2]

Ethyl 7-benzylamino-3-bromopyrazolo[1,5-a]pyrimidine-6-carboxylate

In the same manner as in Example 1, step 4 and using ethyl 3-bromo-7-chloropyrazolo[1,5-a]pyrimidine-6-carboxylate (7.35 g, 24.0 mmol) obtained in step 1, the title compound (8.32 g, 92%) was obtained.

[Step 3]

7-Benzylamino-3-bromopyrazolo[1,5-a]pyrimidine-6-carboxylic acid

In the same manner as in Example 19, step 6 and using ethyl 7-benzylamino-3-bromopyrazolo[1,5-a]pyrimidine-6-carboxylate (2.20 g, 5.86 mmol) obtained in step 2 instead of 3-ethoxycarbonyl-7-(1-phenethylamino)-6-(4-phenylpiperidine-1-carbonyl)pyrazolo[1,5-a]pyrimidine, the title compound (1.36 g, 67%) was obtained.

[Step 4]

7-Benzylamino-3-bromo-6-[4-(2-methoxyphenyl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.150 g, 0.400 mmol) obtained in step 3 and 4-(2-methoxyphenyl)piperidine (0.091 g, 0.480 mmol), the title compound (0.177 g, 80%) was obtained.

[Step 5]

7-Benzylamino-6-[4-(2-methoxyphenyl)piperidine-1-carbonyl]pyrazolo[1,5-a]pyrimidine-3-carboxylic acid In the same manner as in Example 1, step 5 and using 7-benzylamino-3-bromo-6-[4-(2-methoxyphenyl)piperidine-1-carbonyl]pyrazolo[1,5-a]pyrimidine (0.165 g, 0.317 mmol) obtained in step 4, the title compound (0.153 g, 100%) was obtained.

[Step 6]

N-{7-Benzylamino-6-[4-(2-methoxyphenyl)piperidine-1-carbonyl]pyrazolo[1,5-a]pyrimidine-3-carbonyl}methanesulfonamide (compound a-22)

In the same manner as in Example 1, step 6 and using 7-benzylamino-6-[4-(2-methoxyphenyl)piperidine-1-carbonyl]pyrazolo[1,5-a]pyrimidine-3-carboxylic acid (0.153 g, 0.317 mmol) obtained in step 5 and methanesulfonamide (0.175 g, 1.85 mmol), the title compound (0.099 g, 56%) was obtained.

ESI-MS m/z: 564 (M+H)$^+$; $^1$H-NMR (CDCl$_3$, δ): 1.44-1.73 (m, 2H), 1.73-1.98 (m, 2H), 2.49-3.01 (m, 2H), 3.01-3.24 (m, 1H), 3.41 (s, 3H), 3.82 (s, 3H), 4.10-4.69 (m, 2H), 4.89 (d, J=5.4 Hz, 2H), 6.79-7.00 (m, 2H), 7.00-7.14 (m, 1H), 7.14-7.50 (m, 6H), 7.51-7.83 (m, 1H), 8.22 (s, 1H), 8.55 (s, 1H), 10.73 (br s, 1H).

EXAMPLE 23

N-{7-Benzylamino-6-[4-(thiophen-2-yl)piperidine-1-carbonyl]pyrazolo[1,5-a]pyrimidine-3-carbonyl}methanesulfonamide (compound a-23)

[Step 1]

3-Bromo-7-benzylamino-6-[4-(thiophen-2-yl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.10 g, 0.29 mmol) obtained in Example 22, step 3 and 4-(thiophen-2-yl)piperidine hydrochloride (0.07 g, 0.35 mmol), the title compound (0.14 g, 99%) was obtained.

[Step 2]

7-Benzylamino-6-[4-(thiophen-2-yl)piperidine-1-carbonyl]pyrazolo[1,5-a]pyrimidine-3-carboxylic acid In the same manner as in Example 1, step 5 and using 3-bromo-7-benzylamino-6-[4-(thiophen-2-yl)piperidine-1-carbonyl]pyrazolo[1,5-a]pyrimidine (0.14 g, 0.28 mmol) obtained in step 1, the title compound (0.06 g, 44%) was obtained.

[Step 3]

N-{7-Benzylamino-6-[4-(thiophen-2-yl)piperidine-1-carbonyl]pyrazolo[1,5-a]pyrimidine-3-carbonyl}methanesulfonamide (compound a-23)

In the same manner as in Example 1, step 6 and using 7-benzylamino-6-[4-(thiophen-2-yl)piperidine-1-carbonyl]pyrazolo[1,5-a]pyrimidine-3-carboxylic acid (0.06 g, 0.12 mmol) obtained in step 2 and methanesulfonamide (0.057 g, 0.600 mmol), the title compound (0.02 g, 31%) was obtained.

ESI-MS m/z: 539 (M+H)$^+$; $^1$H-NMR (CDCl$_3$, δ): 1.49-1.64 (m, 2H), 1.81-1.91 (m, 2H), 2.60-2.77 (m, 3H), 3.43 (s, 3H), 3.66-3.89 (m, 2H), 4.89 (d, J=4.4 Hz, 2H), 6.77 (d, J=3.0 Hz, 1H), 6.97 (dd, J=3.0, 4.9 Hz, 1H), 7.16 (d, J=4.9 Hz, 1H), 7.15-7.35 (m, 5H), 7.66 (br s, 1H), 8.22 (s, 1H), 8.54 (s, 1H), 10.55 (br s, 1H).

EXAMPLE 24

N-{6-[4-(3-Methyl-1,2,4-oxazol-5-yl)piperidine-1-carbonyl]-7-(2-methylphenylamino)pyrazolo[1,5-a]pyrimidine-3-carbonyl}ethanesulfonamide (compound a-24)

[Step 1]

Ethyl 3-bromo-7-(2-methylphenylamino)pyrazolo[1,5-a]pyrimidine-6-carboxylate

In the same manner as in Example 22, step 2 and using o-toluidine (2.33 mL, 21.8 mmol) instead of benzylamine, the title compound (5.09 g, 94%) was obtained.

[Step 2]

3-Bromo-7-(2-methylphenylamino)pyrazolo[1,5-a]pyrimidine-6-carboxylic acid

In the same manner as in Example 22, step 3 and using ethyl 3-bromo-7-(2-methylphenylamino)pyrazolo[1,5-a]pyrimidine-6-carboxylate (5.09 g, 13.6 mmol) obtained in step 1 instead of ethyl 7-benzylamino-3-bromopyrazolo[1,5-a]pyrimidine-6-carboxylate, the title compound (2.13 g, 45%) was obtained.

[Step 3]

3-Bromo-6-[4-(3-methyl-1,2,4-oxazol-5-yl)piperidine-1-carbonyl]-7-(2-methylphenylamino)pyrazolo[1,5-a]pyrimidine Using 4-(3-methyl-1,2,4-oxazol-5-yl)piperidine hydrochloride (0.193 g, 0.957 mmol), the title compound (0.116 g, 27%) was obtained in the same manner as in Example 22, step 4 from 3-bromo-7-(2-methylphenylamino)pyrazolo[1,5-a]pyrimidine-6-carboxylic acid (0.300 g, 0.869 mmol) obtained in step 2.

[Step 4]

6-[4-(3-Methyl-1,2,4-oxazol-5-yl)piperidine-1-carbonyl]-7-(2-methylphenylamino)pyrazolo[1,5-a]pyrimidine-3-carboxylic acid In the same manner as in Example 1, step 5 and using 3-bromo-6-[4-(3-methyl-1,2,4-oxazo-5-yl)piperidine-1-carbonyl)]-7-(2-methylphenylamino)pyrazolo[1,5-a]pyrimidine (0.122 g, 0.246 mmol) obtained in step 3, the title compound (0.094 g, 82%) was obtained.

[Step 5]

N-{6-[4-(3-Methyl-1,2,4-oxazol-5-yl)piperidine-1-carbonyl]-7-(2-methylphenylamino)pyrazolo[1,5-a]pyrimidine-3-carbonyl}ethanesulfonamide (compound a-24)

In the same manner as in Example 1, step 6 and using 6-[4-(3-methyl-1,2,4-oxazol-5-yl)piperidine-1-carbonyl)]-7-(2-methylphenylamino)pyrazolo[1,5-a]pyrimidine-3-carboxylic acid (0.094 g, 0.203 mmol) obtained in step 4 and ethanesulfonamide (0.110 g, 1.01 mmol), the title compound (0.025 g, 22%) was obtained.

ESI-MS m/z: 554 (M+H)$^+$; $^1$H-NMR (CDCl$_3$, δ):1.46 (t, J=7.3 Hz, 3H), 1.63-1.85 (m, 2H), 1.88-2.12 (m, 2H), 2.40 (s, 6H), 2.55-2.99 (m, 2H), 2.99-3.18 (m, 1H), 3.61 (q, J=7.3 Hz, 2H), 3.70-3.93 (m, 2H), 7.08-7.44 (m, 5H), 8.27 (s, 1H), 8.37 (br s, 1H), 8.63 (s, 1H), 10.51 (br s, 1H).

EXAMPLE 25

N-{7-Benzylamino-6-[4-(1H-pyrazol-1-yl)piperidine-1-carbonyl]pyrazolo[1,5-a]pyrimidine-3-carbonyl}methanesulfonamide (compound a-25)

[Step 1]

7-Benzylamino-3-bromo-6-[4-(1H-pyrazol-1-yl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.215 g, 0.625 mmol) obtained in Example 22, step 3 and 4-(1H-pyrazol-1-yl)piperidine hydrochloride (WO2004/094371, 0.129 g, 0.687 mmol), the title compound (0.155 g, 52%) was obtained.

[Step 2]

7-Benzylamino-6-[4-(1H-pyrazol-1-yl)piperidine-1-carbonyl]pyrazolo[1,5-a]pyrimidine-3-carboxylic acid In the same manner as in Example 22, step 5 and using 7-benzylamino-3-bromo-6-[4-(1H-pyrazol-1-yl)piperidine-1-carbonyl]pyrazolo[1,5-a]pyrimidine (0.125 g, 0.260 mmol) obtained in step 1, the title compound (0.108 g, 93%) was obtained.

[Step 3]

N-{7-Benzylamino-6-[4-(1H-pyrazol-1-yl)piperidine-1-carbonyl]pyrazolo[1,5-a]pyrimidine-3-carbonyl}methanesulfonamide (compound a-25)

In the same manner as in Example 1, step 6 and using 7-benzylamino-6-[4-(1H-pyrazol-1-yl)piperidine-1-carbonyl]pyrazolo[1,5-a]pyrimidine-3-carboxylic acid (0.102 g, 0.229 mmol) obtained in step 2 and methanesulfonamide (0.109 g, 1.14 mmol), the title compound (0.064 g, 53%) was obtained.

ESI-MS m/z: 523 (M+H)$^+$; $^1$H-NMR (CDCl$_3$, δ): 1.74-2.25 (m, 4H), 2.51-3.06 (m, 3H), 3.42 (s, 3H), 4.19-4.41 (m, 2H), 4.81-5.00 (m, 2H), 6.27 (s, 1H), 7.22-7.43 (m, 6H), 7.52 (s, 1H), 7.66-7.90 (m, 1H), 8.20 (s, 1H), 8.58 (s, 1H), 10.70 (br s, 1H).

EXAMPLE 26

N-{7-Benzylamino-6-[4-(4-fluorophenyl)piperidine-1-carbonyl]pyrazolo[1,5-a]pyrimidine-3-carbonyl}methanesulfonamide (compound a-26)

[Step 1]

7-Benzylamino-3-bromo-6-[4-(4-fluorophenyl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.174 g, 0.506 mmol) obtained in Example 22, step 3 and 4-(4-fluorophenyl)piperidine hydrochloride (0.120 g, 0.556 mmol), the title compound (0.231 g, 90%) was obtained.

[Step 2]

7-Benzylamino-6-[4-(4-fluorophenyl)piperidine-1-carbonyl]pyrazolo[1,5-a]pyrimidine-3-carboxylic acid In the same manner as in Example 22, step 5 and using 7-benzylamino-3-bromo-6-[4-(4-fluorophenyl)piperidine-1-carbonyl]pyrazolo[1,5-a]pyrimidine (0.220 g, 0.4331 mmol) obtained in step 1, the title compound (0.183 g, 89%) was obtained.

[Step 3]

N-{7-Benzylamino-6-[4-(4-fluorophenyl)piperidine-1-carbonyl]pyrazolo[1,5-a]pyrimidine-3-carbonyl}methanesulfonamide (compound a-26)

In the same manner as in Example 1, step 6 and using 7-benzylamino-6-[4-(4-fluorophenyl)piperidine-1-carbonyl]pyrazolo[1,5-a]pyrimidine-3-carboxylic acid (0.090 g, 0.190 mmol) obtained in step 2 and methanesulfonamide (0.094 g, 0.951 mmol), the title compound (0.025 g, 24%) was obtained.

ESI-MS m/z: 551 (M+H)$^+$; $^1$H-NMR (CDCl$_3$, δ): 1.32-1.50 (m, 2H), 1.60-1.83 (m, 2H), 2.32-2.74 (m, 3H), 3.29 (s, 3H), 3.68-4.39 (m, 2H), 4.66-4.91 (m, 2H), 6.80-7.08 (m, 4H), 7.08-7.35 (m, 5H), 7.45-7.67 (m, 1H), 8.06 (s, 1H), 8.46 (s, 1H), 10.61 (br s, 1H).

EXAMPLE 27

N-{7-Benzylamino-6-[4-(2-fluorophenyl)piperidine-1-carbonyl]pyrazolo[1,5-a]pyrimidine-3-carbonyl}methanesulfonamide (compound a-27)

[Step 1]

7-Benzylamino-3-bromo-6-[4-(2-fluorophenyl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.174 g, 0.506 mmol) obtained in Example 22, step 3 and 4-(2-fluorophenyl)piperidine hydrochloride (0.120 g, 0.556 mmol), the title compound (0.35 g, 90%) was obtained.

[Step 2]

7-Benzylamino-6-[4-(2-fluorophenyl)piperidine-1-carbonyl]pyrazolo[1,5-a]pyrimidine-3-carboxylic acid In the same manner as in Example 22, step 5 and using 7-benzylamino-3-bromo-6-[4-(2-fluorophenyl)piperidine-1-carbonyl]pyrazolo[1,5-a]pyrimidine (0.220 g, 0.4331 mmol) obtained in step 1, the title compound (0.072 g, 35%) was obtained.

[Step 3]

N-{7-Benzylamino-6-[4-(2-fluorophenyl)piperidine-1-carbonyl]pyrazolo[1,5-a]pyrimidine-3-carbonyl}methanesulfonamide (compound a-27)

In the same manner as in Example 1, step 6 and using 7-benzylamino-6-[4-(2-fluorophenyl)piperidine-1-carbonyl]pyrazolo[1,5-a]pyrimidine-3-carboxylic acid (0.035 g, 0.074 mmol) obtained in step 2 and methanesulfonamide (0.038 g, 0.375 mmol), the title compound (0.011 g, 27%) was obtained.

ESI-MS m/z: 551 (M+H)$^+$; $^1$H-NMR (CDCl$_3$, δ): 1.48-1.75 (m, 2H), 1.75-1.96 (m, 2H), 2.39-2.89 (m, 2H), 2.89-3.15 (m, 1H), 3.41 (s, 3H), 3.84-4.59 (m, 2H), 4.82-4.98 (m, 2H), 6.97-7.49 (m, 9H), 7.61-7.80 (m, 1H), 8.22 (s, 1H), 8.58 (s, 1H), 10.73 (br s, 1H).

EXAMPLE 28

N-{7-Benzylamino-6-[4-(2-methylphenyl)piperidine-1-carbonyl]pyrazolo[1,5-a]pyrimidine-3-carbonyl}methanesulfonamide (compound a-28)

[Step 1]

7-Benzylamino-3-bromo-6-[4-(2-methylphenyl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.20 g, 0.58 mmol) obtained in Example 22, step 3 instead of 7-benzylamino-3-ethoxycarbonylpyrazolo[1,5-a]pyrimidine-6-carboxylic acid and 4-(2-methylphenyl)piperidine hydrochloride (0.15 g, 0.69 mmol), the title compound (0.25 g, 85%) was obtained.

[Step 2]

7-Benzylamino-6-[4-(2-methylphenyl)piperidine-1-carbonyl]pyrazolo[1,5-a]pyrimidine-3-carboxylic acid In the same manner as in Example 1, step 5 and using 7-benzylamino-3-bromo-6-[4-(2-methylphenyl)piperidine-1-carbonyl]pyrazolo[1,5-a]pyrimidine (0.25 g, 0.49 mmol) obtained in step 1, the title compound (0.19 g, 83%) was obtained.

[Step 3]

N-{7-Benzylamino-6-[4-(2-methylphenyl)piperidine-1-carbonyl]pyrazolo[1,5-a]pyrimidine-3-carbonyl}methanesulfonamide (compound a-28)

In the same manner as in Example 1, step 6 and using 7-benzylamino-6-[4-(2-methylphenyl)piperidine-1-carbonyl]pyrazolo[1,5-a]pyrimidine-3-carboxylic acid (0.09 g, 0.19 mmol) obtained in step 2 and methanesulfonamide (0.090 g, 0.950 mmol), the title compound (0.03 g, 30%) was obtained.

ESI-MS m/z: 547 (M+H)⁺; ¹H-NMR (CDCl₃, δ): 1.51-1.59 (m, 2H), 1.80-1.84 (m, 2H), 2.35 (s, 3H), 2.60-2.68 (m, 3H), 3.43 (s, 3H), 4.11-4.36 (m, 2H), 4.93 (br s, 2H), 7.11-7.45, (m, 9H), 7.69 (br s, 1H), 8.24 (s, 1H), 8.57 (s, 1H), 10.73 (br s, 1H).

EXAMPLE 29

N-{7-Benzylamino-6-[4-(3-methylphenyl)piperidine-1-carbonyl]pyrazolo[1,5-a]pyrimidine-3-carbonyl}methanesulfonamide (compound a-29)

[Step 1]

7-Benzylamino-3-bromo-6-[4-(3-methylphenyl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.20 g, 0.58 mmol) obtained in Example 22, step 3 instead of 7-benzylamino-3-ethoxycarbonylpyrazolo[1,5-a]pyrimidine-6-carboxylic acid and 4-(3-methylphenyl)piperidine hydrochloride (0.15 g, 0.69 mmol), the title compound (0.22 g, 77%) was obtained.

[Step 2]

7-Benzylamino-6-[4-(3-methylphenyl)piperidine-1-carbonyl]pyrazolo[1,5-a]pyrimidine-3-carboxylic acid In the same manner as in Example 1, step 5 and using 7-benzylamino-3-bromo-6-[4-(3-methylphenyl)piperidine-1-carbonyl]pyrazolo[1,5-a]pyrimidine (0.22 g, 0.44 mmol) obtained in step 1, the title compound (0.19 g, 92%) was obtained.

[Step 3]

N-{7-Benzylamino-6-[4-(3-methylphenyl)piperidine-1-carbonyl]pyrazolo[1,5-a]pyrimidine-3-carbonyl}methanesulfonamide (compound a-29)

In the same manner as in Example 1, step 6 and using 7-benzylamino-6-[4-(3-methylphenyl)piperidine-1-carbonyl]pyrazolo[1,5-a]pyrimidine-3-carboxylic acid (0.09 g, 0.19 mmol) obtained in step 2 and methanesulfonamide (0.090 g, 0.950 mmol), the title compound (0.04 g, 38%) was obtained.

ESI-MS m/z: 547 (M+H)⁺; ¹H-NMR (CDCl₃, δ): 1.52-1.59 (m, 2H), 1.80-1.84 (m, 2H), 2.34 (s, 3H), 2.60-2.68 (m, 3H), 3.43 (s, 3H), 4.11-4.36 (m, 2H), 4.92 (br s, 2H), 7.11-7.51 (m, 9H), 7.70 (br s, 1H), 8.24 (s, 1H), 8.56 (s, 1H), 10.76 (br s, 1H).

EXAMPLE 30

N-{7-Benzylamino-6-[4-(4-methylphenyl)piperidine-1-carbonyl]pyrazolo[1,5-a]pyrimidine-3-carbonyl}methanesulfonamide (compound a-30)

[Step 1]

7-Benzylamino-3-bromo-6-[4-(4-methylphenyl)piperidine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.20 g, 0.58 mmol) obtained in Example 22, step 3 instead of 7-benzylamino-3-ethoxycarbonylpyrazolo[1,5-a]pyrimidine-6-carboxylic acid and 4-(4-methylphenyl)piperidine hydrochloride (0.15 g, 0.69 mmol), the title compound (0.22 g, 77%) was obtained.

[Step 2]

7-Benzylamino-6-[4-(4-methylphenyl)piperidine-1-carbonyl]pyrazolo[1,5-a]pyrimidine-3-carboxylic acid In the same manner as in Example 1, step 5 and using 7-benzylamino-3-bromo-6-[4-(4-methylphenyl)piperidine-1-carbonyl]pyrazolo[1,5-a]pyrimidine (0.22 g, 0.44 mmol) obtained in step 1, the title compound (0.20 g, 95%) was obtained.

[Step 3]

N-{7-Benzylamino-6-[4-(4-methylphenyl)piperidine-1-carbonyl]pyrazolo[1,5-a]pyrimidine-3-carbonyl}methanesulfonamide (compound a-30)

In the same manner as in Example 1, step 6 and using 7-benzylamino-6-[4-(4-methylphenyl)piperidine-1-carbonyl]pyrazolo[1,5-a]pyrimidine-3-carboxylic acid (0.09 g, 0.19 mmol) obtained in step 2 and methanesulfonamide (0.090 g, 0.950 mmol), the title compound (0.03 g, 28%) was obtained.

ESI-MS m/z: 547 (M+H)⁺; ¹H-NMR (CDCl₃, δ): 1.52-1.59 (m, 2H), 1.77-1.83 (m, 2H), 2.34 (s, 3H), 2.60-2.68 (m, 3H), 3.43 (s, 3H), 4.11-4.36 (m, 2H), 4.92 (br s, 2H), 7.11-7.51 (m, 9H), 7.70 (br s, 1H), 8.24 (s, 1H), 8.56 (s, 1H), 10.76 (br s, 1H).

EXAMPLE 31

N-{7-Benzylamino-6-[4-(pyrimidin-5-yl)piperidine-1-carbonyl]pyrazolo[1,5-a]pyrimidine-3-carbonyl}methanesulfonamide (compound a-31)

[Step 1]

7-Benzylamino-3-ethoxycarbonyl-6-[4-(pyrimidin-5-yl)piperidine-1-carbonyl]pyrazolo[1,5-a]pyrimidine In the same manner as in Example 21, step 5 and using 7-benzylamino-3-ethoxycarbonylpyrazolo[1,5-a]pyrimidine-6-carboxylic acid (0.16 g, 0.47 mmol) obtained in Example 21, step 4 and 4-(pyrimidin-5-yl)piperidine (WO2004/094371, 0.09 g, 0.57 mmol), the title compound (0.20 g, 0.41 mmol) was obtained.

[Step 2]

7-Benzylamino-6-[4-(pyrimidin-5-yl)piperidine-1-carbonyl]pyrazolo[1,5-a]pyrimidine-3-carboxylic acid In the same manner as in Example 19, step 6 and using 7-benzylamino-3-ethoxycarbonyl-6-[4-(pyrimidin-5-yl)piperidine-1-carbonyl]pyrazolo[1,5-a]pyrimidine (0.21 g, 0.41 mmol) obtained in step 1 instead of 3-ethoxycarbonyl-7-(1-phenethylamino)-6-(4-phenylpiperidine-1-carbonyl)pyrazolo[1,5-a]pyrimidine, the title compound (0.14 g, 71%) was obtained.
[Step 3]

N-{7-Benzylamino-6-[4-(pyrimidin-5-yl)piperidine-1-carbonyl]pyrazolo[1,5-a]pyrimidine-3-carbonyl}methanesulfonamide (compound a-31)

In the same manner as in Example 1, step 6 and using 7-benzylamino-6-[4-(pyrimidin-5-yl)piperidine-1-carbonyl]pyrazolo[1,5-a]pyrimidine-3-carboxylic acid (0.14 g, 0.29 mmol) obtained in step 2 and methanesulfonamide (0.138 g, 1.45 mmol), the title compound (0.04 g, 26%) was obtained.
ESI-MS m/z: 535 (M+H)$^+$; $^1$H-NMR (CDCl$_3$, δ): 1.51-1.59 (m, 2H), 1.80-1.84 (m, 2H), 2.60-2.68 (m, 3H), 3.42 (s, 3H), 4.11-4.36 (m, 2H), 4.94 (br s, 2H), 7.25-7.43 (m, 5H), 8.20 (s, 1H), 8.56-8.61 (m, 3H), 9.14 (s, 1H), 10.70 (br s, 1H).

EXAMPLE 32

N-{7-Benzylamino-6-[4-(oxazol-2-yl)piperidine-1-carbonyl]pyrazolo[1,5-a]pyrimidine-3-carbonyl}methanesulfonamide (compound a-32)

[Step 1]

7-Benzylamino-3-ethoxycarbonyl-6-[4-(oxazol-2-yl)piperidine-1-carbonyl]pyrazolo[1,5-a]pyrimidine In the same manner as in Example 21, step 5 and using 7-benzylamino-3-ethoxycarbonylpyrazolo[1,5-a]pyrimidine-6-carboxylic acid (0.20 g, 0.58 mmol) obtained in Example 21, step 4 and 4-(oxazol-2-yl)piperidine (WO2001/036980, 0.11 g, 0.70 mmol), the title compound (0.20 g, 72%) was obtained.
[Step 2]

7-Benzylamino-6-[4-(oxazol-2-yl)piperidine-1-carbonyl]pyrazolo[1,5-a]pyrimidine-3-carboxylic acid In the same manner as in Example 19, step 6 and using 7-benzylamino-3-ethoxycarbonyl-6-[4-(oxazol-2-yl)piperidine-1-carbonyl]pyrazolo[1,5-a]pyrimidine (0.20 g, 0.42 mmol) obtained in step 1 instead of 3-ethoxycarbonyl-7-(1-phenethylamino)-6-(4-phenylpiperidine-1-carbonyl)pyrazolo[1,5-a]pyrimidine, the title compound (0.16 g, 81%) was obtained.
[Step 3]

N-{7-Benzylamino-6-[4-(oxazol-2-yl)piperidine-1-carbonyl]pyrazolo[1,5-a]pyrimidine-3-carbonyl}methanesulfonamide (compound a-32)

In the same manner as in Example 1, step 6 and using 7-benzylamino-6-[4-(oxazol-2-yl)piperidine-1-carbonyl]pyrazolo[1,5-a]pyrimidine-3-carboxylic acid (0.08 g, 0.17 mmol) obtained in step 2 and methanesulfonamide (0.081 g, 0.850 mmol), the title compound (0.04 g, 46%) was obtained.
ESI-MS m/z: 524 (M+H)$^+$; $^1$H-NMR (CDCl$_3$, δ): 1.51-1.59 (m, 2H), 1.80-1.84 (m, 2H), 2.60-2.68 (m, 3H), 3.42 (s, 3H), 4.02-4.21 (m, 2H), 4.87 (br s, 2H), 7.08 (br s, 1H), 7.26-7.38 (m, 5H), 7.62 (br s, 1H), 7.72 (br s, 1H), 8.17 (s, 1H), 8.58 (s, 1H), 10.64 (s, 1H).

EXAMPLE 33

N-{7-Benzylamino-6-[4-(4-chlorophenyl)piperidine-1-carbonyl]pyrazolo[1,5-a]pyrimidine-3-carbonyl}methanesulfonamide (compound a-33)

[Step 1]

7-Benzylamino-6-[4-(4-chlorophenyl)piperidine-1-carbonyl]-3-ethoxycarbonylpyrazolo[1,5-a]pyrimidine In the same manner as in Example 21, step 5 and using 7-benzylamino-3-ethoxycarbonylpyrazolo[1,5-a]pyrimidine-6-carboxylic acid (0.20 g, 0.58 mmol) obtained in Example 21, step 4 and 4-(4-chlorophenyl)piperidine (0.14 g, 0.70 mmol), the title compound (0.24 g, 81%) was obtained.
[Step 2]

7-Benzylamino-6-[4-(4-chlorophenyl)piperidine-1-carbonyl]pyrazolo[1,5-a]pyrimidine-3-carboxylic acid In the same manner as in Example 19, step 6 and using 7-benzylamino-6-[4-(4-chlorophenyl)piperidine-1-carbonyl]-3-ethoxycarbonylpyrazolo[1,5-a]pyrimidine (0.24 g, 0.46 mmol) obtained in step 1 instead of 3-ethoxycarbonyl-7-(1-phenethylamino)-6-(4-phenylpiperidine-1-carbonyl)pyrazolo[1,5-a]pyrimidine, the title compound (0.19 g, 87%) was obtained.
[Step 3]

N-{7-Benzylamino-6-[4-(4-chlorophenyl)piperidine-1-carbonyl]pyrazolo[1,5-a]pyrimidine-3-carbonyl}methanesulfonamide (compound a-33)

In the same manner as in Example 1, step 6 and using 7-benzylamino-6-[4-(4-chlorophenyl)piperidine-1-carbonyl]pyrazolo[1,5-a]pyrimidine-3-carboxylic acid (0.09 g, 0.19 mmol) obtained in step 2 and methanesulfonamide (0.090 g, 0.950 mmol), the title compound (0.05 g, 47%) was obtained.
ESI-MS m/z: 567 (M+H)$^+$; (CDCl$_3$, δ): 1.51-1.59 (m, 2H), 1.80-1.84 (m, 2H), 2.59-2.70 (m, 3H), 3.42 (s, 3H), 3.91-4.15 (m, 2H), 4.91 (d, J=6.6 Hz, 2H), 7.07-7.10 (m, 2H), 7.23-7.43 (m, 7H), 7.72 (br s, 1H), 8.21 (s, 1H), 8.58 (s, 1H), 10.72 (br s, 1H).

EXAMPLE 34

N-[7-(2-Methylphenylamino)-6-(4-methyl-4-phenylpiperidine-1-carbonyl)pyrazolo[1,5-a]pyrimidine-3-carbonyl]ethanesulfonamide (compound a-34)

[Step 1]

3-Ethoxycarbonyl-7-hydroxy-6-(4-methyl-4-phenylpiperidine-1-carbonyl)pyrazolo[1,5-a]pyrimidine In the same manner as in Example 1, step 2 and using 3-ethoxycarbonyl-7-hydroxypyrazolo[1,5-a]pyrimidine-6- carboxylic acid (583 mg, 2.32 mmol) obtained in Example 19, step 2 and 4-methyl-4-phenylpiperidine (Journal of Medicinal Chemistry, vol. 41, page 5320, 590 mg, 2.79 mmol), the title compound (650 mg, 69%) was obtained.
[Step 2]

7-Chloro-3-ethoxycarbonyl-6-(4-methyl-4-phenylpiperidine-1-carbonyl)pyrazolo[1,5-a]pyrimidine In the same manner as in Example 1, step 3 and using 3-ethoxycarbonyl-7-hydroxy-6-(4-methyl-4-phenylpiperidine-1-carbonyl)pyrazolo[1,5-a]pyrimidine (650 mg, 1.59 mmol) obtained in step 1 instead of 3-bromo-7-hydroxy-6-(4-phenylpiperidine-1-carbonyl)pyrazolo[1,5-a]pyrimidine, the title compound (429 mg, 63%) was obtained.
[Step 3]

3-Ethoxycarbonyl-7-(2-methylphenylamino)-6-(4-methyl-4-phenylpiperidine-1-carbonyl)pyrazolo[1,5-a]pyrimidine In the same manner as in Example 19, step 5 and using 7-chloro-3-ethoxycarbonyl-6-(4-methyl-4-phenylpiperidine-1-carbonyl)pyrazolo[1,5-a]pyrimidine (210 mg, 0.49 mmol) obtained in step 2 and o-toluidine (0.08 mL, 0.74 mmol), the title compound (153 mg, 63%) was obtained.
[Step 4]

7-(2-Methylphenylamino)-6-(4-methyl-4-phenylpiperidine-1-carbonyl)pyrazolo[1,5-a]pyrimidine-3-carboxylic acid In the same manner as in Example 19, step 6 and using 3-ethoxycarbonyl-7-(2-methylphenylamino)-6-(4-methyl-4-phenylpiperidine-1-carbonyl)pyrazolo[1,5-a]pyrimidine (153 mg, 0.32 mmol) obtained in step 3, the title compound (107 mg, 72%) was obtained.
[Step 5]

N-[7-(2-Methylphenylamino)-6-(4-methyl-4-phenylpiperidine-1-carbonyl)pyrazolo[1,5-a]pyrimidine-3-carbonyl]ethanesulfonamide (compound a-34)

In the same manner as in Example 1, step 6 and using 7-(2-methylphenylamino)-6-(4-methyl-4-phenylpiperidine-1-carbonyl)pyrazolo[1,5-a]pyrimidine-3-carboxylic acid (60 mg, 0.13 mmol) obtained in step 4 and ethanesulfonamide (56 mg, 0.51 mmol), the title compound (20 mg, 28%) was obtained.
ESI-MS m/z: 561 (M+H)$^+$; $^1$H-NMR (CDCl$_3$, δ): 1.21 (s, 3H), 1.46 (t, J=7.4 Hz, 3H), 1.54 (br s, 4H), 1.98-2.05 (m, 2H), 2.33 (s, 3H), 3.31-3.36 (m, 2H), 3.61 (q, J=7.3 Hz, 2H), 7.08-7.40 (m, 9H), 8.28 (br s, 2H), 8.61 (s, 1H), 10.53 (br s, 1H).

EXAMPLE 35

N-{7-Benzylamino-6-[4-(2-methylphenyl)piperazine-1-carbonyl]pyrazolo[1,5-a]pyrimidine-3-carbonyl}methanesulfonamide (compound a-35)

[Step 1]

7-Benzylamino-3-bromo-6-[4-(2-methylphenyl)piperazine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.150 g, 0.400 mmol) obtained in Example 22, step 3 and 1-(2-methylphenyl)piperazine (0.084 g, 0.480 mmol), the title compound (0.170 g, 79%) was obtained.
[Step 2]

7-Benzylamino-6-[4-(2-methylphenyl)piperazine-1-carbonyl]pyrazolo[1,5-a]pyrimidine-3-carboxylic acid In the same manner as in Example 22, step 5 and using 7-benzylamino-3-bromo-6-[4-(2-methylphenyl)piperazine-1-carbonyl]pyrazolo[1,5-a]pyrimidine (0.160 g, 0.317 mmol) obtained in step 1, the title compound (0.149 g, 100%) was obtained.
[Step 3]

N-{7-Benzylamino-6-[4-(2-methylphenyl)piperazine-1-carbonyl]pyrazolo[1,5-a]pyrimidine-3-carbonyl}methanesulfonamide (compound a-35)

In the same manner as in Example 1, step 6 and using 7-benzylamino-6-[4-(2-methylphenyl)piperazine-1-carbonyl]pyrazolo[1,5-a]pyrimidine-3-carboxylic acid (0.149 g, 0.317 mmol) obtained in step 2 and methanesulfonamide (0.175 g, 1.82 mmol), the title compound (0.072 g, 41%) was obtained.
ESI-MS m/z: 548 (M+H)$^+$; $^1$H-NMR (CDCl$_3$, δ): 2.28 (s, 3H), 2.59-2.97 (m, 4H), 3.12-3.95 (m, 7H), 4.84-4.96 (m, 2H), 6.90-6.98 (m, 1H), 6.98-7.11 (m, 1H), 7.11-7.48 (m, 7H), 7.60-7.85 (m, 1H), 8.22 (s, 1H), 8.58 (s, 1H), 10.69 (br s, 1H).

EXAMPLE 36

N-{7-Benzylamino-6-[4-(2-chlorophenyl)piperazine-1-carbonyl]pyrazolo[1,5-a]pyrimidine-3-carbonyl}methanesulfonamide (compound a-36)

[Step 1]

7-Benzylamino-3-bromo-6-[4-(2-chlorophenyl)piperazine-1-carbonyl]pyrazolo[1,5-a]pyrimidine In the same manner as in Example 21, step 5 and using 7-benzylamino-3-bromopyrazolo[1,5-a]pyrimidine-6-carboxylic acid (0.091 g, 0.243 mmol) obtained in Example 22, step 3 and 1-(2-chlorophenyl)piperazine (0.057 g, 0.239 mmol), the title compound (0.102 g, 69%) was obtained.
[Step 2]

7-Benzylamino-6-[4-(2-chlorophenyl)piperazine-1-carbonyl]pyrazolo[1,5-a]pyrimidine-3-carboxylic acid In the same manner as in Example 22, step 5 and using 7-benzylamino-3-bromo-6-[4-(2-chlorophenyl)piperazine-1-carbonyl]pyrazolo[1,5-a]pyrimidine (0.102 g, 0.184 mmol) obtained in step 1, the title compound (0.087 g, 94%) was obtained.
[Step 3]

N-{7-Benzylamino-6-[4-(2-chlorophenyl)piperazine-1-carbonyl]pyrazolo[1,5-a]pyrimidine-3-carbonyl}methanesulfonamide (compound a-36)

In the same manner as in Example 1, step 6 and using 7-benzylamino-6-[4-(2-chlorophenyl)piperazine-1-carbonyl]pyrazolo[1,5-a]pyrimidine-3-carboxylic acid (0.087 g, 0.177 mmol) obtained in step 2 and methanesulfonamide (0.084 g, 0.855 mmol), the title compound (0.025 g, 25%) was obtained.

ESI-MS m/z: 569 (M+H)$^+$; $^1$H-NMR (CDCl$_3$, δ): 2.80-3.06 (m, 4H), 3.06-3.91 (m, 7H), 4.82-5.01 (m, 2H), 6.90-7.11 (m, 2H), 7.18-7.50 (m, 7H), 7.60-7.86 (m, 1H), 8.21 (s, 1H), 8.60 (s, 1H), 10.70 (br s, 1H).

EXAMPLE 37

N-{6-[4-(2-Chlorophenyl)piperazine-1-carbonyl]-7-(2-methylphenylamino)pyrazolo[1,5-a]pyrimidine-3-carbonyl}ethanesulfonamide (compound a-37)

[Step 1]

3-Bromo-6-[4-(2-chlorophenyl)piperazine-1-carbonyl]-7-(2-methylphenylamino)pyrazolo[1,5-a]pyrimidine In the same manner as in Example 24, step 3 and using 1-(2-chlorophenyl)piperazine (0.135 g, 0.691 mmol) instead of 4-(3-methyl-1,2,4-oxazo-5-yl)piperidine hydrochloride, the title compound (0.291 g, 96%) was obtained.

[Step 2]

6-[4-(2-Chlorophenyl)piperazine-1-carbonyl]-7-(2-methylphenylamino)pyrazolo[1,5-a]pyrimidine-3-carboxylic acid In the same manner as in Example 1, step 5 and using 3-bromo-6-[4-(2-chlorophenyl)piperazine-1-carbonyl]-7-(2-methylphenylamino)pyrazolo[1,5-a]pyrimidine (0.280 g, 0.533 mmol) obtained in step 1, the title compound (0.220 g, 84%) was obtained.

[Step 3]

N-{6-[4-(2-Chlorophenyl)piperazine-1-carbonyl]-7-(2-methylphenylamino)pyrazolo[1,5-a]pyrimidine-3-carbonyl}ethanesulfonamide (compound a-37)

In the same manner as in Example 1, step 6 and using 6-[4-(2-chlorophenyl)piperazine-1-carbonyl]-7-(2-methylphenylamino)pyrazolo[1,5-a]pyrimidine-3-carboxylic acid (0.110 g, 0.224 mmol) obtained in step 2 and ethanesulfonamide (0.049 g, 0.448 mmol), the title compound (0.025 g, 19%) was obtained.

ESI-MS m/z: 583 (M+H)$^+$; $^1$H-NMR (CDCl$_3$, δ): 1.46 (t, J=7.3 Hz, 3H), 2.43 (s, 3H), 2.82-3.00 (m, 4H), 3.26-3.49 (m, 4H), 3.62 (q, J=7.3 Hz, 2H), 6.94-7.06 (m, 2H), 7.16-7.41 (m, 6H), 8.32 (s, 1H), 8.34-8.38 (br s, 1H), 8.64 (s, 1H), 10.53 (br s, 1H).

EXAMPLE 38

N-{7-Benzylamino-6-[4-(4-fluorophenyl)piperazine-1-carbonyl]pyrazolo[1,5-a]pyrimidine-3-carbonyl}methanesulfonamide (compound a-38)

[Step 1]

7-Benzylamino-3-bromo-6-[4-(4-fluorophenyl)piperazine-1-carbonyl]pyrazolo[1,5-a]pyrimidine In the same manner as in Example 21, step 5 and using 7-benzylamino-3-bromopyrazolo[1,5-a]pyrimidine-6-carboxylic acid obtained in Example 22, step 3 instead of 7-benzylamino-3-ethoxycarbonylpyrazolo[1,5-a]pyrimidine-6-carboxylic acid and 1-(4-fluorophenyl)piperazine (0.06 g, 0.35 mmol), the title compound (0.11 g, 62%) was obtained.

[Step 2]

7-Benzylamino-6-[4-(4-fluorophenyl)piperazine-1-carbonyl]pyrazolo[1,5-a]pyrimidine-3-carboxylic acid In the same manner as in Example 1, step 5 and using 7-benzylamino-3-bromo-6-[4-(4-fluorophenyl)piperazine-1-carbonyl]pyrazolo[1,5-a]pyrimidine (0.11 g, 0.22 mmol) obtained in step 1, the title compound (0.04 g, 34%) was obtained.

[Step 3]

N-{7-Benzylamino-6-[4-(4-fluorophenyl)piperazine-1-carbonyl]pyrazolo[1,5-a]pyrimidine-3-carbonyl}methanesulfonamide (compound a-38)

In the same manner as in Example 1, step 6 and using 7-benzylamino-6-[4-(4-fluorophenyl)piperazine-1-carbonyl]pyrazolo[1,5-a]pyrimidine-3-carboxylic acid (0.04 g, 0.08 mmol) obtained in step 2 and methanesulfonamide (0.038 g, 0.400 mmol), the title compound (0.02 g, 48%) was obtained.

ESI-MS m/z: 552 (M+H)$^+$; $^1$H-NMR (CDCl$_3$, δ): 2.91-3.21 (m, 4H), 3.26-3.52 (m, 4H), 3.42 (s, 3H), 4.91 (br s, 2H), 6.95-7.06 (m, 2H), 7.26-7.41 (m, 7H), 7.83 (br s, 1H), 8.19 (s, 1H), 8.58 (s, 1H), 10.67 (br s, 1H).

EXAMPLE 39

N-[7-(2-Methylphenylamino)-6-(4-phenylpiperidine-1-carbonyl)pyrazolo[1,5-a]pyrimidine-3-carbonyl]ethanesulfonamide (compound a-39)

[Step 1]

3-Bromo-7-(2-methylphenylamino)-6-(4-phenylpiperidine-1-carbonyl)pyrazolo[1,5-a]pyrimidine In the same manner as in Example 1, step 4 and using o-toluidine (0.27 mL, 2.50 mmol) instead of benzylamine, the title compound (0.88 g, 99%) was obtained.

[Step 2]

7-(2-Methylphenylamino)-6-(4-phenylpiperidine-1-carbonyl)pyrazolo[1,5-a]pyrimidine-3-carboxylic acid In the same manner as in Example 1, step 5 and using 3-bromo-7-(2-methylphenylamino)-6-(4-phenylpiperidine-1-carbonyl)pyrazolo[1,5-a]pyrimidine (0.88 g, 1.78 mmol) obtained in step 1, the title compound (0.65 g, 81%) was obtained.

[Step 3]

N-[7-(2-Methylphenylamino)-6-(4-phenylpiperidine-1-carbonyl)pyrazolo[1,5-a]pyrimidine-3-carbonyl]ethanesulfonamide (compound a-39)

In the same manner as in Example 1, step 6 and using 7-(2-methylphenylamino)-6-(4-phenylpiperidine-1-carbonyl)pyrazolo[1,5-a]pyrimidine-3-carboxylic acid (0.30 g, 0.66 mmol) obtained in step 2 and ethanesulfonamide (0.35 g, 3.30 mmol), the title compound (0.21 g, 58%) was obtained.

ESI-MS m/z: 547 (M+H)$^+$; $^1$H-NMR (CDCl$_3$, δ): 1.46 (t, J=7.0 Hz, 3H), 1.51-1.59 (m, 2H), 1.79-1.84 (m, 2H), 2.42 (s, 3H), 2.60-2.68 (m, 3H), 3.61 (q, J=7.0 Hz, 2H), 3.85-4.15 (m, 2H), 7.14-7.39 (m, 9H), 8.33 (s, 1H), 8.35 (br s, 1H), 8.63 (s, 1H), 10.54 (s, 1H).

EXAMPLE 40

N-[7-(2-Methylphenylamino)-6-(4-phenylpiperidine-1-carbonyl)pyrazolo[1,5-a]pyrimidine-3-carbonyl] cyclopropanesulfonamide (compound a-40)

In the same manner as in Example 1, step 6 and using 7-(2-methylphenylamino)-6-(4-phenylpiperidine-1-carbonyl)pyrazolo[1,5-a]pyrimidine-3-carboxylic acid (0.30 g, 0.66 mmol) obtained in Example 39, step 2 and cyclopropanesulfonamide (0.40 g, 3.3 mmol), the title compound (0.23 g, 63%) was obtained.

ESI-MS m/z: 559 (M+H)$^+$; $^1$H-NMR (CDCl$_3$, δ): 1.10-1.17 (m, 2H), 1.45-1.59 (m, 4H), 1.79-1.83 (m, 2H), 2.42 (s, 3H), 2.59-2.68 (m, 3H), 3.06-3.15 (m, 1H), 3.89-4.11 (m, 2H), 7.14-7.39 (m, 9H), 8.32 (s, 1H), 8.36 (br s, 1H), 8.63 (s, 1H), 10.64 (s, 1H).

EXAMPLE 41

N-[7-(4-Methylphenylamino)-6-(4-phenylpiperidine-1-carbonyl)pyrazolo[1,5-a]pyrimidine-3-carbonyl] ethanesulfonamide (compound a-41)

[Step 1]

3-Bromo-7-(4-methylphenylamino)-6-(4-phenylpiperidine-1-carbonyl)pyrazolo[1,5-a]pyrimidine In the same manner as in Example 1, step 4 and using p-toluidine (0.77 g, 7.15 mmol) instead of benzylamine, the title compound (0.18 g, 51%) was obtained.

[Step 2]

7-(4-Methylphenylamino)-6-(4-phenylpiperidine-1-carbonyl)pyrazolo[1,5-a]pyrimidine-3-carboxylic acid In the same manner as in Example 1, step 5 and using 3-bromo-7-(4-methylphenylamino)-6-(4-phenylpiperidine-1-carbonyl)pyrazolo[1,5-a]pyrimidine (0.18 g, 0.36 mmol) obtained in step 1, the title compound (0.17 g, 100%) was obtained.

[Step 3]

N-[7-(4-Methylphenylamino)-6-(4-phenylpiperidine-1-carbonyl)pyrazolo[1,5-a]pyrimidine-3-carbonyl] ethanesulfonamide (compound a-41)

In the same manner as in Example 1, step 6 and using 7-(4-methylphenylamino)-6-(4-phenylpiperidine-1-carbonyl)pyrazolo[1,5-a]pyrimidine-3-carboxylic acid (0.17 g, 0.36 mmol) obtained in step 2 and ethanesulfonamide (0.20 g, 1.89 mmol), the title compound (0.03 g, 14%) was obtained.

ESI-MS m/z: 547 (M+H)$^+$)$^+$; $^1$H-NMR (CDCl$_3$, δ): 1.46 (t, J=7.0 Hz, 3H), 1.51-1.59 (m, 2H), 1.76-1.81 (m, 2H), 2.41 (s, 3H), 2.57-2.68 (m, 3H), 3.62 (q, J=7.0 Hz, 2H), 3.85-4.15 (m, 2H), 7.13-7.35 (m, 9H), 8.39 (s, 1H), 8.51 (br s, 1H), 8.62 (s, 1H), 10.52 (s, 1H).

EXAMPLE 42

N-[7-(3-Methylphenylamino)-6-(4-phenylpiperidine-1-carbonyl)pyrazolo[1,5-a]pyrimidine-3-carbonyl] ethanesulfonamide (compound a-42)

[Step 1]

3-Bromo-7-(3-methylphenylamino)-6-(4-phenylpiperidine-1-carbonyl)pyrazolo[1,5-a]pyrimidine In the same manner as in Example 1, step 4 and using m-toluidine (0.077 g, 0.715 mmol) instead of benzylamine, the title compound (0.196 g, 56%) was obtained.

[Step 2]

7-(3-Methylphenylamino)-6-(4-phenylpiperidine-1-carbonyl)pyrazolo[1,5-a]pyrimidine-3-carboxylic acid In the same manner as in Example 1, step 5 and using 3-bromo-7-(3-methylphenylamino)-6-(4-phenylpiperidine-1-carbonyl)pyrazolo[1,5-a]pyrimidine (0.196 g, 0.40 mmol) obtained in step 1, the title compound (0.123 g, 80%) was obtained.

[Step 3]

N-[7-(3-Methylphenylamino)-6-(4-phenylpiperidine-1-carbonyl)pyrazolo[1,5-a]pyrimidine-3-carbonyl] ethanesulfonamide (compound a-42)

In the same manner as in Example 1, step 6 and using 7-(3-methylphenylamino)-6-(4-phenylpiperidine-1-carbonyl)pyrazolo[1,5-a]pyrimidine-3-carboxylic acid (0.061 g, 0.14 mmol) obtained in step 2 and ethanesulfonamide (0.073 g, 0.70 mmol), the title compound (0.021 g, 27%) was obtained.

ESI-MS m/z: 547 (M+H)$^+$; $^1$H-NMR (CDCl$_3$, δ): 1.46 (t, J=7.0 Hz, 3H), 1.51-1.59 (m, 2H), 1.75-1.80 (m, 2H), 2.42 (s, 3H), 2.54-2.63 (m, 3H), 3.61 (q, J=7.0 Hz, 2H), 3.85-4.15 (m, 2H), 7.10-7.38 (m, 9H), 8.44 (s, 1H), 8.56 (br s, 1H), 8.62 (s, 1H), 10.51 (s, 1H).

EXAMPLE 43

N-[7-(2-Chlorophenylamino)-6-(4-phenylpiperidine-1-carbonyl)pyrazolo[1,5-a]pyrimidine-3-carbonyl] ethanesulfonamide (compound a-43)

[Step 1]

3-Bromo-7-(2-chlorophenylamino)-6-(4-phenylpiperidine-1-carbonyl)pyrazolo[1,5-a]pyrimidine In the same manner as in Example 1, step 4 and using 2-chloroaniline (0.23 mL, 2.14 mmol) instead of benzylamine, the title compound (0.61 g, 84%) was obtained.

[Step 2]

7-(2-Chlorophenylamino)-6-(4-phenylpiperidine-1-carbonyl)pyrazolo[1,5-a]pyrimidine-3-carboxylic acid In the same manner as in Example 1, step 5 and using 3-bromo-7-(2-chlorophenylamino)-6-(4-phenylpiperidine- 1-carbonyl)pyrazolo[1,5-a]pyrimidine (0.61 g, 1.19 mmol) obtained in step 1, the title compound (0.51 g, 90%) was obtained.

[Step 3]

N-[7-(2-Chlorophenylamino)-6-(4-phenylpiperidine-1-carbonyl)pyrazolo[1,5-a]pyrimidine-3-carbonyl]ethanesulfonamide (compound a-43)

In the same manner as in Example 1, step 6 and using 7-(2-chlorophenylamino)-6-(4-phenylpiperidine-1-carbonyl)pyrazolo[1,5-a]pyrimidine-3-carboxylic acid (0.25 g, 0.53 mmol) obtained in step 2 and ethanesulfonamide (0.32 g, 2.63 mmol), the title compound (0.14 g, 47%) was obtained.

ESI-MS m/z: 567 (M+H)+; $^1$H-NMR (CDCl$_3$, δ): 1.46 (t, J=7.0 Hz, 3H), 1.51-1.59 (m, 2H), 1.78-1.83 (m, 2H), 2.58-2.67 (m, 3H), 3.62 (q, J=7.0 Hz, 2H), 3.85-4.15 (m, 2H), 7.13-7.43 (m, 8H), 7.55-7.58 (m, 1H), 8.45 (s, 1H), 8.58 (br s, 1H), 8.65 (s, 1H), 10.48 (s, 1H).

EXAMPLE 44

N-[7-(2-Methoxyphenylamino)-6-(4-phenylpiperidine-1-carbonyl)pyrazolo[1,5-a]pyrimidine-3-carbonyl]ethanesulfonamide (compound a-44)

[Step 1]

3-Bromo-7-(2-methoxyphenylamino)-6-(4-phenylpiperidine-1-carbonyl)pyrazolo[1,5-a]pyrimidine In the same manner as in Example 1, step 4 and using 2-methoxyaniline (0.081 mL, 0.71 mmol) instead of benzylamine, the title compound (0.21 g, 88%) was obtained.

[Step 2]

7-(2-Methoxyphenylamino)-6-(4-phenylpiperidine-1-carbonyl)pyrazolo[1,5-a]pyrimidine-3-carboxylic acid In the same manner as in Example 1, step 5 and using 3-bromo-7-(2-methoxyphenylamino)-6-(4-phenylpiperidine-1-carbonyl)pyrazolo[1,5-a]pyrimidine (0.21 g, 0.42 mmol) obtained in step 1, the title compound (0.110 g, 55%) was obtained.

[Step 3]

N-[7-(2-Methoxyphenylamino)-6-(4-phenylpiperidine-1-carbonyl)pyrazolo[1,5-a]pyrimidine-3-carbonyl]ethanesulfonamide (compound a-44)

In the same manner as in Example 1, step 6 and using 7-(2-methoxyphenylamino)-6-(4-phenylpiperidine-1-carbonyl)pyrazolo[1,5-a]pyrimidine-3-carboxylic acid (0.054 g, 0.11 mmol) obtained in step 2 and ethanesulfonamide (0.059 g, 0.55 mmol), the title compound (0.031 g, 34%) was obtained.

ESI-MS m/z: 563 (M+H)+; $^1$H-NMR (CDCl$_3$, δ): 1.28 (t, J=7.0 Hz, 3H), 1.51-1.62 (m, 2H), 1.60-1.69 (m, 2H), 2.58-2.67 (m, 3H), 3.61 (q, J=7.0 Hz, 2H), 3.73 (s, 3H), 3.85-4.15 (m, 2H), 6.95-7.36 (m, 9H), 8.42 (s, 1H), 8.75 (s, 1H), 10.16 (s, 1H).

EXAMPLE 45

N-[7-(2-Methylthiophenylamino)-6-(4-phenylpiperidine-1-carbonyl)pyrazolo[1,5-a]pyrimidine-3-carbonyl]ethanesulfonamide (compound a-45)

[Step 1]

3-Bromo-7-(2-methylthiophenylamino)-6-(4-phenylpiperidine-1-carbonyl)pyrazolo[1,5-a]pyrimidine In the same manner as in Example 1, step 4 and using 2-methylthioaniline (0.090 g, 0.71 mmol) instead of benzylamine, the title compound (0.232 g, 93%) was obtained.

[Step 2]

7-(2-Methylthiophenylamino)-6-(4-phenylpiperidine-1-carbonyl)pyrazolo[1,5-a]pyrimidine-3-carboxylic acid In the same manner as in Example 1, step 5 and using 3-bromo-7-(2-methylthiophenylamino)-6-(4-phenylpiperidine-1-carbonyl)pyrazolo[1,5-a]pyrimidine (0.232 g, 0.44 mmol) obtained in step 1, the title compound (0.157 g, 73%) was obtained.

[Step 3]

N-[7-(2-Methylthiophenylamino)-6-(4-phenylpiperidine-1-carbonyl)pyrazolo[1,5-a]pyrimidine-3-carbonyl]ethanesulfonamide (compound a-45)

In the same manner as in Example 1, step 6 and using 7-(2-methylthiophenylamino)-6-(4-phenylpiperidine-1-carbonyl)pyrazolo[1,5-a]pyrimidine-3-carboxylic acid (0.077 g, 0.16 mmol) obtained in step 2 and ethanesulfonamide (0.084 g, 0.80 mmol), the title compound (0.040 g, 43%) was obtained.

ESI-MS m/z: 579 (M+H)+; $^1$H-NMR (CDCl$_3$, δ): 1.46 (t, J=7.0 Hz, 3H), 1.51-1.59 (m, 2H), 1.76-1.81 (m, 2H), 2.52 (s, 3H), 2.56-2.68 (m, 3H), 3.61 (q, J=7.0 Hz, 2H), 3.85-4.15 (m, 2H), 7.12-7.37 (m, 9H), 8.40 (s, 1H), 8.55 (br s, 1H), 8.64 (s, 1H, 10.52 (s, 1H).

EXAMPLE 46

N-[7-(2-Methanesulfonylphenylamino)-6-(4-phenylpiperidine-1-carbonyl)pyrazolo[1,5-a]pyrimidine-3-carbonyl]ethanesulfonamide (compound a-46)

N-[7-(2-Methylthiophenylamino)-6-(4-phenylpiperidine-1-carbonyl)pyrazolo[1,5-a]pyrimidine-3-carbonyl]ethanesulfonamide (0.02 g, 0.03 mmol) obtained in Example 45, step 3 was dissolved in acetonitrile (1 mL) and water (0.5 mL), OXONE (0.05 mg, 0.08 mmol) was added, and the mixture was stirred at 40° C. for 1 hr. Aqueous sodium thiosulfate solution was added to the reaction mixture, and the mixture was extracted with chloroform. The organic layer was washed with water, and dried over anhydrous magnesium sulfate. The solvent was evaporated under reduced pressure, and the residue was purified by silica gel column chromatography (chloroform/methanol=95/5) to give the title compound (0.02 g, 71%).

ESI-MS m/z: 611 (M+H)+; $^1$H-NMR (CDCl$_3$, δ): 1.46 (t, J=7.0 Hz, 3H), 1.51-1.59 (m, 2H), 1.76-1.81 (m, 2H), 2.56-2.68 (m, 3H), 3.24 (s, 3H), 3.61 (q, J=7.0 Hz, 2H), 3.85-4.15 (m, 2H), 7.12-7.37 (m, 9H), 8.40 (s, 1H), 8.55 (br s, 1H), 8.64 (s, 1H), 10.52 (s, 1H).

EXAMPLE 47

N-[7-(Biphenyl-2-ylamino)-6-(4-phenylpiperidine-1-carbonyl)pyrazolo[1,5-a]pyrimidine-3-carbonyl]cyclopropanesulfonamide (compound a-47)

[Step 1]

7-(Biphenyl-2-ylamino)-3-bromo-6-(4-phenylpiperidine-1-carbonyl)pyrazolo[1,5-a]pyrimidine In the same manner as in Example 1, step 4 and using biphenyl-2-amine (0.120 g, 0.71 mmol) instead of benzylamine, the title compound (0.272 g, 100%) was obtained.

[Step 2]

7-(Biphenyl-2-ylamino)-6-(4-phenylpiperidine-1-carbonyl)pyrazolo[1,5-a]pyrimidine-3-carboxylic acid In the same manner as in Example 1, step 5 and using 7-(biphenyl-2-ylamino)-3-bromo-6-(4-phenylpiperidine-1-carbonyl)pyrazolo[1,5-a]pyrimidine (0.272 g, 0.47 mmol) obtained in step 1, the title compound (0.202 g, 80%) was obtained.

[Step 3]

N-[7-(Biphenyl-2-ylamino)-6-(4-phenylpiperidine-1-carbonyl)pyrazolo[1,5-a]pyrimidine-3-carbonyl]cyclopropanesulfonamide (compound a-47)

In the same manner as in Example 1, step 6 and using 7-(biphenyl-2-ylamino)-6-(4-phenylpiperidine-1-carbonyl)pyrazolo[1,5-a]pyrimidine-3-carboxylic acid (61 mg, 0.14 mmol) obtained in step 2 and cyclopropanesulfonamide (73 mg, 0.70 mmol), the title compound (21 mg, 27%) was obtained.

ESI-MS m/z: 621 (M+H)$^+$; $^1$H-NMR (CDCl$_3$, δ): 1.10-1.14 (m, 2H), 1.46-1.65 (m, 4H), 1.89-1.93 (m, 2H), 2.74-2.89 (m, 3H), 3.06-3.12 (m, 1H), 4.18 (br s, 2H), 7.19-7.55 (m, 14H), 8.34 (s, 1H), 8.48 (br s, 1H), 8.51 (s, 1H), 10.62 (br s, 1H).

EXAMPLE 48

N-[7-(2-Benzyloxyphenylamino)-6-(4-phenylpiperidine-1-carbonyl)pyrazolo[1,5-a]pyrimidine-3-carbonyl]ethanesulfonamide (compound a-48)

[Step 1]

7-(2-Benzyloxyphenylamino)-3-bromo-6-(4-phenylpiperidine-1-carbonyl)pyrazolo[1,5-a]pyrimidine In the same manner as in Example 1, step 4 and using 2-benzyloxyaniline (356 mg, 1.79 mmol) instead of benzylamine, the title compound (696 mg, 99%) was obtained.

[Step 2]

7-(2-Benzyloxyphenylamino)-6-(4-phenylpiperidine-1-carbonyl)pyrazolo[1,5-a]pyrimidine-3-carboxylic acid In the same manner as in Example 1, step 5 and using 7-(2-benzyloxyphenylamino)-3-bromo-6-(4-phenylpiperidine-1-carbonyl)pyrazolo[1,5-a]pyrimidine (690 mg, 1.19 mmol) obtained in step 1, the title compound (469 mg, 72%) was obtained.

[Step 3]

N-[7-(2-Benzyloxyphenylamino)-6-(4-phenylpiperidine-1-carbonyl)pyrazolo[1,5-a]pyrimidine-3-carbonyl]ethanesulfonamide (compound a-48)

In the same manner as in Example 1, step 6 and using 7-(2-benzyloxyphenylamino)-6-(4-phenylpiperidine-1-carbonyl)pyrazolo[1,5-a]pyrimidine-3-carboxylic acid (200 mg, 0.37 mmol) obtained in step 2 and ethanesulfonamide (192 mg, 1.85 mmol), the title compound (146 mg, 63%) was obtained.

ESI-MS m/z: 570 (M+H)$^+$; $^1$H-NMR (CDCl$_3$, δ): 1.40-1.51 (m, 2H), 1.46 (t, J=7.6 Hz, 3H), 1.72-1.81 (m, 2H), 2.52-2.65 (m, 3H), 3.61 (q, J=7.4 Hz, 2H), 3.97 (br s, 2H), 5.04 (s, 2H) 7.02-7.35 (m, 14H), 8.36 (s, 1H), 8.53 (br s, 1H), 9.59 (s, 1H), 10.53 (br s, 1H).

EXAMPLE 49

N-[7-(2-Hydroxyphenylamino)-6-(4-phenylpiperidine-1-carbonyl)pyrazolo[1,5-a]pyrimidine-3-carbonyl]ethanesulfonamide (compound a-49)

N-[7-(2-Benzyloxyphenylamino)-6-(4-phenylpiperidine-1-carbonyl)pyrazolo[1,5-a]pyrimidine-3-carbonyl]ethanesulfonamide (120 mg, 0.19 mmol) obtained in Example 48, step 3 was dissolved in THF (5 mL), 10 wt % palladium-activated carbon (12 mg) was added, and the mixture was stirred at room temperature for 7 hr under a hydrogen atmosphere, and at 60° C. for 1 hr. The mixture was allowed to cool, and the reaction mixture was filtered. The obtained solvent was evaporated under reduced pressure to give the title compound (85 mg, 88%).

ESI-MS m/z: 549 (M+H)$^+$; $^1$H-NMR (DMSO-d$_6$, δ): 1.28 (t, J=7.3 Hz, 3H), 1.59-1.68 (m, 2H), 2.05-2.23 (m, 2H), 2.55-2.69 (m, 1H), 2.89-3.06 (m, 1H), 3.57 (q, J=7.3 Hz, 2H), 3.69-3.84 (m, 1H), 3.95-4.09 (m, 2H), 6.82 (t, J=7.4 Hz, 1H), 6.92 (d, J=7.9 Hz, 1H), 7.13-7.34 (m, 7H), 8.41 (s, 1H), 8.75 (s, 1H), 9.81 (s, 1H), 10.06 (s, 1H), 10.76 (br s, 1H).

EXAMPLE 50

N-[7-(2-Difluoromethoxyphenylamino)-6-(4-phenylpiperidine-1-carbonyl)pyrazolo[1,5-a]pyrimidine-3-carbonyl]ethanesulfonamide (compound a-50)

[Step 1]

3-Bromo-7-(2-difluoromethoxyphenylamino)-6-(4-phenylpiperidine-1-carbonyl)pyrazolo[1,5-a]pyrimidine In the same manner as in Example 1, step 4 and using 2-difluoromethoxyaniline (0.09 mL, 0.48 mmol) instead of benzylamine, the title compound (248 mg, 96%) was obtained.

[Step 2]

7-(2-Difluoromethoxy)-6-(4-phenylpiperidine-1-carbonyl)pyrazolo[1,5-a]pyrimidine-3-carboxylic acid In the same manner as in Example 1, step 5 and using 3-bromo-7-(2-difluoromethoxyphenylamino)-6-(4-phenylpiperidine-1-carbonyl)pyrazolo[1,5-a]pyrimidine (248 mg, 0.46 mmol) obtained in step 1, the title compound (126 mg, 54%) was obtained.

[Step 3]

N-[7-(2-Difluoromethoxyphenylamino)-6-(4-phenylpiperidine-1-carbonyl)pyrazolo[1,5-a]pyrimidine-3-carbonyl]ethanesulfonamide (compound a-50)

In the same manner as in Example 1, step 6 and using 7-(2-difluoromethoxy)-6-(4-phenylpiperidine-1-carbonyl)pyrazolo[1,5-a]pyrimidine-3-carboxylic acid (63 mg, 0.12 mmol) obtained in step 2 and ethanesulfonamide (63 mg, 0.60 mmol), the title compound (45 mg, 63%) was obtained.

ESI-MS m/z: 599 (M+H)$^+$; $^1$H-NMR (CDCl$_3$, δ): 1.46 (t, J=7.5 Hz, 3H), 1.50-1.62 (m, 2H), 1.82-1.87 (m, 2H), 2.54-2.80 (m, 3H), 3.61 (q, J=7.5 Hz, 2H), 4.03 (br s, 2H), 6.64 (t, J=72.8 Hz, 1H), 7.13-7.45 (m, 9H), 8.40 (s, 1H), 8.54 (br s, 1H), 8.63 (s, 1H), 10.50 (br s, 1H).

EXAMPLE 51

N-[7-(4-Fluorophenylamino)-6-(4-phenylpiperidine-1-carbonyl)pyrazolo[1,5-a]pyrimidine-3-carbonyl]cyclopropanesulfonamide (compound a-51)

[Step 1]

3-Bromo-7-(4-fluorophenylamino)-6-(4-phenylpiperidine-1-carbonyl)pyrazolo[1,5-a]pyrimidine In the same manner as in Example 1, step 4 and using 4-fluoroaniline (0.07 mL, 0.71 mmol) instead of benzylamine, the title compound (228 mg, 96%) was obtained.

[Step 2]

7-(4-Fluorophenylamino)-6-(4-phenylpiperidine-1-carbonyl)pyrazolo[1,5-a]pyrimidine-3-carboxylic acid In the same manner as in Example 1, step 5 and using 3-bromo-7-(4-fluorophenylamino)-6-(4-phenylpiperidine-1-carbonyl)pyrazolo[1,5-a]pyrimidine (228 mg, 0.46 mmol) obtained in step 1, the title compound (121 mg, 57%) was obtained.

[Step 3]

N-[7-(4-Fluorophenylamino)-6-(4-phenylpiperidine-1-carbonyl)pyrazolo[1,5-a]pyrimidine-3-carbonyl]cyclopropanesulfonamide (compound a-51)

In the same manner as in Example 1, step 6 and using 7-(4-fluorophenylamino)-6-(4-phenylpiperidine-1-carbonyl)pyrazolo[1,5-a]pyrimidine-3-carboxylic acid (55 mg, 0.12 mmol) obtained in step 2 and cyclopropanesulfonamide (72 mg, 0.59 mmol), the title compound (30 mg, 44%) was obtained.

ESI-MS m/z: 563 (M+H)$^+$; $^1$H-NMR (CDCl$_3$, δ): 1.10-1.17 (m, 2H), 1.45-1.51 (m, 2H), 1.51-1.55 (m, 2H), 1.78-1.87 (m, 2H), 2.59-2.70 (m, 3H), 3.06-3.15 (m, 1H), 3.96-4.22 (m, 2H), 7.13-7.36 (m, 9H), 8.39 (s, 1H), 8.50 (s, 1H), 8.63 (s, 1H), 10.59 (s, 1H).

EXAMPLE 52

N-[7-(2-Methylphenylamino)-6-(4-phenylpiperidine-1-carbonyl)pyrazolo[1,5-a]pyrimidine-3-carbonyl]2,2,2-trifluoroethanesulfonamide (compound a-52)

In the same manner as in Example 1, step 6 and using 7-(2-methylphenylamino)-6-(4-phenylpiperidine-1-carbonyl)pyrazolo[1,5-a]pyrimidine-3-carboxylic acid (0.12 g, 0.27 mmol) obtained in Example 39, step 2 and 2,2,2-trifluoroethanesulfonamide (WO1984/02650, 0.21 g, 1.33 mmol), the title compound (0.07 g, 43%) was obtained.

ESI-MS m/z: 601 (M+H)$^+$; $^1$H-NMR (CDCl$_3$, δ): 1.51-1.59 (m, 2H), 1.79-1.84 (m, 2H), 2.42 (s, 3H), 2.60-2.68 (m, 3H), 3.85-4.15 (m, 2H), 4.38 (q, J=5.4 Hz, 2H), 7.14-7.39 (m, 9H), 8.25 (s, 1H), 8.57 (s, 1H).

Example 53

N-[7-(2-Methylphenylamino)-6-(4-phenylpiperidine-1-carbonyl)pyrazolo[1,5-a]pyrimidine-3-carbonyl]-3,5-dimethylisoxazole-4-sulfonamide (compound a-53)

In the same manner as in Example 1, step 6 and using 7-(2-methylphenylamino)-6-(4-phenylpiperidine-1-carbonyl)pyrazolo[1,5-a]pyrimidine-3-carboxylic acid (0.08 g, 0.18 mmol) obtained in Example 39, step 2 and 3,5-dimethylisoxazole-4-sulfonamide (0.16 g, 0.88 mmol), the title compound (0.07 g, 66%) was obtained.

ESI-MS m/z: 614 (M+H)$^+$; $^1$H-NMR (CDCl$_3$, δ): 1.43-1.57 (m, 2H), 1.82 (d, J=13.2 Hz, 2H), 2.41 (s, 3H), 2.47 (s, 3H), 2.60-2.69 (m, 1H), 2.82 (s, 3H), 3.83-4.28 (m, 4H), 7.15-7.39 (m, 9H), 8.35 (s, 1H), 8.36 (s, 1H), 8.54 (s, 1H), 11.00 (s, 1H).

EXAMPLE 54

N-[7-(o-Tolylamino)-6-(4-phenylpiperidine-1-carbonyl)pyrazolo[1,5-a]pyrimidine-3-carbonyl]-5-chloro-1,3-dimethyl-1H-pyrazole-4-sulfonamide (compound a-54)

In the same manner as in Example 1, step 6 and using 7-(2-methylphenylamino)-6-(4-phenylpiperidine-1-carbonyl)pyrazolo[1,5-a]pyrimidine-3-carboxylic acid (0.08 g, 0.18 mmol) obtained in Example 39, step 2 and 5-chloro-1,3-dimethyl-1H-pyrazole-4-sulfonamide (0.18 g, 0.88 mmol), the title compound (0.10 g, 90%) was obtained.

ESI-MS m/z: 647 (M+H)$^+$; $^1$H-NMR (CDCl$_3$, δ): 1.40-1.53 (m, 2H), 1.81 (d, J=13.6 Hz, 2H), 2.41 (s, 3H), 2.55 (s, 3H), 2.60-2.68 (m, 1H), 3.81 (s, 3H), 3.87-4.21 (m, 4H), 7.15-7.39 (m, 9H), 8.32 (s, 1H), 8.36 (s, 1H), 8.55 (s, 1H), 11.00 (s, 1H).

EXAMPLE 55

N-[7-(3-Fluoro-2-methylphenylamino)-6-(4-phenylpiperidine-1-carbonyl)pyrazolo[1,5-a]pyrimidine-3-carbonyl]ethanesulfonamide (compound a-55)

[Step 1]

3-Bromo-7-(3-fluoro-2-methylphenylamino)-6-(4-phenylpiperidine-1-carbonyl)pyrazolo[1,5-a]pyrimidine In the same manner as in Example 1, step 4 and using 3-fluoro-2-methylaniline (134 mg, 1.07 mmol) instead of benzylamine, the title compound (356 mg, 97%) was obtained.

[Step 2]

7-(3-Fluoro-2-methylphenylamino)-6-(4-phenylpiperidine-1-carbonyl)pyrazolo[1,5-a]pyrimidine-3-carboxylic acid In the same manner as in Example 1, step 5 and using 3-bromo-7-(3-fluoro-2-methylphenylamino)-6-(4-phenylpiperidine-1-carbonyl)pyrazolo[1,5-a]pyrimidine (350 mg, 0.69 mmol) obtained in step 1, the title compound (251 mg, 65%) was obtained.

[Step 3]

N-[7-(3-Fluoro-2-methylphenylamino)-6-(4-phenylpiperidine-1-carbonyl)pyrazolo[1,5-a]pyrimidine-3-carbonyl]ethanesulfonamide (compound a-55)

In the same manner as in Example 1, step 6 and using 7-(3-fluoro-2-methylphenylamino)-6-(4-phenylpiperidine-1-carbonyl)pyrazolo[1,5-a]pyrimidine-3-carboxylic acid (125 mg, 0.26 mmol) obtained in step 2 and ethanesulfonamide (139 mg, 1.32 mmol), the title compound (53 mg, 36%) was obtained.

ESI-MS m/z: 565 (M+H)$^+$; $^1$H-NMR (CDCl$_3$, δ): 1.46 (t, J=7.4 Hz, 3H), 1.54-1.57 (m, 2H), 1.82-1.87 (m, 2H), 2.34 (br s, 3H), 2.65-2.69 (m, 3H), 3.61 (q, J=7.4 Hz, 2H), 3.85-4.20 (m, 2H), 7.00-7.36 (m, 8H), 8.36-8.38 (m, 2H), 8.63 (s, 1H), 10.51 (s, 1H).

EXAMPLE 56

N-[7-(3-Fluoro-2-methylphenylamino)-6-(4-phenylpiperidine-1-carbonyl)pyrazolo[1,5-a]pyrimidine-3-carbonyl]cyclopropanesulfonamide (compound a-56)

In the same manner as in Example 1, step 6 and using 7-(3-fluoro-2-methylphenylamino)-6-(4-phenylpiperidine-1-carbonyl)pyrazolo[1,5-a]pyrimidine-3-carboxylic acid (125 mg, 0.26 mmol) obtained in Example 55, step 2 and cyclopropanesulfonamide (160 mg, 1.32 mmol), the title compound (17 mg, 11%) was obtained.

ESI-MS m/z: 577 (M+H)$^+$; $^1$H-NMR (CDCl$_3$, δ): 1.10-1.15 (n, 2H), 1.47-1.50 (m, 2H), 1.50-1.54 (m, 2H), 1.82-1.86 (m, 2H), 2.34 (d, J=1.8 Hz, 3H), 2.65-2.72 (m, 3H), 3.07-3.15 (m, 1H, 3.80-4.20 (m, 2H), 7.00-7.36 (m, 8H), 8.35 (m, 2H), 8.64 (s, 1H), 10.60 (s, 1H).

EXAMPLE 57

N-[7-(4-Fluoro-2-methylphenylamino)-6-(4-phenylpiperidine-1-carbonyl)pyrazolo[1,5-a]pyrimidine-3-carbonyl]ethanesulfonamide (compound a-57)

[Step 1]

3-Bromo-7-(4-fluoro-2-methylphenylamino)-6-(4-phenylpiperidine-1-carbonyl)pyrazolo[1,5-a]pyrimidine In the same manner as in Example 1, step 4 and using 4-fluoro-2-methylaniline (0.06 mL, 0.54 mmol) instead of benzylamine, the title compound (176 mg, 96%) was obtained.

[Step 2]

7-(4-Fluoro-2-methylphenylamino)-6-(4-phenylpiperidine-1-carbonyl)pyrazolo[1,5-a]pyrimidine-3-carboxylic acid In the same manner as in Example 1, step 5 and using 3-bromo-7-(4-fluoro-2-methylphenylamino)-6-(4-phenylpiperidine-1-carbonyl)pyrazolo[1,5-a]pyrimidine (176 mg, 0.35 mmol) obtained in step 1, the title compound (94 mg, 57%) was obtained.

[Step 3]

N-[7-(4-Fluoro-2-methylphenylamino)-6-(4-phenylpiperidine-1-carbonyl)pyrazolo[1,5-a]pyrimidine-3-carbonyl]ethanesulfonamide (compound a-57)

In the same manner as in Example 1, step 6 and using 7-(4-fluoro-2-methylphenylamino)-6-(4-phenylpiperidine-1-carbonyl)pyrazolo[1,5-a]pyrimidine-3-carboxylic acid (47 mg, 0.10 mmol) obtained in step 2 and ethanesulfonamide (52 mg, 0.5 mmol), the title compound (16 mg, 28%) was obtained.

ESI-MS m/z: 565 (M+H)$^+$; $^1$H-NMR (CDCl$_3$, δ): 1.45 (t, J=7.3 Hz, 3H), 1.55-1.68 (m, 2H), 1.83-1.87 (m, 2H), 2.40 (s, 3H), 2.64-2.73 (m, 3H), 3.61 (q, J=7.4 Hz, 2H), 4.07 (br s, 2H), 6.97 (dt, J=2.8, 8.2 Hz, 1H), 7.09 (dd, J=2.6, 8.9 Hz, 1H), 7.16-7.37 (m, 6H), 8.26 (br s, 1H), 8.30 (s, 1H), 8.62 (s, 1H), 10.52 (br s, 1H).

EXAMPLE 58

N-[7-(3-Chloro-2-methylphenylamino)-6-(4-phenylpiperidine-1-carbonyl)pyrazolo[1,5-a]pyrimidine-3-carbonyl]ethanesulfonamide (compound a-58)

[Step 1]

3-Bromo-7-(3-chloro-2-methylphenylamino)-6-(4-phenylpiperidine-1-carbonyl)pyrazolo[1,5-a]pyrimidine In the same manner as in Example 1, step 4 and using 3-chloro-2-methylaniline (0.07 mL, 0.54 mmol) instead of benzylamine, the title compound (165 mg, 88%) was obtained.

[Step 2]

7-(3-Chloro-2-methylphenylamino)-6-(4-phenylpiperidine-1-carbonyl)pyrazolo[1,5-a]pyrimidine-3-carboxylic acid In the same manner as in Example 1, step 5 and using 3-bromo-7-(3-chloro-2-methylphenylamino)-6-(4-phenylpiperidine-1-carbonyl)pyrazolo[1,5-a]pyrimidine (165 mg, 0.32 mmol) obtained in step 1, the title compound (106 mg, 68%) was obtained.

[Step 3]

N-[7-(3-Chloro-2-methylphenylamino)-6-(4-phenylpiperidine-1-carbonyl)pyrazolo[1,5-a]pyrimidine-3-carbonyl]ethanesulfonamide (compound a-58)

In the same manner as in Example 1, step 6 and using 7-(3-chloro-2-methylphenylamino)-6-(4-phenylpiperidine-1-carbonyl)pyrazolo[1,5-a]pyrimidine-3-carboxylic acid (53 mg, 0.11 mmol) obtained in step 2 and ethanesulfonamide (58 mg,' 0.55 mmol), the title compound (32 mg, 50%) was obtained.

ESI-MS m/z: 582 (M+H)$^+$; $^1$H-NMR (CDCl$_3$, δ): 1.46 (t, J=7.4 Hz, 3H), 1.48-1.56 (m, 2H), 1.83-1.87 (m, 2H), 1.97 (br s, 2H), 2.46 (s, 3H), 2.62-2.71 (m, 1H), 3.61 (q, J=7.3 Hz, 2H), 4.05 (br s, 2H), 7.14-7.46 (m, 8H), 8.35 (s, 1H), 8.41 (br s, 1H), 8.63 (s, 1H), 10.50 (br s, 1H).

EXAMPLE 59

N-[7-(2-Fluoro-5-methylphenylamino)-6-(4-phenylpiperidine-1-carbonyl)pyrazolo[1,5-a]pyrimidine-3-carbonyl]ethanesulfonamide (compound a-59)

[Step 1]

3-Bromo-7-(2-fluoro-5-methylphenylamino)-6-(4-phenylpiperidine-1-carbonyl)pyrazolo[1,5-a]pyrimidine In the same manner as in Example 1, step 4 and using 2-fluoro-5-methylaniline (0.08 mL, 0.71 mmol) instead of benzylamine, the title compound (238 mg, 98%) was obtained.

[Step 2]

7-(2-Fluoro-5-methylphenylamino)-6-(4-phenylpiperidine-1-carbonyl)pyrazolo[1,5-a]pyrimidine-3-carboxylic acid In the same manner as in Example 1, step 5 and using 3-bromo-7-(2-fluoro-5-methylphenylamino)-6-(4-phenylpiperidine-1-carbonyl)pyrazolo[1,5-a]pyrimidine (237 mg, 0.47 mmol) obtained in step 1, the title compound (176 mg, 79%) was obtained.

[Step 3]

N-[7-(2-Fluoro-5-methylphenylamino)-6-(4-phenylpiperidine-1-carbonyl)pyrazolo[1,5-a]pyrimidine-3-carbonyl]ethanesulfonamide (compound a-59)

In the same manner as in Example 1, step 6 and using 7-(2-fluoro-5-methylphenylamino)-6-(4-phenylpiperidine-1-carbonyl)pyrazolo[1,5-a]pyrimidine-3-carboxylic acid (87 mg, 0.18 mmol) obtained in step 2 and ethanesulfonamide (94 mg, 0.90 mmol), the title compound (25 mg, 25%) was obtained.

ESI-MS m/z: 565 (M+H)$^+$; $^1$H-NMR (CDCl$_3$, δ): 1.46 (t, J=7.4 Hz, 3H), 1.48-1.59 (m, 2H), 1.85-1.97 (m, 2H), 2.37 (s, 3H), 2.62-2.70 (m, 3H), 3.61 (q, J=7.4 Hz, 2H), 4.03 (br s, 2H), 7.08-7.35 (m, 8H), 8.42 (br s, 2H), 8.64 (s, 1H), 10.50 (br s, 1H).

EXAMPLE 60

N-[7-(2-Fluoro-5-methylphenylamino)-6-(4-phenylpiperidine-1-carbonyl)pyrazolo[1,5-a]pyrimidine-3-carbonyl]cyclopropanesulfonamide (compound a-60)

In the same manner as in Example 1, step 6 and using 7-(2-fluoro-5-methylphenylamino)-6-(4-phenylpiperidine-1-carbonyl)pyrazolo[1,5-a]pyrimidine-3-carboxylic acid (87 mg, 0.18 mmol) obtained in Example 59, step 2 and cyclopropanesulfonamide (109 mg, 0.90 mmol), the title compound (62 mg, 59%) was obtained.

ESI-MS m/z: 577 (M+H)$^+$; $^1$H-NMR (CDCl$_3$, δ): 1.12-1.16 (m, 2H), 1.46-1.56 (m, 4H), 1.80-1.85 (m, 2H), 2.37 (s, 3H), 2.61-2.65 (m, 3H), 3.08-3.14 (m, 1H), 4.04 (br s, 2H), 7.07-7.35 (m, 8H), 8.42 (br s, 2H), 8.65 (s, 1H), 10.50 (br s, 1H).

EXAMPLE 61

N-[7-(2,5-Dimethylphenylamino)-6-(4-phenylpiperidine-1-carbonyl)pyrazolo[1,5-a]pyrimidine-3-carbonyl]ethanesulfonamide (compound a-61)

[Step 1]

3-Bromo-7-(2,5-dimethylphenylamino)-6-(4-phenylpiperidine-1-carbonyl)pyrazolo[1,5-a]pyrimidine In the same manner as in Example 1, step 4 and using 2,5-dimethylaniline (0.09 mL, 0.71 mmol) instead of benzylamine, the title compound (230 mg, 95%) was obtained.

[Step 2]

7-(2,5-Dimethylphenylamino)-6-(4-phenylpiperidine-1-carbonyl)pyrazolo[1,5-a]pyrimidine-3-carboxylic acid In the same manner as in Example 1, step 5 and using 3-bromo-7-(2,5-dimethylphenylamino)-6-(4-phenylpiperidine-1-carbonyl)pyrazolo[1,5-a]pyrimidine (229 mg, 0.45 mmol) obtained in step 1, the title compound (199 mg, 94%) was obtained.

[Step 3]

N-[7-(2,5-Dimethylphenylamino)-6-(4-phenylpiperidine-1-carbonyl)pyrazolo[1,5-a]pyrimidine-3-carbonyl]ethanesulfonamide (compound a-61)

In the same manner as in Example 1, step 6 and using 7-(2,5-dimethylphenylamino)-6-(4-phenylpiperidine-1-carbonyl)pyrazolo[1,5-a]pyrimidine-3-carboxylic acid (99 mg, 0.21 mmol) obtained in step 2 and ethanesulfonamide (110 mg, 1.05 mmol), the title compound (50 mg, 42%) was obtained.

ESI-MS m/z: 561 (M+H)$^+$; $^1$H-NMR (CDCl$_3$, δ): 1.46 (t, J=7.4 Hz, 3H), 1.48-1.59 (m, 2H), 1.77-1.82 (m, 2H), 2.35 (s, 3H), 2.37 (s, 3H), 2.55-2.64 (m, 3H), 3.61 (q, J=7.4 Hz, 2H), 4.03 (br s, 2H), 7.06-7.34 (m, 8H), 8.33 (br s, 1H), 8.36 (s, 1H), 8.62 (s, 1H), 10.55 (br s, 1H).

EXAMPLE 62

N-[7-(2-Methyl-5-trifluoromthylphenylamino)-6-(4-phenylpiperidine-1-carbonyl)pyrazolo[1,5-a]pyrimidine-3-carbonyl]cyclopropanesulfonamide (compound a-62)

[Step 1]

3-Bromo-7-(2-methyl-5-trifluoromethylphenylamino)-6-(4-phenylpiperidine-1-carbonyl)pyrazolo[1,5-a]pyrimidine In the same manner as in Example 1, step 4 and using 2-methyl-5-trifluoromethylaniline (126 mg, 0.72 mmol) instead of benzylamine, the title compound (259 mg, 97%) was obtained.

[Step 2]

7-(2-Methyl-5-trifluoromethylphenylamino)-6-(4-phenylpiperidine-1-carbonyl)pyrazolo[1,5-a]pyrimidine-3-carboxylic acid In the same manner as in Example 1, step 5 and using 3-bromo-7-(2-methyl-5-trifluoromethylphenylamino)-6-(4- phenylpiperidine-1-carbonyl)pyrazolo[1,5-a]pyrimidine (259 mg, 0.46 mmol) obtained in step 1, the title compound (212 mg, 88%) was obtained.

[Step 3]

N-[7-(2-Methyl-5-trifluoromethylphenylamino)-6-(4-phenylpiperidine-1-carbonyl)pyrazolo[1,5-a]pyrimidine-3-carbonyl]cyclopropanesulfonamide (compound a-62)

In the same manner as in Example 1, step 6 and using 7-(2-methyl-5-trifluoromethylphenylamino)-6-(4-phenylpiperidine-1-carbonyl)pyrazolo[1,5-a]pyrimidine-3-carboxylic acid (100 mg, 0.19 mmol) obtained in step 2 and cyclopropanesulfonamide (115 mg, 0.95 mmol), the title compound (54 mg, 45%) was obtained.

ESI-MS m/z: 627 (M+H)$^+$; $^1$H-NMR (CDCl$_3$, δ): 1.10-1.18 (m, 2H), 1.45-1.60 (m, 4H), 1.85-1.90 (m, 2H), 2.49 (s, 3H), 2.63-2.72 (m, 3H), 3.07-3.13 (m, 1H), 4.05 (br s, 2H), 7.17-7.59 (m, 8H), 8.36 (s, 1H), 8.41 (br s, 1H), 8.63 (s, 1H), 10.60 (br s, 1H).

EXAMPLE 63

N-[7-(4-Fluoro-3-methylphenylamino)-6-(4-phenylpiperidine-1-carbonyl)pyrazolo[1,5-a]pyrimidine-3-carbonyl]ethanesulfonamide (compound a-63)

[Step 1]

3-Ethoxycarbonyl-7-(4-fluoro-3-methylphenylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (100 mg, 0.24 mmol) obtained in Example 19, step 4 and 4-fluoro-3-methylaniline (46 mg, 0.36 mmol), the title compound (120 mg, 99%) was obtained.

[Step 2]

7-(4-Fluoro-3-methylphenylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(4-fluoro-3-methylphenylamino)-6-(4-phenylpiperidine-1-carbonyl)pyrazolo[1,5-a]pyrimidine (120 mg, 0.24 mmol) obtained in step 1, the title compound (94 mg, 83%) was obtained.

[Step 3]

N-[7-(4-Fluoro-3-methylphenylamino)-6-(4-phenylpiperidine-1-carbonyl)pyrazolo[1,5-a]pyrimidine-3-carbonyl]ethanesulfonamide (compound a-63)

In the same manner as in Example 1, step 6 and using 7-(4-fluoro-3-methylphenylamino)-6-(4-phenylpiperidine-1-carbonyl)pyrazolo[1,5-a]pyrimidine-3-carboxylic acid (60 mg, 0.13 mmol) obtained in step 2 and ethanesulfonamide (56 mg, 0.51 mmol), the title compound (0.041 g, 57%) was obtained.

ESI-MS m/z: 565 (M+H)$^+$; $^1$H-NMR (CDCl$_3$, δ): 1.46 (t, J=7.3 Hz, 3H), 1.48-1.59 (m, 2H), 1.80-1.84 (m, 2H), 2.33 (d, J=1.3 Hz, 3H), 2.58-2.67 (m, 3H), 3.61 (q, J=7.5 Hz, 2H), 4.03 (br s, 2H), 6.87-7.35 (m, 8H), 8.40 (s, 1H), 8.47 (s, 1H), 8.62 (s, 1H), 10.49 (br s, 1H).

EXAMPLE 64

N-[7-(2-Fluoro-3-methylphenylamino)-6-(4-phenylpiperidine-1-carbonyl)pyrazolo[1,5-a]pyrimidine-3-carbonyl]ethanesulfonamide (compound a-64)

[Step 1]

3-Ethoxycarbonyl-7-(2-fluoro-3-methylphenylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (100 mg, 0.24 mmol) obtained in Example 19, step 4 and 2-fluoro-3-methylaniline (46 mg, 0.36 mmol), the title compound (120 mg, 99%) was obtained.

[Step 2]

7-(2-Fluoro-3-methylphenylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(2-fluoro-3-methylphenylamino)-6-(4-phenylpiperidine-1-carbonyl)pyrazolo[1,5-a]pyrimidine (120 mg, 0.24 mmol) obtained in step 1, the title compound (75 mg, 66%) was obtained.

[Step 3]

N-[7-(2-Fluoro-3-methylphenylamino)-6-(4-phenylpiperidine-1-carbonyl)pyrazolo[1,5-a]pyrimidine-3-carbonyl]ethanesulfonamide (compound a-64)

In the same manner as in Example 1, step 6 and using 7-(2-fluoro-3-methylphenylamino)-6-(4-phenylpiperidine-1-carbonyl)pyrazolo[1,5-a]pyrimidine-3-carboxylic acid (35 mg, 0.074 mmol) obtained in step 2 and ethanesulfonamide (33 mg, 0.30 mmol), the title compound (30 mg, 73%) was obtained.

ESI-MS m/z: 565 (M+H)$^+$; $^1$H-NMR (CDCl$_3$, δ): 1.46 (t, J=7.4 Hz, 3H), 1.48-1.59 (m, 2H), 1.81-1.86 (m, 2H), 2.36 (d, J=2.0 Hz, 3H), 2.61-2.70 (m, 3H), 3.61 (q, J=7.4 Hz, 2H), 4.04 (br s, 2H), 7.09-7.36 (m, 8H), 8.42 (s, 1H), 8.45 (br s, 1H), 8.64 (s, 1H), 10.50 (br s, 1H).

EXAMPLE 65

N-[7-(2-Chloro-3-fluorophenylamino)-6-(4-phenylpiperidine-1-carbonyl)pyrazolo[1,5-a]pyrimidine-3-carbonyl]ethanesulfonamide (compound a-65)

[Step 1]

3-Bromo-7-(2-chloro-3-fluorophenylamino)-6-(4-phenylpiperidine-1-carbonyl)pyrazolo[1,5-a]pyrimidine In the same manner as in Example 1, step 4 and using 2-chloro-3-fluoroaniline (0.13 mL, 1.07 mmol) instead of benzylamine, the title compound (228 mg, 60%) was obtained.

[Step 2]

7-(2-Chloro-3-fluorophenylamino)-6-(4-phenylpiperidine-1-carbonyl)pyrazolo[1,5-a]pyrimidine-3-carboxylic acid In the same manner as in Example 1, step 5 and using 3-bromo-7-(2-chloro-3-fluorophenylamino)-6-(4-phenylpiperidine-1-carbonyl)pyrazolo[1,5-a]pyrimidine (228 mg, 0.43 mmol) obtained in step 1, the title compound (154 mg, 73%) was obtained.

[Step 3]

N-[7-(2-Chloro-3-fluorophenylamino)-6-(4-phenylpiperidine-1-carbonyl)pyrazolo[1,5-a]pyrimidine-3-carbonyl]ethanesulfonamide (compound a-65)

In the same manner as in Example 1, step 6 and using 7-(2-chloro-3-fluorophenylamino)-6-(4-phenylpiperidine-1-carbonyl)pyrazolo[1,5-a]pyrimidine-3-carboxylic acid (77 mg, 0.16 mmol) obtained in step 2 and ethanesulfonamide (84 mg, 0.80 mmol), the title compound (28 mg, 28%) was obtained.

ESI-MS m/z: 586 (M+H)$^+$; $^1$H-NMR (CDCl$_3$, δ): 1.36-1.55 (m, 3H), 1.46 (t, J=7.4 Hz, 3H), 1.82-1.87 (m, 2H), 2.62-2.71 (m, 2H), 3.62 (q, J=7.5 Hz, 2H), 4.05 (br s, 2H), 7.13-7.39 (m, 8H), 8.47(s, 1H), 8.63(s, 1H), 8.66 (s, 1H), 10.44 (s, 1H).

EXAMPLE 66

N-[7-(2-Chloro-5-methylphenylamino)-6-(4-phenylpiperidine-1-carbonyl)pyrazolo[1,5-a]pyrimidine-3-carbonyl]ethanesulfonamide (compound a-66)

[Step 1]

Methyl 7-(2-chloro-5-methylphenylamino)-3-ethoxycarbonylpyrazolo[1,5-a]pyrimidine-6-carboxylate In the same manner as in Example 1, step 4 and using methyl 7-chloro-3-ethoxycarbonylpyrazolo[1,5-a]pyrimidine-6-carboxylate (2.2 g, 7.13 mmol) obtained in Example 21, step 2 and 2-chloro-5-methylaniline (1.64 g, 11.6 mmol), the title compound (2.78 g, 92%) was obtained.

[Step 2]

7-(2-Chloro-5-methylphenylamino)-3-ethoxycarbonylpyrazolo[1,5-a]pyrimidine-6-carboxylic acid In the same manner as in Example 21, step 4 and using methyl 7-(2-chloro-5-methylphenylamino)-3-ethoxycarbonylpyrazolo[1,5-a]pyrimidine-6-carboxylate (2.78 g, 7.15 mmol) obtained in step 1, the title compound (2.48 g, 92%) was obtained.

[Step 3]

7-(2-Chloro-5-methylphenylamino)-3-ethoxycarbonyl-6-(4-phenylpiperidine-1-carbonyl)pyrazolo[1,5-a]pyrimidine In the same manner as in Example 21, step 5 and using 7-(2-chloro-5-methylphenylamino)-3-ethoxycarbonylpyrazolo[1,5-a]pyrimidine-6-carboxylic acid (72 mg, 0.17 mmol) obtained in step 2 and 4-phenylpiperidine (37 mg, 0.26 mmol), the title compound (72 mg, 84%) was obtained.

[Step 4]

7-(2-Chloro-5-methylphenylamino)-6-(4-phenylpiperidine-1-carbonyl)pyrazolo[1,5-a]pyrimidine-3-carboxylic acid In the same manner as in Example 19, step 6 and using 7-(2-chloro-5-methylphenylamino)-3-ethoxycarbonyl-6-(4-phenylpiperidine-1-carbonyl)pyrazolo[1,5-a]pyrimidine (72 mg, 0.14 mmol) obtained in step 3, the title compound (44 mg, 65%) was obtained.

[Step 5]

N-[7-(2-Chloro-5-methylphenylamino)-6-(4-phenylpiperidine-1-carbonyl)pyrazolo[1,5-a]pyrimidine-3-carbonyl]ethanesulfonamide (compound a-66)

In the same manner as in Example 1, step 6 and using 7-(2-chloro-5-methylphenylamino)-6-(4-phenylpiperidine-1-carbonyl)pyrazolo[1,5-a]pyrimidine-3-carboxylic acid (40 mg, 0.08 mmol) obtained in step 4 and ethanesulfonamide (36 mg, 0.33 mmol), the title compound (17 mg, 36%) was obtained.

ESI-MS m/z: 582 (M+H)$^+$; $^1$H-NMR (CDCl$_3$, δ): 1.40-1.49 (m, 2H), 1.46 (t, J=7.4 Hz, 3H), 1.76-1.81 (m, 2H), 2.38 (s, 3H), 2.55-2.64 (m, 3H), 3.62 (q, J=7.6 Hz, 2H), 4.04 (br s, 2H), 7.11-7.44 (m, 8H), 8.47 (s, 1H), 8.54 (br s, 1H), 8.64 (s, 1H), 10.48 (br s, 1H).

EXAMPLE 67

N-[7-(2-Chloro-4-fluorophenylamino)-6-(4-phenylpiperidine-1-carbonyl)pyrazolo[1,5-a]pyrimidine-3-carbonyl]ethanesulfonamide (compound a-67)

[Step 1]

3-Bromo-7-(2-chloro-4-fluorophenylamino)-6-(4-phenylpiperidine-1-carbonyl)pyrazolo[1,5-a]pyrimidine In the same manner as in Example 1, step 4 and using 2-chloro-4-fluoroaniline (0.13 mL, 1.07 mmol) instead of benzylamine, the title compound (315 mg, 83%) was obtained.

[Step 2]

7-(2-Chloro-4-fluorophenylamino)-6-(4-phenylpiperidine-1-carbonyl)pyrazolo[1,5-a]pyrimidine-3-carboxylic acid In the same manner as in Example 1, step 5 and using 3-bromo-7-(2-chloro-4-fluorophenylamino)-6-(4-phenylpiperidine-1-carbonyl)pyrazolo[1,5-a]pyrimidine (310 mg, 0.59 mmol) obtained in step 1, the title compound (230 mg, 79%) was obtained.

[Step 3]

N-[7-(2-Chloro-4-fluorophenylamino)-6-(4-phenylpiperidine-1-carbonyl)pyrazolo[1,5-a]pyrimidine-3-carbonyl]ethanesulfonamide (compound a-67)

In the same manner as in Example 1, step 6 and using 7-(2-chloro-4-fluorophenylamino)-6-(4-phenylpiperidine-1-carbonyl)pyrazolo[1,5-a]pyrimidine-3-carboxylic acid (115 mg, 0.23 mmol) obtained in step 2 and ethanesulfonamide (123 mg, 1.17 mmol), the title compound (53 mg, 39%) was obtained.

ESI-MS m/z: 585 (M+H)$^+$; $^1$H-NMR (CDCl$_3$, δ): 1.46 (t, J=7.4 Hz, 3H), 1.51-1.55 (m, 2H), 1.82-1.91 (m, 2H), 2.61-2.76 (m, 3H), 3.61 (q, J=7.4 Hz, 2H), 3.92-4.22 (m, 2H), 7.05-7.51 (m, 8H), 8.39 (s, 1H), 8.51 (s, 1H), 8.64 (s, 1H), 10.47 (s, 1H).

EXAMPLE 68

N-[7-(2,3-Dihydro-1H-inden-4-ylamino)-6-(4-phenylpiperidine-1-carbonyl)pyrazolo[1,5-a]pyrimidine-3-carbonyl]ethanesulfonamide (compound a-68)

[Step 1]

3-Bromo-7-(2,3-dihydro-1H-inden-4-ylamino)-6-(4-phenylpiperidine-1-carbonyl)pyrazolo[1,5-a]pyrimidine In the same manner as in Example 1, step 4 and using 4-aminoindane (0.137 mL, 1.07 mmol) instead of benzylamine, the title compound (344 mg, 93%) was obtained.

[Step 2]

7-(2,3-Dihydro-1H-inden-4-ylamino)-6-(4-phenylpiperidine-1-carbonyl)pyrazolo[1,5-a]pyrimidine-3-carboxylic acid In the same manner as in Example 1, step 5 and using 3-bromo-7-(2,3-dihydro-1H-inden-4-ylamino)-6-(4-phenylpiperidine-1-carbonyl)pyrazolo[1,5-a]pyrimidine (325 mg, 0.63 mmol) obtained in step 1, the title compound (190 mg, 63%) was obtained.

[Step 3]

N-[7-(2,3-Dihydro-1H-inden-4-ylamino)-6-(4-phenylpiperidine-1-carbonyl)pyrazolo[1,5-a]pyrimidine-3-carbonyl]ethanesulfonamide (compound a-68)

In the same manner as in Example 1, step 6 and using 7-(2,3-dihydro-1H-inden-4-ylamino)-6-(4-phenylpiperidine-1-carbonyl)pyrazolo[1,5-a]pyrimidine-3-carboxylic acid (90 mg, 0.19 mmol) obtained in step 2 and ethanesulfonamide (99 mg, 0.94 mmol), the title compound (78 mg, 74%) was obtained.

ESI-MS m/z: 573 (M+H)$^+$; $^1$H-NMR (CDCl$_3$, δ): 1.37-1.52 (m, 3H), 1.46 (t, J=7.3 Hz, 3H), 1.77-1.81 (m, 3H), 2.09-2.19 (m, 2H), 2.56-2.65 (m, 1H), 2.91-3.04 (m, 4H), 3.61 (q, J=7.3 Hz, 2H), 3.99 (br s, 2H), 7.03-7.34 (m, 8H), 8.38 (s, 1H), 8.41 (br s, 1H), 8.62 (s, 1H), 10.54 (br s, 1H).

EXAMPLE 69

N-[7-(1-Methylpyrazol-5-yl)amino-6-(4-phenylpiperidine-1-carbonyl)pyrazolo[1,5-a]pyrimidine-3-carbonyl]ethanesulfonamide (compound a-69)

[Step 1]

3-Bromo-7-(1-methylpyrazol-5-yl)amino-6-(4-phenylpiperidine-1-carbonyl)pyrazolo[1,5-a]pyrimidine In the same manner as in Example 1, step 4 and using 1-methyl-5-aminopyrazole (0.035 g, 0.358 mmol) instead of benzylamine, the title compound (0.095 g, 84%) was obtained.

[Step 2]

7-(1-Methylpyrazol-5-yl)amino-6-(4-phenylpiperidine-1-carbonyl)pyrazolo[1,5-a]pyrimidine-3-carboxylic acid In the same manner as in Example 1, step 5 and using 3-bromo-7-(1-methylpyrazol-5-yl)amino-6-(4-phenylpiperidine-1-carbonyl)pyrazolo[1,5-a]pyrimidine (0.080 g, 0.167 mmol) obtained in step 1, the title compound (0.074 g, 100%) was obtained.

[Step 3]

N-[7-(1-Methylpyrazol-5-yl)amino-6-(4-phenylpiperidine-1-carbonyl)pyrazolo[1,5-a]pyrimidine-3-carbonyl]ethanesulfonamide (compound a-69)

In the same manner as in Example 1, step 6 and using 7-(1-methylpyrazol-5-yl)amino-6-(4-phenylpiperidine-1-carbonyl)pyrazolo[1,5-a]pyrimidine-3-carboxylic acid (0.074 g, 0.167 mmol) obtained in step 2 and ethanesulfonamide (0.091 g, 0.833 mmol), the title compound (0.027 g, 30%) was obtained.

ESI-MS m/z: 537 (M+H)$^+$; $^1$H-NMR (CDCl$_3$, δ): 1.45 (t, J=7.3 Hz, 3H), 1.59-1.75 (m, 2H), 1.80-1.99 (m, 2H), 2.52-3.02 (m, 3H), 3.61 (q, J=7.3 Hz, 2H), 3.90 (s, 3H), 4.00-4.62 (m, 2H), 7.11-7.43 (m, 7H), 7.54 (s, 1H), 8.34 (s, 1H), 8.67 (s, 1H).

EXAMPLE 70

N-[7-(2-Methyl-3-pyridylamino)-6-(4-phenylpiperidine-1-carbonyl)pyrazolo[1,5-a]pyrimidine-3-carbonyl]ethanesulfonamide (compound a-70)

[Step 1]

3-Ethoxycarbonyl-7-(2-methyl-3-pyridylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.20 g, 0.48 mmol) obtained in Example 19, step 4 and 3-amino-2-methylpyridine (0.105 g, 0.97 mmol), the title compound (0.150 g, 64%) was obtained.

[Step 2]

7-(2-Methyl-3-pyridylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(2-methyl-3-pyridylamino)-6-(4-phenylpiperidine-1-carbonyl)pyrazolo[1,5-a]pyrimidine (0.150 g, 0.31 mmol) obtained in step 1, the title compound (0.115 g, 81%) was obtained.

[Step 3]

N-[7-(2-Methyl-3-pyridylamino)-6-(4-phenylpiperidine-1-carbonyl)pyrazolo[1,5-a]pyrimidine-3-carbonyl]ethanesulfonamide (compound a-70)

In the same manner as in Example 1, step 6 and using 7-(2-methyl-3-pyridylamino)-6-(4-phenylpiperidine-1-carbonyl)pyrazolo[1,5-a]pyrimidine-3-carboxylic acid (0.05 g, 0.11 mmol) obtained in step 2 and ethanesulfonamide (0.052 g, 0.55 mmol), the title compound (0.019 g, 31%) was obtained.

ESI-MS m/z: 548 (M+H)$^+$; $^1$H-NMR (CDCl$_3$, δ): 1.31-1.65 (m, 2H), 1.46 (t, J=7.3 Hz, 3H), 1.76-1.91 (m, 2H), 2.40-2.82 (m, 2H), 2.65 (s, 3H), 3.23-3.60 (m, 1H), 3.62 (q, J=7.3 Hz, 2H), 3.84-4.24 (m, 2H), 7.11-7.40 (m, 6H), 7.58 (dd, J=8.2, 1.3 Hz, 1H), 8.36 (s, 1H), 8.45 (s, 1H), 8.57 (dd, J=4.6, 1.6 Hz, 35 1H), 8.64 (s, 1H), 10.48 (s, 1H).

EXAMPLE 71

N-[7-(4-Methyl-3-thienylamino)-6-(4-phenylpiperidine-1-carbonyl)pyrazolo[1,5-a]pyrimidine-3-carbonyl]cyclopropanesulfonamide (compound a-71)

[Step 1]

3-Ethoxycarbonyl-7-(4-methyl-3-thienylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.20 g, 0.48 mmol) obtained in Example 19, step 4 and 3-amino-4-methylthiophene (0.110 g, 0.97 mmol), the title compound (0.099 g, 42%) was obtained.

[Step 2]

7-(4-Methyl-3-thienylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(4-methyl-3-thienylamino)-6-(4-phenylpiperidine-1-carbonyl)pyrazolo[1,5-a]pyrimidine (0.099 g, 0.20 mmol) obtained in step 1, the title compound (0.076 g, 80%) was obtained.

[Step 3]

N-[7-(4-Methyl-3-thienylamino)-6-(4-phenylpiperidine-1-carbonyl)pyrazolo[1,5-a]pyrimidine-3-carbonyl]cyclopropanesulfonamide (compound a-71)

In the same manner as in Example 1, step 6 and using 7-(4-methyl-3-thienylamino)-6-(4-phenylpiperidine-1-carbonyl)pyrazolo[1,5-a]pyrimidine-3-carboxylic acid (0.05 g, 0.11 mmol) obtained in step 2 and cyclopropanesulfonamide (0.048 g, 0.44 mmol), the title compound (0.005 g, 8%) was obtained.

ESI-MS m/z: 565 (M+H)$^+$; $^1$H-NMR (CDCl$_3$, δ): 1.09-1.19 (m, 2H), 1.42-1.66 (m, 4H), 1.77-1.92 (m, 2H), 2.26 (s, 3H), 2.58-2.78 (m, 2H), 3.00-3.20 (m, 1H), 3.24-4.82 (m, 3H), 7.01-7.41 (m, 7H), 8.13 (s, 1H), 8.32 (s, 1H), 8.64 (s, 1H), 10.61 (s, 1H).

EXAMPLE 72

N-[7-(4-Indolylamino)-6-(4-phenylpiperidine-1-carbonyl)pyrazolo[1,5-a]pyrimidine-3-carbonyl]ethanesulfonamide (compound a-72)

[Step 1]

3-Ethoxycarbonyl-7-(4-indolylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.20 g, 0.48 mmol) obtained in Example 19, step 4 and 4-aminoindole (0.128 g, 0.97 mmol), the title compound (0.240 g, 98%) was obtained.

[Step 2]

7-(4-Indolylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(4-indolylamino)-6-(4-phenylpiperidine-1-carbonyl)pyrazolo[1,5-a]pyrimidine (0.240 g, 0.47 mmol) obtained in step 1, the title compound (0.197 g, 85%) was obtained.

[Step 3]

N-[7-(4-Indolylamino)-6-(4-phenylpiperidine-1-carbonyl)pyrazolo[1,5-a]pyrimidine-3-carbonyl]ethanesulfonamide (compound a-72)

In the same manner as in Example 1, step 6 and using 7-(4-indolylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.050 g, 0.46 mmol), the title compound (0.009 g, 15%) was obtained.

ESI-MS m/z: 572 (M+H)$^+$; $^1$H-NMR (CDCl$_3$, δ): 1.03-1.72 (m, 4H), 1.47 (t, J=7.3 Hz, 3H), 2.32-2.48 (m, 2H), 2.51-4.38 (m, 3H), 3.62 (q, J=7.3 Hz, 2H), 6.59 (s, 1H), 6.89-7.50 (m, 9H), 8.39 (s, 1H), 8.52 (s, 1H), 8.63 (s, 1H), 8.73 (s, 1H), 10.55 (s, 1H).

EXAMPLE 73

N-[7-(7-Indolylamino)-6-(4-phenylpiperidine-1-carbonyl)pyrazolo[1,5-a]pyrimidine-3-carbonyl]ethanesulfonamide (compound a-73)

[Step 1]

3-Ethoxycarbonyl-7-(7-indolylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.25 g, 0.61 mmol) obtained in Example 19, step 4 and 7-aminoindole (0.128 g, 0.97 mmol), the title compound (0.310 g, 99%) was obtained.

[Step 2]

7-(7-Indolylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(7-indolylamino)-6-(4-phenylpiperidine-1-carbonyl)pyrazolo[1,5-a]pyrimidine (0.310 g, 0.61 mmol) obtained in step 1, the title compound (0.269 g, 92%) was obtained.

[Step 3]

N-[7-(7-Indolylamino)-6-(4-phenylpiperidine-1-carbonyl)pyrazolo[1,5-a]pyrimidine-3-carbonyl]ethanesulfonamide (compound a-73)

In the same manner as in Example 1, step 6 and using 7-(7-indolylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.080 g, 0.73 mmol), the title compound (0.015 g, 27%) was obtained.

ESI-MS m/z: 572 (M+H)⁺; ¹H-NMR (CDCl₃, δ): 1.08-1.74 (m, 4H), 1.44 (t, J=7.5 Hz, 3H), 2.38-2.55 (m, 2H), 2.56-4.15 (m, 3H), 3.58 (q, J=7.5 Hz, 2H), 6.68 (dd, J=3.1, 2.0 Hz, 1H), 7.04-7.39 (m, 8H), 7.71 (dd, J=6.4, 2.4 Hz, 1H), 8.29 (s, 1H), 8.51 (s, 1H), 8.57 (s, 1H), 8.85 (s, 1H), 10.55 (s, 1H).

EXAMPLE 74

N-[7-(5-Indolylamino)-6-(4-phenylpiperidine-1-carbonyl)pyrazolo[1,5-a]pyrimidine-3-carbonyl]ethanesulfonamide (compound a-74)

[Step 1]

3-Ethoxycarbonyl-7-(5-indolylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.15 g, 0.36 mmol) obtained in Example 19, step 4 and 5-aminoindole (0.072 g, 0.54 mmol), the title compound (0.184 g, 99%) was obtained.

[Step 2]

7-(5-Indolylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(5-indolylamino)-6-(4-phenylpiperidine-1-carbonyl)pyrazolo[1,5-a]pyrimidine (0.184 g, 0.36 mmol) obtained in step 1, the title compound (0.170 g, 98%) was obtained.

[Step 3]

N-[7-(5-Indolylamino)-6-(4-phenylpiperidine-1-carbonyl)pyrazolo[1,5-a]pyrimidine-3-carbonyl]ethanesulfonamide (compound a-74)

In the same manner as in Example 1, step 6 and using 7-(5-indolylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.092 g, 0.84 mmol), the title compound (0.020 g, 35%) was obtained. ESI-MS m/z: 572 (M+H)⁺; ¹H-NMR (CDCl₃, δ): 1.15-1.82 (m, 4H), 1.46 (t, J=7.3 Hz, 3H), 2.40-2.59 (m, 2H), 2.60-4.15 (m, 3H), 3.62 (q, J=7.3 Hz, 2H), 6.61 (s, 1H), 7.00-7.37 (m, 7H), 7.47 (d, J=8.4 Hz, 1H), 7.58 (s, 1H), 8.33 (s, 1H), 8.37 (s, 1H), 8.63 (s, 1H), 8.64 (s, 1H), 10.58 (s, 1H).

EXAMPLE 75

N-[7-(6-Indolylamino)-6-(4-phenylpiperidine-1-carbonyl)pyrazolo[1,5-a]pyrimidine-3-carbonyl]ethanesulfonamide (compound a-75)

[Step 1]

3-Ethoxycarbonyl-7-(6-indolylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.15 g, 0.36 mmol) obtained in Example 19, step 4 and 6-aminoindole (0.054 g, 0.72 mmol), the title compound (0.179 g, 98%) was obtained.

[Step 2]

7-(6-Indolylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(6-indolylamino)-6-(4-phenylpiperidine-1-carbonyl)pyrazolo[1,5-a]pyrimidine (0.179 g, 0.35 mmol) obtained in step 1, the title compound (0.168 g, 98%) was obtained.

[Step 3]

N-[7-(6-Indolylamino)-6-(4-phenylpiperidine-1-carbonyl)pyrazolo[1,5-a]pyrimidine-3-carbonyl]ethanesulfonamide (compound a-75)

In the same manner as in Example 1, step 6 and using 7-(6-indolylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.092 g, 0.84 mmol), the title compound (0.020 g, 36%) was obtained.
ESI-MS m/z: 572 (M+H)⁺; ¹H-NMR (CDCl₃, δ): 1.17-1.87 (m, 4H), 1.46 (t, J=7.3 Hz, 3H), 2.34-3.06 (m, 3H), 3.11-4.26 (m, 2H), 3.62 (q, J=7.3 Hz, 2H), 6.62 (s, 1H), 6.99-7.49 (m, 8H), 7.69 (d, J=8.1 Hz, 1H), 8.37 (s, 1H), 8.47 (s, 1H), 8.63 (s, 1H), 8.68 (s, 1H), 10.56 (s, 1H).

EXAMPLE 76

N-[7-(1-Methyl-5-indolylamino)-6-(4-phenylpiperidine-1-carbonyl)pyrazolo[1,5-a]pyrimidine-3-carbonyl]ethanesulfonamide (compound a-76)

[Step 1]

3-Ethoxycarbonyl-7-(1-methyl-5-indolylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.15 g, 0.36 mmol) obtained in Example 19, step 4 and 1-methyl-5-aminoindole (0.072 g, 0.49 mmol), the title compound (0.169 g, 90%) was obtained.

[Step 2]

7-(1-Methyl-5-indolylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(1-methyl-5-indolylamino)-6-(4-phenylpiperidine-1-carbonyl)pyrazolo[1,5-a]pyrimidine (0.169 g, 0.32 mmol) obtained in step 1, the title compound (0.134 g, 84%) was obtained.

[Step 3]

N-[7-(1-Methyl-5-indolylamino)-6-(4-phenylpiperidine-1-carbonyl)pyrazolo[1,5-a]pyrimidine-3-carbonyl]ethanesulfonamide (compound a-76)

In the same manner as in Example 1, step 6 and using 7-(1-methyl-5-indolylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.065 g, 0.6 mmol), the title compound (0.028 g, 47%) was obtained.

ESI-MS m/z: 586 (M+H)+; $^1$H-NMR (CDCl$_3$, δ): 1.08-1.93 (m, 4H), 1.46 (t, J=7.3 Hz, 3H), 2.39-3.29 (m, 3H), 3.31-4.56 (m, 2H), 3.62 (q, J=7.5 Hz, 2H), 3.84 (s, 3H), 6.53 (t, J=1.6 Hz, 1H), 7.00-7.44 (m, 8H), 7.55 (d, J=2.2 Hz, 1H), 8.33 (s, 1H), 8.63 (s, 1H), 8.65 (s, 1H), 10.59 (s, 1H).

EXAMPLE 77

N-[7-(1-Methyl-4-indolylamino)-6-(4-phenylpiperidine-1-carbonyl)pyrazolo[1,5-a]pyrimidine-3-carbonyl]ethanesulfonamide (compound a-77)

[Step 1]

3-Ethoxycarbonyl-7-(1-methyl-4-indolylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.15 g, 0.36 mmol) obtained in Example 19, step 4 and 1-methyl-4-aminoindole (0.076 g, 0.52 mmol), the title compound (0.169 g, 90%) was obtained.

[Step 2]

7-(1-Methyl-4-indolylamino)-6-(4-phenylpiperidine-1-carbonyl)pyrazolo[1,5-a]pyrimidine-3-carboxylic acid In the same manner as in Example 19, step 6 and using 3-ethoxycarbonyl-7-(1-methyl-4-indolylamino)-6-(4-phenylpiperidine-1-carbonyl)pyrazolo[1,5-a]pyrimidine (0.169 g, 0.32 mmol) obtained in step 1, the title compound (0.133 g, 84%) was obtained.

[Step 3]

N-[7-(1-Methyl-4-indolylamino)-6-(4-phenylpiperidine-1-carbonyl)pyrazolo[1,5-a]pyrimidine-3-carbonyl]ethanesulfonamide (compound a-77)

In the same manner as in Example 1, step 6 and using 7-(1-methyl-4-indolylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.065 g, 0.6 mmol), the title compound (0.026 g, 44%) was obtained.

ESI-MS m/z: 586 (M+H)+; $^1$H-NMR (CDCl$_3$, δ): 0.92-1.67 (m, 4H), 1.47 (t, J=7.5 Hz, 3H), 2.28-3.00 (m, 3H), 3.10-4.73 (m, 2H), 3.62 (q, J=7.3 Hz, 2H), 3.85 (s, 3H), 6.52 (d, J=3.3 Hz, 1H), 6.89-7.41 (m, 9H), 8.40 (s, 1H), 8.65 (s, 1H), 8.73 (s, 1H), 10.57 (s, 1H).

EXAMPLE 78

N-[6-(4-Phenylpiperidine-1-carbonyl)-7-(5-quinolylamino)pyrazolo[1,5-a]pyrimidine-3-carbonyl]ethanesulfonamide (compound a-78)

[Step 1]

3-Ethoxycarbonyl-6-(4-phenylpiperidine-1-carbonyl)-7-(5-quinolylamino)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.10 g, 0.24 mmol) obtained in Example 19, step 4 and 5-aminoquinoline (0.069 g, 0.48 mmol), the title compound (0.108 g, 86%) was obtained.

[Step 2]

6-(4-Phenylpiperidine-1-carbonyl)-7-(5-quinolylamino)pyrazolo[1,5-a]pyrimidine-3-carboxylic acid In the same manner as in Example 19, step 6 and using 3-ethoxycarbonyl-6-(4-phenylpiperidine-1-carbonyl)-7-(5-quinolylamino)pyrazolo[1,5-a]pyrimidine (0.108 g, 0.21 mmol) obtained in step 1, the title compound (0.092 g, 88%) was obtained.

[Step 3]

N-[6-(4-Phenylpiperidine-1-carbonyl)-7-(5-quinolylamino)pyrazolo[1,5-a]pyrimidine-3-carbonyl]ethanesulfonamide (compound a-78)

In the same manner as in Example 1, step 6 and using 6-(4-phenylpiperidine-1-carbonyl)-7-(5-quinolylamino)pyrazolo[1,5-a]pyrimidine-3-carboxylic acid (0.05 g, 0.10 mmol) obtained in step 2 and ethanesulfonamide (0.065 g, 0.6 mmol), the title compound (0.002 g, 3%) was obtained.

ESI-MS m/z: 584 (M+H)+; $^1$H-NMR (CDCl$_3$, δ): 1.11-1.79 (m, 4H), 1.47 (t, J=7.4 Hz, 3H), 2.37-3.05 (m, 3H), 3.45-4.45 (m, 2H), 3.63 (q, J=7.4 Hz, 2H), 7.03 (d, J=6.9 Hz, 2H), 7.19-7.35 (m, 3H), 7.53-7.59 (m, 2H), 7.78 (t, J=8.1 Hz, 1H), 8.23 (d, J=8.3 Hz, 1H), 8.34 (s, 1H), 8.43 (d, J=8.6 Hz, 1H), 8.68 (s, 1H), 8.76 (s, 1H), 9.06 (dd, J=4.1, 1.5 Hz, 1H), 10.50 (s, 1H).

EXAMPLE 79

N-[6-(4-Phenylpiperidine-1-carbonyl)-7-(8-quinolylamino)pyrazolo[1,5-a]pyrimidine-3-carbonyl]ethanesulfonamide (compound a-79)

[Step 1]

3-Ethoxycarbonyl-6-(4-phenylpiperidine-1-carbonyl)-7-(8-quinolylamino)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.10 g, 0.24 mmol) obtained in Example 19, step 4 and 8-aminoquinoline (0.069 g, 0.48 mmol), the title compound (0.125 g, 99%) was obtained.

[Step 2]

6-(4-Phenylpiperidine-1-carbonyl)-7-(8-quinolylamino)pyrazolo[1,5-a]pyrimidine-3-carboxylic acid In the same manner as in Example 19, step 6 and using 3-ethoxycarbonyl-6-(4-phenylpiperidine-1-carbonyl)-7-(8-quinolylamino)pyrazolo[1,5-a]pyrimidine (0.125 g, 0.24 mmol) obtained in step 1, the title compound (0.091 g, 64%) was obtained.

[Step 3]

N-[6-(4-Phenylpiperidine-1-carbonyl)-7-(8-quinolylamino)pyrazolo[1,5-a]pyrimidine-3-carbonyl]ethanesulfonamide (compound a-79)

In the same manner as in Example 1, step 6 and using 6-(4-phenylpiperidine-1-carbonyl)-7-(8-quinolylamino)pyrazolo[1,5-a]pyrimidine-3-carboxylic acid (0.04 g, 0.08 mmol) obtained in step 2 and ethanesulfonamide (0.055 g, 0.5 mmol), the title compound (0.014 g, 30%) was obtained.

ESI-MS m/z: 584 (M+H)$^+$; $^1$H-NMR (CDCl$_3$, δ): 1.12-1.69 (m, 4H), 1.48 (t, J=7.4 Hz, 3H), 2.15-2.85 (m, 3H), 3.11-4.15 (m, 2H), 3.63 (q, J=7.3 Hz, 2H), 6.58-6.75 (m, 2H), 7.12-7.21 (m, 3H), 7.54-7.80 (m, 4H), 8.30 (dd, J=8.2, 1.6 Hz, 1H), 8.58 (s, 1H), 8.71 (s, 1H), 8.97 (dd, J=4.3, 1.6 Hz, 1H), 10.07 (s, 1H), 10.54 (s, 1H).

EXAMPLE 80

N-[7-(2,2-Dimethyl-2,3-dihydrobenzofuran-7-ylamino)-6-(4-phenylpiperidine-1-carbonyl)pyrazolo [1,5-a]pyrimidine-3-carbonyl]ethanesulfonamide (compound a-80)

[Step 1]

3-Ethoxycarbonyl-7-(2,2-dimethyl-2,3-dihydrobenzofuran-7- ylamino)-6-(4-phenylpiperidine-1-carbonyl)pyrazolo[1,5-a]pyrimidine In the same manner as in Example 19, step 5 and using 7-chloro-3-ethoxycarbonyl-6-(4-phenylpiperidine-1-carbonyl)pyrazolo[1,5-a]pyrimidine (0.15 g, 0.36 mmol) obtained in Example 19, step 4 and 2,2-dimethyl-2,3-dihydro-1-benzofuran-7-amine (0.088 g, 0.54 mmol), the title compound (0.194 g, 99%) was obtained.

[Step 2]

7-(2,2-Dimethyl-2,3-dihydrobenzofuran-7-ylamino)-6-(4- phenylpiperidine-1-carbonyl)pyrazolo[1,5-a] pyrimidine-3-carboxylic acid In the same manner as in Example 19, step 6 and using 3-ethoxycarbonyl-7-(2,2-dimethyl-2,3-dihydrobenzofuran-7-ylamino)-6-(4-phenylpiperidine-1-carbonyl)pyrazolo[1,5-a]pyrimidine (0.194 g, 0.36 mmol) obtained in step 1, the title compound (0.153 g, 83%) was obtained.

[Step 3]

N-[7-(2,2-Dimethyl-2,3-dihydrobenzofuran-7-ylamino)-6-(4-phenylpiperidine-1-carbonyl)pyrazolo [1,5-a]pyrimidine-3-carbonyl]ethanesulfonamide (compound a-80)

In the same manner as in Example 1, step 6 and using 7-(2,2-dimethyl-2,3-dihydrobenzofuran-7-ylamino)-6-(4-phenylpiperidine-1-carbonyl)pyrazolo[1,5-a]pyrimidine-3-carboxylic acid (0.05 g, 0.10 mmol) obtained in step 2 and ethanesulfonamide (0.063 g, 0.58 mmol), the title compound (0.027 g, 44%) was obtained.

ESI-MS m/z: 603 (M+H)$^+$: $^1$H-NMR (CDCl$_3$, δ): 1.32-1.86 (m, 4H), 1.47 (s, 3H), 1.47 (t, J=3.7 Hz, 6H), 2.47-2.95 (m, 3H), 3.09 (s, 2H), 3.23-4.38 (m, 2H), 3.61 (q, J=7.5 Hz, 2H), 6.82-7.37 (m, 8H), 8.37 (s, 1H), 8.43 (s, 1H), 8.62 (s, 1H), 10.55 (s, 1H).

EXAMPLE 81

N-{7-(2-Fluoro-5-methylphenylamino)-6-[4-(4-fluorophenyl)piperidine-1-carbonyl]pyrazolo[1,5-a]pyrimidine-3-carbonyl}ethanesulfonamide (compound a-81)

[Step 1]

3-Ethoxycarbonyl-6-[4-(4-fluorophenyl)piperidine-1-carbonyl]-7-hydroxypyrazolo[1,5-a]pyrimidine In the same manner as in Example 1, step 2 and using 3-ethoxycarbonyl-7-hydroxypyrazolo[1,5-a]pyrimidine-6-carboxylic acid (1.17 g, 4.65 mmol) obtained in Example 19, step 2 and 4-(4-fluorophenyl)piperidine (1.0 g, 5.58 mmol), the title compound (1.18 g, 62%) was obtained.

[Step 2]

7-Chloro-3-ethoxycarbonyl-6-[4-(4-fluorophenyl) piperidine-1-carbonyl]pyrazolo[1,5-a]pyrimidine In the same manner as in Example 1, step 3 and using 3-ethoxycarbonyl-6-[4-(4-fluorophenyl)piperidine-1-carbonyl]-7-hydroxypyrazolo[1,5-a]pyrimidine (1.17 g, 2.85 mmol) obtained in step 1 instead of 3-bromo-7-hydroxy-6-(4-phenylpiperidine-1-carbonyl)pyrazolo[1,5-a]pyrimidine, the title compound (0.183 g, 15%) was obtained.

[Step 3]

3-Ethoxycarbonyl-7-(2-fluoro-5-methylphenylamino)-6-[4-(4-fluorophenyl)piperidine-1-carbonyl] pyrazolo[1,5-a]pyrimidine In the same manner as in Example 19, step 5 and using 7-chloro-3-ethoxycarbonyl-6-[4-(4-fluorophenyl)piperidine-1-carbonyl]pyrazolo[1,5-a]pyrimidine (0.090 g, 0.21 mmol) obtained in step 2 and 2-fluoro-5-methylaniline (0.053 g, 0.42 mmol), the title compound (0.109 g, 99%) was obtained.

[Step 4]

7-(2-Fluoro-5-methylphenylamino)-6-[4-(4-fluorophenyl)piperidine-1-carbonyl]pyrazolo[1,5-a]pyrimidine-3-carboxylic acid In the same manner as in Example 19, step 6 and using 3-ethoxycarbonyl-7-(2-fluoro-5-methylanilino)-6-[4-(4-fluorophenyl)piperidine-1-carbonyl]pyrazolo[1,5-a]pyrimidine (0.109 g, 0.21 mmol) obtained in step 3, the title compound (0.082 g, 80%) was obtained.

[Step 5]

N-{7-(2-Fluoro-5-methylphenylamino)-6-[4-(4-fluorophenyl)piperidine-1-carbonyl]pyrazolo[1,5-a]pyrimidine-3-carbonyl}ethanesulfonamide (compound a-81)

In the same manner as in Example 1, step 6 and using 7-(2-fluoro-5-methylphenylamino)-6-[4-(4-fluorophenyl) piperidine-1-carbonyl]pyrazolo[1,5-a]pyrimidine-3-carboxylic acid (0.04 g, 0.081 mmol) obtained in step 4 and ethanesulfonamide (0.053 g, 0.49 mmol), the title compound (0.021 g, 46%) was obtained.

ESI-MS m/z: 583 (M+H)$^+$; $^1$H-NMR (CDCl$_3$, δ): 1.22-1.91 (m, 4H), 1.46 (t, J=7.3 Hz, 3H), 2.37 (s, 3H), 2.52-3.23 (m, 3H), 3.55-4.45 (m, 2H), 3.61 (q, J=7.3 Hz, 2H), 6.95-7.31 (m, 7H), 8.42 (s, 1H), 8.43 (s, 1H), 8.64 (s, 1H), 10.49 (s, 1H).

EXAMPLE 82

N-{7-(2-Fluoro-5-methylphenylamino)-6-[4-(4-fluorophenyl)piperidine-1-carbonyl]pyrazolo[1,5-a]pyrimidine-3-carbonyl}cyclopropanesulfonamide (compound a-82)

In the same manner as in Example 1, step 6 and using 7-(2-fluoro-5-methylphenylamino)-6-[4-(4- fluorophenyl) piperidine-1-carbonyl]pyrazolo[1,5-a]pyrimidine-3-carboxylic acid (68 mg, 0.14 mmol) obtained in Example 81, step 4 and cyclopropanesulfonamide (84 mg, 0.69 mmol), the title compound (45 mg, 55%) was obtained.
ESI-MS m/z: 595 (M+H)$^+$; $^1$H-NMR (CDCl$_3$, δ): 1.09-1.18 (m, 2H), 1.31-1.57 (m, 4H), 1.71-1.89 (m, 2H), 2.37 (s, 3H), 2.55-2.71 (m, 3H), 3.05-3.17 (m, 1H), 3.95-4.14 (m, 2H), 6.95-7.05 (m, 2H), 7.06-7.15 (m, 4H), 7.16-7.23 (m, 1H), 8.41 (s, 1H), 8.43 (br s, 1H), 8.65 (s, 1H), 10.59 (br s, 1H).

EXAMPLE 83

N-{6-[4-(4-Fluorophenyl)piperidine-1-carbonyl]-7-(3-methylphenylamino)pyrazolo[1,5-a]pyrimidine-3-carbonyl}ethanesulfonamide (compound a-83)

[Step 1]

3-Ethoxycarbonyl-6-[4-(4-fluorophenyl)piperidine-1-carbonyl]-7-(3-methylphenylamino)pyrazolo[1,5-a]pyrimidine In the same manner as in Example 19, step 5 and using 7-chloro-3-ethoxycarbonyl-6-[4-(4-fluorophenyl)piperidine-1-carbonyl]pyrazolo[1,5-a]pyrimidine (0.10 g, 0.23 mmol) obtained in Example 81, step 2 and 3-methylaniline (0.038 g, 0.35 mmol), the title compound (0.113 g, 98%) was obtained.

[Step 2]

6-[4-(4-Fluorophenyl)piperidine-1-carbonyl]-7-(3-methylphenylamino)pyrazolo[1,5-a]pyrimidine-3-carboxylic acid In the same manner as in Example 19, step 6 and using 3-ethoxycarbonyl-6-[4-(4-fluorophenyl)piperidine-1-carbonyl]-7-(3-methylphenylamino)pyrazolo[1,5-a]pyrimidine (0.113 g, 0.23 mmol) obtained in step 1, the title compound (0.103 g, 94%) was obtained.

[Step 3]

N-{6-[4-(4-Fluorophenyl)piperidine-1-carbonyl]-7-(3-methylphenylamino)pyrazolo[1,5-a]pyrimidine-3-carbonyl}ethanesulfonamide (compound a-83)

In the same manner as in Example 1, step 6 and using 6-[4-(4-fluorophenyl)piperidine-1-carbonyl]-7-(3-methylphenylamino)pyrazolo[1,5-a]pyrimidine-3-carboxylic acid (0.05 g, 0.11 mmol) obtained in step 2 and ethanesulfonamide (0.070 g, 0.64 mmol), the title compound (0.022 g, 37%) was obtained.
ESI-MS m/z: 565 (M+H)$^+$; $^1$H-NMR (CDCl$_3$, δ): 1.31-1.83 (m, 4H), 1.46 (t, J=7.3 Hz, 3H), 2.41 (s, 3H), 2.47-3.05 (m, 3H), 3.30-4.97 (m, 2H), 3.61 (q, J=7.3 Hz, 2H), 6.93-7.40 (m, 8H), 8.43 (s, 1H), 8.55 (s, 1H), 8.63 (s, 1H), 10.51 (s, 1H).

EXAMPLE 84

N-{7-(4-Fluoro-2-methylphenylamino)-6-[4-(4-fluorophenyl)piperidine-1-carbonyl]pyrazolo[1,5-a]pyrimidine-3-carbonyl}ethanesulfonamide (compound a-84)

[Step 1]

3-Ethoxycarbonyl-7-(4-fluoro-2-methylphenylamino)-6-[4-(4-fluorophenyl)piperidine-1-carbonyl]pyrazolo[1,5-a]pyrimidine In the same manner as in Example 19, step 5 and using 7-chloro-3-ethoxycarbonyl-6-[4-(4-fluorophenyl)piperidine-1-carbonyl]pyrazolo[1,5-a]pyrimidine (0.10 g, 0.23 mmol) obtained in Example 81, step 2 and 4-fluoro-2-methylaniline (0.044 g, 0.35 mmol), the title compound (0.114 g, 96%) was obtained.

[Step 2]

7-(4-Fluoro-2-methylphenylamino)-6-[4-(4-fluorophenyl)piperidine-1-carbonyl]pyrazolo[1,5-a]pyrimidine-3-carboxylic acid In the same manner as in Example 19, step 6 and using 3-ethoxycarbonyl-7-(4-fluoro-2-methylphenylamino)-6-[4-(4-fluorophenyl)piperidine-1-carbonyl]pyrazolo[1,5-a]pyrimidine (0.114 g, 0.22 mmol) obtained in step 1, the title compound (0.082 g, 72%) was obtained.

[Step 3]

N-{7-(4-Fluoro-2-methylphenylamino)-6-[4-(4-fluorophenyl)piperidine-1-carbonyl]pyrazolo[1,5-a]pyrimidine-3-carbonyl}ethanesulfonamide (compound a-84)

In the same manner as in Example 1, step 6 and using 7-(4-fluoro-2-methylphenylamino)-6-[4-(4-fluorophenyl)piperidine-1-carbonyl]pyrazolo[1,5-a]pyrimidine-3-carboxylic acid (0.05 g, 0.10 mmol) obtained in step 2 and ethanesulfonamide (0.067 g, 0.61 mmol), the title compound (0.023 g, 39%) was obtained.
ESI-MS m/z: 583 (M+H)$^+$; $^1$H-NMR (CDCl$_3$, δ): 1.32-1.91 (m, 4H), 1.46 (t, J=7.3 Hz, 3H), 2.40 (s, 3H), 2.55-3.18 (m, 3H), 3.48-4.68 (m, 2H), 3.61 (q, J=7.3 Hz, 2H), 6.83-7.39 (m, 7H), 8.25 (s, 1H), 8.29 (s, 1H), 8.63 (s, 1H), 10.51 (s, 1H).

Example 85

N-{7-(4-Fluoro-3-methylphenylamino)-6-[4-(4-fluorophenyl)piperidine-1-carbonyl]pyrazolo[1,5-a]pyrimidine-3-carbonyl}ethanesulfonamide (compound a-85)

[Step 1]

3-Ethoxycarbonyl-7-(4-fluoro-3-methylphenylamino)-6-[4-(4-fluorophenyl)piperidine-1-carbonyl]pyrazolo[1,5-a]pyrimidine In the same manner as in Example 19, step 5 and using 7-chloro-3-ethoxycarbonyl-6-[4-(4-fluorophenyl)piperidine-1-carbonyl]pyrazolo[1,5-a]pyrimidine (0.10 g, 0.23 mmol) obtained in Example 81, step 2 and 4-fluoro-3-methylaniline (0.044 g, 0.35 mmol), the title compound (0.119 g, 99%) was obtained.

[Step 2]

7-(4-Fluoro-3-methylphenylamino)-6-[4-(4-fluorophenyl)piperidine-1-carbonyl]pyrazolo[1,5-a]pyrimidine-3-carboxylic acid In the same manner as in Example 19, step 6 and using 3-ethoxycarbonyl-7-(4-fluoro-3-methylphenylamino)-6-[4-(4-fluorophenyl)piperidine-1-carbonyl]pyrazolo[1,5-a]pyrimidine (0.119 g, 0.23 mmol) obtained in step 1, the title compound (0.103 g, 91%) was obtained.

[Step 3]

N-{7-(4-Fluoro-3-methylphenylamino)-6-[4-(4-fluorophenyl)piperidine-1-carbonyl]pyrazolo[1,5-a]pyrimidine-3-carbonyl}ethanesulfonamide (compound a-85)

In the same manner as in Example 1, step 6 and using 7-(4-fluoro-3-methylphenylamino)-6-[4-(4-fluorophenyl)piperidine-1-carbonyl]pyrazolo[1,5-a]pyrimidine-3-carboxylic acid (0.05 g, 0.10 mmol) obtained in step 2 and ethanesulfonamide (0.067 g, 0.61 mmol), the title compound (0.038 g, 64%) was obtained.

ESI-MS m/z: 583 (M+H)$^+$; $^1$H-NMR (CDCl$_3$, δ): 1.33-1.88 (m, 4H), 1.46 (t, J=7.3 Hz, 3H), 2.33 (d, J=1.8 Hz, 3H), 2.52-3.07 (m, 3H), 3.61 (q, J=7.3 Hz, 2H), 3.68-4.46 (m, 2H), 6.95-7.32 (m, 7H), 8.39 (s, 1H), 8.48 (s, 1H), 8.62 (s, 1H), 10.49 (s, 1H).

EXAMPLE 86

N-{7-(2,5-Dimethylphenylamino)-6-[4-(4-fluorophenyl)piperidine-1-carbonyl]pyrazolo[1,5-a]pyrimidine-3-carbonyl}ethanesulfonamide (compound a-86)

[Step 1]

7-(2,5-Dimethylphenylamino)-3-ethoxycarbonyl-6-(4- phenylpiperidine-1-carbonyl)pyrazolo[1,5-a]pyrimidine In the same manner as in Example 19, step 5 and using 7-chloro-3-ethoxycarbonyl-6-[4-(4-fluorophenyl)piperidine-1-carbonyl]pyrazolo[1,5-a]pyrimidine (0.10 g, 0.23 mmol) obtained in Example 81, step 2 and 2,5-dimethylaniline (0.042 g, 0.35 mmol), the title compound (0.118 g, 99%) was obtained.

[Step 2]

7-(2,5-Dimethylphenylamino)-6-[4-(4-fluorophenyl)piperidine-1-carbonyl]pyrazolo[1,5-a]pyrimidine-3-carboxylic acid In the same manner as in Example 19, step 6 and using 7-(2,5-dimethylphenylamino)-3-ethoxycarbonyl-6-(4-phenylpiperidine-1-carbonyl)pyrazolo[1,5-a]pyrimidine (0.118 g, 0.23 mmol) obtained in step 1, the title compound (0.066 g, 59%) was obtained.

[Step 3]

N-{7-(2,5-Dimethylphenylamino)-6-[4-(4-fluorophenyl)piperidine-1-carbonyl]pyrazolo[1,5-a]pyrimidine-3-carbonyl}ethanesulfonamide (compound a-86)

In the same manner as in Example 1, step 6 and using 7-(2,5-dimethylphenylamino)-6-[4-(4-fluorophenyl)piperidine-1-carbonyl]pyrazolo[1,5-a]pyrimidine-3-carboxylic acid (0.05 g, 0.10 mmol) obtained in step 2 and ethanesulfonamide (0.067 g, 0.62 mmol), the title compound (0.039 g, 65%) was obtained.

ESI-MS m/z: 579 (M+H)$^+$; $^1$H-NMR (CDCl$_3$, δ): 1.34-1.87 (m, 4H), 1.46 (t, J=7.3 Hz, 3H), 2.16-2.96 (m, 3H), 2.35 (s, 3H), 2.36 (s, 3H), 3.61 (q, J=7.3 Hz, 2H), 3.71-4.33 (m, 2H), 6.93-7.33 (m, 7H), 8.33 (s, 1H), 8.35 (s, 1H), 8.62 (s, 1H), 10.54 (s, 1H).

EXAMPLE 87

N-{7-(2,5-Dimethylphenylamino)-6-[4-(4-fluorophenyl)piperidine-1-carbonyl]pyrazolo[1,5-a]pyrimidine-3-carbonyl}cyclopropanesulfonamide (compound a-87)

In the same manner as in Example 1, step 6 and using 7-(2,5-dimethylphenylamino)-6-[4-(4-fluorophenyl)piperidine-1-carbonyl]pyrazolo[1,5-a]pyrimidine-3-carboxylic acid (97 mg, 0.20 mmol) obtained in Example 86, step 2 and cyclopropanesulfonamide (120 mg, 1.00 mmol), the title compound (37 mg, 32%) was obtained.

ESI-MS m/z: 591 (M+H)$^+$; (CDCl$_3$, δ): 1.08-1.19 (m, 2H), 1.30-1.53 (m, 4H), 1.69-1.85 (m, 2H), 2.35 (s, 3H), 2.36 (s, 3H), 2.50-2.65 (m, 3H), 3.05-3.18 (m, 1H), 3.90-4.08 (m, 2H), 6.94-7.16 (m, 6H), 7.23 (s, 1H), 8.33 (br s, 1H), 8.35 (s, 1H), 8.64 (s, 1H), 10.64 (br s, 1H).

EXAMPLE 88

N-{6-[4-(3,4-Difluorophenyl)piperidine-1-carbonyl]-7-(2,5-dimethylphenylamino)pyrazolo[1,5-a]pyrimidine-3-carbonyl]ethanesulfonamide (compound a-88)

[Step 1]

Methyl 7-(2,5-dimethylphenylamino)-3-ethoxycarbonylpyrazolo[1,5-a]pyrimidine-6-carboxylate In the same manner as in Example 1, step 4 and using methyl 7-chloro-3-ethoxycarbonylpyrazolo[1,5-a]pyrimidine-6-carboxylate (2.8 g, 9.9 mmol) obtained in Example 21, step 2 and 2,5-dimethylaniline (1.5 mL, 11.8 mmol), the title compound (2.99 g, 81%) was obtained.

[Step 2]

7-(2,5-Dimethylphenylamino)-3-ethoxycarbonylpyrazolo[1,5-a]pyrimidine-6-carboxylic acid In the same manner as in Example 21, step 4 and using methyl 7-(2,5-dimethylphenylamino)-3-ethoxycarbonylpyrazolo[1,5-a]pyrimidine-6-carboxylate (2.99 g, 8.13 mmol) obtained in step 1, the title compound (2.5 g, 87%) was obtained.

[Step 3]

6-[4-(3,4-Difluorophenyl)piperidine-1-carbonyl]-7-(2,5-dimethylphenylamino)-3-ethoxycarbonylpyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (220 mg, 0.62 mmol) obtained in step 2 and 4-(3,4-difluorophenyl)piperidine hydrochloride (WO2004/069798, 217 mg, 0.93 mmol), the title compound (232 mg, 70%) was obtained.

[Step 4]

6-[4-(3,4-Difluorophenyl)piperidine-1-carbonyl]-7-(2,5-dimethylphenylamino)pyrazolo[1,5-a]pyrimidine-3-carboxylic acid In the same manner as in Example 19, step 6 and using 6-[4-(3,4-difluorophenyl)piperidine-1-carbonyl]-7-(2,5-dimethylphenylamino)-3-ethoxycarbonylpyrazolo[1,5-a]pyrimidine (232 mg, 0.43 mmol) obtained in step 3, the title compound (202 mg, 93%) was obtained.
[Step 5]

N-{6-[4-(3,4-Difluorophenyl)piperidine-1-carbonyl]-7-(2,5-dimethylphenylamino)pyrazolo[1,5-a]pyrimidine-3-carbonyl}ethanesulfonamide (compound a-88)

In the same manner as in Example 1, step 6 and using 6-[4-(3,4-difluorophenyl)piperidine-1-carbonyl]-7-(2,5-dimethylphenylamino)pyrazolo[1,5-a]pyrimidine-3-carboxylic acid (100 mg, 0.20 mmol) obtained in step 4 and ethanesulfonamide (105 mg, 1.0 mmol), the title compound (79 mg, 66%) was obtained.
ESI-MS m/z: 597 (M+H)$^+$; $^1$H-NMR (CDCl$_3$,δ): 1.35-1.39 (m, 2H), 1.46 (t, J=7.4 Hz, 3H), 1.76-1.80 (m, 2H), 2.35 (s, 3H), 2.37 (s, 3H), 2.52-2.61 (m, 3H), 3.61 (q, J=7.4 Hz, 2H), 4.01 (br s, 2H), 6.83-6.96 (m, 2H), 7.05-7.14 (m, 3H), 7.25 (d, J=8.9 Hz, 1H), 8.35 (br s, 2H), 8.62 (s, 1H), 10.53 (br s, 1H).

EXAMPLE 89

N-{6-[4-(3,4-Difluorophenyl)piperidine-1-carbonyl]-7-(2,5-dimethylphenylamino)pyrazolo[1,5-a]pyrimidine-3-carbonyl}cyclopropanesulfonamide (compound a-89)

In the same manner as in Example 1, step 6 and using 6-[4-(3,4-difluorophenyl)piperidine-1-carbonyl]-7-(2,5-dimethylphenylamino)pyrazolo[1,5-a]pyrimidine-3-carboxylic acid (100 mg, 0.20 mmol) obtained in Example 88, step 4 and cyclopropanesulfonamide (121 mg, 1.0 mmol), the title compound (79 mg, 65%) was obtained.
ESI-MS m/z: 609 (M+H)$^+$; $^1$H-NMR (CDCl$_3$, δ): 1.11-1.16 (m, 2H), 1.35-1.38 (m, 2H), 1.46-1.51 (m, 2H), 1.75-1.80 (m, 2H), 2.35 (s, 3H), 2.37 (s, 3H), 2.52-2.61 (m, 3H), 3.09-3.16 (m, 1H), 4.01 (br s, 2H), 6.86-6.96 (m, 2H), 7.06-7.13 (m, 3H), 7.24 (d, J=8.9 Hz, 1H), 8.35 (br s, 2H), 8.64 (s, 1H), 10.64 (br s, 1H).

EXAMPLE 90

N-{6-[4-(3,4-Difluorophenyl)piperidine-1-carbonyl]-7-(2-fluoro-5-methylphenylamino)pyrazolo[1,5-a]pyrimidine-3-carbonyl}ethanesulfonamide (compound a-90)

[Step 1]

Methyl 3-ethoxycarbonyl-7-(2-fluoro-5-methylphenylamino)pyrazolo[1,5-a]pyrimidine-6-carboxylate In the same manner as in Example 1, step 4 and using methyl 7-chloro-3-ethoxycarbonylpyrazolo[1,5-a]pyrimidine-6-carboxylate (4.0 g, 14.0 mmol) obtained in Example 21, step 2 and 2-fluoro-5-methylaniline (2.4 mL, 20.9 mmol), the title compound (2.45 g, 47%) was obtained.
[Step 2]

3-Ethoxycarbonyl-7-(2-fluoro-5-methylphenylamino)pyrazolo[1,5-a]pyrimidine-6-carboxylic acid In the same manner as in Example 21, step 4 and using methyl 3-ethoxycarbonyl-7-(2-fluoro-5-methylphenylamino)pyrazolo[1,5-a]pyrimidine-6-carboxylate (2.45 g, 6.6 mmol) obtained in step 1, the title compound (1.98 g, 84%) was obtained.
[Step 3]

6-[4-(3,4-Difluorophenyl)piperidine-1-carbonyl]-3-ethoxycarbonyl-7-(2-fluoro-5-methylphenylamino)pyrazolo[1,5-a]pyrimidine In the same manner as in Example 21, step 5 and using 3-ethoxycarbonyl-7-(2-fluoro-5-methylphenylamino)pyrazolo[1,5-a]pyrimidine-6-carboxylic acid (150 mg, 0.42 mmol) obtained in step 2 and 4-(3,4-difluorophenyl)piperidine hydrochloride (WO2004/069798, 127 mg, 0.55 mmol), the title compound (63 mg, 28%) was obtained.
[Step 4]

6-[4-(3,4-Difluorophenyl)piperidine-1-carbonyl]-7-(2-fluoro-5-methylphenylamino)pyrazolo[1,5-a]pyrimidine-3-carboxylic acid In the same manner as in Example 19, step 6 and using 6-[4-(3,4-difluorophenyl)piperidine-1-carbonyl]-3-ethoxycarbonyl-7-(2-fluoro-5-methylphenylamino)pyrazolo[1,5-a]pyrimidine (63 mg, 0.12 mmol) obtained in step 3, the title compound (57 mg, 93%) was obtained.
[Step 5]

N-[6-[4-(3,4-Difluorophenyl)piperidine-1-carbonyl]-7-(2-fluoro-5-methylphenylamino)pyrazolo[1,5-a]pyrimidine-3-carbonyl]ethanesulfonamide (compound a-90)

In the same manner as in Example 1, step 6 and using 6-[4-(3,4-difluorophenyl)piperidine-1-carbonyl]-7-(2-fluoro-5-methylphenylamino)pyrazolo[1,5-a]pyrimidine-3-carboxylic acid (57 mg, 0.11 mmol) obtained in step 4 and ethanesulfonamide (58 mg, 0.55 mmol), the title compound (39 mg, 59%) was obtained.
ESI-MS m/z: 601 (M+H)$^+$; $^1$H-NMR (CDCl$_3$,δ): 1.39-1.45 (m, $^4$H), 1.46 (t, J=7.4 Hz, 3H), 1.71-1.83 (m, 2H), 2.37 (s, 3H), 2.58-2.67 (m, 1H), 3.62 (q, J=7.5 Hz, 2H), 4.05 (br s, $^2$H), 6.85-6.99 (m, 2H), 7.05-7.29 (m, 4H), 8.41 (s, 1H), 8.44 (br s, 1H), 8.64 (s, 1H), 10.49 (br s, 1H).

EXAMPLE 91

N-{6-[4-(2,4-Difluorophenyl)piperidine-1-carbonyl]-7-(2-fluoro-5-methylphenylamino)pyrazolo[1,5-a]pyrimidine-3-carbonyl}ethanesulfonamide (compound a-91)

[Step 1]

6-[4-(2,4-Difluorophenyl)piperidine-1-carbonyl]-3-ethoxycarbonyl-7-(2-fluoro-5-methylphenylamino)pyrazolo[1,5-a]pyrimidine In the same manner as in Example 21, step 5 and using 3-ethoxycarbonyl-7-(2-fluoro-5-methylphenylamino)pyrazolo[1,5-a]pyrimidine-6-carboxylic acid (160 mg, 0.46 mmol) obtained in Example 90, step 2 and 4-(2,4-difluorophenyl)piperidine hydrochloride (WO2007/018998, 160 mg, 0.69 mmol), the title compound (117 mg, 47%) was obtained.

[Step 2]

6-[4-(3,4-Difluorophenyl)piperidine-1-carbonyl]-7-(2-fluoro-5-methylphenylamino)pyrazolo[1,5-a]pyrimidine-3-carboxylic acid In the same manner as in Example 19, step 6 and using 6-[4-(2,4-difluorophenyl)piperidine-1-carbonyl]-3-ethoxycarbonyl-7-(2-fluoro-5-methylphenylamino)pyrazolo[1,5-a]pyrimidine (117 mg, 0.22 mmol) obtained in step 1, the title compound (97 mg, 86%) was obtained.

[Step 3]

N-[6-[4-(2,4-Difluorophenyl)piperidine-1-carbonyl]-7-(2-fluoro-5-methylphenylamino)pyrazolo[1,5-a]pyrimidine-3-carbonyl]ethanesulfonamide (compound a-91)

In the same manner as in Example 1, step 6 and using 6-[4-(2,4-difluorophenyl)piperidine-1-carbonyl]-7-(2-fluoro-5-methylphenylamino)pyrazolo[1,5-a]pyrimidine-3-carboxylic acid (48 mg, 0.09 mmol) obtained in step 2 and ethanesulfonamide (47 mg, 0.45 mmol), the title compound (33 mg, 62%) was obtained.

ESI-MS m/z: 601 (M+H)$^+$; $^1$H-NMR (CDCl$_3$,δ): 1.46 (t, J=7.4 Hz, 3H), 1.52-1.58 (m, 2H), 1.72-1.82 (m, 2H), 2.37 (s, 3H), 2.62 (br s, 2H), 2.90-2.99 (m, 1H), 3.61 (q, J=7.4 Hz, 2H), 4.04 (br s, 2H), 6.75-6.88 (m, 2H), 7.06-7.21 (m, 4H), 8.41 (s, 1H), 8.43 (br s, 1H), 8.64 (s, 1H), 10.49 (br s, 1H).

EXAMPLE 92

N-{7-(2-Fluoro-5-methylphenylamino)-6-[4-(4-methoxyphenyl)piperidine-1-carbonyl]pyrazolo[1,5-a]pyrimidine-3-carbonyl}ethanesulfonamide (compound a-92)

[Step 1]

3-Ethoxycarbonyl-7-(2-fluoro-5-methylphenylamino)-6-[4-(4-methoxyphenyl)piperidine-1-carbonyl]pyrazolo[1,5-a]pyrimidine In the same manner as in Example 21, step 5 and using 3-ethoxycarbonyl-7-(2-fluoro-5-methylphenylamino)pyrazolo[1,5-a]pyrimidine-6-carboxylic acid (0.5 g, 1.40 mmol) obtained in Example 90, step 2 and 4-(4-methoxyphenyl)piperidine hydrochloride (0.38 mg, 1.67 mmol), the title compound (0.58 mg, 78%) was obtained.

[Step 2]

7-(2-Fluoro-5-methylphenylamino)-6-[4-(4-methoxyphenyl)piperidine-1-carbonyl]pyrazolo[1,5-a]pyrimidine-3-carboxylic acid In the same manner as in Example 19, step 6 and using 3-ethoxycarbonyl-7-(2-fluoro-5-methylphenylamino)-6-[4-(4-methoxyphenyl)piperidine-1-carbonyl]pyrazolo[1,5-a]pyrimidine (0.58 mg, 1.10 mmol) obtained in step 1, the title compound (0.56 g, 100%) was obtained.

[Step 3]

N-{7-(2-Fluoro-5-methylphenylamino)-6-[4-(4-methoxyphenyl)piperidine-1-carbonyl]pyrazolo[1,5-a]pyrimidine-3-carbonyl}ethanesulfonamide (compound a-92)

In the same manner as in Example 1, step 6 and using 7-(2-fluoro-5-methylphenylamino)-6-[4-(4-methoxyphenyl)piperidine-1-carbonyl]pyrazolo[1,5-a]pyrimidine-3-carboxylic acid (0.3 g, 0.60 mmol) obtained in step 2 and ethanesulfonamide (0.31 g, 2.98 mmol), the title compound (0.27 g, 75%) was obtained.

ESI-MS m/z: 595 (M+H)$^+$; $^1$H-NMR (CDCl$_3$,δ):1.36-1.50 (m, 2H), 1.46 (t, J=7.3 Hz, 3H), 1.80 (d, J=11.9 Hz, 2H), 2.37 (s, 3H), 2.60 (t, J=12.1 Hz, 1H), 3.62 (q, J=7.2 Hz, 2H), 3.80 (d, J=1.3 Hz, 3H), 3.90-4.18 (m, 4H), 6.86 (d, J=7.3 Hz, 2H), 7.06-7.22 (m, 5H), 8.42 (d, J=1.3 Hz, 1H), 8.43 (s, 1H), 8.64 (d, J=1.7 Hz, 1H), 10.50 (s, 1H).

EXAMPLE 93

N-{7-(2-Fluoro-5-methylphenylamino)-6-[4-(2-naphthyl)piperidine-1-carbonyl]pyrazolo[1,5-a]pyrimidine-3-carbonyl}ethanesulfonamide (compound a-93)

[Step 1]

3-Ethoxycarbonyl-7-(2-fluoro-5-methylphenylamino)-6-[4-(2-naphthyl)piperidine-1-carbonyl]pyrazolo[1,5-a]pyrimidine In the same manner as in Example 21, step 5 and using 3-ethoxycarbonyl-7-(2-fluoro-5-methylphenylamino)pyrazolo[1,5-a]pyrimidine-6-carboxylic acid (120 mg, 0.33 mmol) obtained in Example 90, step 2 and 4-(2-naphthyl)piperidine hydrochloride (WO1997/037979, 100 mg, 0.40 mmol), the title compound (89 mg, 49%) was obtained.

[Step 2]

7-(2-Fluoro-5-methylphenylamino)-6-[4-(2-naphthyl)piperidine-1-carbonyl]pyrazolo[1,5-a]pyrimidine-3-carboxylic acid In the same manner as in Example 19, step 6 and using 3-ethoxycarbonyl-7-(2-fluoro-5-methylphenylamino)-6-[4-(2-naphthyl)piperidine-1-carbonyl]pyrazolo[1,5-a]pyrimidine (89 mg, 0.16 mmol) obtained in step 1, the title compound (69 mg, 82%) was obtained.

[Step 3]

N-{7-(2-Fluoro-5-methylphenylamino)-6-[4-(2-naphthyl)piperidine-1-carbonyl]pyrazolo[1,5-a]pyrimidine-3-carbonyl}ethanesulfonamide (compound a-93)

In the same manner as in Example 1, step 6 and using 7-(2-fluoro-5-methylphenylamino)-6-[4-(2-naphthyl)piperidine-1-carbonyl]pyrazolo[1,5-a]pyrimidine-3-carboxylic acid (69 mg, 0.13 mmol) obtained in step 2 and ethanesulfonamide (68 mg, 0.65 mmol), the title compound (48 mg, 60%) was obtained.

ESI-MS m/z: 614 (M+H)$^+$; $^1$H-NMR (CDCl$_3$,δ): 1.46 (t, J=7.4 Hz, 3H), 1.55-1.73 (m, 2H), 1.91-1.95 (m, 2H), 2.39 (s, 3H), 2.62-2.91 (m, 3H), 3.62 (q, J=7.3 Hz, 2H), 4.10 (br s, 2H), 7.09-7.32 (m, 4H), 7.42-7.51 (m, 2H), 7.60 (s, 1H), 7.80-7.83 (m, 3H), 8.45 (br s, 2H), 8.65 (s, 1H), 10.51 (br s, 1H).

EXAMPLE 94

N-{7-(2,5-Dimethylphenylamino)-6-[4-(2-fluoropyridin-5-yl)piperidine-1-carbonyl]pyrazolo[1,5-a]pyrimidine-3-carbonyl}cyclopropanesulfonamide (compound a-94)

[Step 1]

7-(2,5-Dimethylphenylamino)-3-ethoxycarbonyl-6-[4-(2-fluoropyridin-5-yl)piperidine-1-carbonyl]pyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (100 mg, 0.29 mmol) obtained in Example 88, step 2 and 4-(2-fluoropyridin-5-yl)piperidine (WO2004/069798, 87 mg, 0.34 mmol), the title compound (100 mg, 71%) was obtained.

[Step 2]

7-(2,5-Dimethylphenylamino)-6-[4-(2-fluoropyridin-5-yl)piperidine-1-carbonyl]pyrazolo[1,5-a]pyrimidine-3-carboxylic acid In the same manner as in Example 19, step 6 and using 7-(2,5-dimethylphenylamino)-3-ethoxycarbonyl-6-[4-(2-fluoropyridin-5-yl)piperidine-1-carbonyl]pyrazolo[1,5-a]pyrimidine (100 mg, 0.20 mmol) obtained in step 1, the title compound (83 mg, 84%) was obtained.

[Step 3]

N-{7-(2,5-Dimethylphenylamino)-6-[4-(2-fluoropyridin-5-yl)piperidine-1-carbonyl]pyrazolo[1,5-a]pyrimidine-3-carbonyl}cyclopropanesulfonamide (compound a-94)

In the same manner as in Example 1, step 6 and using 7-(2,5-dimethylphenylamino)-6-[4-(2-fluoropyridin-5-yl)piperidine-1-carbonyl]pyrazolo[1,5-a]pyrimidine-3-carboxylic acid (82 mg, 0.17 mmol) obtained in step 2 and cyclopropanesulfonamide (100 mg, 0.84 mmol), the title compound (21 mg, 22%) was obtained.

ESI-MS m/z: 590 (M+H)$^+$; $^1$H-NMR (DMSO-d$_6$, δ): 1.01-1.25 (m, 4H), 1.55-1.75 (m, 2H), 2.22 (s, 3H), 2.28 (s, 3H), 2.65-2.92 (m, 5H), 3.09-3.22 (m, 1H), 3.78-3.92 (m, 1H), 3.92-4.08 (m, 1H), 7.01-7.20 (m, 4H), 7.82-7.98 (m, 1H), 8.12 (s, 1H), 8.42 (s, 1H), 8.70 (s, 1H), 10.35 (s, 1H), 10.90 (br s, 1H).

EXAMPLE 95

N-[6-(4-Cyclohexylpiperidine-1-carbonyl)-7-(2,5-dimethylphenylamino)pyrazolo[1,5-a]pyrimidine-3-carbonyl]ethanesulfonamide (compound a-95)

[Step 1]

6-(4-Cyclohexylpiperidine-1-carbonyl)-7-(2,5-dimethylphenylamino)-3-ethoxycarbonylpyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (150 mg, 0.42 mmol) obtained in Example 88, step 2 and 4-cyclohexylpiperidine (U.S. Pat. No. 4,308,382, 120 mg, 0.72 mmol), the title compound (211 mg, 99%) was obtained.

[Step 2]

6-(4-Cyclohexylpiperidine-1-carbonyl)-7-(2,5-dimethylphenylamino)pyrazolo[1,5-a]pyrimidine-3-carboxylic acid In the same manner as in Example 19, step 6 and using 6-(4-cyclohexylpiperidine-1-carbonyl)-7-(2,5-dimethylphenylamino)-3-ethoxycarbonylpyrazolo[1,5-a]pyrimidine (211 mg, 0.42 mmol) obtained in step 1, the title compound (152 mg, 76%) was obtained.

[Step 3]

N-[6-(4-Cyclohexylpiperidine-1-carbonyl)-7-(2,5-dimethylphenylamino)pyrazolo[1,5-a]pyrimidine-3-carbonyl]ethanesulfonamide (compound a-95)

In the same manner as in Example 1, step 6 and using 6-(4-cyclohexylpiperidine-1-carbonyl)-7-(2,5-dimethylphenylamino)pyrazolo[1,5-a]pyrimidine-3-carboxylic acid (75 mg, 0.16 mmol) obtained in step 2 and ethanesulfonamide (84 mg, 0.80 mmol), the title compound (50 mg, 55%) was obtained.

ESI-MS m/z: 568 (M+H)$^+$; $^1$H-NMR (CDCl$_3$, δ): 0.87-1.22 (m, 9H), 1.46 (t, J=7.4 Hz, 3H), 1.55-1.74 (m, 11H), 2.33 (s, 6H), 3.61 (q, J=7.5 Hz, 2H), 7.01 (s, 1H), 7.08 (d, J=7.9 Hz, 1H), 7.20 (d, J=7.6 Hz, 1H), 8.28 (s, 1H), 8.29 (br s, 1H), 8.61 (s, 1H), 10.56 (br s, 1H).

EXAMPLE 96

N-[7-Benzylamino-6-(4-fluoro-4-phenylpiperidine-1-carbonyl)pyrazolo[1,5-a]pyrimidine-3-carbonyl]methanesulfonamide (compound a-96)

[Step 1]

7-Benzylamino-3-bromo-6-(4-fluoro-4-phenylpiperidine-1-carbonyl)pyrazolo[1,5-a]pyrimidine In the same manner as in Example 21, step 5 and using 7-benzylamino-3-bromopyrazolo[1,5-a]pyrimidine-6-carboxylic acid (0.500 g, 1.44 mmol) obtained in Example 22, step 3 and 4-fluoro-4-phenylpiperidine (WO2002/13824, 0.340 g, 1.73 mmol), the title compound (0.630 g, 86%) was obtained.

[Step 2]

7-Benzylamino-6-(4-fluoro-4-phenylpiperidine-1-carbonyl)pyrazolo[1,5-a]pyrimidine-3-carboxylic acid In the same manner as in Example 1, step 5 and using 7-benzylamino-3-bromo-6-(4-fluoro-4-phenylpiperidine-1-carbonyl)pyrazolo[1,5-a]pyrimidine (0.700 g, 1.38 mmol) obtained in step 1, the title compound (0.406 g, 62%) was obtained.

[Step 3]

N-[7-Benzylamino-6-(4-fluoro-4-phenylpiperidine-1-carbonyl)pyrazolo[1,5-a]pyrimidine-3-carbonyl]methanesulfonamide (compound a-96)

In the same manner as in Example 1, step 6 and using 7-benzylamino-6-(4-fluoro-4-phenylpiperidine-1-carbonyl)

pyrazolo[1,5-a]pyrimidine-3-carboxylic acid (0.030 g, 0.634 mmol) obtained in step 2 and methanesulfonamide (0.064 g, 0.676 mmol), the title compound (0.263 g, 75%) was obtained.

ESI-MS m/z: 551 (M+H)$^+$; $^1$H-NMR (CDCl$_3$,δ): 1.71-2.17 (m, 4H), 2.78-3.29 (m, 2H), 3.42 (s, 3H), 3.98-4.67 (m, 2H), 4.81-5.06 (m, 2H), 7.19-7.50 (m, 10H), 7.67-7.86 (m, 1H), 8.24 (s, 1H), 8.59 (s, 1H), 10.71 (br s, 1H).

EXAMPLE 97

N-[7-(4-Fluoro-2-methylphenylamino)-6-(4-fluoro-4-phenylpiperidine-1-carbonyl)pyrazolo[1,5-a]pyrimidine-3-carbonyl]ethanesulfonamide (compound a-97)

[Step 1]

3-Ethoxycarbonyl-6-(4-fluoro-4-phenylpiperidine-1-carbonyl)-7-hydroxypyrazolo[1,5-a]pyrimidine In the same manner as in Example 1, step 2 and using 3-ethoxycarbonyl-7-hydroxypyrazolo[1,5-a]pyrimidine-6-carboxylic acid (1.55 g, 6.18 mmol) obtained in Example 19, step 2 and 4-fluoro-4-phenylpiperidine hydrochloride (2.0 g, 9.27 mmol), the title compound (1.72 g, 68%) was obtained.

[Step 2]

7-Chloro-3-ethoxycarbonyl-6-(4-fluoro-4-phenylpiperidine-1-carbonyl)pyrazolo[1,5-a]pyrimidine In the same manner as in Example 1, step 3 and using 3-ethoxycarbonyl-6-(4-fluoro-4-phenylpiperidine-1-carbonyl)-7-hydroxypyrazolo[1,5-a]pyrimidine (1.66 g, 4.03 mmol) obtained in step 1, the title compound (515 mg, 30%) was obtained.

[Step 3]

3-Ethoxycarbonyl-7-(4-fluoro-2-methylphenylamino)-6-(4-fluoro-4-phenylpiperidine-1-carbonyl)pyrazolo[1,5-a]pyrimidine In the same manner as in Example 19, step 5 and using 7-chloro-3-ethoxycarbonyl-6-(4-fluoro-4-phenylpiperidine-1-carbonyl)pyrazolo[1,5-a]pyrimidine (250 mg, 0.58 mmol) obtained in step 2 and 4-fluoro-2-methylaniline (0.1 mL, 0.87 mmol), the title compound (219 mg, 73%) was obtained.

[Step 4]

7-(4-Fluoro-2-methylphenylamino)-6-(4-fluoro-4-phenylpiperidine-1-carbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(4-fluoro-4-phenylpiperidine-1-carbonyl)pyrazolo[1,5-a]pyrimidine (219 mg, 0.42 mmol) obtained in step 3, the title compound (189 mg, 92%) was obtained.

[Step 5]

N-[7-(4-Fluoro-2-methylphenylamino)-6-(4-fluoro-4-phenylpiperidine-1-carbonyl)pyrazolo[1,5-a]pyrimidine-3-carbonyl]ethanesulfonamide (compound a-97)

In the same manner as in Example 1, step 6 and using 7-(4-fluoro-2-methylphenylamino)-6-(4-fluoro-4-phenylpiperidine-1-carbonyl)pyrazolo[1,5-a]pyrimidine-3-carboxylic acid (95 mg, 0.19 mmol) obtained in step 4 and ethanesulfonamide (100 mg, 0.95 mmol), the title compound (32 mg, 29%) was obtained.

ESI-MS m/z: 583 (M+H)$^+$; $^1$H-NMR (CDCl$_3$,δ): 1.46 (t, J=7.4 Hz, 3H), 1.69-1.99 (m, 4H), 2.41 (s, 3H), 2.99 (br s, 2H), 3.61 (q, J=7.5 Hz, 2H), 3.98 (br s, 2H), 6.95-7.44 (m, 8H), 8.28 (br s, 1H), 8.31 (s, 1H), 8.63 (s, 1H), 10.50 (br s, 1H).

EXAMPLE 98

N-[7-(4-Fluoro-2-methylphenylamino)-6-(4-fluoro-4-phenylpiperidine-1-carbonyl)pyrazolo[1,5-a]pyrimidine-3-carbonyl]cyclopropanesulfonamide (compound a-98)

In the same manner as in Example 1, step 6 and using 7-(4-fluoro-2-methylphenylamino)-6-(4-fluoro-4-phenylpiperidine-1-carbonyl)pyrazolo[1,5-a]pyrimidine-3-carboxylic acid (95 mg, 0.19 mmol) obtained in Example 97, step 4 and cyclopropanesulfonamide (115 mg, 0.95 mmol), the title compound (21 mg, 19%) was obtained.

ESI-MS m/z: 595 (M+H)$^+$; $^1$H-NMR (CDCl$_3$, δ): 1.12-1.14 (m, 2H), 1.45-1.50 (m, 2H), 1.79-2.00 (m, 4H), 2.40 (s, 3H), 3.06-3.16 (m, 3H), 3.91 (br s, 2H), 6.94-7.44 (m, 8H), 8.26 (br s, 1H), 8.31 (s, 1H), 8.65 (s, 1H), 10.60 (br s, 1H).

EXAMPLE 99

N-[7-(2-Fluoro-5-methylphenylamino)-6-(4-fluoro-4-phenylpiperidine-1-carbonyl)pyrazolo[1,5-a]pyrimidine-3-carbonyl]ethanesulfonamide (compound a-99)

[Step 1]

Ethyl 3-bromo-7-(2-fluoro-5-methylphenylamino)pyrazolo[1,5-a]pyrimidine-6-carboxylate In the same manner as in Example 1, step 4 and using ethyl 3-bromo-7-chloropyrazolo[1,5-a]pyrimidine-6-carboxylate (400 mg, 1.31 mmol) obtained in Example 22, step 1 and 2-fluoro-5-methylaniline (0.18 mL, 1.57 mmol), the title compound (410 mg, 91%) was obtained.

[Step 2]

3-Bromo-7-(2-fluoro-5-methylphenylamino)pyrazolo[1,5-a]pyrimidine-6-carboxylic acid In the same manner as in Example 19, step 6 and using ethyl 3-bromo-7-(2-fluoro-5-methylphenylamino)pyrazolo[1,5-a]pyrimidine-6-carboxylate (470 mg, 1.19 mmol) obtained in step 1, the title compound (333 mg, 77%) was obtained.

[Step 3]

3-Bromo-7-(2-fluoro-5-methylphenylamino)-6-(4-fluoro-4-phenylpiperidine-1-carbonyl)pyrazolo[1,5-a]pyrimidine In the same manner as in Example 21, step 5 and using 3-bromo-7-(2-fluoro-5-methylphenylamino)pyrazolo[1,5-a]pyrimidine-6-carboxylic acid (333 mg, 0.91 mmol) obtained in step 2 and 4-fluoro-4-phenylpiperidine hydrochloride (296 mg, 1.37 mmol), the title compound (1-39 mg, 29%) was obtained.

[Step 4]

7-(2-Fluoro-5-methylphenylamino)-6-(4-fluoro-4-phenylpiperidine-1-carbonyl)pyrazolo[1,5-a]pyrimidine-3-carboxylic acid In the same manner as in Example 1, step 5 and using 3-bromo-7-(2-fluoro-5-methylphenylamino)-6-(4-fluoro-4-phenylpiperidine-1-carbonyl)pyrazolo[1,5-a]pyrimidine (138 mg, 0.26 mmol) obtained in step 3, the title compound (71 mg, 56%) was obtained.

[Step 5]

N-[7-(2-Fluoro-5-methylphenylamino)-6-(4-fluoro-4-phenylpiperidine-1-carbonyl)pyrazolo[1,5-a]pyrimidine-3-carbonyl]ethanesulfonamide (compound a-99)

In the same manner as in Example 1, step 6 and using 7-(2-fluoro-5-methylphenylamino)-6-(4-fluoro-4-phenylpiperidine-1-carbonyl)pyrazolo[1,5-a]pyrimidine-3-carboxylic acid (71 mg, 0.14 mmol) obtained in step 4 and ethanesulfonamide (73 mg, 0.70 mmol), the title compound (35 mg, 43%) was obtained.

ESI-MS m/z: 584 (M+H)$^+$; $^1$H-NMR (CDCl$_3$,δ): 1.46 (t, J=7.4 Hz, 3H), 1.79-1.99 (m, 4H), 2.38 (s, 3H), 2.98 (br s, 2H), 3.61 (q, J=7.5 Hz, 2H), 3.92 (br s, 2H), 7.09-7.43 (m, 8H), 8.42 (s, 1H), 8.44 (br s, 1H), 8.64 (s, 1H), 10.47 (br s, 1H).

EXAMPLE 100

N-[7-(2,5-Dimethylphenylamino)-6-(4-fluoro-4-phenylpiperidine-1-carbonyl)pyrazolo[1,5-a]pyrimidine-3-carbonyl]ethanesulfonamide (compound a-100)

[Step 1]

Ethyl 3-bromo-7-(2,5-dimethylphenylamino)pyrazolo[1,5-a]pyrimidine-6-carboxylate In the same manner as in Example 1, step 4 and using ethyl 3-bromo-7-chloropyrazolo[1,5-a]pyrimidine-6-carboxylate (400 mg, 1.31 mmol) obtained in Example 22, step 1 and 2,5-dimethylaniline (0.19 mL, 1.57 mmol), the title compound (345 mg, 68%) was obtained.

[Step 2]

3-Bromo-7-(2,5-dimethylphenylamino)pyrazolo[1,5-a]pyrimidine-6-carboxylic acid

In the same manner as in Example 19, step 6 and using ethyl 3-bromo-7-(2,5-dimethylphenylamino)pyrazolo[1,5-a]pyrimidine-6-carboxylate (331 mg, 0.85 mmol) obtained in step 1, the title compound (231 mg, 75%) was obtained.

[Step 3]

3-Bromo-7-(2,5-dimethylphenylamino)-6-(4-fluoro-4-phenylpiperidine-1-carbonyl)pyrazolo[1,5-a]pyrimidine In the same manner as in Example 21, step 5 and using 3-bromo-7-(2,5-dimethylphenylamino)pyrazolo[1,5-a]pyrimidine-6-carboxylic acid (231 mg, 0.64 mmol) obtained in step 2 and 4-fluoro-4-phenylpiperidine hydrochloride (207 mg, 0.96 mmol), the title compound (208 mg, 62%) was obtained.

[Step 4]

7-(2,5-Dimethylphenylamino)-6-(4-fluoro-4-phenylpiperidine-1-carbonyl)pyrazolo[1,5-a]pyrimidine-3-carboxylic acid In the same manner as in Example 1, step 5 and using 3-bromo-7-(2,5-dimethylphenylamino)-6-(4-fluoro-4-phenylpiperidine-1-carbonyl)pyrazolo[1,5-a]pyrimidine (208 mg, 0.40 mmol) obtained in step 3, the title compound (91 mg, 47%) was obtained.

[Step 5]

N-[7-(2,5-Dimethylphenylamino)-6-(4-fluoro-4-phenylpiperidine-1-carbonyl)pyrazolo[1,5-a]pyrimidine-3-carbonyl]ethanesulfonamide (compound a-100)

In the same manner as in Example 1, step 6and using 7-(2,5-dimethylphenylamino)-6-(4-fluoro-4-phenylpiperidine-1-carbonyl)pyrazolo[1,5-a]pyrimidine-3-carboxylic acid (91 mg, 0.19 mmol) obtained in step 4 and ethanesulfonamide (100 mg, 0.95 mmol), the title compound (38 mg, 35%) was obtained.

ESI-MS m/z: 579 (M+H)$^+$; $^1$H-NMR (CDCl$_3$,δ): 1.46 (t, J=7.5 Hz, 3H), 1.71-1.99 (m, 4H), 2.36 (s, 6H), 2.98 (br s, 2H), 3.61 (q, J=7.3 Hz, 2H), 3.87 (br s, 2H), 7.06-7.41 (m, 8H), 8.34 (br s, 1H), 8.36 (s, 1H), 8.63 (s, 1H), 10.52 (br s, 1H).

EXAMPLE 101

N-[7-(2-Chloro-5-methylphenylamino)-6-(4-fluoro-4-phenylpiperidine-1-carbonyl)pyrazolo[1,5-a]pyrimidine-3-carbonyl]ethanesulfonamide (compound a-101)

[Step 1]

7-(2-Chloro-5-methylphenylamino)-3-ethoxycarbonyl-6-(4-fluoro-4-phenylpiperidine-1-carbonyl)pyrazolo[1,5-a]pyrimidine In the same manner as in Example 21, step 5 and using 7-(2-chloro-5-methylphenylamino)-3-ethoxycarbonylpyrazolo[1,5-a]pyrimidine-6-carboxylic acid (100 mg, 0.27 mmol) obtained in Example 66, step 2 and 4-fluoro-4-phenylpiperidine hydrochloride (86 mg, 0.40 mmol), the title compound (103 mg, 72%) was obtained.

[Step 2]

7-(2-Chloro-5-methylphenylamino)-6-(4-fluoro-4-phenylpiperidine-1-carbonyl)pyrazolo[1,5-a]pyrimidine-3-carboxylic acid In the same manner as in Example 19, step 6 and using 7-(2-chloro-5-methylphenylamino)-3-ethoxycarbonyl-6-(4-fluoro-4-phenylpiperidine-1-carbonyl)pyrazolo[1,5-a]pyrimidine (103 mg, 0.19 mmol) obtained in step 1, the title compound (72 mg, 74%) was obtained.

[Step 3]

N-[7-(2-Chloro-5-methylphenylamino)-6-(4-fluoro-4-phenylpiperidine-1-carbonyl)pyrazolo[1,5-a]pyrimidine-3-carbonyl]ethanesulfonamide (compound a-101)

In the same manner as in Example 1, step 6 and using 7-(2-chloro-5-methylphenylamino)-6-(4-fluoro-4-phenylpiperidine-1-carbonyl)pyrazolo[1,5-a]pyrimidine-3-carboxylic acid (71 mg, 0.14 mmol) obtained in step 2 and ethanesulfonamide (74 mg, 0.7 mmol), the title compound (18 mg, 22%) was obtained.

ESI-MS m/z: 600 (M+H)$^+$; $^1$H-NMR (CDCl$_3$,δ): 1.46 (t, J=7.4 Hz, 3H), 1.69-1.98 (m, 4H), 2.38 (s, 3H), 2.98 (br s, 2H), 3.62 (q, J=7.4 Hz, 2H), 3.92 (br s, 2H), 7.14-7.46 (m, 8H), 8.47 (s, 1H), 8.55 (br s, 1H), 8.66 (s, 1H), 10.47 (br s, 1H).

EXAMPLE 102

N-{6-[4-Fluoro-4-(4-fluorophenyl)piperidine-1-carbonyl]-7-(4-fluoro-2-methylphenylamino)pyrazolo[1,5-a]pyrimidine-3-carbonyl}ethanesulfonamide (compound a-102)

[Step 1]

Ethyl 3-bromo-7-(4-fluoro-2-methylphenylamino)pyrazolo[1,5-a]pyrimidine-6-carboxylate In the same manner as in Example 1, step 4 and using ethyl 3-bromo-7-chloropyrazolo[1,5-a]pyrimidine-6-carboxylate (3.5 g, 11.4 mmol) obtained in Example 22, step 1 and 4-fluoro-2-methylaniline (1.53 mL, 22.8 mmol), the title compound (4.48 g, 99%) was obtained.

[Step 2]

3-Bromo-7-(4-fluoro-2-methylphenylamino)pyrazolo[1,5-a]pyrimidine-6-carboxylic acid In the same manner as in Example 19, step 6 and using ethyl 3-bromo-7-(4-fluoro-2-methylphenylamino)pyrazolo[1,5-a]pyrimidine-6-carboxylate (4.48 g, 11.4 mmol) obtained in step 1, the title compound (3.03 g, 73%) was obtained.

[Step 3]

3-Bromo-6-[4-fluoro-4-(4-fluorophenyl)piperidine-1-carbonyl]-7-(4-fluoro-2-methylphenylamino)pyrazolo[1,5-a]pyrimidine In the same manner as in Example 21, step 5 and using 3-bromo-7-(4-fluoro-2-methylphenylamino)pyrazolo[1,5-a]pyrimidine-6-carboxylic acid (100 mg, 0.27 mmol) obtained in step 2 and 4-fluoro-4-(4-fluorophenyl)piperidine hydrochloride (WO2008/012622, 71 mg, 0.33 mmol), the title compound (71 mg, 48%) was obtained.

[Step 4]

6-[4-Fluoro-4-(4-fluorophenyl)piperidine-1-carbonyl]-7-(4-fluoro-2-methylphenylamino)pyrazolo[1,5-a]pyrimidine-3-carboxylic acid In the same manner as in Example 1, step 5 and using 3-bromo-6-[4-fluoro-4-(4-fluorophenyl)piperidine-1-carbonyl]-7-(4-fluoro-2-methylphenylamino)pyrazolo[1,5-a]pyrimidine (71 mg, 0.13 mmol) obtained in step 3, the title compound (26 mg, 40%) was obtained.

[Step 5]

N-{6-[4-Fluoro-4-(4-fluorophenyl)piperidine-1-carbonyl]-7-(4-fluoro-2-methylphenylamino)pyrazolo[1,5-a]pyrimidine-3-carbonyl}ethanesulfonamide (compound a-102)

In the same manner as in Example 1, step 6 and using 6-[4-fluoro-4-(4-fluorophenyl)piperidine-1-carbonyl]-7-(4-fluoro-2-methylphenylamino)pyrazolo[1,5-a]pyrimidine-3-carboxylic acid (26 mg, 0.05 mmol) obtained in step 4 and ethanesulfonamide (27 mg, 0.26 mmol), the title compound (9 mg, 30%) was obtained.

ESI-MS m/z: 601 (M+H)$^+$; $^1$H-NMR (CDCl$_3$,δ): 1.45 (t, J=7.4 Hz, 3H), 1.71-2.20 (m, 4H), 2.40 (s, 3H), 2.99 (br s, 2H), 3.61 (q, J=7.5 Hz, 2H), 3.93 (br s, 2H), 6.92-7.01 (m, 1H), 7.05-7.14 (m, 3H), 7.19 (dd, J=8.6, 5.3 Hz, 1H), 7.32 (dd, J=8.9, 5.3 Hz, 2H), 8.29 (br s, 1H), 8.30 (s, 1H), 8.63 (s, 1H), 10.49 (br s, 1H).

EXAMPLE 103

N-{7-(2,5-Dimethylphenylamino)-6-[4-fluoro-4-(4-fluorophenyl)piperidine-1-carbonyl]pyrazolo[1,5-a]pyrimidine-3-carbonyl}ethanesulfonamide (compound a-103)

[Step 1]

7-(2,5-Dimethylphenylamino)-3-ethoxycarbonyl-6-[4-fluoro-4-(4-fluorophenyl)piperidine-1-carbonyl]pyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (100 mg, 0.28 mmol) obtained in Example 88, step 2 and 4-fluoro-4-(4-fluorophenyl)piperidine hydrochloride (79 mg, 0.34 mmol), the title compound (80 mg, 54%) was obtained.

[Step 2]

7-(2,5-Dimethylphenylamino)-6-[4-fluoro-4-(4-fluorophenyl)piperidine-1-carbonyl]pyrazolo[1,5-a]pyrimidine-3-carboxylic acid In the same manner as in Example 19, step 6 and using 7-(2,5-dimethylphenylamino)-3-ethoxycarbonyl-6-[4-fluoro-4-(4-fluorophenyl)piperidine-1-carbonyl]pyrazolo[1,5-a]pyrimidine (80 mg, 0.15 mmol) obtained in step 1, the title compound (64 mg, 81%) was obtained.

[Step 3]

N-{7-(2,5-Dimethylphenylamino)-6-[4-fluoro-4-(4-fluorophenyl)piperidine-1-carbonyl]pyrazolo[1,5-a]pyrimidine-3-carbonyl}ethanesulfonamide (compound a-103)

In the same manner as in Example 1, step 6 and using 7-(2,5-dimethylphenylamino)-6-[4-fluoro-4-(4-fluorophenyl)piperidine-1-carbonyl]pyrazolo[1,5-a]pyrimidine-3-carboxylic acid (64 mg, 0.12 mmol) obtained in step 2 and ethanesulfonamide (51 mg, 0.48 mmol), the title compound (18 mg, 25%) was obtained.

ESI-MS m/z: 597 (M+H)$^+$; $^1$H-NMR (CDCl$_3$,δ): 1.46 (t, J=7.3 Hz, 3H), 1.67-2.00 (m, 4H), 2.36 (s, 6H), 2.99 (br s,

2H), 3.62 (q, J=7.5 Hz, 2H), 3.93 (br s, 2H), 7.04-7.16 (m, 4H), 7.21-7.32 (m, 3H), 8.34 (br s, 1H), 8.35 (s, 1H), 8.63 (s, 1H), 10.52 (br s, 1H).

EXAMPLE 104

N-{7-(2,5-Dimethylphenylamino)-6-[4-(4-fluorophenyl)-1,2,3,6-tetrahydropyridine-1-carbonyl]pyrazolo[1,5-a]pyrimidine-3-carbonyl}ethanesulfonamide (compound a-104)

[Step 1]

7-(2,5-Dimethylphenylamino)-3-ethoxycarbonyl-6-[4-(4-fluorophenyl)-1,2,3,6-tetrahydropyridine-1-carbonyl]pyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (110 mg, 0.31 mmol) obtained in Example 88, step 2 and 4-(4-fluorophenyl)-1,2,3,6-tetrahydropyridine hydrochloride (79 mg, 0.37 mmol), the title compound (119 mg, 75%) was obtained.

[Step 2]

7-(2,5-Dimethylphenylamino)-6-[4-(4-fluorophenyl)-1,2,3,6-tetrahydropyridine-1-carbonyl]pyrazolo[1,5-a]pyrimidine-3-carboxylic acid In the same manner as in Example 19, step 6 and using 7-(2,5-dimethylphenylamino)-3-ethoxycarbonyl-6-[4-(4-fluorophenyl)-1,2,3,6-tetrahydropyridine-1-carbonyl]pyrazolo[1,5-a]pyrimidine (119 mg, 0.23 mmol) obtained in step 1, the title compound (107 mg, 95%) was obtained.

[Step 3]

N-{7-(2,5-Dimethylphenylamino)-6-[4-(4-fluorophenyl)-1,2,3,6-tetrahydropyridine-1-carbonyl]pyrazolo[1,5-a]pyrimidine-3-carbonyl}ethanesulfonamide (compound a-104)

In the same manner as in Example 1, step 6 and using 7-(2,5-dimethylphenylamino)-6-[4-(4-fluorophenyl)-1,2,3,6-tetrahydropyridine-1-carbonyl]pyrazolo[1,5-a]pyrimidine-3-carboxylic acid (45 mg, 0.09 mmol) obtained in step 2 and ethanesulfonamide (49 mg, 0.47 mmol), the title compound (21 mg, 39%) was obtained.
ESI-MS m/z: 577 (M+H)$^+$; $^1$H-NMR (CDCl$_3$,δ): 1.47 (t, J=7.3 Hz, 3H), 2.23 (br s, 2H), 2.34 (s, 6H), 3.48 (br s, 2H), 3.62 (q, J=7.3 Hz, 2H), 3.86 (br s, 2H), 5.88 (br s, 1H), 6.99-7.32 (m, 7H), 8.32 (br s, 2H), 8.63 (br s, 1H), 10.54 (br s, 1H).

EXAMPLE 105

N-[7-Benzylamino-6-(spiro[inden-1,4'-piperidine]-1'-ylcarbonyl)pyrazolo[1,5-a]pyrimidine-3-carbonyl]methanesulfonamide (compound a-105)

[Step 1]

7-Benzylamino-3-bromo-6-(spiro[inden-1,4'-piperidine]-1'-ylcarbonyl)pyrazolo[1,5-a]pyrimidine In the same manner as in Example 22, step 4 and using 7-benzylamino-3-bromopyrazolo[1,5-a]pyrimidine-6-carboxylic acid (0.091 g, 0.242 mmol) obtained in Example 22, step 3 and spiro[inden-1,4'-piperidine]hydrochloride (WO2004/028459, 0.059 g, 0.267 mmol), the title compound (0.127 g, 95%) was obtained.

[Step 2]

7-Benzylamino-6-(spiro[inden-1,4'-piperidine]-1'-ylcarbonyl)pyrazolo[1,5-a]pyrimidine-3-carboxylic acid In the same manner as in Example 1, step 5 and using 7-benzylamino-3-bromo-6-(spiro[inden-1,4'-piperidine]-1'-ylcarbonyl)pyrazolo[1,5-a]pyrimidine (0.150 g, 0.276 mmol) obtained in step 1, the title compound (0.132 g, 100%) was obtained.

[Step 3]

N-[7-Benzylamino-6-(spiro[inden-1,4'-piperidine]-1'-ylcarbonyl)pyrazolo[1,5-a]pyrimidine-3-carbonyl]methanesulfonamide (compound a-105)

In the same manner as in Example 1, step 6 and using 7-benzylamino-6-(spiro[inden-1,4'-piperidine]-1'-ylcarbonyl)pyrazolo[1,5-a]pyrimidine-3-carboxylic acid (0.125 g, 0.260 mmol) obtained in step 2 and methanesulfonamide (0.123 g, 1.30 mmol), the title compound (0.043 g, 29%) was obtained.
ESI-MS m/z: 557 (M+H)$^+$; $^1$H-NMR (CDCl$_3$,δ): 1.12-1.48 (m, 2H), 1.78-2.10 (m, 2H), 2.40-3.26 (m, 2H), 3.42 (s, 3H), 3.96-4.52 (m, 2H), 4.84-5.07 (m, 2H), 6.64 (d, J=6.0 Hz, 1H), 6.81 (d, J=6.0 Hz, 1H), 7.14-7.55 (m, 9H), 7.62-7.95 (m, 1H), 8.27 (s, 1H), 8.60 (s, 1H), 10.71 (br s, 1H).

EXAMPLE 106

N-[7-(2-Methylphenyl)amino-6-(spiro[inden-1,4'-piperidine]-1'-ylcarbonyl)pyrazolo[1,5-a]pyrimidine-3-carbonyl]methanesulfonamide (compound a-106)

[Step 1]

3-Bromo-7-(2-methylphenyl)amino-6-(spiro[inden-1,4'-piperidine]-1'-ylcarbonyl)pyrazolo[1,5-a]pyrimidine In the same manner as in Example 24, step 3 and using spiro[inden-1,4'-piperidine]hydrochloride (0.800 g, 3.61 mmol) instead of 4-(3-methyl-1,2,4-oxazol-5-yl)piperidine hydrochloride, the title compound (1.10 g, 65%) was obtained.

[Step 2]

7-(2-Methylphenyl)amino-6-(spiro[inden-1,4'-piperidine]-1'-ylcarbonyl)pyrazolo[1,5-a]pyrimidine-3-carboxylic acid In the same manner as in Example 1, step 5 and using 3-bromo-7-(2-methylphenyl)amino-6-(spiro[inden-1,4'-piperidine]-1'-ylcarbonyl)pyrazolo[1,5-a]pyrimidine (1.1 g, 2.15 mmol) obtained in step 1, the title compound (0.742 g, 72%) was obtained.

[Step 3]

N-[7-(2-Methylphenyl)amino-6-(spiro[inden-1,4'-piperidine]-1'-ylcarbonyl)pyrazolo[1,5-a]pyrimidine-3-carbonyl]methanesulfonamide (compound a-106)

In the same manner as in Example 1, step 6 and using 7-(2-methylphenyl)amino-6-(spiro[inden-1,4'-piperidine]-

1'-ylcarbonyl)pyrazolo[1,5-a]pyrimidine-3-carboxylic acid (0.080 g, 0.167 mmol) obtained in step 2 and methanesulfonamide (0.080 g, 0.834 mmol), the title compound (0.007 g, 7.5%) was obtained.

ESI-MS m/z: 557 (M+H)$^+$; $^1$H-NMR (CDCl$_3$, δ): 1.74-2.16 (m, 4H), 2.45 (s, 3H), 2.63-3.24 (m, 2H), 3.45 (s, 3H), 3.69-4.20 (m, 2H), 6.67 (d, J=5.6 Hz, 1H), 6.82 (d, J=5.6 Hz, 1H), 7.20-7.54 (m, 8H), 8.31-8.48 (m, 2H), 8.64 (s, 1H), 10.70 (br s, 1H).

EXAMPLE 107

N-[7-(2-Methylphenyl)amino-6-(spiro[inden-1,4'-piperidine]-1'-ylcarbonyl)pyrazolo[1,5-a]pyrimidine-3-carbonyl]ethanesulfonamide (compound a-107)

In the same manner as in Example 1, step 6 and using 7-(2-methylphenyl)amino-6-(spiro[inden-1,4'-piperidine]-1'-ylcarbonyl)pyrazolo[1,5-a]pyrimidine-3-carboxylic acid (0.249 g, 0.520 mmol) obtained in Example 106, step 2 and ethanesulfonamide (0.238 g, 2.60 mmol), the title compound (0.036 g, 11%) was obtained.

ESI-MS m/z: 571 (M+H)$^+$; $^1$H-NMR (CDCl$_3$, δ): 1.18-1.39 (m, 2H), 1.48 (t, J=7.3 Hz, 3H), 1.55-1.97 (m, 2H), 2.39-2.53 (m, $^2$H), 2.68-3.28 (m, 3H), 3.62 (q, J=7.3 Hz, 2H), 3.87-4.02 (m, 2H), 6.67 (d, J=5.4 Hz, 1H), 6.81 (d, J=5.4 Hz, 1H), 7.13-7.55 (m, 8H), 8.32-8.52 (m, 2H), 8.67 (s, 1H), 10.57 (br s, 1H).

EXAMPLE 108

N-[7-(2-Fluoro-5-methylphenylamino)-6-(spiro[inden-1,4'-piperidine]-1'-ylcarbonyl)pyrazolo[1,5-a]pyrimidine-3-carbonyl]cyclopropanesulfonamide (compound a-108)

[Step 1]

3-Ethoxycarbonyl-7-hydroxy-6-(spiro[inden-1,4'-piperidine]-1'-ylcarbonyl)pyrazolo[1,5-a]pyrimidine In the same manner as in Example 1, step 2 and using 3-ethoxycarbonyl-7-hydroxypyrazolo[1,5-a]pyrimidine-6-carboxylic acid (0.420 g, 1.68 mmol) obtained in Example 19, step 2 and spiro[inden-1,4'-piperidine]hydrochloride (0.450 g, 2.02 mmol), the title compound (0.300 g, 43%) was obtained.

[Step 2]

7-Chloro-3-ethoxycarbonyl-6-(spiro[inden-1,4'-piperidine]-1'-ylcarbonyl)pyrazolo[1,5-a]pyrimidine In the same manner as in Example 1, step 3 and using 3-ethoxycarbonyl-7-hydroxy-6-(spiro[inden-1,4'-piperidine]-1'-ylcarbonyl)pyrazolo[1,5-a]pyrimidine (0.300 g, 0.730 mmol) obtained in step 1, the title compound (0.210 g, 65%) was obtained.

[Step 3]

3-Ethoxycarbonyl-7-(2-fluoro-5-methylphenylamino)-6-(spiro[inden-1,4'-piperidine]-1'-ylcarbonyl)pyrazolo[1,5-a]pyrimidine In the same manner as in Example 19, step 5 and using 7-chloro-3-ethoxycarbonyl-6-(spiro[inden-1,4'-piperidine]-1'-ylcarbonyl)pyrazolo[1,5-a]pyrimidine (0.070 g, 0.160 mmol) obtained in step 2 and 2-fluoro-5-methylaniline (0.030 g, 0.240 mmol), the title compound (0.074 g, 87%) was obtained.

[Step 4]

7-(2-Fluoro-3-methylphenylamino)-6-(spiro[inden-1,4'-piperidine]-1'-ylcarbonyl)pyrazolo[1,5-a]pyrimidine-3-carboxylic acid In the same manner as in Example 19, step 6 and using 3-ethoxycarbonyl-7-(2-fluoro-5-methylphenylamino)-6-(spiro[inden-1,4'-piperidine]-1'-ylcarbonyl)pyrazolo[1,5-a] pyrimidine (0.740 g, 0.14 mmol) obtained in step 3, the title compound (0.053 g, 77%) was obtained.

[Step 5]

N-[7-(2-Fluoro-5-methylphenylamino)-6-(spiro[inden-1,4'-piperidine]-1'-ylcarbonyl)pyrazolo[1,5-a]pyrimidine-3-carbonyl]cyclopropanesulfonamide (compound a-108)

In the same manner as in Example 1, step 6 and using 7-(2-fluoro-3-methylphenylamino)-6-(spiro[inden-1,4'-piperidine]-1'-ylcarbonyl)pyrazolo[1,5-a]pyrimidine-3-carboxylic acid (0.053 g, 0.11 mmol) obtained in step 4 and cyclopropanesulfonamide (0.07 g, 0.43 mmol), the title compound (0.051 g, 79%) was obtained.

ESI-MS m/z: 601 (M+H)$^+$; $^1$H-NMR (CDCl$_3$, δ):1.10-1.17 (m, 2H), 1.32 (d, J=13.6 Hz, 2H), 1.46-1.50 (m, 2H), 1.87 (t, J=10.6 Hz, 2H), 2.41 (s, 3H), 3.07-3.15 (m, 1H), 3.86-4.05 (m, 4H), 6.67 (d, J=5.5 Hz, 1H), 6.81 (d, J=5.9 Hz, 1H), 7.19-7.35 (m, 7H), 8.48 (s, 1H), 8.65 (s, 1H).

EXAMPLE 109

N-[7-(4-Fluoro-2-methylphenylamino)-6-(spiro[inden-1,4'-piperidine]-1'-ylcarbonyl)pyrazolo[1,5-a]pyrimidine-3-carbonyl]ethanesulfonamide (compound a-109)

[Step 1]

3-Ethoxycarbonyl-7-(4-fluoro-2-methylphenylamino)-6-(spiro[inden-1,4'-piperidine]-1'-ylcarbonyl)pyrazolo[1,5-a]pyrimidine In the same manner as in Example 19, step 5 and using 7-chloro-3-ethoxycarbonyl-6-(spiro[inden-1,4'-piperidine]-1'-ylcarbonyl)pyrazolo[1,5-a]pyrimidine (0.07 g, 0.16 mmol) obtained in Example 108, step 2 and 4-fluoro-2-methylaniline (0.03 g, 0.24 mmol), the title compound (0.073 g, 88%) was obtained.

[Step 2]

7-(4-Fluoro-2-methylphenylamino)-6-(spiro[inden-1,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(spiro[inden-1,4'-piperidine]-1'-ylcarbonyl)pyrazolo[1,5-a] pyrimidine (0.073 g, 0.14 mmol) obtained in step 1, the title compound (0.063 g, 91%) was obtained.

[Step 3]

N-[7-(4-Fluoro-2-methylphenylamino)-6-(spiro[inden-1,4'-piperidine]-1'-ylcarbonyl)pyrazolo[1,5-a]pyrimidine-3-carbonyl]ethanesulfonamide (compound a-109)

In the same manner as in Example 1, step 6 and using 7-(4-fluoro-2-methylphenylamino)-6-(spiro[inden-1,4'-piperidine]-1'-ylcarbonyl)pyrazolo[1,5-a]pyrimidine-3-carboxylic acid (0.03 g, 0.06 mmol) obtained in step 2 and ethanesulfonamide (0.032 g, 0.30 mmol), the title compound (0.013 g, 37%) was obtained.

ESI-MS m/z: 589 (M+H)$^+$; $^1$H-NMR (CDCl$_3$,δ):1.35 (d, J=14.3 Hz, 2H), 1.46 (t, J=7.5 Hz, 3H), 1.89 (t, J=11.2 Hz, 2H), 2.43 (s, 3H), 3.61 (q, J=7.3 Hz, 2H), 3.77-4.10 (m, 4H), 6.70 (d, J=5.5 Hz, 1H), 6.83 (d, J=5.5 Hz, 1H), 7.02-7.08 (m, 1H), 7.14 (dd, J=9.0, 3.1 Hz, 1H), 7.22-7.37 (m, 5H), 8.37 (s, 1H), 8.64 (s, 1H).

EXAMPLE 110

N-[7-(4-Fluoro-2-methylphenylamino)-6-(spiro[inden-1,4'-piperidine]-1'-ylcarbonyl)pyrazolo[1,5-a]pyrimidine-3-carbonyl]cyclopropanesulfonamide (compound a-110)

In the same manner as in Example 1, step 6 and using 7-(4-fluoro-2-methylphenylamino)-6-(spiro[inden-1,4'-piperidine]-1'-ylcarbonyl)pyrazolo[1,5-a]pyrimidine-3-carboxylic acid (0.03 g, 0.06 mmol) obtained in Example 109, step 2 and cyclopropanesulfonamide (0.037 g, 0.30 mmol), the 30 title compound (0.021 g, 58%) was obtained.

ESI-MS m/z: 601 (M+H)$^+$; $^1$H-NMR (CDCl$_3$,δ):1.10-1.18 (m, 2H), 1.35 (d, J=12.5 Hz, 2H), 1.46-1.51 (m, 2H), 1.88 (t, J=10.4 Hz, 2H), 2.62 (s, 3H), 3.07-3.15 (m, 1H), 3.85-4.11 (m, 4H), 6.70 (d, J=5.9 Hz, 1H), 6.83 (d, J=5.5 Hz, 1H), 7.05 (td, J=8.2, 2.9 Hz, 1H), 7.14 (dd, J=8.8, 2.6 Hz, 1H), 7.22-7.36 (m, 5H), 8.28 (s, 1H), 8.36 (s, 1H), 8.65 (s, 1H), 10.61 (s, 1H).

EXAMPLE 111

N-[7-Benzylamino-6-(3-methylspiro[inden-1,4'-piperidine]-1'-ylcarbonyl)pyrazolo[1,5-a]pyrimidine-3-carbonyl]methanesulfonamide (compound a-111)

[Step 1]

7-Benzylamino-3-ethoxycarbonyl-6-(3-methylspiro[inden-1,4'-piperidine]-1'-ylcarbonyl)pyrazolo[1,5-a]pyrimidine In the same manner as in Example 21, step 5 and using 7-benzylamino-3-ethoxycarbonylpyrazolo[1,5-a]pyrimidine-6-carboxylic acid (0.138 g, 0.406 mmol) obtained in Example 21, step 4 and 3-methylspiro[inden-1,4'-piperidine] (Reference Example 7, 0.097 g, 0.447 mmol), the title compound (0.180 g, 85%) was obtained.

[Step 2]

7-Benzylamino-6-(3-methylspiro[inden-1,4'-piperidine]-1'-ylcarbonyl)pyrazolo[1,5-a]pyrimidine-3-carboxylic acid In the same manner as in Example 19, step 6 and using 7-benzylamino-3-ethoxycarbonyl-6-(3-methylspiro[inden-1,4'-piperidine]-1'-ylcarbonyl)pyrazolo[1,5-a]pyrimidine (0.180 g, 0.346 mmol) obtained in step 1, the title compound (0.130 g, 76%) was obtained.

[Step 3]

N-[7-Benzylamino-6-(3-methylspiro[inden-1,4'-piperidine]-1'-ylcarbonyl)pyrazolo[1,5-a]pyrimidine-3-carbonyl]methanesulfonamide (compound a-111)

In the same manner as in Example 1, step 6 and using 7-benzylamino-6-(3-methylspiro[inden-1,4'-piperidine]-1'-ylcarbonyl)pyrazolo[1,5-a]pyrimidine-3-carboxylic acid (0.130 g, 0.264 mmol) obtained in step 2 and methanesulfonamide (0.126 g, 1.32 mmol), the title compound (0.096 g, 64%) was obtained.

ESI-MS m/z: 571 (M+H)$^+$; $^1$H-NMR (CDCl$_3$,δ): 1.20-1.51 (m, 2H), 1.80-2.09 (m, 2H), 2.09-2.30 (m, 3H), 2.59-3.26 (m, 2H), 3.45 (s, 3H), 4.04-4.55 (m, 2H), 4.86-5.08 (m, 2H), 6.33 (s, 1H), 7.17-7.59 (m, 9H), 7.64-7.89 (m, 1H), 8.28 (s, 1H), 8.59 (s, 1H), 10.74 (br s, 1H).

EXAMPLE 112

N-[7-Benzylamino-6-(2-methylspiro[inden-1,4'-piperidine]-1'-ylcarbonyl)pyrazolo[1,5-a]pyrimidine-3-carbonyl]methanesulfonamide (compound a-112)

[Step 1]

7-Benzylamino-3-ethoxycarbonyl-6-(2-methylspiro[inden-1,4'-piperidine]-1'-ylcarbonyl)pyrazolo[1,5-a]pyrimidine In the same manner as in Example 21, step 5 and using 7-benzylamino-3-ethoxycarbonylpyrazolo[1,5-a]pyrimidine-6-carboxylic acid (0.100 g, 0.2949 mmol) obtained in Example 21, step 4 and 2-methylspiro[inden-1,4'-piperidine] (Reference Example 6, 0.064 g, 0.324 mmol), the title compound (0.103 g, 67%) was obtained.

[Step 2]

7-Benzylamino-6-(2-methylspiro[inden-1,4'-piperidine]-1'-ylcarbonyl)pyrazolo[1,5-a]pyrimidine-3-carboxylic acid In the same manner as in Example 19, step 6 and using 7-benzylamino-3-ethoxycarbonyl-6-(2-methylspiro[inden-1,4'-piperidine]-1'-ylcarbonyl)pyrazolo[1,5-a]pyrimidine (0.100 g, 0.346 mmol) obtained in step 1, the title compound (0.078 g, 82%) was obtained.

[Step 3]

N-[7-Benzylamino-6-(2-methylspiro[inden-1,4'-piperidine]-1'-ylcarbonyl)pyrazolo[1,5-a]pyrimidine-3-carbonyl]methanesulfonamide (compound a-112)

In the same manner as in Example 1, step 6 and using 7-benzylamino-6-(2-methylspiro[inden-1,4'-piperidine]-1'-ylcarbonyl)pyrazolo[1,5-a]pyrimidine-3-carboxylic acid (0.078 g, 0.158 mmol) obtained in step 2 and methanesulfonamide (0.075 g, 0.791 mmol), the title compound (0.055 g, 61%) was obtained.

ESI-MS m/z: 571 (M+H)$^+$; $^1$H-NMR (CDCl$_3$,δ): 1.12-1.38 (m, 2H), 1.77-2.05 (m, 5H), 2.94-3.36 (m, 2H), 3.42 (s, 3H), 4.14-4.67 (m, 2H), 4.99 (s, 2H), 6.43 (s, 1H), 7.05-7.20 (m, 1H), 7.20-7.54 (m, 8H), 7.66-7.89 (m, 1H), 8.26 (s, 1H), 8.61 (s, 1H), 10.73 (br s, 1H).

EXAMPLE 113

N-[7-(2,5-Dimethylphenylamino)-6-(2-methylspiro[inden-1,4'-piperidine]-1'-ylcarbonyl)pyrazolo[1,5-a]pyrimidine-3-carbonyl]ethanesulfonamide (compound a-113)

[Step 1]

7-(2,5-Dimethylphenylamino)-3-ethoxycarbonyl-6-(2-methylspiro[inden-1,4'-piperidine]-1'-ylcarbonyl)pyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (0.100 g, 0.282 mmol) obtained in Example 88, step 2 and 2-methylspiro[inden-1,4'-piperidine] (0.062 g, 0.313 mmol), the title compound (0.098 g, 65%) was obtained.

[Step 2]

7-(2,5-Dimethylphenylamino)-6-(2-methylspiro[inden-1,4'-piperidine]-1'-ylcarbonyl)pyrazolo[1,5-a]pyrimidine-3-carboxylic acid In the same manner as in Example 19, step 6 and using 7-(2,5-dimethylphenylamino)-3-ethoxycarbonyl-6-(2-methylspiro[inden-1,4'-piperidine]-1'-ylcarbonyl)pyrazolo[1,5-a]pyrimidine (0.095 g, 0.178 mmol) obtained in step 1, the title compound (0.053 g, 59%) was obtained.

[Step 3]

N-[7-(2, 5-Dimethylphenylamino)-6-(2-methylspiro[inden-1,4'-piperidine]-1'-ylcarbonyl)pyrazolo[1,5-a]pyrimidine-3-carbonyl]ethanesulfonamide (compound a-113)

In the same manner as in Example 1, step 6 and using 7-(2,5-dimethylphenylamino)-6-(2-methylspiro[inden-1,4'-piperidine]-1'-ylcarbonyl)pyrazolo[1,5-a]pyrimidine-3-carboxylic acid (0.053 g, 0.105 mmol) obtained in step 2 and ethanesulfonamide (0.057 g, 0.587 mmol), the title compound (0.033 g, 52%) was obtained.

ESI-MS m/z: 599 (M+H)$^+$; $^1$H-NMR (CDCl$_3$,δ): 1.09-1.18 (m, 2H), 1.46 (t, J=7.4 Hz, 3H), 1.67-1.86 (m, 2H), 1.86-1.97 (m, 3H), 2.40 (s, 3H), 2.43 (s, 3H), 3.08-3.52 (m, 2H), 3.62 (q, J=7.4 Hz, 2H), 3.94-4.37 (m, 2H), 6.40 (s, 1H), 7.03-7.31 (m, 6H), 7.31-7.44 (m, 1H), 8.36-8.45 (m, 1H), 8.50 (s, 1H), 8.63 (s, 1H), 10.55 (br s, 1H).

EXAMPLE 114

N-[6-(2-Methylspiro[inden-1,4'-piperidine]-1'-ylcarbonyl)-7-phenylaminopyrazolo[1,5-a]pyrimidine-3-carbonyl]methanesulfonamide (compound a-114)

[Step 1]

3-Ethoxycarbonyl-7-hydroxy-6-(2-methylspiro[inden-1,4'-piperidine]-1'-ylcarbonyl)pyrazolo[1,5-a]pyrimidine In the same manner as in Example 19, step 3 and using 3-ethoxycarbonyl-7-hydroxypyrazolo[1,5-a]pyrimidine-6-carboxylic acid (0.533 g, 2.12 mmol) obtained in Example 19, step 2 and 2-methylspiro[inden-1,4'-piperidine] (0.465 g, 2.34 mmol), the title compound (0.712 g, 70%) was obtained.

[Step 2]

7-Chloro-3-ethoxycarbonyl-6-(2-methylspiro[inden-1,4'-piperidine]-1'-ylcarbonyl)pyrazolo[1,5-a]pyrimidine In the same manner as in Example 1, step 3 and using 3-ethoxycarbonyl-7-hydroxy-6-(2-methylspiro[inden-1,4'-piperidine]-1'-ylcarbonyl)pyrazolo[1,5-a]pyrimidine (0.712 g, 1.65 mmol) obtained in step 1, the title compound (0.660 g, 88%) was obtained.

[Step 3]

3-Ethoxycarbonyl-6-(2-methylspiro[inden-1,4'-piperidine]-1'-ylcarbonyl)-7-phenylaminopyrazolo[1,5-a]pyrimidine In the same manner as in Example 19, step 5 and using 7-chloro-3-ethoxycarbonyl-6-(2-methylspiro[inden-1,4'-piperidine]-1'-ylcarbonyl)pyrazolo[1,5-a]pyrimidine (0.220 g, 0.488 mmol) obtained in step 2 and aniline (0.054 mL, 0.585 mmol), the title compound (0.191 g, 79%) was obtained.

[Step 4]

6-(2-Methylspiro[inden-1,4'-piperidine]-1'-ylcarbonyl)-7-phenylaminopyrazolo[1,5-a]pyrimidine-3-carboxylic acid In the same manner as in Example 19, step 6 and using 3-ethoxycarbonyl-6-(2-methylspiro[inden-1,4'-piperidine]-1'-ylcarbonyl)-7-phenylaminopyrazolo[1,5-a]pyrimidine (0.197 g, 0.389 mmol) obtained in step 3, the title compound (0.153 g, 82%) was obtained.

[Step 5]

N-[6-(2-Methylspiro[inden-1,4'-piperidine]-1'-ylcarbonyl)-7-phenylaminopyrazolo[1,5-a]pyrimidine-3-carbonyl]methanesulfonamide (compound a-114)

In the same manner as in Example 1, step 6 and using 6-(2-methylspiro[inden-1,4'-piperidine]-1'-ylcarbonyl)-7-phenylaminopyrazolo[1,5-a]pyrimidine-3-carboxylic acid (0.030 g, 0.063 mmol) obtained in step 4 and methanesulfonamide (0.030 g, 0.313 mmol), the title compound (0.026 g, 60%) was obtained.

ESI-MS m/z: 557 (M+H)$^+$; $^1$H-NMR (CDCl$_3$,δ): 1.50-1.85 (m, 4H), 1.90 (s, 3H), 3.29-3.61 (m, 5H), 3.95-4.27 (m, 2H), 6.40'(s, 1H), 7.06-7.17 (m, 1H), 7.22-7.34 (m, 3H), 7.36-7.53 (m, 3H), 7.53-7.66 (m, 2H), 8.53 (s, 1H), 8.58-8.73 (m, 2H), 10.66 (s, 1H).

EXAMPLE 115

N-[6-(2-Methylspiro[inden-1,4'-piperidine]-1'-ylcarbonyl)-7-phenylaminopyrazolo[1,5-a]pyrimidine-3-carbonyl]ethanesulfonamide (compound a-115)

In the same manner as in Example 1, step 6 and using 6-(2-methylspiro[inden-1,4'-piperidine]-1'-ylcarbonyl)-7-phenylaminopyrazolo[1,5-a]pyrimidine-3-carboxylic acid (0.090 g, 0.188 mmol) obtained in Example 114, step 4 and ethanesulfonamide (0.102 g, 0.939 mmol), the title compound (0.068 g, 63%) was obtained.

ESI-MS m/z: 571 (M+H)$^+$; $^1$H-NMR (CDCl$_3$, δ): 1.45 (t, J=7.3 Hz, 3H), 1.55-1.85 (m, 4H), 1.91 (s, 3H), 3.33-3.77 (m, 4H), 3.83-4.35 (m, 2H), 6.38-6.42 (m, 1H), 7.08-7.17 (m,

1H), 7.20-7.34 (m, 3 H), 7.35-7.52 (m, 3H), 7.52-7.69 (m, 2H), 8.47-8.58 (m, 2H), 8.69 (s, 1H), 10.49 (s, 1H).

EXAMPLE 116

N-[7-(4-Fluorophenylamino)-6-(2-methylspiro[inden-1,4'-piperidine]-1'-ylcarbonyl)pyrazolo[1,5-a]pyrimidine-3-carbonyl]methanesulfonamide (compound a-116)

[Step 1]

3-Ethoxycarbonyl-7-(4-fluorophenylamino)-6-(2-methylspiro[inden-1,4'-piperidine]-1'-ylcarbonyl)pyrazolo[1,5-a]pyrimidine In the same manner as in Example 114, step 3 and using 4-fluoroaniline (0.056 mL, 0.585 mmol) instead of aniline, the title compound (0.200 g, 78%) was obtained.

[Step 2]

7-(4-Fluorophenylamino)-6-(2-methylspiro[inden-1,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluorophenylamino)-6-(2-methylspiro[inden-1,4'-piperidine]-1'-ylcarbonyl)pyrazolo[1,5-a]pyrimidine (0.200 g, 0.380 mmol) obtained in step 1, the title compound (0.180 g, 95%) was obtained.

[Step 3]

N-[7-(4-Fluorophenylamino)-6-(2-methylspiro[inden-1,4'-piperidine]-1'-ylcarbonyl)pyrazolo[1,5-a]pyrimidine-3-carbonyl]methanesulfonamide (compound a-116)

In the same manner as in Example 1, step 6 and using 7-(4-fluorophenylamino)-6-(2-methylspiro[inden-1,4'-piperidine]-1'-ylcarbonyl)pyrazolo[1,5-a]pyrimidine-3-carboxylic acid (0.040 g, 0.083 mmol) obtained in step 2 and methanesulfonamide (0.040 g, 0.417 mmol), the title compound (0.034 g, 71%) was obtained.

ESI-MS m/z: 575 (M+H)$^+$; $^1$H-NMR (CDCl$_3$,δ): 1.64-1.89 (m, 4H), 1.94 (s, 3H), 3.27-3.79 (m, 5H), 3.98-4.36 (m, 2H), 6.40-6.44 (m, 1H), 7.08-7.20 (m, 1H), 7.20-7.46 (m, 7H), 8.47 (s, 1H), 8.57 (s, 1H), 8.64 (s, 1H), 10.64 (br s, 1H).

EXAMPLE 117

N-[7-(4-Fluorophenylamino)-6-(2-methylspiro[inden-1,4'-piperidine]-1'-ylcarbonyl)pyrazolo[1,5-a]pyrimidine-3-carbonyl]ethanesulfonamide (compound a-117)

In the same manner as in Example 1, step 6 and using 7-(4-fluorophenylamino)-6-(2-methylspiro[inden-1,4'-piperidine]-1'-ylcarbonyl)pyrazolo[1,5-a]pyrimidine-3-carboxylic acid (0.100 g, 0.209 mmol) obtained in Example 116, step 2 and ethanesulfonamide (0.113 g, 1.04 mmol), the title compound (0.031 g, 25%) was obtained.

ESI-MS m/z: 589 (M+H)$^+$; $^1$H-NMR (CDCl$_3$, δ): 1.15-1.37 (m, 2H), 1.46 (t, J=7.3 Hz, 3H), 1.72-1.89 (m, 2H), 1.95 (s, 3H), 3.32-3.79 (m, 4H), 4.05-4.45 (m, 2H), 6.38-6.46 (m, 1H), 7.07-7.22 (m, 1 H), 7.22-7.50 (m, 7H), 8.48 (s, 1H), 8.55 (s, 1H), 8.63 (s, 1H), 10.50 (br s, 1H).

EXAMPLE 118

N-[7-Benzylamino-6-(3'-methylspiro[inden-1,4'-piperidine]-1'-ylcarbonyl)pyrazolo[1,5-a]pyrimidine-3-carbonyl]methanesulfonamide (compound a-118)

[Step 1]

7-Benzylamino-3-ethoxycarbonyl-6-(3'-methylspiro[inden-1,4'-piperidine]-1'-ylcarbonyl)pyrazolo[1,5-a]pyrimidine In the same manner as in Example 21, step 5 and using 7-benzylamino-3-ethoxycarbonylpyrazolo[1,5-a]pyrimidine-6-carboxylic acid (0.066 g, 0.194 mmol) obtained in Example 21, step 4 and 3'-methylspiro[inden-1,4'-piperidine] (WO2004/028459, 0.043 g, 0.213 mmol), the title compound (0.091 g, 90%) was obtained.

[Step 2]

7-Benzylamino-6-(3'-methylspiro[inden-1,4'-piperidine]-1'-ylcarbonyl)pyrazolo[1,5-a]pyrimidine-3-carboxylic acid In the same manner as in Example 19, step 6 and using 7-benzylamino-3-ethoxycarbonyl-6-(3'-methylspiro[inden-1,4'-piperidine]-1'-ylcarbonyl)pyrazolo[1,5-a]pyrimidine (0.075 g, 0.144 mmol) obtained in step 1, the title compound (0.049 g, 69%) was obtained.

[Step 3]

N-[7-Benzylamino-6-(3'-methylspiro[inden-1,4'-piperidine]-1'-ylcarbonyl)pyrazolo[1,5-a]pyrimidine-3-carbonyl]methanesulfonamide (compound a-118)

In the same manner as in Example 1, step 6 and using 7-benzylamino-6-(3'-methylspiro[inden-1,4'-piperidine]-1'-ylcarbonyl)pyrazolo[1,5-a]pyrimidine-3-carboxylic acid (0.049 g, 0.0825 mmol) obtained in step 2 and methanesulfonamide (0.039 g, 0.413 mmol), the title compound (0.037 g, 79%) was obtained.

ESI-MS m/z: 571 (M+H)$^+$; $^1$H-NMR (CDCl$_3$,δ): 0.15-0.45 (m, 3H), 1.20-1.37 (m, 1H), 1.90-2.25 (m, 2H), 2.40-3.00 (m, 2H), 3.42 (s, 3H), 4.15-4.66 (m, 2H), 4.85-5.04 (m, 2H), 6.41-6.58 (m, 1H), 6.88 (d, J=5.6 Hz, 1H), 7.10-7.53 (m, 9H), 7.66-7.83 (m, 1H), 8.27 (s, 1H), 8.59 (s, 1H), 10.72 (br s, 1H).

EXAMPLE 119

N-[7-Benzylamino-6-(spiro[indane-1,4'-piperidine]-1'-ylcarbonyl)pyrazolo[1,5-a]pyrimidine-3-carbonyl]methanesulfonamide (compound a-119)

[Step 1]

7-Benzylamino-3-bromo-6-(spiro[indane-1,4'-piperidine]-1'-ylcarbonyl)pyrazolo[1,5-a]pyrimidine In the same manner as in Example 22, step 4 and using spiro[indane-1,4'-piperidine]hydrochloride (WO2006/023852, 0.092 g, 0.412 mmol) instead of 4-(2-methoxyphenyl)piperidine, the title compound (0.156 g, 81%) was obtained.

[Step 2]

7-Benzylamino-6-(spiro[indane-1,4'-piperidine]-1'-ylcarbonyl)pyrazolo[1,5-a]pyrimidine-3-carboxylic acid In the same manner as in Example 1, step 5 and using 7-benzylamino-3-bromo-6-(spiro[indane-1,4'-piperidine]-1'-ylcarbonyl)pyrazolo[1,5-a]pyrimidine (0.150 g, 0.291 mmol) obtained in step 1, the title compound (0.090 g, 64%) was obtained.

[Step 3]

N-[7-Benzylamino-6-(spiro[indane-1,4'-piperidine]-1'-ylcarbonyl)pyrazolo[1,5-a]pyrimidine-3-carbonyl]methanesulfonamide (compound a-119)

In the same manner as in Example 1, step 6 and using 7-benzylamino-6-(spiro[indane-1,4'-piperidine]-1'-ylcarbonyl)pyrazolo[1,5-a]pyrimidine-3-carboxylic acid (0.090 g, 0.187 mmol) obtained in step 2 and methanesulfonamide (0.039 mg, 0.412 mmol), the title compound (0.070 g, 67%) was obtained.
ESI-MS m/z: 559 (M+H)$^+$; $^1$H-NMR (CDCl$_3$,δ): 1.23-1.37 (m, 2H), 1.64-1.90 (m, 2H), 1.90-2.14 (m, 2H), 2.56-3.06 (m, 4H), 3.38-3.49 (m, 3H), 3.93-4.28 (m, 2H), 4.85-5.01 (m, 2H), 7.01-7.14 (m, 1H), 7.14-7.56 (m, 8H), 7.73 (br s, 1H), 8.25 (s, 1H), 8.62 (s, 1H), 10.73 (br s, 1H).

EXAMPLE 120

N-[7-(2-Methylphenylamino)-6-(spiro[indane-1,4'-piperidine]-1'-ylcarbonyl)pyrazolo[1,5-a]pyrimidine-3-carbonyl]ethanesulfonamide (compound a-120)

[Step 1]

3-Ethoxycarbonyl-7-hydroxy-6-(spiro[indane-1,4'-piperidine]-1'-ylcarbonyl)pyrazolo[1,5-a]pyrimidine In the same manner as in Example 1, step 2 and using 3-ethoxycarbonyl-7-hydroxypyrazolo[1,5-a]pyrimidine-6-carboxylic acid (0.27 g, 1.06 mmol) obtained in Example 19, step 2 and spiro[indane-1,4'-piperidine]hydrochloride (0.3 g, 1.32 mmol), the title compound (0.29 g, 64%) was obtained.

[Step 2]

7-Chloro-3-ethoxycarbonyl-6-(spiro[indane-1,4'-piperidine]-1'-ylcarbonyl)pyrazolo[1,5-a]pyrimidine In the same manner as in Example 1, step 3 and using 3-ethoxycarbonyl-7-hydroxy-6-(spiro[indane-1,4'-piperidine]-1'-ylcarbonyl)pyrazolo[1,5-a]pyrimidine (0.29 g, 0.68 mmol) obtained in step 1, the title compound (0.15 g, 49%) was obtained.

[Step 3]

3-Ethoxycarbonyl-7-(2-methylphenylamino)-6-(spiro[indane-1,4'-piperidine]-1'-ylcarbonyl)pyrazolo[1,5-a]pyrimidine In the same manner as in Example 19, step 5 and using 7-chloro-3-ethoxycarbonyl-6-(spiro[indane-1,4'-piperidine]-1'-ylcarbonyl)pyrazolo[1,5-a]pyrimidine (0.15 g, 0.33 mmol) obtained in step 2 and o-toluidine (0.053 g, 0.5 mmol), the title compound (0.14 g, 85%) was obtained.

[Step 4]

7-(2-Methylphenylamino)-6-(spiro[indane-1,4'-piperidine]-1'-ylcarbonyl)pyrazolo[1,5-a]pyrimidine-3-carboxylic acid In the same manner as in Example 19, step 6 and using 3-ethoxycarbonyl-7-(2-methylphenylamino)-6-(spiro[indane-1,4'-piperidine]-1'-ylcarbonyl)pyrazolo[1,5-a]pyrimidine (0.14 g, 0.28 mmol) obtained in step 3, the title compound (0.12 g, 90%) was obtained.

[Step 5]

N-[7-(2-Methylphenylamino)-6-(spiro[indane-1,4'-piperidine]-1'-ylcarbonyl)pyrazolo[1,5-a]pyrimidine-3-carbonyl]ethanesulfonamide (compound a-120)

In the same manner as in Example 1, step 6 and using 7-(2-methylphenylamino)-6-(spiro[indane-1,4'-piperidine]-1'-ylcarbonyl)pyrazolo[1,5-a]pyrimidine-3-carboxylic acid (0.06 g, 0.13 mmol) obtained in step 4 and ethanesulfonamide (0.066 g, 0.62 mmol), the title compound (0.073 g, 100%) was obtained. ESI-MS m/z: 573 (M+H)$^+$; $^1$H-NMR (CDCl$_3$, δ):1.46 (t, J=7.3 Hz, 3H), 1.46-1.53 (m, 2H), 1.57-1.70 (m, 2H), 1.98 (t, J=7.3 Hz, 2H), 2.43 (s, 3H), 2.92 (t, J=7.1 Hz, 2H), 3.61 (q, J=7.5 Hz, 2H), 3.70-4.06 (m, 4H), 7.09-7.23 (m, 4H), 7.29-7.42 (m, 4H), 8.35 (s, 1H), 8.35 (s, 1H), 8.63 (s, 1H), 10.54 (s, 1H).

EXAMPLE 121

N-[7-(4-Fluoro-2-methylphenylamino)-6-(spiro[indane-1,4'-piperidine]-1'-ylcarbonyl)pyrazolo[1,5-a]pyrimidine-3-carbonyl]cyclopropanesulfonamide (compound a-121)

[Step 1]

3-Ethoxycarbonyl-7-(4-fluoro-2-methylphenylamino)-6-(spiro[indane-1,4'-piperidine]-1'-ylcarbonyl)pyrazolo[1,5-a]pyrimidine In the same manner as in Example 19, step 5 and using 7-chloro-3-ethoxycarbonyl-6-(spiro[indane-1,4'-piperidine]-1'-ylcarbonyl)pyrazolo[1,5-a]pyrimidine (0.08 g, 0.18 mmol) obtained in Example 120, step 2 and 4-fluoro-2-methylaniline (0.034 g, 0.27 mmol), the title compound (0.088 g, 91%) was obtained.

[Step 2]

7-(4-Fluoro-2-methylphenylamino)-6-(spiro[indane-1,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(spiro[indane-1,4'-piperidine]-1'-ylcarbonyl)pyrazolo[1,5-a]pyrimidine (0.088 g, 0.17 mmol) obtained in step 1, the title compound (0.063 g, 76%) was obtained.

[Step 3]

N-[7-(4-Fluoro-2-methylphenylamino)-6-(spiro[indane-1,4'-piperidine]-1'-ylcarbonyl)pyrazolo[1,5-a]pyrimidine-3-carbonyl]cyclopropanesulfonamide (compound a-121)

In the same manner as in Example 1, step 6 and using 7-(4-fluoro-2-methylphenylamino)-6-(spiro[indane-1,4'-piperidine]-1'-ylcarbonyl)pyrazolo[1,5-a]pyrimidine-3-carboxylic acid (0.04 g, 0.08 mmol) obtained in step 2 and cyclopropanesulfonamide (0.049 g, 0.40 mmol), the title compound (0.043 g, 88%) was obtained.

ESI-MS m/z: 603 (M+H)$^+$; $^1$H-NMR (CDCl$_3$,δ):1.09-1.18 (m, 2H), 1.45-1.51 (m, 2H), 1.49-1.57 (m, 2H), 1.62-1.73 (m, 2H), 2.02 (t, J=7.1 Hz, 2H), 2.41 (s, 3H), 2.94 (t, J=7.3 Hz, 2H), 3.06-3.15 (m, 1H), 3.74-4.06 (m, 4H), 7.00 (td, J=8.1, 3.0 Hz, 1H), 7.09-7.13 (m, 2H), 7.18-7.25 (m, 4H), 8.26 (s, 1H), 8.32 (s, 1H), 8.63 (s, 1H), 10.62 (s, 1H).

EXAMPLE 122

N-[7-(2-Fluoro-5-methylphenylamino)-6-(spiro[indane-1,4'-piperidine]-1'-ylcarbonyl)pyrazolo[1,5-a]pyrimidine-3-carbonyl]ethanesulfonamide (compound a-122)

[Step 1]

3-Ethoxycarbonyl-7-(2-fluoro-5-methylphenylamino)-6-(spiro[indane-1,4'-piperidine]-1'-ylcarbonyl)pyrazolo[1,5-a]pyrimidine In the same manner as in Example 19, step 5 and using 7-chloro-3-ethoxycarbonyl-6-(spiro[indane-1,4'-piperidine]-1'-ylcarbonyl)pyrazolo[1,5-a]pyrimidine (0.10 g, 0.23 mmol) obtained in Example 120, step 2 and 2-fluoro-5-methylaniline (0.043 g, 0.34 mmol), the title compound (0.108 g, 90%) was obtained.

[Step 2]

7-(2-Fluoro-5-methylphenylamino)-6-(spiro[indane-1,4'-piperidine]-1'-ylcarbonyl)pyrazolo[1,5-a]pyrimidine-3-carboxylic acid In the same manner as in Example 19, step 6 and using 3-ethoxycarbonyl-7-(2-fluoro-5-methylphenylamino)-6-(spiro[indane-1,4'-piperidine]-1'-ylcarbonyl)pyrazolo[1,5-a]pyrimidine (0.108 g, 0.21 mmol) obtained in step 1, the title compound (0.083 g, 81%) was obtained.

[Step 3]

N-[7-(2-Fluoro-5-methylphenylamino)-6-(spiro[indane-1,4'-piperidine]-1'-ylcarbonyl)pyrazolo[1,5-a]pyrimidine-3-carbonyl]ethanesulfonamide (compound a-122)

In the same manner as in Example 1, step 6 and using 7-(2-fluoro-5-methylphenylamino)-6-(spiro[indane-1,4'-piperidine]-1'-ylcarbonyl)pyrazolo[1,5-a]pyrimidine-3-carboxylic acid (0.042 g, 0.085 mmol) obtained in step 2 and ethanesulfonamide (0.045 g, 0.42 mmol), the title compound (0.041 g, 82%) was obtained.

ESI-MS m/z: 591 (M+H)$^+$; $^1$H-NMR (CDCl$_3$,δ):1.46 (t, J=7.5 Hz, 3H), 1.63-1.77 (m, 4H), 1.99 (t, J=7.1 Hz, 2H), 2.39 (s, 3H), 2.92 (t, J=7.3 Hz, 2H), 3.61 (q, J=7.5 Hz, 2H), 3.68-4.06 (m, 4H), 7.08-7.25 (m, 7H), 8.44 (s, 1H), 8.45 (s, 1H), 8.63 (s, 1H), 10.50 (s, 1H).

EXAMPLE 123

N-[7-Benzylamino-6-(3-methylspiro[indane-1,4'-piperidine]-1'-ylcarbonyl)pyrazolo[1,5-a]pyrimidine-3-carbonyl]methanesulfonamide (compound a-123)

N-[7-Benzylamino-6-(3-methylspiro[inden-1,4'-piperidine]-1'-ylcarbonyl)pyrazolo[1,5-a]pyrimidine-3-carbonyl]methanesulfonamide (0.035 g, 0.061 mmol) obtained in Example 111, step 3 was dissolved in ethanol (2.0 ml), 10% palladium-carbon (0.079 g, 0.382 mmol) was added, and the mixture was stirred at room temperature for 4 hr. The reaction mixture was filtered through celite and washed with chloroform, and the filtrate was concentrated under reduced pressure to give a residue. Diisopropyl ether was added to the residue and the precipitated crystals were collected by filtration to give the title compound (0.011 g, 32%).

ESI-MS m/z: 573 (M+H)$^+$; $^1$H-NMR (CDCl$_3$,δ): 1.35 (d, J=7.0 Hz, 3H), 1.46-1.69 (m, 4H), 1.89-2.08 (m, 1H), 2.29-2.50 (m, 1H), 2.59-2.98 (m, 2H), 3.15-3.33 (m, 1H), 3.43 (s, 3H), 4.05-4.48 (m, 2H), 4.82-5.04 (m, 2H), 6.96-7.14 (m, 1H), 7.14-7.50 (m, 8H), 7.59-7.80 (m, 1H), 8.24 (s, 1H), 8.58 (s, 1H), 10.70 (br s, 1H).

EXAMPLE 124

N-[7-Benzylamino-6-(3-hydroxyspiro[indane-1,4'-piperidine]-1'-ylcarbonyl)pyrazolo[1,5-a]pyrimidine-3-carbonyl]methanesulfonamide (compound a-124) and N-[7-benzylamino-6-(3-oxospiro[indane-1,4'-piperidine]-1'-ylcarbonyl)pyrazolo[1,5-a]pyrimidine]methanesulfonamide (compound a-158)

[Step 1]

7-Benzylamino-3-ethoxycarbonyl-6-(3-oxospiro[indane-1,4'-piperidine]-1'-ylcarbonyl)pyrazolo[1,5-a]pyrimidine In the same manner as in Example 21, step 5 and using 7-benzylamino-3-ethoxycarbonylpyrazolo[1,5-a]pyrimidine-6-carboxylic acid (0.184 g, 0.544 mmol) obtained in Example 21, step 4 and 1-oxospiro[indane-3,4'-piperidine] (WO2004/028459, 0.160 g, 0.598 mmol), the title compound (0.280 g, 98%) was obtained.

[Step 2]

7-Benzylamino-6-(3-oxospiro[indane-1,4'-piperidine]-1'-ylcarbonyl)pyrazolo[1,5-a]pyrimidine-3-carboxylic acid In the same manner as in Example 19, step 6 and using 7-benzylamino-3-ethoxycarbonyl-6-(3-oxospiro[indane-1,4'-piperidine]-1'-ylcarbonyl)pyrazolo[1,5-a]pyrimidine (0.280 g, 0.535 mmol) obtained in step 1, the title compound (0.135 g, 50%) was obtained.

[Step 3]

N-[7-Benzylamino-6-(3-oxospiro[indane-1,4'-piperidine]-1'-ylcarbonyl)pyrazolo[1,5-a]pyrimidine]methanesulfonamide (compound a-158)

In the same manner as in Example 1, step 6 and using 7-benzylamino-6-(3-oxospiro[indane-1,4'-piperidine]-1'-ylcarbonyl)pyrazolo[1,5-a]pyrimidine-3-carboxylic acid (0.135 g, 0.273 mmol) obtained in step 2 and methanesulfonamide (0.129 g, 1.36 mmol), the title compound (0.052 g, 33%) was obtained.

[Step 4]

N-[7-Benzylamino-6-(3-hydroxyspiro[indane-1,4'-piperidine]-1'-ylcarbonyl)pyrazolo[1,5-a]pyrimidine]methanesulfonamide (compound a-124)

N-[7-Benzylamino-6-(3-oxospiro[indane-1,4'-piperidine]-1'-ylcarbonyl)pyrazolo[1,5-a]pyrimidine]methanesulfonamide (0.031 g, 0.054 mmol) obtained in step 3 was dissolved in methanol (1.0 mL), sodium borohydride (0.008 g, 0.217 mmol) was added, and the mixture was stirred overnight. The reaction mixture was concentrated under reduced pressure, and the obtained residue was purified by thin layer silica gel chromatography (chloroform/methanol=9/1) to give the title compound (0.008 g, 27%).

ESI-MS m/z: 575 (M+H)$^+$; $^1$H-NMR (CDCl$_3$,δ): 1.35-2.05 (m, 6H), 2.32-2.96 (m, 3H), 3.71 (s, 3H), 3.88-4.50 (m, 2H), 4.82-5.01 (m, 2H), 7.04-7.19 (m, 1H), 7.19-7.50 (m, 8H), 7.65-7.89 (m, 1H), 8.24 (s, 1H), 8.58 (s, 1H), 10.72 (br s, 1H).

EXAMPLE 125

N-[7-Benzylamino-6-(2H-spiro[benzofuran-3,4'-piperidine]-1'-ylcarbonyl)pyrazolo[1,5-a]pyrimidine-3-carbonyl]methanesulfonamide (compound a-125)

[Step 1]

7-Benzylamino-3-bromo-6-(2H-spiro[benzofuran-3,4'-piperidine]-1'-ylcarbonyl)pyrazolo[1,5-a]pyrimidine In the same manner as in Example 21, step 5 and using 7-benzylamino-3-bromopyrazolo[1,5-a]pyrimidine-6-carboxylic acid (0.278 g, 0.808 mmol) obtained in Example 22, step 3 and 2H-spiro[benzofuran-3,4'-piperidine]hydrochloride (0.200 g, 0.889 mmol) obtained in Reference Example 1, the title compound (0.372 g, 89%) was obtained.

[Step 2]

7-Benzylamino-6-(2H-spiro[benzofuran-3,4'-piperidine]-1'-ylcarbonyl)pyrazolo[1,5-a]pyrimidine-3-carboxylic acid In the same manner as in Example 1, step 5 and using 7 benzylamino-3-bromo-6-(2H-spiro[benzofuran-3,4'-piperidine]-1'-ylcarbonyl)pyrazolo[1,5-a]pyrimidine (0.370 g, 0.714 mmol) obtained in step 1, the title compound (0.217 g, 63%) was obtained.

[Step 3]

N-[7-Benzylamino-6-(2H-spiro[benzofuran-3,4'-piperidine]-1'-ylcarbonyl)pyrazolo[1,5-a]pyrimidine-3-carbonyl]methanesulfonamide (compound a-125)

In the same manner as in Example 1, step 6 and using 7-benzylamino-6-(2H-spiro[benzofuran-3,4'-piperidine]-1'-ylcarbonyl)pyrazolo[1,5-a]pyrimidine-3-carboxylic acid (0.105 g, 0.217 mmol) obtained in step 2 and methanesulfonamide (0.103 g, 1.09 mmol), the title compound (0.058 g, 47%) was obtained.

ESI-MS m/z: 561 (M+H)$^+$; $^1$H-NMR (CDCl$_3$,δ): 1.59-1.89 (m, 4H), 2.36-3.15 (m,2H), 3.42 (s, 3H), 3.63-4.17 (m, 2H), 4.30 (s, 2H), 4.81-5.08 (m, 2H), 6.74-6.98 (m, 2H), 6.98-7.55 (m, 7H), 7.62-7.87 (m, 1H), 8.23 (s, 1H), 8.62 (s, 1H), 10.70 (br s, 1H).

EXAMPLE 126

N-[7-Benzylamino-6-(2H-spiro[benzofuran-3,4'-piperidine]-1'-ylcarbonyl)pyrazolo[1,5-a]pyrimidine-3-carbonyl]cyclopropanesulfonamide (compound a-126)

In the same manner as in Example 1, step 6 and using 7-benzylamino-6-(2H-spiro[benzofuran-3,4'-piperidine]-1'-ylcarbonyl)pyrazolo[1,5-a]pyrimidine-3-carboxylic acid (0.105 g, 0.217 mmol) obtained in Example 125, step 2 and cyclopropanesulfonamide (0.131 g, 1.09 mmol), the title compound (0.059 g, 47%) was obtained.

ESI-MS m/z: 587 (M+H)$^+$; $^1$H-NMR (CDCl$_3$, δ): 1.03-1.19 (m, 2H), 1.41-1.51 (m, 2H), 1.60-1.93 (m, 4H), 2.34-2.95 (m, 2H), 2.98-3.17 (m, 1H), 3.47-4.09 (m, 2H), 4.29 (s, 2H), 4.84-5.01 (m, 2H), 6.77-6.86 (m, 1H), 6.86-6.99 (m, 1H), 7.01-7.11 (m, 1 H), 7.11-7.23 (m, 1H), 7.23-7.50 (m, 5H), 7.67-7.85 (m, 1H), 8.22 (s, 1H), 8.59 (s, 1H), 10.66 (br s, 1H).

EXAMPLE 127

N-[7-Benzylamino-6-(2H-spiro[benzofuran-3,4'-piperidine]-1'-ylcarbonyl)pyrazolo[1,5-a]pyrimidine-3-carbonyl]ethanesulfonamide (compound a-127)

In the same manner as in Example 1, step 6 and using 7-benzylamino-6-(2H-spiro[benzofuran-3,4'-piperidine]-1'-ylcarbonyl)pyrazolo[1,5-a]pyrimidine-3-carboxylic acid (0.055 g, 0.114 mmol) obtained in Example 125, step 2 and ethanesulfonamide (0.062 g, 0.569 mmol), the title compound (0.026 g, 47%) was obtained.

ESI-MS m/z: 575 (M+H)$^+$; $^1$H-NMR (CDCl$_3$, δ): 1.44 (t, J=7.2 Hz, 3H), 1.62-1.91 (m, 4H), 2.37-3.07 (m, 2H), 3.60 (q, J=7.2 Hz, 2H), 3.73-4.18 (m, 2H), 4.29 (s, 2H), 4.83-5.02 (m, 2H), 6.77-6.86 (m, 1H), 6.86-6.98 (m, 1H), 6.99-7.12 (m, 1H), 7.12-7.24 (m, 1H), 7.24-7.51 (m, 5H), 7.66-7.86 (m, 1H), 8.21 (s, 1H), 8.59 (s, 1H), 10.57 (br s, 1H).

EXAMPLE 128

N-[7-(2-Fluoro-5-methylphenylamino)-6-(2H-spiro[benzofuran-3,4'-piperidine]-1'-ylcarbonyl)pyrazolo[1,5-a]pyrimidine-3-carbonyl]cyclopropanesulfonamide (compound a-128)

[Step 1]

3-Ethoxycarbonyl-7-hydroxy-6-(2H-spiro[benzofuran-3,4'-piperidine]-1'-ylcarbonyl)pyrazolo[1,5-a]pyrimidine In the same manner as in Example 1, step 2 and using 3-ethoxycarbonyl-7-hydroxypyrazolo[1,5-a]pyrimidine-6-carboxylic acid (0.5 g, 1.99 mmol) obtained in Example 19, step 2 and 2H-spiro[benzofuran-3,4'-piperidine]hydrochloride (0.54 g, 2.39 mmol), the title compound (0.49 g, 59%) was obtained.

[Step 2]

7-Chloro-3-ethoxycarbonyl-6-(2H-spiro[benzofuran-3,4'-piperidine]-1'-ylcarbonyl)pyrazolo[1,5-a]pyrimidine In the same manner as in Example 1, step 3 and using 3-ethoxycarbonyl-7-hydroxy-6-(2H-spiro[benzofuran-3,4'-piperidine]-1'-ylcarbonyl)pyrazolo[1,5-a]pyrimidine (0.5 g, 1.18 mmol) obtained in step 1, the title compound (0.48 g, 93%) was obtained.

[Step 3]

3-Ethoxycarbonyl-7-(2-fluoro-5-methylphenylamino)-6-(2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(2H-spiro[benzofuran-3,4'-piperidine]-1'-ylcarbonyl)pyrazolo[1,5-a]pyrimidine (0.24 g, 0.54 mmol) obtained in step 2 and 2-fluoro-5-methylaniline (0.1 g, 0.82 mmol), the title compound (0.25 g, 88%) was obtained.

[Step 4]

7-(2-Fluoro-5-methylphenylamino)-6-(2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(2-fluoro-5-methylphenylamino)-6-(2H-spiro[benzofuran-3,4'-piperidine]-1'-ylcarbonyl)pyrazolo[1,5-a]pyrimidine (0.25 g, 0.47 mmol) obtained in step 3, the title compound (0.19 g, 81%) was obtained.

[Step 5]

N-[7-(2-Fluoro-5-methylphenylamino)-6-(2H-spiro[benzofuran-3,4'-piperidine]-1'-ylcarbonyl)pyrazolo[1,5-a]pyrimidine-3-carbonyl]cyclopropanesulfonamide (compound a-128)

In the same manner as in Example 1, step 6 and using 7-(2-fluoro-5-methylphenylamino)-6-(2H-spiro[benzofuran-3,4'-piperidine]-1'-ylcarbonyl)pyrazolo[1,5-a]pyrimidine-3-carboxylic acid (0.095 g, 0.19 mmol) obtained in step 4 and cyclopropanesulfonamide (0.12 g, 0.95 mmol), the title compound (0.076 g, 66%) was obtained.

ESI-MS m/z: 605 (M+H)$^+$; $^1$H-NMR (CDCl$_3$,δ):1.10-1.18 (m, 2H), 1.47-1.50 (m, 2H), 1.68-1.76 (m, 4H), 2.39 (s, 3H), 2.72-2.77 (m, 2H), 3.06-3.16 (m, 1H), 3.79-3.86 (m, 2H), 4.32 (s, 2H), 6.80-7.23 (m, 7H), 8.41-8.45 (m, 2H), 8.65 (s, 1H), 10.57 (s, 1H).

EXAMPLE 129

N-[7-(2,5-Dimethylphenylamino)-6-(2H-spiro[benzofuran-3,4'-piperidine]-1'-ylcarbonyl)pyrazolo[1,5-a]pyrimidine-3-carbonyl]ethanesulfonamide (compound a-129)

[Step 1]

7-(2,5-Dimethylphenylamino)-3-ethoxycarbonyl-6-(2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(2H-spiro[benzofuran-3,4'-piperidine]-1'-ylcarbonyl)pyrazolo[1,5-a]pyrimidine (0.24 g, 0.54 mmol) obtained in Example 128, step 2 and 2,5-dimethylaniline (0.098 g, 0.81 mmol), the title compound (0.25 g, 86%) was obtained.

[Step 2]

7-(2,5-Dimethylphenylamino)-6-(2H-spiro[benzofuran-3,4'-piperidine]-1'-ylcarbonyl)pyrazolo[1,5-a]pyrimidine-3-carboxylic acid In the same manner as in Example 19, step 6 and using 7-(2,5-dimethylphenylamino)-3-ethoxycarbonyl-6-(2H-spiro[benzofuran-3,4'-piperidine]-1'-ylcarbonyl)pyrazolo[1,5-a]pyrimidine (0.24 g, 0.46 mmol) obtained in step 1, the title compound (0.13 g, 58%) was obtained.

[Step 3]

N-[7-(2,5-Dimethylphenylamino)-6-(2H-spiro[benzofuran-3,4'-piperidine]-1'-ylcarbonyl)pyrazolo[1,5-a]pyrimidine-3-carbonyl]ethanesulfonamide (compound a-129)

In the same manner as in Example 1, step 6 and using 7-(2,5-dimethylphenylamino)-6-(2H-spiro[benzofuran-3,4'-piperidine]-1'-ylcarbonyl)pyrazolo[1,5-a]pyrimidine-3-carboxylic acid (0.065 g, 0.13 mmol) obtained in step 2 and ethanesulfonamide (0.068 g, 0.65 mmol), the title compound (0.033 g, 43%) was obtained.

ESI-MS m/z: 589 (M+H)$^+$; $^1$H-NMR (CDCl$_3$,δ):1.46 (t, J=7.4 Hz, 3H), 1.63-1.72 (m, 4H), 2.38 (s, 6H), 2.55-2.70 (m,2H), 3.61 (q, J=7.5 Hz, 2H), 3.62-3.80 (m, 2H), 4.27 (s, 2H), 6.80-7.30 (m, 7H), 8.35 (br s, 1H), 8.38 (s, 1H), 8.63 (s, $^1$H), 10.52 (s, 1H).

EXAMPLE 130

N-[7-(2,5-Dimethylphenylamino)-6-(2H-spiro[benzofuran-3,4'-piperidine]-1'-ylcarbonyl)pyrazolo[1,5-a]pyrimidine-3-carbonyl]cyclopropanesulfonamide (compound a-130)

In the same manner as in Example 1, step 6 and using 7-(2,5-dimethylphenylamino)-6-(2H-spiro[benzofuran-3,4'-piperidine]-1'-ylcarbonyl)pyrazolo[1,5-a]pyrimidine-3-carboxylic acid (0.065 g, 0.13 mmol) obtained in Example 129, step 2 and cyclopropanesulfonamide (0.079 g, 0.65 mmol), the title compound (0.043 g, 55%) was obtained.

ESI-MS m/z: 601 (M+H)$^+$; $^1$H-NMR (CDCl$_3$, δ): 1.11-1.16 (m, 2H), 1.47-1.50 (m, 2H), 1.64-1.70 (m, 4H), 2.37 (s, 6H), 2.50-2.80 (m, 2H), 3.06-3.16 (m, 1H), 3.58-3.86 (m, 2H), 4.27 (s, 2H), 6.75-7.23 (m, 7H), 8.35 (s, 1H), 8.38 (s, 1H), 8.64 (s, 1H), 10.61 (s, 1H).

EXAMPLE 131

N-[7-(2-Methylphenylamino)-6-(2H-spiro[benzofuran-3,4'-piperidine]-1'-ylcarbonyl)pyrazolo[1,5-a]pyrimidine-3-carbonyl]ethanesulfonamide

[Step 1]

3-Bromo-7-(2-methylphenylamino)-6-(2H-spiro[benzofuran-3,4'-piperidine]-1'-ylcarbonyl)pyrazolo[1,5-a]pyrimidine In the same manner as in Example 21, step 5 and using 3-bromo-7-(2-methylphenylamino)-pyrazolo[1,5-a]pyrimidine-6-carboxylic acid (0.2 g, 0.58 mmol) obtained in Example 24, step 2 and 2H-spiro[benzofuran-3,4'-piperidine] hydrochloride (0.15 g, 0.69 mmol), the title compound (0.28 g, 93%) was obtained.

[Step 2]

7-(2-Methylphenylamino)-6-(2H-spiro[benzofuran-3,4'-piperidine]-1'-ylcarbonyl)pyrazolo[1,5-a]pyrimidine-3-carboxylic acid In the same manner as in Example 1, step 5 and using 3-bromo-7-(2-methylphenylamino)-6-(2H-spiro[benzofuran-3,4'-piperidine]-1'-ylcarbonyl)pyrazolo[1,5-a]pyrimidine (0.27 g, 0.52 mmol) obtained in step 1, the title compound (0.14 g, 56%) was obtained.

[Step 3]

N-[7-(2-Methylphenylamino)-6-(2H-spiro[benzofuran-3,4'-piperidine]-1'-ylcarbonyl)pyrazolo[1,5-a]pyrimidine-3-carbonyl]ethanesulfonamide (compound a-131)

In the same manner as in Example 1, step 6 and using 7-(2-methylphenylamino)-6-(2H-spiro[benzofuran-3,4'-piperidine]-1'-ylcarbonyl)pyrazolo[1,5-a]pyrimidine-3-carboxylic acid (0.07 g, 0.14 mmol) obtained in step 2 and ethanesulfonamide (0.076 g, 0.72 mmol), the title compound (0.04 g, 50%) was obtained.
ESI-MS m/z: 575 (M+H)$^+$; $^1$H-NMR (CDCl$_3$,δ): 1.46 (t, J=7.5 Hz, 3H), 1.66-1.72 (m, 4H), 2.43 (s, 3H), 2.54-2.86 (m, 2H), 3.61 (q, J=7.5 Hz, 2H), 3.71-3.85 (m, 2H), 4.31 (s, 2H), 6.82 (d, J=8.1 Hz, 1H), 6.90-6.95 (m, 1H), 7.05-7.09 (m, 1H), 7.15-7.43 (m, 5H), 8.34 (s, 1H), 8.37 (s, 1H), 8.63 (s, 1H), 10.51 (s, 1H).

EXAMPLE 132

N-[7-(3-Methylphenylamino)-6-(2H-spiro[benzofuran-3,4'-piperidine]-1'-ylcarbonyl)pyrazolo[1,5-a]pyrimidine-3-carbonyl]ethanesulfonamide (compound a-132)

[Step 1]

3-Ethoxycarbonyl-7-(3-methylphenylamino)-6-(2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(2H-spiro[benzofuran-3,4'-piperidine]-1'-ylcarbonyl)pyrazolo[1,5-a]pyrimidine (0.2 g, 0.45 mmol) obtained in Example 128, step 2 and m-toluidine (0.073 g, 0.68 mmol), the title compound (0.21 g, 92%) was obtained.
[Step 2]

7-(3-Methylphenylamino)-6-(2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(3-methylphenylamino)-6-(2H-spiro[benzofuran-3,4'-piperidine]-1'-ylcarbonyl)pyrazolo[1,5-a]pyrimidine (0.21 g, 0.41 mmol) obtained in step 1, the title compound (0.15 g, 75%) was obtained.
[Step 3]

N-[7-(3-Methylphenylamino)-6-(2H-spiro[benzofuran-3,4'-piperidine]-1'-ylcarbonyl)pyrazolo[1,5-a]pyrimidine-3-carbonyl]ethanesulfonamide (compound a-132)

In the same manner as in Example 1, step 6 and using 7-(3-methylphenylamino)-6-(2H-spiro[benzofuran-3,4'-piperidine]-1'-ylcarbonyl)pyrazolo[1,5-a]pyrimidine-3-carboxylic acid (0.75 g, 0.16 mmol) obtained in step 2 and ethanesulfonamide (0.082 g, 0.78 mmol), the title compound (0.057 g, 66%) was obtained.
ESI-MS m/z: 575 (M+H)$^+$; $^1$H-NMR (CDCl$_3$,δ): 1.46 (t, J=7.6 Hz, 3H), 1.60-1.70 (m, 4H), 2.45 (s, 3H), 2.54-2.86 (m, 2H), 3.61 (q, J=7.5 Hz, 2H), 3.65-3.69 (m, 2H), 4.25 (s, 2H), 6.81 (d, J=8.3 Hz, 1H), 6.87-6.93 (m, 1H), 7.01-7.04 (m, 1H), 7.11-7.23 (m, 4H), 7.39 (t, J=7.6 Hz, 1H), 8.46 (s, 1H), 8.59 (s, 1H), 8.61 (s, 1H), 10.49 (s, 1H).

EXAMPLE 133

N-[7-(2-Fluoro-3-methylphenylamino)-6-(2H-spiro[benzofuran-3,4'-piperidine]-1'-ylcarbonyl)pyrazolo[1,5-a]pyrimidine-3-carbonyl]ethanesulfonamide (compound a-133)

[Step 1]

3-Ethoxycarbonyl-7-(2-fluoro-3-methylphenylamino)-6-(2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(2H-spiro[benzofuran-3,4'-piperidine]-1'-ylcarbonyl)pyrazolo[1,5-a]pyrimidine (0.2 g, 0.45 mmol) obtained in Example 128, step 2 and 2-fluoro-3-methylaniline (0.085 g, 0.68 mmol), the title compound (0.2 g, 85%) was obtained.
[Step 2]

7-(2-Fluoro-3-methylphenylamino)-6-(2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(2-fluoro-3-methylphenylamino)-6-(2H-spiro[benzofuran-3,4'-piperidine]-1'-ylcarbonyl)pyrazolo[1,5-a]pyrimidine (0.2 g, 0.38 mmol) obtained in step 1, the title compound (0.15 g, 77%) was obtained.
[Step 3]

N-[7-(2-Fluoro-3-methylphenylamino)-6-(2H-spiro[benzofuran-3,4'-piperidine]-1'-ylcarbonyl)pyrazolo[1,5-a]pyrimidine-3-carbonyl]ethanesulfonamide (compound a-133)

In the same manner as in Example 1, step 6 and using 7-(2-fluoro-3-methylphenylamino)-6-(2H-spiro[benzofuran-3,4'-piperidine]-1'-ylcarbonyl)pyrazolo[1,5-a]pyrimidine-3-carboxylic acid (0.07 g, 0.14 mmol) obtained in step 2 and ethanesulfonamide (0.074 g, 0.7 mmol), the title compound (0.044 g, 53%) was obtained.
ESI-MS m/z: 593 (M+H)$^+$; $^1$H-NMR (CDCl$_3$, δ) :1.46 (t, J=7.3 Hz, 3H), 1.67-1.76 (m, 4H), 2.41 (d, J=1.8 Hz, 3H), 2.61-2.88 (m, 2H), 3.61 (q, J=7.5 Hz, 2H), 3.71-3.88 (m, 2H), 4.31 (s, 2H), 6.81-7.25 (m, 7H), 8.43 (s, 1H), 8.46 (s, 1H), 8.64 (s, 1H), 10.47 (s, 1H).

EXAMPLE 134

N-[7-Benzylamino-6-(6-fluoro-2H-spiro[benzofuran-3,4'-piperidine]-1'-ylcarbonyl)pyrazolo[1,5-a]pyrimidine-3-carbonyl]methanesulfonamide (compound a-134)

[Step 1]

7-Benzylamino-3-bromo-6-(6-fluoro-2H-spiro[benzofuran-3,4'-piperidine]-1'-ylcarbonyl)pyrazolo[1,5-a]pyrimidine In the same manner as in Example 21, step 5 and using 7-benzylamino-3-bromopyrazolo[1,5-a]pyrimidine-6-carboxylic acid (0.193 g, 0.556 mmol) obtained in Example 22, step 3 and 6-fluoro-2H-spiro[benzofuran-3,4'-piperidine]hydrochloride (0.150 g, 0.616 mmol) obtained in Reference Example 4, the title compound (0.232 g, 77%) was obtained.
[Step 2]

7-Benzylamino-6-(6-fluoro-2H-spiro[benzofuran-3, 4'-piperidine]-1'-ylcarbonyl)pyrazolo[1,5-a]pyrimidine-3-carboxylic acid In the same manner as in Example 1, step 5 and using 7-benzylamino-3-bromo-6-(6-fluoro-2H-spiro[benzofuran-3,4'-piperidine]-1'-ylcarbonyl)pyrazolo[1,5-a]pyrimidine (0.220 g, 0.410 mmol) obtained in step 1, the title compound (0.165 g, 80%) was obtained.
[Step 3]

N-[7-Benzylamino-6-(6-fluoro-2H-spiro[benzofuran-3,4'-piperidine]-1'-ylcarbonyl)pyrazolo[1,5-a]pyrimidine-3-carbonyl]methanesulfonamide (compound a-134)

In the same manner as in Example 1, step 6 and using 7-benzylamino-6-(6-fluoro-2H-spiro[benzofuran-3,4'-piperidine]-1'-ylcarbonyl)pyrazolo[1,5-a]pyrimidine-3-carboxylic acid (0.075 g, 0.149 mmol) obtained in step 2 and methanesulfonamide (0.070 g, 0.745 mmol), the title compound (0.041 g, 47%) was obtained.
ESI-MS m/z: 578 (M+H)$^+$; $^1$H-NMR (CDCl$_3$, δ): 1.58-1.96 (m, 4H), 2.11-2.45 (m, 2H), 3.42 (s, 3H), 3.63-4.14 (m, 2H), 4.33 (s, 2H), 4.86-5.02 (m, 2H), 6.49-6.69 (m, 2H), 6.89-7.03 (m, 1H), 7.22-7.50 (m, 5H), 7.68-7.90 (m, 1H), 8.21 (s, 1H), 8.58 (s, 1H), 10.70 (br s, 1H).

EXAMPLE 135

N-[6-(6-Fluoro-2H-spiro[benzofuran-3,4'-piperidine]-1'-ylcarbonyl)-7-(3-methylphenylamino)pyrazolo[1,5-a]pyrimidine-3-carbonyl]ethanesulfonamide (compound a-135)

[Step 1]

Methyl 3-ethoxycarbonyl-7-(3-methylphenylamino) pyrazolo[1,5-a]pyrimidine-6-carboxylate In the same manner as in Example 19, step 5 and using methyl 7-chloro-3-ethoxycarbonylpyrazolo[1,5-a]pyrimidine-6-carboxylate (3.00 g, 10.6 mmol) obtained in Example 21, step 2 and m-toluidine (1.70 g, 1.73 mmol), the title compound (3.51 g, 94%) was obtained.
[Step 2]

3-Ethoxycarbonyl-7-(3-methylphenylamino)pyrazolo[1,5-a]pyrimidine-6-carboxylic acid In the same manner as in Example 21, step 4 and using methyl 3-ethoxycarbonyl-7-(3-methylphenylamino)pyrazolo[1,5-a]pyrimidine-6-carboxylate (3.51 g, 9.90 mmol) obtained in step 1 instead of methyl 7-benzylamino-3-ethoxycarbonylpyrazolo[1,5-a]pyrimidine-6-carboxylate, the title compound (2.66 g, 79%) was obtained.
[Step 3]

3-Ethoxycarbonyl-6-(6-fluoro-2H-spiro[benzofuran-3,4'-piperidine]-1'-ylcarbonyl)-7-(3-methylphenylamino)pyrazolo[1,5-a]pyrimidine In the same manner as in Example 21, step 5 and using 3-ethoxycarbonyl-7-(3-methylphenylamino)pyrazolo[1,5-a]pyrimidine-6-carboxylic acid (0.130 g, 0.382 mmol) obtained in step 2 and 6-fluoro-2H-spiro[benzofuran-3,4'-piperidine]hydrochloride (0.087 g, 0.420 mmol), the title compound (0.130 g, 64%) was obtained.
[Step 4]

6-(6-Fluoro-2H-spiro[benzofuran-3,4'-piperidine]-1'-ylcarbonyl)-7-(3-methylphenylamino)pyrazolo[1,5-a]pyrimidine-3-carboxylic acid In the same manner as in Example 19, step 6 and using 3-ethoxycarbonyl-6-(6-fluoro-2H-spiro[benzofuran-3,4'-piperidine]-1'-ylcarbonyl)-7-(3-methylphenylamino)pyrazolo[1,5-a]pyrimidine (0.130 g, 0.246 mmol) obtained in step 3, the title compound (0.070 g, 57%) was obtained.
[Step 5]

N-[6-(6-Fluoro-2H-spiro[benzofuran-3,4'-piperidine]-1'-ylcarbonyl)-7-(3-methylphenylamino)pyrazolo[1,5-a]pyrimidine-3-carbonyl]ethanesulfonamide (compound a-135)

In the same manner as in Example 1, step 6 and using 6-(6-fluoro-2H-spiro[benzofuran-3,4'-piperidine]-1'-ylcarbonyl)-7-(3-methylphenylamino)pyrazolo[1,5-a]pyrimidine-3-carboxylic acid (0.070 g, 0.140 mmol) obtained in step 4 and ethanesulfonamide (0.076 g, 0.699 mmol), the title compound (0.040 g, 48%) was obtained.
ESI-MS m/z: 593 (M+H)$^+$; $^1$H-NMR (CDCl$_3$, δ): 1.46 (t, J=7.3 Hz, 3H), 1.56-1.69 (m, 4H), 2.44 (s, 3H), 2.50-2.97 (m, 2H), 3.42-3.93 (m, 4H), 4.30 (s, 2H), 6.46-6.68 (m, 2H), 6.85-6.99 (m, 1H), 7.06-7.30 (m, 3H), 7.31-7.46 (m, 1H), 8.46 (s, 1H), 8.55-8.66 (m, 2H), 10.49 (br s, 1H).

EXAMPLE 136

N-[7-(2-Fluoro-5-methylphenylamino)-6-(6-fluoro-2H-spiro[benzofuran-3,4'-piperidine]-1'-ylcarbonyl) pyrazolo[1,5-a]pyrimidine-3-carbonyl]ethanesulfonamide (compound a-136)

[Step 1]

3-Ethoxycarbonyl-7-(2-fluoro-5-methylphenylamino)-6-(6-fluoro-2H-spiro[benzofuran-3,4'-piperidine]-1'-ylcarbonyl)pyrazolo[1,5-a]pyrimidine In the same manner as in Example 21, step 5 and using 3-ethoxycarbonyl-7-(2-fluoro-5-methylphenylamino)pyrazolo[1,5-a]pyrimidine-6-carboxylic acid (0.130 g, 0.363 mmol) obtained in Example 90, step 2 and 6-fluoro-2H-spiro [benzofuran-3,4'-piperidine]hydrochloride (0.082 g, 0.399 mmol), the title compound (0.148 g, 74%) was obtained.
[Step 2]

7-(2-Fluoro-5-methylphenylamino)-6-(6-fluoro-2H-spiro[benzofuran-3,4'-piperidine]-1'-ylcarbonyl) pyrazolo[1,5-a]pyrimidine-3-carboxylic acid In the same manner as in Example 19, step 6 and using 3-ethoxycarbonyl-7-(2-fluoro-5-methylphenylamino)-6-(6-fluoro-2H-spiro[benzofuran-3,4'-piperidine]-1-ylcarbonyl) pyrazolo[1,5-a]pyrimidine (0.145 g, 0.265 mmol) obtained in step 1, the title compound (0.109 g, 76%) was obtained.

[Step 3]

N-[7-(2-Fluoro-5-methylphenylamino)-6-(6-fluoro-2H-spiro[benzofuran-3,4'-piperidine]-1'-ylcarbonyl)pyrazolo[1,5-a]pyrimidine-3-carbonyl]ethanesulfonamide (compound a-136)

In the same manner as in Example 1, step 6 and using 7-(2-fluoro-5-methylphenylamino)-6-(6-fluoro-2H-spiro[benzofuran-3,4'-piperidine]-1'-ylcarbonyl)pyrazolo[1,5-a]pyrimidine-3-carboxylic acid (0.109 g, 0.210 mmol) obtained in step 2 and ethanesulfonamide (0.114 g, 1.05 mmol), the title compound (0.061 g, 48%) was obtained.

ESI-MS m/z: 611 (M+H)$^+$; $^1$H-NMR (CDCl$_3$, δ): 1.46 (t, J=7.3 Hz, 3H), 1.61-1.88 (m, 4H), 2.38 (s, 3H), 2.54-2.90 (m, 2H), 3.60 (q, J=7.3 Hz, 2H), 3.70-3.99 (m, 2H), 4.37 (s, 2H), 6.47-6.69 (m, 2H), 6.91-7.04 (m, 1H), 7.10-7.25 (m, 3H), 8.43 (s, 2H), 8.65 (s, 1H), 10.47 (br s, 1H).

EXAMPLE 137

N-[7-(2,5-Dimethylphenylamino)-6-(6-fluoro-2H-spiro[benzofuran-3,4'-piperidine]-1'-ylcarbonyl)pyrazolo[1,5-a]pyrimidine-3-carbonyl]ethanesulfonamide (compound a-137)

[Step 1]

7-(2,5-Dimethylphenylamino)-3-ethoxycarbonyl-6-(6-fluoro-2H-spiro[benzofuran-3,4'-piperidine]-1'-ylcarbonyl)pyrazolo[1,5-a]pyrimidine In the same manner as in Example 21, step 5 and using 7-(2,5-dimethylphenylamino)-3-ethoxycarbonylpyrazolo[1,5-a]pyrimidine-6-carboxylic acid (0.123 g, 0.347 mmol) obtained in Example 88, step 2 and 6-fluoro-2H-spiro[benzofuran-3,4'-piperidine]hydrochloride (0.079 g, 0.382 mmol), the title compound (0.142 g, 76%) was obtained.

[Step 2]

7-(2,5-Dimethylphenylamino)-6-(6-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 7-(2,5-dimethylphenylamino)-3-ethoxycarbonyl-6-(6-fluoro-2H-spiro[benzofuran-3,4'-piperidine]-1'-ylcarbonyl)pyrazolo[1,5-a]pyrimidine (0.142 g, 0.261 mmol) obtained in step 1, the title compound (0.115 g, 85%) was obtained.

[Step 3]

N-[7-(2,5-Dimethylphenylamino)-6-(6-fluoro-2H-spiro[benzofuran-3,4'-piperidine]-1'-ylcarbonyl)pyrazolo[1,5-a]pyrimidine-3-carbonyl]ethanesulfonamide (compound a-137)

In the same manner as in Example 1, step 6 and using 7-(2,5-dimethylphenylamino)-6-(6-fluoro-2H-spiro[benzofuran-3,4'-piperidine]-1'-ylcarbonyl)pyrazolo[1,5-a]pyrimidine-3-carboxylic acid (0.100 g, 0.194 mmol) obtained in step 2 and ethanesulfonamide (0.105 g, 0.969 mmol), the title compound (0.031 g, 27%) was obtained.

ESI-MS m/z: 607 (M+H)$^+$; $^1$H-NMR (CDCl$_3$, δ): 1.46 (t, J=7.3 Hz, 3H), 1.54-1.76 (m, 4H), 2.37 (s, 6H), 2.46-2.89 (m, 2H), 3.52-3.94 (m, 4H), 4.24-4.39 (m, 2H), 6.45-6.71 (m, 2H), 6.86-7.23 (m, 3H), 7.24-7.34 (m, 1H), 8.30-8.44 (m, 2H), 8.63 (s, 1H), 10.53 (br s, 1H)

EXAMPLE 138

N-[7-(2,5-Dimethylphenylamino)-6-(6-fluoro-2H-spiro[benzofuran-3,4'-piperidine]-1'-ylcarbonyl)pyrazolo[1,5-a]pyrimidine-3-carbonyl]cyclopropanesulfonamide (compound a-138)

In the same manner as in Example 137, step 3 and using cyclopropanesulfonamide (0.052 g, 0.349 mmol) instead of ethanesulfonamide, the title compound (0.030 g, 55%) was obtained.

ESI-MS m/z: 619 (M+H)$^+$; $^1$H-NMR (CDCl$_3$, δ): 1.08-1.19 (m, 2H), 1.44-1.54 (m, 2H), 1.55-1.80 (m, 4H), 2.37 (s, 6H), 2.45-2.89 (m, 2H), 3.00-3.19 (m, 1H), 3.53-3.94 (m, 2H), 4.31 (s, 2H), 6.44-6.67 (m, 2H), 6.85-7.01 (m, 1H), 7.04-7.11 (m, 1H), 7.11-7.20 (m, 1H), 7.21-7.35 (m, 1H), 8.31-8.46 (m, 2H), 8.62 (s, 1H), 10.62 (br s, 1H).

EXAMPLE 139

N-[7-(4-Fluoro-2-methylphenylamino)-6-(6-fluoro-2H-spiro[benzofuran-3,4'-piperidine]-1'-ylcarbonyl]ethanesulfonamide (compound a-139)

[Step 1]

Methyl 3-ethoxycarbonyl-7-(4-fluoro-2-methylphenylamino)pyrazolo[1,5-a]pyrimidine-6-carboxylate In the same manner as in Example 1, step 4 and using methyl 7-chloro-3-ethoxycarbonylpyrazolo[1,5-a]pyrimidine-6-carboxylate (2.80 g, 9.87 mmol) obtained in Example 21, step 2 and 4-fluoro-2-methylaniline (1.85 g, 14.8 mmol), the title compound (3.69 g, 100%) was obtained.

[Step 2]

3-Ethoxycarbonyl-7-(4-fluoro-2-methylphenylamino)pyrazolo[1,5-a]pyrimidine-6-carboxylic acid In the same manner as in Example 21, step 4 and using methyl 3-ethoxycarbonyl-7-(4-fluoro-2-methylphenylamino)pyrazolo[1,5-a]pyrimidine-6-carboxylate (3.69 g, 9.87 mmol) obtained in step 1, the title compound (2.70 g, 76%) was obtained.

[Step 3]

3-Ethoxycarbonyl-7-(4-fluoro-2-methylphenylamino)-6-(6-fluoro-2H-spiro[benzofuran-3,4'-piperidine]-1'-ylcarbonyl)pyrazolo[1,5-a]pyrimidine In the same manner as in Example 21, step 5 and using 3-ethoxycarbonyl-7-(4-fluoro-2-methylphenylamino)pyrazolo[1,5-a]pyrimidine-6-carboxylic acid (0.130 g, 0.363 mmol) obtained in step 2 and 6-fluoro-2H-spiro[benzofuran-3,4'-piperidine]hydrochloride (0.082 g, 0.399 mmol), the title compound (0.150 g, 75%) was obtained.

[Step 4]

7-(4-Fluoro-2-methylphenylamino)-6-(6-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(6- fluoro-2H-spiro[benzofuran-3,4'-piperidine]-1'-ylcarbonyl) pyrazolo[1,5-a]pyrimidine (0.148 g, 0.271 mmol) obtained in step 3, the title compound (0.115 g, 82%) was obtained.
[Step 5]

N-[7-(4-Fluoro-2-methylphenylamino)-6-(6-fluoro-2H-spiro[benzofuran-3,4'-piperidine]-1'-ylcarbonyl]ethanesulfonamide (compound a-139)

In the same manner as in Example 1, step 6 and using 7-(4-fluoro-2-methylphenylamino)-6-(6-fluoro-2H-spiro[benzofuran-3,4'-piperidine]-1'-ylcarbonyl)pyrazolo[1,5-a]pyrimidine-3-carboxylic acid (0.110 g, 0.212 mmol) obtained in step 4 and ethanesulfonamide (0.115 g, 1.06 mmol), the title compound (0.065 g, 50%) was obtained.
ESI-MS m/z: 611 (M+H)$^+$; $^1$H-NMR (CDCl$_3$, δ): 1.45 (t, J=7.3 Hz, 3H), 1.63-1.77 (m, 4H), 2.41 (s, 3H), 2.60-2.89 (m, 2H), 3.60 (q, J=7.3 Hz, 2H), 3.75-3.98 (m, 2H), 4.39 (s, 2H), 6.50-6.58 (m, 1H), 6.58-6.69 (m, 1H), 6.93-7.04 (m, 2H), 7.06-7.16 (m, 1H), 7.16-7.24 (m, 1H), 8.23-8.38 (m, 2H), 8.61 (s, 1H), 10.49 (br s, 1H).

EXAMPLE 140

N-[7-(3-Fluoro-4-methylphenylamino)-6-(6-fluoro-2H-spiro[benzofuran-3,4'-piperidine]-1'-ylcarbonyl]ethanesulfonamide (compound a-140)

[Step 1]

Methyl 3-ethoxycarbonyl-7-(3-fluoro-4-methylphenylamino)pyrazolo[1,5-a]pyrimidine-6-carboxylate In the same manner as in Example 1, step 4 and using methyl 7-chloro-3-ethoxycarbonylpyrazolo[1,5-a]pyrimidine-6-carboxylate (3.00 g, 10.6 mmol) obtained in Example 21, step 2 and 3-fluoro-4-methylaniline (1.43 ml, 12.7 mmol), the title compound (3.67 g, 94%) was obtained.
[Step 2]

3-Ethoxycarbonyl-7-(3-fluoro-4-methylphenylamino)pyrazolo[1,5-a]pyrimidine-6-carboxylic acid In the same manner as in Example 21, step 4 and using methyl 3-ethoxycarbonyl-7-(3-fluoro-4-methylphenylamino)pyrazolo[1,5-a]pyrimidine-6-carboxylate (2.80 g, 7.52 mmol) obtained in step 1, the title compound (1.65 g, 61%) was obtained.
[Step 3]

3-Ethoxycarbonyl-7-(3-fluoro-4-methylphenylamino)-6-(6-fluoro-2H-spiro[benzofuran-3,4'-piperidine]-1'-ylcarbonyl)pyrazolo[1,5-a]pyrimidine In the same manner as in Example 21, step 5 and using 3-ethoxycarbonyl-7-(3-fluoro-4-methylphenylamino)pyrazolo[1,5-a]pyrimidine-6-carboxylic acid (0.130 g, 0.363 mmol) obtained in step 2 and 6-fluoro-2H-spiro[benzofuran-3,4'-piperidine]hydrochloride (0.082 g, 0.399 mmol), the title compound (0.191 g, 96%) was obtained.
[Step 4]

7-(3-Fluoro-4-methylphenylamino)-6-(6-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(3-fluoro-4-methylphenylamino)-6-(6-fluoro-2H-spiro[benzofuran-3,4'-piperidine]-1'-ylcarbonyl)pyrazolo[1,5-a]pyrimidine (0.185 g, 0.338 mmol) obtained in step 3, the title compound (0.145 g, 83%) was obtained.
[Step 5]

N-[7-(3-Fluoro-4-methylphenylamino)-6-(6-fluoro-2H-spiro[benzofuran-3,4'-piperidine]-1'-ylcarbonyl]ethanesulfonamide (compound a-140)

In the same manner as in Example 1, step 6 and using 7-(3-fluoro-4-methylphenylamino)-6-(6-fluoro-2H-spiro[benzofuran-3,4'-piperidine]-1'-ylcarbonyl)pyrazolo[1,5-a]pyrimidine-3-carboxylic acid (0.140 g, 0.269 mmol) obtained in step 4 and ethanesulfonamide (0.146 g, 1.35 mmol), the title compound (0.102 g, 82%) was obtained.
ESI-MS m/z: 611 (M+H)$^+$; $^1$H-NMR (CDCl$_3$, δ): 1.44 (t, J=7.3 Hz, 3H), 1.54-1.87 (m, 4H), 2.35 (s, 3H), 2.56-3.18 (m, 2H), 3.58 (q, J=7.3 Hz, 2H), 3.68-4.03 (m, 2H), 4.38 (s, 2H), 6.54 (dd, J=9.0, 2.2 Hz, 1H), 6.62 (td, J=9.0, 2.2 Hz, 1H), 6.91-7.13 (m, 3H), 7.20-7.39 (m, 1H), 8.38 (s, 1H), 8.56 (s, 1H), 8.65 (br s, 1H), 10.42 (s, 1H).

EXAMPLE 141

N-[7-(3-Fluoro-4-methylphenylamino)-6-(6-fluoro-2H-spiro[benzofuran-3,4'-piperidine]-1'-ylcarbonyl]cyclopropanesulfonamide (compound a-141)

In the same manner as in Example 1, step 6 and using 7-(3-fluoro-4-methylphenylamino)-6-(6-fluoro-2H-spiro[benzofuran-3,4'-piperidine]-1'-ylcarbonyl)pyrazolo[1,5-a]pyrimidine-3-carboxylic acid (0.113 g, 0.218 mmol) obtained in Example 140, step 4 and cyclopropanesulfonamide (0.131 g, 1.09 mmol), the title compound (0.089 g, 66%) was obtained.
ESI-MS m/z: 623 (M+H)$^+$; $^1$H-NMR (DMSO-d$_6$, δ): 1.04-1.22 (m, 2H), 1.39-1.53 (m, 2H), 1.62-1.77 (m, 4H), 2.35 (s, 3H), 2.46-2.92 (m, 2H), 3.02-3.20 (m, 1H), 3.53-3.98 (m, 2H), 4.33 (s, 2H), 6.46-6.69 (m, 2H), 6.86-7.01 (m, 1H), 7.04-7.33 (m, 3H), 8.41 (s, 1H), 8.50-8.54 (m, 1H), 8.63 (s, 1H), 10.58 (br s, 1H).

EXAMPLE 142

N-[7-(2-Chloro-5-methylphenylamino)-6-(6-fluoro-2H-spiro[benzofuran-3,4'-piperidine]-1'-ylcarbonyl)pyrazolo[1,5-a]pyrimidine-3-carbonyl]ethanesulfonamide (compound a-142)

[Step 1]

7-(2-Chloro-5-methylphenylamino)-3-ethoxycarbonyl-6-(6-fluoro-2H-spiro[benzofuran-3,4'-piperidine]-1'-ylcarbonyl)pyrazolo[1,5-a]pyrimidine In the same manner as in Example 21, step 5 and using 7-(2-chloro-5-methylphenylamino)-3-ethoxycarbonylpyrazolo[1,5-a]pyrimidine-6-carboxylic acid (0.130 g, 0.347 mmol) obtained in Example 66, step 2 and 6-fluoro-2H-spiro[benzofuran-3,4'-piperidine]hydrochloride (0.079 g, 0.382 mmol), the title compound (0.195 g, 100%) was obtained.
[Step 2]

7-(2-Chloro-5-methylphenylamino)-6-(6-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 7-(2-chloro-5-methylphenylamino)-3-ethoxycarbonyl-6-(6- fluoro-2H-spiro[benzofuran-3,4'-piperidine]-1'-ylcarbonyl)pyrazolo[1,5-a]pyrimidine (0.200 g, 0.355 mmol) obtained in step 1, the title compound (0.146 g, 77%) was obtained.
[Step 3]

N-[7-(2-Chloro-5-methylphenylamino)-6-(6-fluoro-2H-spiro[benzofuran-3,4'-piperidine]-1'-ylcarbonyl)pyrazolo[1,5-a]pyrimidine-3-carbonyl]ethanesulfonamide (compound a-142)

In the same manner as in Example 1, step 6 and using 7-(2-chloro-5-methylphenylamino)-6-(6-fluoro-2H-spiro[benzofuran-3,4'-piperidine]-1'-ylcarbonyl)pyrazolo[1,5-a]pyrimidine-3-carboxylic acid (0.140 g, 0.262 mmol) obtained in step 2 and ethanesulfonamide (0.142 g, 1.31 mmol), the title compound (0.071 g, 43%) was obtained.
ESI-MS m/z: 628 (M+H)$^+$; $^1$H-NMR (CDCl$_3$, δ): 1.46 (t, J=7.3 Hz, 3H), 1.54-1.69 (m, 4H), 2.37 (s, 3H), 2.46-2.87 (m, 2H), 3.49-3.97 (m, 4H), 4.30 (s, 2H), 6.51-6.68 (m, 2H), 6.87-6.98 (m, 1H), 7.09-7.28 (m, 2H), 7.41-7.52 (m, 1H), 8.45-8.60 (m, 2H), 8.64 (s, 1H), 10.46 (br s, 1H).

EXAMPLE 143

N-[7-(2-Chloro-5-methylphenylamino)-6-(6-fluoro-2H-spiro[benzofuran-3,4'-piperidine]-1'-ylcarbonyl)pyrazolo[1,5-a]pyrimidine-3-carbonyl]cyclopropanesulfonamide (compound a-143)

In the same manner as in Example 1, step 6 and using 7-(2-chloro-5-methylphenylamino)-6-(6-fluoro-2H-spiro[benzofuran-3,4'-piperidine]-1'-ylcarbonyl)pyrazolo[1,5-a]pyrimidine-3-carboxylic acid (0.160 g, 0.282 mmol) obtained in Example 142, step 2 and cyclopropanesulfonamide (0.170 g, 1.41 mmol), the title compound (0.087 g, 48%) was obtained.
ESI-MS m/z: 640 (M+H)$^+$; $^1$H-NMR (CDCl$_3$, δ): 1.03-1.24 (m, 2H), 1.41-1.77 (m, 6H), 2.36 (s, 3H), 2.48-2.94 (m, 2H), 3.01-3.21 (m, 1H), 3.36-3.99 (m, 2H), 4.31 (s, 2H), 6.42-6.68 (m, 2H), 6.84-6.99 (m, 1H), 7.12-7.20 (m, 1H), 7.21-7.28 (m, 1H), 7.41-7.53 (m, 1H), 8.35-8.75 (m, 3H), 10.56 (br s, 1H).

EXAMPLE 144

N-[6-(6-Fluoro-2H-spiro[benzofuran-3,4'-piperidine]-1'-ylcarbonyl)-7-(4-methylphenylamino)pyrazolo[1,5-a]pyrimidine-3-carbonyl]ethanesulfonamide (compound a-144)

[Step 1]

Methyl 3-ethoxycarbonyl-7-(4-methylphenylamino)pyrazolo[1,5-a]pyrimidine-6-carboxylate In the same manner as in Example 1, step 4 and using methyl 7-chloro-3-ethoxycarbonylpyrazolo[1,5-a]pyrimidine-6-carboxylate (0.400 g, 1.51 mmol) obtained in Example 21, step 2 and 4-methylaniline (0.242 g, 2.26 mmol), the title compound (0.191 g, 35%) was obtained.
[Step 2]

3-Ethoxycarbonyl-7-(4-methylphenylamino)pyrazolo[1,5-a]pyrimidine-6-carboxylic acid In the same manner as in Example 21, step 4 and using methyl 3-ethoxycarbonyl-7-(4-methylphenylamino)pyrazolo[1,5-a]pyrimidine-6-carboxylate (0.110 g, 0.311 mmol) obtained in step 1, the title compound (0.060 g, 32%) was obtained.
[Step 3]

3-Ethoxycarbonyl-6-(6-fluoro-2H-spiro[benzofuran-3,4'-piperidine]-1'-ylcarbonyl)-7-(4-methylphenylamino)pyrazolo[1,5-a]pyrimidine In the same manner as in Example 21, step 5 and using 3-ethoxycarbonyl-7-(4-methylphenylamino)pyrazolo[1,5-a]pyrimidine-6-carboxylic acid (0.060 g, 0.176 mmol) obtained in step 2 and 6-fluoro-2H-spiro[benzofuran-3,4'-piperidine]hydrochloride (0.040 mg, 0.194 mmol), the title compound (0.083 g, 89%) was obtained.
[Step 4]

6-(6-Fluoro-2H-spiro[benzofuran-3,4'-piperidine]-1'-ylcarbonyl)-7-(4-methylphenylamino)pyrazolo[1,5-a]pyrimidine-3-carboxylic acid In the same manner as in Example 19, step 6 and using 3-ethoxycarbonyl-6-(6-fluoro-2H-spiro[benzofuran-3,4'-piperidine]-1'-ylcarbonyl)-7-(4-methylphenylamino)pyrazolo[1,5-a]pyrimidine (0.080 g, 0.151 mmol) obtained in step 3, the title compound (0.031 g, 41%) was obtained.
[Step 5]

N-[6-(6-Fluoro-2H-spiro[benzofuran-3,4'-piperidine]-1'-ylcarbonyl)-7-(4-methylphenylamino)pyrazolo[1,5-a]pyrimidine-3-carbonyl]ethanesulfonamide (compound a-144)

In the same manner as in Example 1, step 6 and using 6-(6-fluoro-2H-spiro[benzofuran-3,4'-piperidine]-1'-ylcarbonyl)-7-(4-methylphenylamino)pyrazolo[1,5-a]pyrimidine-3-carboxylic acid (0.031 g, 0.062 mmol) obtained in step 4 and ethanesulfonamide (0.034 g, 0.309 mmol), the title compound (0.022 g, 60%) was obtained.
ESI-MS m/z: 593 (M+H)$^+$; $^1$H-NMR (CDCl$_3$, δ): 1.45 (t, J=7.3 Hz, 3H), 1.55-1.82 (m, 4H), 2.43 (s, 3H), 2.56-3.13 (m, 2H), 3.46-3.91 (m, 4H), 4.30 (s, 2H), 6.45-6.56 (m, 1H), 6.56-6.70 (m, 1H), 6.86-7.00 (m, 1H), 7.16-7.35 (m, 4H), 8.40 (s, 1H), 8.51-8.66 (m, 2H), 10.49 (br s, 1H).

EXAMPLE 145

N-[7-Benzylamino-6-(7-fluoro-2H-spiro[benzofuran-3,4'-piperidine]-1'-ylcarbonyl)pyrazolo[1,5-a]pyrimidine-3-carbonyl]methanesulfonamide (compound a-145)

[Step 1]

3-Ethoxycarbonyl-6-(7-fluoro-2H-spiro[benzofuran-3,4'-piperidine]-1'-ylcarbonyl)-7-hydroxypyrazolo[1,5-a]pyrimidine In the same manner as in Example 19, step 3 and using 3-ethoxycarbonyl-7-hydroxypyrazolo[1,5-a]pyrimidine-6-carboxylic acid (0.416 g, 1.66 mmol) obtained in Example 19, step 2 and 7-fluoro-2H-spiro[benzofuran-3,4'-piperidine]hydrochloride (0.500 g, 1.99 mmol) obtained in Reference Example 5, the title compound (0.570 g, 79%) was obtained.

[Step 2]

7-Chloro-3-ethoxycarbonyl-6-(7-fluoro-2H-spiro[benzofuran-3,4'-piperidine]-1'-ylcarbonyl)pyrazolo[1,5-a]pyrimidine In the same manner as in Example 1, step 3 and using 3-ethoxycarbonyl-6-(7-fluoro-2H-spiro[benzofuran-3,4'-piperidine]-1'-ylcarbonyl)-7-hydroxypyrazolo[1,5-a]pyrimidine (0.570 g, 1.30 mmol) obtained in step 1, the title compound (0.510 g, 72%) was obtained.

[Step 3]

7-Benzylamino-3-ethoxycarbonyl-6-(7-fluoro-2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(7-fluoro-2H-spiro[benzofuran-3,4'-piperidine]-1'-ylcarbonyl)pyrazolo[1,5-a]pyrimidine (0.250 g, 0.546 mmol) obtained in step 2 and benzylamine (0.150 mL, 1.37 mmol), the title compound (0.091 g, 31%) was obtained.

[Step 4]

7-Benzylamino-6-(7-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 7-benzylamino-3-ethoxycarbonyl-6-(7-fluoro-2H-spiro[benzofuran-3,4'-piperidine]-1'-ylcarbonyl)pyrazolo[1,5-a]pyrimidine (0.090 g, 0.170 mmol) obtained in step 3, the title compound (0.075 g, 88%) was obtained.

[Step 5]

N-[7-Benzylamino-6-(7-fluoro-2H-spiro[benzofuran-3,4'-piperidine]-1'-ylcarbonyl)pyrazolo[1,5-a]pyrimidine-3-carbonyl]methanesulfonamide (compound a-145)

In the same manner as in Example 1, step 6 and using 7-benzylamino-6-(7-fluoro-2H-spiro[benzofuran-3,4'-piperidine]-1'-ylcarbonyl)pyrazolo[1,5-a]pyrimidine-3-carboxylic acid (0.075 g, 0.746 mmol) obtained in step 4 and methanesulfonamide (0.071 g, 0.749 mmol), the title compound (0.026 g, 30%) was obtained.

ESI-MS m/z: 579 (M+H)$^+$; $^1$H-NMR (CDCl$_3$, δ): 1.61-1.91 (m, 4H), 2.47-3.01 (m, 2H), 3.41 (s, 3H), 3.69-4.11 (m, 2H), 4.38 (s, 2H), 4.84-5.01 (m, 2H), 6.75-7.03 (m, 3H), 7.19-7.50 (m, 5H), 7.71-7.87 (m, 1H), 8.22 (s, 1H), 8.60 (s, 1H), 10.68 (br s, 1H).

EXAMPLE 146

N-[7-(2-Fluoro-5-methylphenylamino)-6-(7-fluoro-2H-spiro[benzofuran-3,4'-piperidine]-1'-ylcarbonyl)pyrazolo[1,5-a]pyrimidine-3-carbonyl]cyclopropanesulfonamide (compound a-146)

[Step 1]

3-Ethoxycarbonyl-7-(2-fluoro-5-methylphenylamino)-6-(7-fluoro-2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(7-fluoro-2H-spiro[benzofuran-3,4'-piperidine]-1'-ylcarbonyl)pyrazolo[1,5-a]pyrimidine (0.250 g, 0.546 mmol) obtained in Example 145, step 2 and 2-fluoro-5-methylphenylamine (0.150 mL, 1.37 mmol), the title compound (0.155 g, 52%) was obtained.

[Step 2]

7-(2-Fluoro-5-methylphenylamino)-6-(7-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(2-fluoro-5-methylphenylamine)-6-(7-fluoro-2H-spiro[benzofuran-3,4'-piperidine]-1'-ylcarbonyl)pyrazolo[1,5-a]pyrimidine (0.155 g, 0.283 mmol) obtained in step 1, the title compound (0.130 g, 88%) was obtained.

[Step 3]

N-[7-(2-Fluoro-5-methylphenylamino)-6-(7-fluoro-2H-spiro[benzofuran-3,4'-piperidine]-1'-ylcarbonyl)pyrazolo[1,5-a]pyrimidine-3-carbonyl]cyclopropanesulfonamide (compound a-146)

In the same manner as in Example 1, step 6 and using 7-(2-fluoro-5-methylphenylamino)-6-(7-fluoro-2H-spiro[benzofuran-3,4'-piperidine]-1'-ylcarbonyl)pyrazolo[1,5-a]pyrimidine-3-carboxylic acid (0.130 g, 0.251 mmol) obtained in step 2 and cyclopropanesulfonamide (0.155 g, 0.125 mmol), the title compound (0.066 g, 42%) was obtained.

ESI-MS m/z: 623 (M+H)$^+$; $^1$H-NMR (CDCl$_3$, δ): 1.08-1.22 (m, 2H), 1.43-1.55 (m, 2H), 1.64-1.82 (m, 4H), 2.32-2.46 (m, 3H), 2.55-2.97 (m, 2H), 3.03-3.22 (m, 1H), 3.71-4.01 (m, 2H), 4.43 (s, 2H), 6.79-7.04 (m, 3H), 7.09-7.34 (m, 3H), 8.37-8.51 (m, 2H), 8.67 (s, 1H), 10.57 (br s, 1H).

EXAMPLE 147

N-[7-(2,5-Dimethylphenylamino)-6-(7-fluoro-2H-spiro[benzofuran-3,4'-piperidine]-1'-ylcarbonyl)pyrazolo[1,5-a]pyrimidine-3-carbonyl]ethanesulfonamide (compound a-147)

[Step 1]

7-(2,5-Dimethylphenylamino)-3-ethoxycarbonyl-6-(7-fluoro-2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(7-fluoro-2H-spiro[benzofuran-3,4'-piperidine]-1'-ylcarbonyl)pyrazolo[1,5-a]pyrimidine (0.145 g, 0.318 mmol) obtained in Example 145, step 2 and 2,5-dimethylphenylamine (0.046 mL, 0.372 mmol), the title compound (0.105 g, 61%) was obtained.

[Step 2]

7-(2,5-Dimethylphenylamino)-6-(7-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 7-(2,5-dimethylphenylamino)-3-ethoxycarbonyl-6-(7-fluoro-2H-spiro[benzofuran-3,4'-piperidine]-1'-ylcarbonyl)pyrazolo[1,5-a]pyrimidine (0.095 g, 0.175 mmol) obtained in step 1, the title compound (0.063 g, 70%) was obtained.

[Step 3]

N-[7-(2,5-Dimethylphenylamino)-6-(7-fluoro-2H-spiro[benzofuran-3,4'-piperidine]-1'-ylcarbonyl)pyrazolo[1,5-a]pyrimidine-3-carbonyl]ethanesulfonamide (compound a-147)

In the same manner as in Example 1, step 6 and using 7-(2,5-dimethylphenylamino)-6-(7-fluoro-2H-spiro[benzofuran-3,4'-piperidine]-1'-ylcarbonyl)pyrazolo[1,5-a]pyrimidine-3-carboxylic acid (0.063 g, 0.122 mmol) obtained in step 2 and ethanesulfonamide (0.066 g, 0.610 mmol), the title compound (0.049 g, 66%) was obtained.
ESI-MS m/z: 607 (M+H)$^+$; $^1$H-NMR (CDCl$_3$, δ): 1.45 (t, J=7.4 Hz, 3H), 1.52-1.77 (m, 4H), 2.37 (s, 6H), 2.43-2.89 (m, 2H), 3.45-3.87 (m, 4H), 4.37 (s, 2H), 6.74-7.32 (m, 6H), 8.33-8.43 (m, 2H), 8.62 (s, 1H), 10.50 (br s, 1H).

EXAMPLE 148

N-[7-(4-Fluoro-2-methylphenylamino)-6-(7-fluoro-2H-spiro[benzofuran-3,4'-piperidine]-1'-ylcarbonyl)pyrazolo[1,5-a]pyrimidine-3-carbonyl]cyclopropanesulfonamide (compound a-148)

[Step 1]

3-Ethoxycarbonyl-7-(4-fluoro-2-methylphenylamino)-6-(7-fluoro-2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(7-fluoro-2H-spiro[benzofuran-3,4'-piperidine]-1'-ylcarbonyl)pyrazolo[1,5-a]pyrimidine (0.145 g, 0.318 mmol) obtained in Example 145, step 2 and 4-fluoro-2-methylphenylamine (0.041 mL, 0.372 mmol), the title compound (0.095 g, 54%) was obtained.

[Step 2]

7-(4-Fluoro-2-methylphenylamino)-6-(7-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(7-fluoro-2H-spiro[benzofuran-3,4'-piperidine]-1'-ylcarbonyl)pyrazolo[1,5-a]pyrimidine (0.105 g, 0.192 mmol) obtained in step 1, the title compound (0.079 g, 79%) was obtained.

[Step 3]

N-[7-(4-Fluoro-2-methylphenylamino)-6-(7-fluoro-2H-spiro[benzofuran-3,4'-piperidine]-1'-ylcarbonyl)pyrazolo[1,5-a]pyrimidine-3-carbonyl]cyclopropanesulfonamide (compound a-148)

In the same manner as in Example 1, step 6 and using 7-(4-fluoro-2-methylphenylamino)-6-(7-fluoro-2H-spiro[benzofuran-3,4'-piperidine]-1'-ylcarbonyl)pyrazolo[1,5-a]pyrimidine-3-carboxylic acid (0.079 g, 0.152 mmol) obtained in step 2 and cyclopropanesulfonamide (0.092 g, 0.760 mmol), the title compound (0.051 g, 64%) was obtained.
ESI-MS m/z: 623 (M+H)$^+$; $^1$H-NMR (CDCl$_3$, δ): 1.08-1.20 (m, 2H), 1.40-1.53 (m, 2H), 1.66-1.85 (m, 4H), 2.41 (s, 3H), 2.53-2.91 (m, 2H), 3.02-3.18 (m, 1H), 3.70-4.08 (m, 2H), 4.46 (s, 2H), 6.83-7.24 (m, 6H), 8.30 (s, 1H), 8.63 (s, 1H), 10.58 (br s, 1H).

EXAMPLE 149

N-[7-(4-Fluoro-2-methylphenylamino)-6-(4-fluoro-2H-spiro[benzofuran-3,4'-piperidine]-1'-ylcarbonyl)pyrazolo[1,5-a]pyrimidine-3-carbonyl]ethanesulfonamide (compound a-149)

[Step 1]

3-Ethoxycarbonyl-6-(4-fluoro-2H-spiro[benzofuran-3,4'-piperidine]-1'-ylcarbonyl)-7-hydroxypyrazolo[1,5-a]pyrimidine In the same manner as in Example 1, step 2 and using 3-ethoxycarbonyl-7-hydroxypyrazolo[1,5-a]pyrimidine-6-carboxylic acid (0.430 g, 1.71 mmol) obtained in Example 19, step 2 and 4-fluoro-2H-spiro[benzofuran-3,4'-piperidine] hydrochloride (0.500 g, 2.05 mmol) obtained in Reference Example 2, the title compound (0.260 g, 35%) was obtained.

[Step 2]

7-Chloro-3-ethoxycarbonyl-6-(4-fluoro-2H-spiro[benzofuran-3,4'-piperidine]-1-ylcarbonyl)pyrazolo[1,5-a]pyrimidine In the same manner as in Example 1, step 3 and using 3-ethoxycarbonyl-6-(4-fluoro-2H-spiro[benzofuran-3,4'-piperidine]-1'-ylcarbonyl)-7-hydroxypyrazolo[1,5-a]pyrimidine (0.260 g, 0.591 mmol) obtained in step 1, the title compound (0.175 g, 65%) was obtained.

[Step 3]

3-Ethoxycarbonyl-7-(4-fluoro-2-methylphenylamino)-6-(4-fluoro-2H-spiro[benzofuran-3,4'-piperidine]-1'-ylcarbonyl)pyrazolo[1,5-a]pyrimidine In the same manner as in Example 19, step 5 and using 7-chloro-3-ethoxycarbonyl-6-(4-fluoro-2H-spiro[benzofuran-3,4'-piperidine]-1'-ylcarbonyl)pyrazolo[1,5-a]pyrimidine (0.171 g, 0.372 mmol) obtained in step 2 and 4-fluoro-2-methylaniline (0.050 mL, 0.446 mmol), the title compound (0.035 g, 17%) was obtained.

[Step 4]

7-(4-Fluoro-2-methylphenylamino)-6-(4-fluoro-2H-spiro[benzofuran-3,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(4-fluoro-2H-spiro[benzofuran-3,4'-piperidine]-1'-ylcarbonyl)pyrazolo[1,5-a]pyrimidine (0.035 g, 0.064 mmol) obtained in step 3, the title compound (0.025 g, 72%) was obtained.

[Step 5]

N-[7-(4-Fluoro-2-methylphenylamino)-6-(4-fluoro-2H-spiro[benzofuran-3,4'-piperidine]-1'-ylcarbonyl)pyrazolo[1,5-a]pyrimidine-3-carbonyl]ethanesulfonamide (compound a-149)

In the same manner as in Example 1, step 6 and using 7-(4-fluoro-2-methylphenylamino)-6-(4-fluoro-2H-spiro[benzofuran-3,4'-piperidine]-1'-ylcarbonyl)pyrazolo[1,5-a]pyrimidine-3-carboxylic acid (0.025 g, 0.048 mmol) obtained in step 4 and ethanesulfonamide (0.026 g, 0.241 mmol), the title compound (0.008 g, 27%) was obtained.

ESI-MS m/z: 611 (M+H)$^+$; $^1$H-NMR (CDCl$_3$, δ): 1.44 (t, J=7.3 Hz, 3H), 1.59-1.88 (m, 2H), 1.95-2.21 (m, 2H), 2.41 (s, 3H), 2.51-3.01 (m, 2H), 3.61 (q, J=7.3 Hz, 2H), 3.79-4.14 (m, 2H), 4.41 (s, 2H), 6.52-6.71 (m, 2H), 6.93-7.25 (m, 4H), 8.22-8.39 (m, 2H), 8.61 (s, 1H), 10.49 (br s, 1H).

EXAMPLE 150

N-[6-(5-Fluoro-2H-spiro[benzofuran-3,4'-piperidine]-1'-ylcarbonyl)-7-(2-methylphenylamino)pyrazolo[1,5-a]pyrimidine-3-carbonyl]ethanesulfonamide (compound a-150)

[Step 1]

3-Ethoxycarbonyl-6-(5-fluoro-2H-spiro[benzofuran-3,4'-piperidine]-1'-ylcarbonyl)-7-hydroxypyrazolo[1,5-a]pyrimidine In the same manner as in Example 1, step 2 and using 3-ethoxycarbonyl-7-hydroxypyrazolo[1,5-a]pyrimidine-6-carboxylic acid (0.416 g, 1.66 mmol) obtained in Example 19, step 2 and 5-fluoro-2H-spiro[benzofuran-3,4'-piperidine] hydrochloride (0.500 g, 1.99 mmol) obtained in Reference Example 3, the title compound (0.470 g, 54%) was obtained.

[Step 2]

7-Chloro-3-ethoxycarbonyl-6-(5-fluoro-2H-spiro[benzofuran-3,4'-piperidine]-1'-ylcarbonyl)pyrazolo[1,5-a]pyrimidine In the same manner as in Example 1, step 3 and using 3-ethoxycarbonyl-6-(5-fluoro-2H-spiro[benzofuran-3,4'-piperidine]-1'-ylcarbonyl)-7-hydroxypyrazolo[1,5-a]pyrimidine (0.470 g, 1.07 mmol) obtained in step 1, the title compound (0.489 g, 100%) was obtained.

[Step 3]

3-Ethoxycarbonyl-6-(5-fluoro-2H-spiro[benzofuran-3,4'-piperidine]-1'-ylcarbonyl)-7-(2-methylphenylamino)pyrazolo[1,5-a]pyrimidine In the same manner as in Example 19, step 5 and using 7-chloro-3-ethoxycarbonyl-6-(5-fluoro-2H-spiro[benzofuran-3,4'-piperidine]-1'-ylcarbonyl)pyrazolo[1,5-a]pyrimidine (0.260 g, 0.569 mmol) obtained in step 2 and 2-methylaniline (0.091 mL, 0.853 mmol), the title compound (0.151 g, 50%) was obtained.

[Step 4]

6-(5-Fluoro-2H-spiro[benzofuran-3,4'-piperidine]-1'-ylcarbonyl)-7-(2-methylphenylamino)pyrazolo[1,5-a]pyrimidine-3-carboxylic acid In the same manner as in Example 19, step 6 and using 3-ethoxycarbonyl-6-(5-fluoro-2H-spiro[benzofuran-3,4'-piperidine]-1'-ylcarbonyl)-7-(2-methylphenylamino)pyrazolo[1,5-a]pyrimidine (0.145 g, 0.274 mmol) obtained in step 3, the title compound (0.123 g, 89%) was obtained.

[Step 5]

N-[6-(5-Fluoro-2H-spiro[benzofuran-3,4'-piperidine]-1'-ylcarbonyl)-7-(2-methylphenylamino)pyrazolo[1,5-a]pyrimidine-3-carbonyl]ethanesulfonamide (compound a-150)

In the same manner as in Example 1, step 6 and using 6-(5-fluoro-2H-spiro[benzofuran-3,4'-piperidine]-1'-ylcarbonyl)-7-(2-methylphenylamino)pyrazolo[1,5-a]pyrimidine-3-carboxylic acid (0.122 g, 0.243 mmol) obtained in step 4 and ethanesulfonamide (0.133 g, 1.23 mmol), the title compound (0.121 g, 84%) was obtained.

ESI-MS m/z: 593 (M+H)$^+$; $^1$H-NMR (CDCl$_3$, δ): 1.37-1.54 (m, 3H), 1.58-1.91 (m, 4H), 2.35-2.48 (m, 3H), 2.59-3.04 (m, 2H), 3.44-3.87 (m, 4H), 4.24-4.40 (m, 2H), 6.63-6.96 (m, 3H), 7.15-7.52 (m, 4H), 8.27-8.54 (m, 2H), 8.57-8.69 (m, 1H), 10.21-10.74 (m, 1H)

EXAMPLE 151

N-[7-Benzylamino-6-(3-oxo-3H-spiro[isobenzofuran-1,4'-piperidine]-1'-ylcarbonyl)pyrazolo[1,5-a]pyrimidine-3-carbonyl]methanesulfonamide (compound a-151)

[Step 1]

3-Ethoxycarbonyl-7-hydroxy-6-(3-oxo-3H-spiro[isobenzofuran-1,4'-piperidine]-1'-ylcarbonyl)pyrazolo[1,5-a]pyrimidine In the same manner as in Example 1, step 2 and using 3-ethoxycarbonyl-7-hydroxypyrazolo[1,5-a]pyrimidine-6-carboxylic acid (0.436 g, 1.74 mmol) obtained in Example 19, step 2 and 3-oxo-3H-spiro[isobenzofuran-1,4'-piperidine]hydrochloride (Journal of Organic Chemistry, 1976, vol. 15, item 2628, 0.500 g, 2.09 mmol), the title compound (0.680 g, 89%) was obtained.

[Step 2]

7-Chloro-3-ethoxycarbonyl-6-(3-oxo-3H-spiro[isobenzofuran-1,4'-piperidine]-1'-ylcarbonyl)pyrazolo[1,5-a]pyrimidine In the same manner as in Example 1, step 3 and using 3-ethoxycarbonyl-7-hydroxy-6-(3-oxo-3H-spiro[isobenzofuran-1,4'-piperidine]-1'-ylcarbonyl)pyrazolo[1,5-a]pyrimidine (0.350 g, 0.803 mmol) obtained in step 1, the title compound (0.166 g, 45%) was obtained.

[Step 3]

7-Benzylamino-3-ethoxycarbonyl-6-(3-oxo-3H-spiro[isobenzofuran-1,4'-piperidine]-1'-ylcarbonyl)pyrazolo[1,5-a]pyrimidine In the same manner as in Example 19, step 5 and using 7-chloro-3-ethoxycarbonyl-6-(3-oxo-3H-spiro[isobenzofuran-1,4'-piperidine]-1'-ylcarbonyl)pyrazolo[1,5-a]pyrimidine (0.160 g, 0.352 mmol) obtained in step 2 and benzylamine (0.100 mL, 0.881 mmol), the title compound (0.142 g, 76%) was obtained.

[Step 4]

7-Benzylamino-6-(3-oxo-3H-spiro[isobenzofuran-1,4'-piperidine]-1'-ylcarbonyl)pyrazolo[1,5-a]pyrimidine-3-carboxylic acid After an operation similar to that in Example 19, step 6 with using 7 benzylamino-3-ethoxycarbonyl-6-(3-oxo-3H-spiro[isobenzofuran-1,4'-piperidine]-1'-ylcarbonyl)pyrazolo[1,5-a]pyrimidine (0.140 g, 0.266 mmol) obtained in step 3, the mixture was heated under reflux for 2 hr with 1 mol/L hydrochloric acid to give the title compound (0.120 g, 90%).

[Step 5]

N-[7-Benzylamino-6-(3-oxo-3H-spiro[isobenzofuran-1,4'-piperidine]-1'-ylcarbonyl)pyrazolo[1,5-a]pyrimidine-3-carbonyl]methanesulfonamide (compound a-151)

In the same manner as in Example 1, step 6 and using 7-benzylamino-6-(3-oxo-3H-spiro[isobenzofuran-1,4'-piperidine]-1'-ylcarbonyl)pyrazolo[1,5-a]pyrimidine-3-carboxylic acid (0.100 g, 0.201 mmol) obtained in step 4 and methanesulfonamide (0.096 g, 1.01 mmol), the title compound (0.099 g, 85%) was obtained.

ESI-MS m/z: 575 (M+H)$^+$; $^1$H-NMR (CDCl$_3$, δ): 1.66-1.86 (m, 2H), 1.90-2.16 (m, 2H), 2.92-3.26 (m, 2H), 3.33-3.50 (m, 3H), 3.83-4.67 (m, 2H), 4.81-5.02 (m, 2H), 7.19-7.52 (m, 6H), 7.52-7.65 (m, 1H), 7.65-7.87 (m, 2H), 7.87-7.99 (m, 1H), 8.25 (s, 1H), 8.59 (s, 1H), 10.69 (br s, 1H).

EXAMPLE 152

N-[7-Benzylamino-6-(3H-spiro[isobenzofuran-1,4'-piperidine]-1'-ylcarbonyl)pyrazolo[1,5-a]pyrimidine-3-carbonyl]methanesulfonamide (compound a-152)

[Step 1]

7-Benzylamino-3-bromo-6-(3H-spiro[isobenzofuran-1,4'-piperidine]-1'-ylcarbonyl)pyrazolo[1,5-a]pyrimidine In the same manner as in Example 21, step 5 and using 7-benzylamino-3-bromopyrazolo[1,5-a]pyrimidine-6-carboxylic acid (0.754 g, 2.18 mmol) obtained in Example 22, step 3 and 3H-spiro[isobenzofuran-1,4'-piperidine]hydrochloride (Journal of Organic Chemistry, 1976, vol. 15, item 2628, 0.491 g, 0.218 mmol), the title compound (0.484 g, 94%) was obtained.

[Step 2]

7-Benzylamino-6-(3H-spiro[isobenzofuran-1,4'-piperidine]-1'-ylcarbonyl)pyrazolo[1,5-a]pyrimidine-3-carboxylic acid In the same manner as in Example 1, step 5 and using 7-benzylamino-3-bromo-6-(3H-spiro[isobenzofuran-1,4'-piperidine]-1'-ylcarbonyl)pyrazolo[1,5-a]pyrimidine (0.480 g, 0.923 mmol) obtained in step 1, the title compound (0.270 g, 56%) was obtained.

[Step 3]

N-[7-Benzylamino-6-(3H-spiro[isobenzofuran-1,4'-piperidine]-1'-ylcarbonyl)pyrazolo[1,5-a]pyrimidine-3-carbonyl]methanesulfonamide (compound a-152)

In the same manner as in Example 1, step 6 and using 7-benzylamino-6-(3H-spiro[isobenzofuran-1,4'-piperidine]-1'-ylcarbonyl)pyrazolo[1,5-a]pyrimidine-3-carboxylic acid (0.130 g, 0.269 mmol) obtained in step 2 and methanesulfonamide (0.127 g, 1.34 mmol), the title compound (0.050 g, 33%) was obtained.

ESI-MS m/z: 561 (M+H)$^+$; $^1$H-NMR (CDCl$_3$, δ): 1.64-2.00 (m, 4H), 3.03-3.32 (m, 2H), 3.45 (s, 3H), 3.85-4.56 (m, 2H), 4.90-4.98 (m, 2H), 5.13 (s, 2H), 6.95-7.16 (m, 1H), 7.16-7.57 (m, 8H), 7.56-7.81 (m, 1H), 8.28 (s, 1H), 8.59 (s, 1H), 10.76 (br s, 1H).

EXAMPLE 153

N-[7-Benzylamino-6-(2H-spiro[2,3-dihydrobenzo[b]thiophene-3,4'-piperidine]-1'-ylcarbonyl)pyrazolo[1,5-a]pyrimidine-3-carbonyl]methanesulfonamide (compound a-153)

[Step 1]

7-Benzylamino-3-ethoxycarbonyl-6-(2H-spiro[2,3-dihydrobenzo[b]thiophene-3,4'-piperidine]-1'-ylcarbonyl)pyrazolo[1,5-a]pyrimidine In the same manner as in Example 21, step 5 and using 7-benzylamino-3-ethoxycarbonylpyrazolo[1,5-a]pyrimidine-6-carboxylic acid (0.28 g, 0.82 mmol) obtained in Example 21, step 4 and 2H-spiro[2,3-dihydrobenzo[b]thiophene-3,4'-piperidine] (U.S. Pat. No. 6,013,652, 0.24 g, 0.99 mmol), the title compound (0.30 g, 70%) was obtained.

[Step 2]

7-Benzylamino-6-(2H-spiro[2,3-dihydrobenzo[b]thiophene-3,4'-piperidine]-1'-ylcarbonyl)pyrazolo[1,5-a]pyrimidine-3-carboxylic acid In the same manner as in Example 19, step 6 and using 7-benzylamino-3-ethoxycarbonyl-6-(2H-spiro[2,3-dihydrobenzo[b]thiophene-3,4'-piperidine]-1'-ylcarbonyl)pyrazolo[1,5-a]pyrimidine (0.302 g, 0.57 mmol) obtained in step 1, the title compound (0.18 g, 62%) was obtained.

[Step 3]

N-[7-Benzylamino-6-(2H-spiro[2,3-dihydrobenzo[b]thiophene-3,4'-piperidine]-1'-ylcarbonyl)pyrazolo[1,5-a]pyrimidine-3-carbonyl]methanesulfonamide (compound a-153)

In the same manner as in Example 1, step 6 and using 7-benzylamino-6-(2H-spiro[2,3-dihydrobenzo[b]thiophene-3,4'-piperidine]-1'-ylcarbonyl)pyrazolo[1,5-a]pyrimidine-3-carboxylic acid (0.18 g, 0.36 mmol) obtained in step 2 and methanesulfonamide (0.170 g, 1.79 mmpl), the title compound (0.079 g, 76%) was obtained.

ESI-MS m/z: 577 (M+H)$^+$; $^1$H-NMR (CDCl$_3$, δ):1.27-1.37 (m, 2H), 1.77-1.95 (m, 2H), 3.20 (s, 2H), 3.42 (s, 3H), 3.82-4.28 (m, 4H), 4.93 (s, 2H), 6.91-7.45 (m, 9H), 7.75 (s, 1H), 8.22 (s, 1H), 8.59 (s, 1H), 10.70 (s, 1H).

EXAMPLE 154

N-[7-Benzylamino-6-(2H-spiro[2,3-dihydrobenzo[b]thiophene-1,1-dioxide-3,4'-piperidine]-1'-ylcarbonyl)pyrazolo[1,5-a]pyrimidine-3-carbonyl]methanesulfonamide (compound a-154)

N-[7-Benzylamino-6-(2H-spiro[2,3-dihydrobenzo[b]thiophene-3,4'-piperidine]-1'-ylcarbonyl)pyrazolo[1,5-a]pyrimidine-3-carbonyl]methanesulfonamide (0.048 g, 0.084 mmol) obtained in Example 153, step 3 was dissolved in acetonitrile (2.5 mL), and water (1.25 mL) was added. Oxone (0.113 g, 0.18 mmol) was added, and the mixture was stirred at room temperature for 16 hr, and saturated aqueous sodium thiosulfate solution was added to quench the reaction. The organic layer was separated, and the aqueous layer was extracted with chloroform. The organic layers were combined, washed with saturated brine, dried over anhydrous sodium sulfate, and concentrated under reduced pressure.

The obtained crude product was purified by silica gel column chromatography (chloroform/methanol=90/10) to give the title compound (0.029 g, 57%).

ESI-MS m/z: 609 (M+H)$^+$; $^1$H-NMR (CDCl$_3$, δ):1.20-1.39 (m, 2H), 1.76-2.06 (m, 2H), 3.29 (s, 2H), 3.43 (s, 3H), 3.95-4.62 (m, 4H), 4.94 (s, 2H), 7.26-7.58 (m, 6H), 7.64-7.85 (m, 3H), 8.20 (s, 1H), 8.61 (s, 1H).

EXAMPLE 155

N-[7-(4-Fluoro-2-methylphenylamino)-6-(2H-spiro[2,3-dihydrobenzo[b]thiophene-3,4'-piperidine]-1'-ylcarbonyl)pyrazolo[1,5-a]pyrimidine-3-carbonyl]cyclopropanesulfonamide (compound a-155)

[Step 1]

3-Ethoxycarbonyl-7-hydroxy-6-(2H-spiro[2,3-dihydrobenzo[b]thiophene-3,4'-piperidine]-1'-ylcarbonyl)pyrazolo[1,5-a]pyrimidine In the same manner as in Example 1, step 2 and using 3-ethoxycarbonyl-7-hydroxypyrazolo[1,5-a]pyrimidine-6-carboxylic acid (0.4 g, 1.59 mmol) obtained in Example 19, step 2 and 2H-spiro[2,3-dihydrobenzo[b]thiophene-3,4'-piperidine] (0.5 g, 2.07 mmol), the title compound (0.39 g, 55%) was obtained.

[Step 2]

7-Chloro-3-ethoxycarbonyl-6-(2H-spiro[2,3-dihydrobenzo[b]thiophene-3,4'-piperidine]-1'-ylcarbonyl)pyrazolo[1,5-a]pyrimidine In the same manner as in Example 1, step 3 and using 3-ethoxycarbonyl-7-hydroxy-6-(2H-spiro[2,3-dihydrobenzo[b]thiophene-3,4'-piperidine]-1'-ylcarbonyl)pyrazolo[1,5-a]pyrimidine (0.39 g, 0.88 mmol) obtained in step 1, the title compound (0.088 g, 22%) was obtained.

[Step 3]

3-Ethoxycarbonyl-7-(4-fluoro-2-methylphenylamino)-6-(2H-spiro[2,3-dihydrobenzo[b]thiophene-3,4'-piperidine]-1'-ylcarbonyl)pyrazolo[1,5-a]pyrimidine In the same manner as in Example 19, step 5 and using 7-chloro-3-ethoxycarbonyl-6-(2H-spiro[2,3-dihydrobenzo[b]thiophene-3,4'-piperidine]-1'-ylcarbonyl)pyrazolo[1,5-a]pyrimidine (0.088 g, 0.19 mmol) obtained in step 2 and 4-fluoro-2-methylaniline (0.037 g, 0.29 mmol), the title compound (0.088 g, 83%) was obtained.

[Step 4]

7-(4-Fluoro-2-methylphenylamino)-6-(2H-spiro[2,3-dihydrobenzo[b]thiophene-3,4'-piperidine]-1'-ylcarbonyl)pyrazolo[1,5-a]pyrimidine-3-carboxylic acid In the same manner as in Example 19, step 6 and using 3-ethoxycarbonyl-7-(4-fluoro-2-methylphenylamino)-6-(2H-spiro[2,3-dihydrobenzo[b]thiophene-3,4'-piperidine]-1'-ylcarbonyl)pyrazolo[1,5-a]pyrimidine (0.088 g, 0.16 mmol) obtained in step 3, the title compound (0.069 g, 82%) was obtained.

[Step 5]

N-[7-(4-Fluoro-2-methylphenylamino)-6-(2H-spiro[2,3-dihydrobenzo[b]thiophene-3,4'-piperidine]-1'-ylcarbonyl)pyrazolo[1,5-a]pyrimidine-3-carbonyl]cyclopropanesulfonamide (compound a-155)

In the same manner as in Example 1, step 6 and using 7-(4-fluoro-2-methylphenylamino)-6-(2H-spiro[2,3-dihydrobenzo[b]thiophene-3,4'-piperidine]-1'-ylcarbonyl)pyrazolo[1,5-a]pyrimidine-3-carboxylic acid (0.068 g, 0.13 mmol) obtained in step 4 and cyclopropanesulfonamide (0.08 g, 0.66 mmol), the title compound (0.069 g, 84%) was obtained.

ESI-MS m/z: 621 (M+H)$^+$; $^1$H-NMR (CDCl$_3$, δ):1.11-1.17 (m, 2H), 1.45-1.51 (m, 2H), 1.68 (dd, J=12.8, 4.0 Hz, 2H), 1.85 (d, J=13.9 Hz, 2H), 2.40 (s, 3H), 3.08-3.13 (m, 1H), 3.26 (s, 2H), 3.77-4.07 (m, 4H), 6.95-7.22 (m, 7H), 8.30 (s, 1H), 8.64 (s, 1H).

EXAMPLE 156

N-[7-Benzylamino-6-(spiro[indoline-3,4'-piperidine]-1'-ylcarbonyl)pyrazolo[1,5-a]pyrimidine-3-carbonyl]methanesulfonamide (compound a-156) and N-[7-benzylamino-6-(1-(tert-butoxycarbonyl)spiro[indoline-3,4'-piperidine]-1'-ylcarbonyl)pyrazolo[1,5-a]pyrimidine-3-carbonyl]methanesulfonamide (compound a-159)

[Step 1]

7-Benzylamino-6-(1-(tert-butoxycarbonyl)spiro[indoline-3,4'-piperidine]-1'-ylcarbonyl)-3-ethoxycarbonylpyrazolo[1,5-a]pyrimidine In the same manner as in Example 21, step 5 and using 7-benzylamino-3-ethoxycarbonylpyrazolo[1,5-a]pyrimidine-6-carboxylic acid (0.363 g, 1.07 mmol) obtained in Example 21, step 4 and tert-butyl spiro[indoline-3,4'-piperidine]-1-carboxylate (0.370 g, 1.28 mmmol) obtained in Reference Example 8, the title compound (0.518 g, 79%) was obtained.

[Step 2]

7-Benzylamino-6-(1-(tert-butoxycarbonyl)spiro[indoline-3,4'-piperidine]-1'-ylcarbonyl)pyrazolo[1,5-a]pyrimidine-3-carboxylic acid In the same manner as in Example 19, step 6 and using 7-benzylamino-6-(1-(tert-butoxycarbonyl)spiro[indoline-3,4'-piperidine]-1'-ylcarbonyl)-3-ethoxycarbonylpyrazolo[1,5-a]pyrimidine (0.300 g, 0.492 mmol) obtained in step 1, the title compound (0.076 g, 27%) was obtained.

[Step 3]

N-[7-Benzylamino-6-(1-(tert-butoxycarbonyl)spiro[indoline-3,4'-piperidine]-1'-ylcarbonyl)pyrazolo[1,5-a]pyrimidine-3-carbonyl]methanesulfonamide (compound a-159)

In the same manner as in Example 1, step 6 and using 7-benzylamino-6-(1-(tert-butoxycarbonyl)spiro[indoline-3,4'-piperidine]-1'-ylcarbonyl)pyrazolo[1,5-a]pyrimidine-3-carboxylic acid (0.150 g, 0.258 mmol) obtained in step 2 and methanesulfonamide (0.122 g, 1.29 mmol), the title compound (0.062 g, 25%) was obtained.

[Step 4]

N-[7-Benzylamino-6-(spiro[indoline-3,4'-piperidine]-1'-ylcarbonyl)pyrazolo[1,5-a]pyrimidine-3-carbonyl]methanesulfonamide (compound a-156)

N-[7-Benzylamino-6-(1-(tert-butoxycarbonyl)spiro[indoline-3,4'-piperidine]-1'-ylcarbonyl)pyrazolo[1,5-a]pyrimidine-3-carbonyl]methanesulfonamide (0.062 g, 0.094 mmol) obtained in step 3 was dissolved in 4 mol/L hydrogen chloride-dioxane solution, and the mixture was stirred at room temperature for 2 hr. The reaction mixture was concentrated under reduced pressure, ethyl acetate was added to the obtained crystals and the mixture was suction-filtered to give the title compound (0.036 g, 42%).

ESI-MS m/z: 560 (M+H)$^+$; $^1$H-NMR (CDCl$_3$, δ): 1.37-1.92 (m, 4H), 3.35-3.70 (m, 8H), 4.17-4.63 (m, 2H), 4.81 (s, 2H), 7.18-7.55 (m, 9H), 8.44 (s, 1H), 8.78 (s, 1H), 9.41-9.55 (m, 1H), 10.74-10.98 (m, 1H).

EXAMPLE 157

N-[7-(4-Fluoro-2-methylphenylamino)-6-(3,3-dimethyl-3H-spiro[isobenzofuran-1,4'-piperidine]-1'-ylcarbonyl)pyrazolo[1,5-a]pyrimidine-3-carbonyl]ethanesulfonamide (compound a-157)

[Step 1]

7-(4-Fluoro-2-methylphenylamino)-3-ethoxycarbonyl-6-(3,3-dimethyl-3H-spiro[isobenzofuran-1,4'-piperidine]-1'-ylcarbonyl)pyrazolo[1,5-a]pyrimidine In the same manner as in Example 21, step 5 and using 3-ethoxycarbonyl-7-(4-fluoro-2-methylphenylamino)pyrazolo[1,5-a]pyrimidine-6-carboxylic acid (0.14 g, 0.39 mmol) obtained in Example 139, step 2 and 3,3-dimethyl-3H-spiro[isobenzofuran-1,4'-piperidine] (WO2005/092895, 0.12 g, 0.47 mmol), the title compound (0.17 g, 77%) was obtained.

[Step 2]

7-(4-Fluoro-2-methylphenylamino)-6-(3,3-dimethyl-3H-spiro[isobenzofuran-1,4'-piperidine]-1'-ylcarbonyl)pyrazolo[1,5-a]pyrimidine-3-carboxylic acid In the same manner as in Example 19, step 6 and using 7-(4-fluoro-2-methylphenylamino)-3-ethoxycarbonyl-6-(3,3-dimethyl-3H-spiro[isobenzofuran-1,4'-piperidine]-1'-ylcarbonyl)pyrazolo[1,5-a]pyrimidine (0.17 g, 0.30 mmol) obtained in step 1, the title compound (0.12 g, 78%) was obtained.

[Step 3]

N-[7-(4-Fluoro-2-methylphenylamino)-6-(3,3-dimethyl-3H-spiro[isobenzofuran-1,4'-piperidine]-1'-ylcarbonyl)pyrazolo[1,5-a]pyrimidine-3-carbonyl]ethanesulfonamide (compound a-157)

In the same manner as in Example 1, step 6 and using 7-(4-fluoro-2-methylphenylamino)-6-(3,3-dimethyl-3H-spiro[isobenzofuran-1,4'-piperidine]-1'-ylcarbonyl)pyrazolo[1,5-a]pyrimidine-3-carboxylic acid (0.12 g, 0.23 mmol) obtained in step 2 and ethanesulfonamide (0.12 g, 1.17 mmol), the title compound (0.084 g, 58%) was obtained.

ESI-MS m/z: 621 (M+H)$^+$; $^1$H-NMR (CDCl$_3$, δ):1.46 (t, J=7.4 Hz, 3H), 1.50 (s, 6H), 1.63-1.81 (m, 4H), 2.41 (s, 3H), 3.61 (q, J=7.5 Hz, 2H), 3.80-4.37 (m, 4H), 6.99-7.13 (m, 5H), 7.19-7.24 (m, 1H), 7.30-7.34 (m, 1H), 8.27 (s, 1H), 8.31 (s, 1H), 8.63 (s, 1H), 10.52 (s, 1H).

Formulation Examples of the compound of the present invention are shown in the following.

FORMULATION EXAMPLE 1

Tablets having the following composition are prepared according to a conventional method. Compound a-1 (40 g), lactose (286.8 g) and potato starch (60 g) are mixed, and 10% aqueous solution (120 g) of hydroxypropylcellulose is added thereto. The mixture is kneaded, granulated, dried and sieved according to a conventional method to give granules for tableting. Magnesium stearate (1.2 g) is added thereto and they are mixed. The mixture is tableted by a tableting machine having a punch with diameter 8 mm (RT-15 type manufactured by KIKUSUI SEISAKUSHO LTD.) to give tablets (containing 20 mg of active ingredient per tablet).

| Formulation compound a-1 | 20 mg |
|---|---|
| lactose | 143.4 mg |
| potato starch | 30 mg |
| hydroxypropylcellulose | 6 mg |
| magnesium stearate | 0.6 mg |
| | 200 mg |

FORMULATION EXAMPLE 2

Injection having the following composition is prepared according to a conventional method. Compound a-1 (1 g) and D-mannitol (5 g) are added to distilled water for injection and they are mixed. Furthermore, the mixture is adjusted to pH 6 with hydrochloric acid and aqueous sodium hydroxide solution, and distilled water for injection is added to the total amount of 1000 mL. The obtained mixture is aseptically filled in a glass vial by 2 mL to give an injection (containing 2 mg of active ingredient per vial).

| Formulation compound a-1 | 2 mg |
|---|---|
| D-mannitol | 10 mg |
| hydrochloric acid | e.q. |
| aqueous sodium hydroxide solution | e.q. |
| distilled water for injection | e.q. |
| | 2.00 ml |

REFERENCE EXAMPLE 1

2H-Spiro[benzofuran-3,4'-piperidine]hydrochloride

[Step 1]

4-[(2-Iodophenoxy)methyl]pyridine

4-Picolyl chloride hydrochloride (4.00 g, 24.4 mmol) was dissolved in acetone (55 mL), potassium carbonate (10.1 g, 73.2 mmol) and o-iodophenol (6.97 g, 31.7 mmol) were added, and the mixture was heated under reflux for 24 hr. The reaction mixture was concentrated under reduced pressure, ethyl acetate was added to the obtained crystals, and the mixture was suction-filtered. The filtrate was concentrated under reduced pressure, and the obtained residue was purified by silica gel column chromatography (hexane/ethyl acetate=1/2) to give the title compound (4.02 g, 53%).
[Step 2]

1-Benzyl-4-[(2-iodophenoxy)methyl]-1,2,3,6-tetrahydropyridine

4-[(2-Iodophenoxy)methyl]pyridine (4.00 g, 12.9 mmol) obtained in step 1 was dissolved in acetonitrile (40 mL), benzyl chloride (1.77 mL 15.4 mmol) was added, and the mixture was heated under reflux for 6 hr. The reaction mixture was concentrated under reduced pressure, and the residue was dissolved in methanol (40 mL). Sodium borohydride (0.486 g, 12.9 mmol) was added at −20° C., and the mixture was heated to room temperature. Acetic acid (3.0 mL) was added to the reaction mixture, and the mixture was stirred for 30 min. Saturated aqueous sodium hydrogen carbonate solution was added, and the mixture was extracted several times with ethyl acetate. The combined organic layers were dried over magnesium sulfate, and the solvent was evaporated under reduced pressure. The obtained residue was purified by silica gel column chromatography (hexane/ethyl acetate=1/2) to give the title compound (1.1 g, 21%).
[Step 3]

2H-Spiro[benzofuran-3,4'-piperidine]hydrochloride

1-Benzyl-4-[(2-iodophenoxy)methyl]-1,2,3,6-tetrahydropyridine (1.09 g, 2.69 mmol) obtained in step 2 was dissolved in toluene (26 mL), tributyltin hydride (1.66 mL, 6.19 mmol) was added, and the mixture was heated under reflux for 2 hr. The reaction mixture was concentrated under reduced pressure, and the obtained oil was dissolved in methylene chloride (7.0 mL). 1-Chloroethyl (0.29 mL, 2.69 mmol) was added dropwise at 0° C., and the mixture was stirred at room temperature for 1 hr. Methylene chloride was evaporated under reduced pressure, methanol (10 mL) was added, and the mixture was heated under reflux for 1 hr. The reaction mixture was concentrated under reduced pressure, and the precipitated white crystals were suspended in ethyl acetate and the suspension was suction-filtered to give the title compound (0.489 mg, 80%).
ESI-MS m/z: 190 (M+H)$^+$; $^1$H-NMR (DMSO-d$_6$, δ): 1.99-2.23 (m, 2H), 2.25-2.52 (m, 2H), 3.16-3.40 (m, 2H), 3.50-3.70 (m, 2H), 4.77 (s, 2H), 7.07-7.14 (m, 1H), 7.16-7.26 (m, 1H), 7.37-7.53 (m, 2H), 9.22-9.53 (m, 1H).

REFERENCE EXAMPLE 2

4-Fluoro-2H-spiro[benzofuran-3,4'-piperidine]hydrochloride

[Step 1]

4-[(2-Bromo-3-fluorophenoxy)methyl]pyridine

In the same manner as in Reference Example 1, step 1 and using 2-bromo-3-fluorophenol (2.10 g, 12.8 mmol) instead of o-iodophenol, the title compound (3.33 g, 69%) was obtained.
[Step 2]

1-Benzyl-4-[(2-bromo-3-fluorophenoxy)methyl]-1,2,3,6-tetrahydropyridine

In the same manner as in Reference Example 1, step 2 and using 4-[(2-bromo-3-fluorophenoxy)methyl]pyridine (3.33 g, 8.86 mmol) instead of 4-[(2-iodophenoxy)methyl]pyridine, the title compound (1.07 g, 32%) was obtained.
[Step 3]

4-Fluoro-2H-spiro[benzofuran-3,4'-piperidine]hydrochloride

In the same manner as in Reference Example 1, step 3 and using 1-benzyl-4-[(2-bromo-3-fluorophenoxy)methyl]-1,2,3,6-tetrahydropyridine (1.07 g, 2.84 mmol) instead of 1-benzyl-4-[(2-iodophenoxy)methyl]-1,2,3,6-tetrahydropyridine, the title compound (0.650 g, 93%) was obtained.
ESI-MS m/z: 208 (M+H)$^+$; $^1$H-NMR (DMSO-d$_6$, δ): 1.81-2.07 (m, 2H), 2.19-2.47 (m, 2H), 2.84-3.24 (m, 2H), 3.25-3.41 (m, 2H), 4.56 (s, 2H), 6.61-6.80 (m, 2H), 7.08-7.28 (m, 1H), 8.99-9.17 (m, 1H).

REFERENCE EXAMPLE 3

5-Fluoro-2H-spiro[benzofuran-3,4'-piperidine]hydrochloride

[Step 1]

4-[(2-Bromo-4-fluorophenoxy)methyl]pyridine

In the same manner as in Reference Example 1, step 1 and using 2-bromo-4-fluorophenol (4.70 g, 24.4 mmol) instead of o-iodophenol, the title compound (3.26 g, 89%) was obtained.
[Step 2]

1-Benzyl-4-[(2-bromo-4-fluorophenoxy)methyl]-1,2,3,6-tetrahydropyridine

In the same manner as in Reference Example 1, step 2 and using 4-[(2-bromo-4-fluorophenoxy)methyl]pyridine (3.25 g, 11.5 mmol) instead of 4-[(2-iodophenoxy)methyl]pyridine, the title compound (1.76 g, 39%) was obtained.
[Step 3]

5-Fluoro-2H-spiro[benzofuran-3,4'-piperidine]hydrochloride

In the same manner as in Reference Example 1, step 3 and using 1-benzyl-4-[(2-bromo-4-fluorophenoxy)methyl]-1,2,3,6-tetrahydropyridine (1.76 g, 4.69 mmol) instead of 1-benzyl-4-[(2-iodophenoxy)methyl]-1,2,3,6-tetrahydropyridine, the title compound (0.900 mg, 78%) was obtained.
ESI-MS m/z: 208 (M+H)$^+$; $^1$H-NMR (DMSO-d$_6$, δ): 1.74-1.91 (m, 2H), 1.97-2.21 (m, 21H), 2.85-3.08 (m, 2H), 3.20-3.43 (m, 2H), 4.51 (s, 2H), 6.72-6.90 (m, 1H), 6.92-7.07 (m, 2H), 8.83-9.27 (m, 1H).

REFERENCE EXAMPLE 4

6-Fluoro-2H-spiro[benzofuran-3,4'-piperidine]hydrochloride

[Step 1]

4-[(2-Bromo-5-fluorophenoxy)methyl]pyridine

In the same manner as in Reference Example 1, step 1 and using 2-bromo-5-fluorophenol (12.0 g, 62.8 mmol) instead of o-iodophenol, the title compound (7.65 g, 64%) was obtained.

[Step 2]

1-Benzyl-4-[(2-bromo-5-fluorophenoxy)methyl]-1,2,3,6-tetrahydropyridine

In the same manner as in Reference Example 1, step 2 and using 4-[(2-bromo-5-fluorophenoxy)methyl]pyridine (7.65 g, 20.4 mmol) instead of 4-[(2-iodophenoxy)methyl]pyridine, the title compound (1.1 g, 14%) was obtained.

[Step 3]

6-Fluoro-2H-spiro[benzofuran-3,4'-piperidine]hydrochloride

In the same manner as in Reference Example 1, step 3 and using 1-benzyl-4-((2-bromo-5-fluorophenoxy)methyl)-1,2,3,6-tetrahydropyridine (8.77 g, 23.3 mmol) instead of 1-benzyl-4-[(2-iodophenoxy)methyl]-1,2,3,6-tetrahydropyridine, the title compound (0.483 g, 8%) was obtained.

ESI-MS m/z: 208 (M+H)$^+$; $^1$H-NMR (CDCl$_3$, δ): 1.63-1.77 (m, 2H), 1.77-1.90 (m, 3H), 2.58-2.80 (m, 2H), 3.03-3.18 (m, 2H), 4.44 (s, 2H), 6.42-6.66 (m, 2H), 6.98-7.10 (m, 1H).

REFERENCE EXAMPLE 5

7-Fluoro-2H-spiro[benzofuran-3,4'-piperidine]hydrochloride

[Step 1]

4-[(2-Bromo-6-fluorophenoxy)methyl]pyridine

In the same manner as in Reference Example 1, step 1 and using 2-bromo-6-fluorophenol (4.70 g, 24.4 mmol) instead of o-iodophenol, the title compound (3.25 g, 89%) was obtained.

[Step 2]

1-Benzyl-4-[(2-bromo-6-fluorophenoxy)methyl]-1,2,3,6-tetrahydropyridine

In the same manner as in Reference Example 1, step 2 and using 4-[(2-bromo-6-fluorophenoxy)methyl]pyridine (3.25 g, 11.5 mmol) instead of 4-[(2-iodophenoxy)methyl]pyridine, the title compound (3.45 g, 76%) was obtained.

[Step 3]

7-Fluoro-2H-spiro[benzofuran-3,4'-piperidine]hydrochloride

In the same manner as in Reference Example 1, step 3 and using 1-benzyl-4-[(2-bromo-6-fluorophenoxy)methyl]-1,2,3,6-tetrahydropyridine (1.76 g, 4.69 mmol) instead of 1-benzyl-4-[(2-iodophenoxy)methyl]-1,2,3,6-tetrahydropyridine, the title compound (1.06 g, 93%) was obtained.

ESI-MS m/z: 208 (M+H)$^+$; $^1$H-NMR (DMSO-d$_6$, δ): 1.78-1.98 (m, 2H), 1.98-2.20 (m, 2H), 2.86-3.13 (m, 2H), 3.23-3.43 (m, 2H), 4.63 (s, 2H), 6.84-7.03 (m, 2H), 7.03-7.19 (m, 1H), 8.88-9.22 (m, 1H).

REFERENCE EXAMPLE 6

2-Methylspiro[inden-1,4'-piperidine]

[Step 1]

tert-Butyl bis(2-chloroethyl)carbamate

Bis(2-chloroethyl)amine hydrochloride (5.00 g, 28.0 mmol) was dissolved in methylene chloride (50 mL), di-tert-butyl bicarbonate (6.62 g, 30.8 mmol) and triethylamine (3.89 mL, 28.0 mmol) were added, and the mixture was stirred at room temperature for 3 hr. The reaction mixture was concentrated under reduced pressure, and the obtained residue was purified by silica gel column chromatography (hexane/ethyl acetate=4/1) to give the title compound (5.84 g, 86%).

[Step 2]

tert-Butyl 2-methylspiro[inden-1,4'-piperidine]-1'-carboxylate tert-Butyl bis(2-chloroethyl)carbamate (1.33 g, 5.49 mmol) obtained in step 1 was dissolved in THF, 2-methylinden (1.00 g, 7.69 mmol) and sodium hydride (2.16 g, 49.4 mmol) were added under ice-cooling, and the mixture was heated under reflux for 3 hr. The reaction mixture was added dropwise to saturated aqueous sodium hydrogen carbonate solution under ice-cooling, and the mixture was extracted several times with ethyl acetate. The combined organic layers were dried over magnesium sulfate, and evaporated under reduced pressure. The obtained residue was purified by silica gel column chromatography (hexane/ethyl acetate=2/1) to give the title compound (1.19 g, 51%).

[Step 3]

2-Methylspiro[inden-1,4'-piperidine]

tert-Butyl 2-methylspiro[inden-1,4'-piperidine]-1'-carboxylate (1.19 g, 3.98 mmol) obtained in step 2 was dissolved in 4 mol/L hydrogen chloride-1,4-dioxane (6 mL), and the mixture was stirred at room temperature for 2 hr. The reaction mixture was concentrated under reduced pressure, ethyl acetate was added to the obtained residue, and the mixture was suction-filtered to give white crystals. Saturated aqueous sodium hydrogen carbonate solution was added to the white crystals, and the mixture was extracted with ethyl acetate. The combined organic layers were dried over magnesium sulfate, and concentrated under reduced pressure to give the title compound (0.790 g, 72%).

ESI-MS m/z: 200 (M+H)$^+$; $^1$H-NMR (CDCl$_3$, δ): 1.68-1.96 (m, 5H), 2.01 (s, 3H), 3.06-3.21 (m, 2H), 3.31-3.51 (m, 2H), 6.36-6.44 (m, 1H), 7.05-7.17 (m, 1H), 7.20-7.31 (m, 2H), 7.78-7.90 (m, 1H).

REFERENCE EXAMPLE 7

3-Methylspiro[inden-1,4'-piperidine]

[Step 1]

tert-Butyl 1-methyl-1-hydroxyspiro[indane-3,4'-piperidine]-1'-carboxylate tert-Butyl 1-oxospiro[indane-3,4'-piperidine]-1'-carboxylate (0.202 g, 0.671 mmol) was dissolved in THF (3 mL), 3 mmol/L methylmagnesium chloride-THF solution (0.450 mL, 1.34 mmol) was added under ice-cooling, and the mixture was stirred for 1 hr. Saturated aqueous ammonium chloride solution was added dropwise to the reaction mixture, and the mixture was extracted several times with ethyl acetate. The combined organic layers were dried over magnesium sulfate, and concentrated under reduced pressure. The obtained residue was purified by silica gel column chromatography (hexane/ethyl acetate=2/1) to give the title compound (0.141 g, 66%).

[Step 2]

tert-Butyl 3-methylspiro[inden-1,4'-piperidine]-1'-carboxylate tert-Butyl 1-methyl-1-hydroxyspiro[indane-3,4'-piperidine]-1'-carboxylate (0.140 g, 0.441 mmol) obtained in step 1 was dissolved in methylene chloride (2 mL), toluenesulfonic acid monohydrate (0.008 g, 0.044 mmol) was added, and the mixture was stirred at room temperature for 3 hr. Saturated aqueous ammonium chloride solution was added dropwise to the reaction mixture, and the mixture was extracted several times with ethyl acetate. The combined organic layers were dried over magnesium sulfate and concentrated under reduced pressure to give the title compound (0.108 g, 81%).

[Step 3]

3-Methylspiro[inden-1,4'-piperidine]

tert-Butyl 3-methylspiro[inden-1,4'-piperidine]-1'-carboxylate (0.155 g, 0.518 mmol) obtained in step 3 was dissolved in 4 mol/L hydrogen chloride-1,4-dioxane (2 mL), and the mixture was stirred at room temperature for 1 hr. The reaction mixture was concentrated under reduced pressure, ethyl acetate was added to the obtained residue, and the mixture was suction-filtered to give white crystals. Saturated aqueous sodium hydrogen carbonate solution was added to the white crystals, and the mixture was extracted with ethyl acetate. The combined organic layers were dried over magnesium sulfate, and concentrated under reduced pressure to give the title compound (0.097 g, 94%).

ESI-MS m/z: 200 (M+H)$^+$; $^1$H-NMR (CDCl$_3$, δ): 1.22-1.45 (m, 2H), 2.07-2.24 (m, 4H), 2.95-3.18 (m, 2H), 3.22-3.40 (m, 2H), 3.71 (s, 2H), 6.48-6.57 (m, 1H), 7.17-7.32 (m, 3H), 7.34-7.46 (m, 1H).

REFERENCE EXAMPLE 8 tert-Butylspiro[indoline-3,4'-piperidine]-1-carboxylate

[Step 1]

Benzyl 1-tert-butyloxycarbonylspiro[indoline-3,4'-piperidine]-1'-carboxylate

Benzylspiro[indoline-3,4'-piperidine]-1'-carboxylate (Tetrahedron, 1997, vol. 32, item 10983, 1.00 g, 3.11 mmol) was dissolved in methylene chloride (10 mL), di-tert-butyl bicarbonate (1.00 g, 4.65 mmol) and triethylamine (0.860 mL, 6.21 mmol) were added, and the mixture was stirred at room temperature for 1 hr. The reaction mixture was concentrated under reduced pressure, and the obtained residue was purified by silica gel column chromatography (hexane/ethyl acetate=1/2) to give the title compound (1.14 g, 87%).

[Step 2]

tert-Butylspiro[indoline-3,4'-piperidine]-1-carboxylate

Benzyl 1-tert-butyloxycarbonylspiro[indoline-3,4'-piperidine]-1'-carboxylate (0.500 g, 1.18 mmol) obtained in step 1 was dissolved in ethanol (6 mL), 10% palladium-carbon (0.125 g) was added, and the mixture was stirred at room temperature for 4 hr under a hydrogen atmosphere. The system was substituted with nitrogen, and the reaction mixture was filtered through celite and washed with ethanol. The obtained filtrate was concentrated under reduced pressure to give the title compound (0.339 g, 100%).

ESI-MS m/z: 289 (M+H)$^+$; $^1$H-NMR (CDCl$_3$, δ): 1.52-1.71 (m, 12H), 1.72-1.91 (m, 2H), 2.66-2.85 (m, 2H), 3.02-3.16 (m, 2H), 3.87 (s, 2H), 6.92-7.03 (m, 1H), 7.11-7.24 (m, 2H), 7.43-7.87 (m, 1H).

Industrial Applicability

The present invention can provide an agent for the prevention and/or treatment of a skin disease, containing, as an active ingredient, a pyrazolopyrimidine derivative or a pharmacologically acceptable salt thereof, and the like.

This application is based on a patent application No. 2007-252804 filed in Japan, the contents of which are incorporated in full herein by this reference.

The invention claimed is:

1. A compound of formula

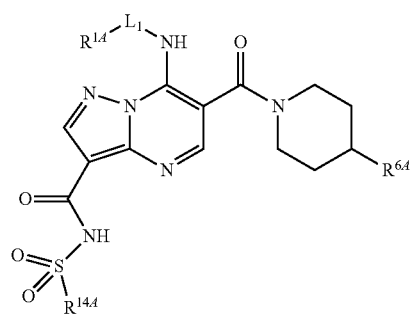

wherein
L$^1$ is a single bond or methylene,
R$^{1A}$ is aryl optionally having substituent(s),
R$^{6A}$ is aryl optionally having substituent(s), and
R$^{14A}$ is lower alkyl or cycloalkyl;
or a pharmacologically acceptable salt thereof.

2. The compound of claim 1, wherein R$^{1A}$ is phenyl optionally having substituent(s), R$^{6A}$ is phenyl optionally having substituent(s), and R$^{14A}$ is lower alkyl, or a pharmacologically acceptable salt thereof.

3. The compound of claim 1 that is

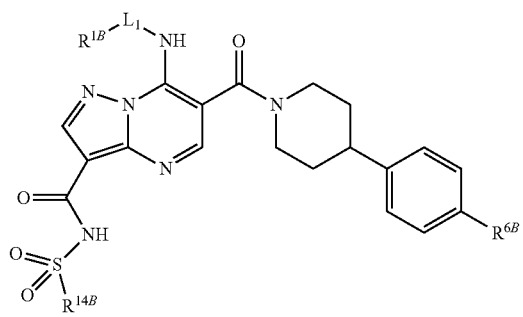

wherein
L$^1$ is a single bond or methylene,
R$^{1B}$ is phenyl optionally having substituent(s), wherein the substituent(s) are 1 to 2 substituents which are the same or different, and each is selected from a fluorine atom or methyl,
R$^{6B}$ is a hydrogen atom or a fluorine atom, and
R$^{14B}$ is methyl or ethyl,
or a pharmacologically acceptable salt thereof.

4. The compound of claim 1 that is N-[7-benzylamino-6-(4-phenylpiperidine-1-carbonyl)pyrazolo[1,5-a]pyrimidine-3-carbonyl]methanesulfonamide (compound a-1) or a pharmacologically acceptable salt thereof.

5. The compound of claim 1 that is N-[7-(4-fluoro-2-methylphenylamino) -6-(4-phenylpiperidine-1-carbonyl)pyrazolo[1,5-a]pyrimidine-3-carbonyl]ethanesulfonamide (compound a-57) or a pharmacologically acceptable salt thereof.

6. The compound of claim 1 that is N-{7-(2-fluoro-5-methylphenylamino)-6-[4-(4-fluorophenyl)piperidine-1-carbonyl]pyrazolo[1,5-a]pyrimidine-3-carbonyl}ethanesulfonamide (compound a-81) or a pharmacologically acceptable salt thereof.

7. The compound of claim 1 that is N-{7-(4-fluoro-2-methylphenylamino)-6-[4-(4-fluorophenyl)piperidine-1-carbonyl]pyrazolo[1,5-a]pyrimidine-3-carbonyl }ethanesulfonamide (compound a-84) or a pharmacologically acceptable salt thereof.

8. A pharmaceutical composition comprising (a) the compound of claim 1 or a pharmacologically acceptable salt thereof and (b) a pharmaceutically acceptable carrier.

9. The pharmaceutical composition of claim 8, wherein the compound is
N-[7-benzylamino-6-(4-phenylpiperidine-1-carbonyl)pyrazolo[1,5-a]pyrimidine-3-carbonyl]methanesulfonamide (compound a-1),
N-[7-(4-fluoro-2-methylphenylamino)-6-(4-phenylpiperidine-1-carbonyl)pyrazolo[1,5-a]pyrimidine-3-carbonyl]ethanesulfonamide (compound a-57),
N-{7-(2-fluoro-5-methylphenylamino)-6-[4-(4-fluorophenyl)piperidine-1-carbonyl]pyrazolo[1,5-a]pyrimidine-3-carbonyl}ethanesulfonamide (compound a-81), or
N-{7-(4-fluoro-2-methylphenylamino)-6[4-(4-fluorophenyl)piperidine-1-carbonyl]pyrazolo[1,5-a]pyrimidine-3-carbonyl}ethanesulfonamide (compound a-84).

10. A pharmaceutical composition comprising (a) the compound of claim 2 or a pharmacologically acceptable salt thereof and (b) a pharmaceutically acceptable carrier.

11. A pharmaceutical composition comprising (a) the compound of claim 3 or a pharmacologically acceptable salt thereof and (b) a pharmaceutically acceptable carrier.

* * * * *